US011253525B2

(12) United States Patent
Balog et al.

(10) Patent No.: US 11,253,525 B2
(45) Date of Patent: Feb. 22, 2022

(54) INHIBITORS OF INDOLEAMINE 2,3-DIOXYGENASE AND METHODS OF THEIR USE

(71) Applicant: BRISTOL-MYERS SQUIBB COMPANY, Princeton, NJ (US)

(72) Inventors: James Aaron Balog, Lambertville, NJ (US); Steven P. Seitz, Swarthmore, PA (US); Susheel Jethanand Nara, Mumbai (IN); Saumya Roy, Bangalore (IN); Srinivasan Thangathirupathy, Hosur (IN); Soodamani Thangavel, Krishnagiri (IN); Srinivas Cheruku, Bangalore (IN)

(73) Assignee: Bristol-Myers Squibb Company, Princeton, NJ (US)

(*) Notice: Subject to any disclaimer, the term of this patent is extended or adjusted under 35 U.S.C. 154(b) by 0 days.

(21) Appl. No.: 16/555,431

(22) Filed: Aug. 29, 2019

(65) Prior Publication Data
US 2020/0069695 A1    Mar. 5, 2020

Related U.S. Application Data

(60) Provisional application No. 62/724,404, filed on Aug. 29, 2018.

(51) Int. Cl.
| | |
|---|---|
| *A61P 35/00* | (2006.01) |
| *A61K 31/17* | (2006.01) |
| *A61K 31/44* | (2006.01) |
| *A61K 31/50* | (2006.01) |
| *A61K 31/136* | (2006.01) |
| *A61K 31/275* | (2006.01) |
| *A61K 31/351* | (2006.01) |
| *A61K 31/428* | (2006.01) |
| *A61K 31/4965* | (2006.01) |
| *A61K 31/505* | (2006.01) |
| *A61K 31/5375* | (2006.01) |
| *A61K 31/5377* | (2006.01) |
| *C07C 211/54* | (2006.01) |
| *C07C 229/42* | (2006.01) |
| *C07C 255/58* | (2006.01) |
| *C07C 275/42* | (2006.01) |
| *C07D 213/90* | (2006.01) |
| *C07D 237/22* | (2006.01) |
| *C07D 239/42* | (2006.01) |
| *C07D 239/47* | (2006.01) |
| *C07D 241/18* | (2006.01) |
| *C07D 265/30* | (2006.01) |
| *C07D 277/64* | (2006.01) |
| *C07D 295/03* | (2006.01) |
| *C07D 407/12* | (2006.01) |
| *C07D 413/12* | (2006.01) |

(52) U.S. Cl.
CPC ........ *A61K 31/5377* (2013.01); *A61K 31/136* (2013.01); *A61K 31/17* (2013.01); *A61K 31/275* (2013.01); *A61K 31/428* (2013.01); *A61K 31/4965* (2013.01); *A61K 31/505* (2013.01); *A61K 31/5375* (2013.01); *C07C 211/54* (2013.01); *C07C 275/42* (2013.01); *C07D 239/42* (2013.01); *C07D 239/47* (2013.01); *C07D 241/18* (2013.01); *C07D 277/64* (2013.01); *C07D 295/03* (2013.01); *C07D 413/12* (2013.01)

(58) Field of Classification Search
CPC ......... A61P 35/00; A61K 31/17; A61K 31/44; A61K 31/50; A61K 31/136; A61K 31/275; A61K 31/351; A61K 31/428; A61K 31/4965; A61K 31/505; A61K 31/5375; A61K 31/5377; C07C 211/54; C07C 229/42; C07C 255/58; C07C 275/42; C07D 213/90; C07D 237/22; C07D 239/42; C07D 239/47; C07D 241/18; C07D 265/30; C07D 277/64; C07D 295/03; C07D 407/12; C07D 413/12

See application file for complete search history.

(56) References Cited

U.S. PATENT DOCUMENTS

| | | |
|---|---|---|
| 9,598,422 B2 | 3/2017 | Beck et al. |
| 2007/0167426 A1 | 7/2007 | Siddiqui et al. |
| 2009/0155311 A1 | 6/2009 | Chen et al. |

FOREIGN PATENT DOCUMENTS

| | | |
|---|---|---|
| WO | 2004/022529 A2 | 3/2004 |
| WO | 2004/094409 A1 | 11/2004 |
| WO | 2006/029879 | 3/2006 |
| WO | 2006/105021 A2 | 10/2006 |
| WO | 2006/122150 A1 | 11/2006 |
| WO | 2007/005874 A2 | 1/2007 |
| WO | 2007/075598 A2 | 7/2007 |
| WO | 2008/036642 A2 | 3/2008 |
| WO | 2008/036653 A2 | 3/2008 |

(Continued)

OTHER PUBLICATIONS

Ball et al., Characterization of an indoleamine 2, 3-dioxygenase-like protein found in humans and mice, Gene, Jul. 1, 2007;396(1):203-213.

(Continued)

*Primary Examiner* — Brenda L Coleman
(74) *Attorney, Agent, or Firm* — BakerHostetler

(57) ABSTRACT

There are disclosed compounds that modulate or inhibit the enzymatic activity of indoleamine 2,3-dioxygenase (IDO), pharmaceutical compositions containing said compounds and methods of treating proliferative disorders, such as cancer, viral infections and/or inflammatory disorders utilizing the compounds of the disclosure.

32 Claims, No Drawings

(56) References Cited

FOREIGN PATENT DOCUMENTS

| WO | 2009/009116 | | 1/2009 |
|---|---|---|---|
| WO | 2009/044273 | | 4/2009 |
| WO | 2009/073620 | A2 | 6/2009 |
| WO | 2010/019570 | | 2/2010 |
| WO | 2010/077634 | A1 | 7/2010 |
| WO | 2011/028683 | | 3/2011 |
| WO | 2011/056652 | | 5/2011 |
| WO | 2011/070024 | | 6/2011 |
| WO | 2011/107553 | A1 | 9/2011 |
| WO | 2011/131407 | A1 | 10/2011 |
| WO | 2011/140249 | A2 | 11/2011 |
| WO | 2012/032433 | | 3/2012 |
| WO | 2012/142237 | A1 | 10/2012 |
| WO | 2012/145493 | A1 | 10/2012 |
| WO | 2013/079174 | | 6/2013 |
| WO | 2013/087699 | | 6/2013 |
| WO | 2013/119716 | A1 | 8/2013 |
| WO | 2013/132044 | A1 | 9/2013 |
| WO | 2013/169264 | A1 | 11/2013 |
| WO | 2014/008218 | | 1/2014 |
| WO | 2014/036357 | A1 | 3/2014 |
| WO | 2016/073738 | A2 | 5/2016 |
| WO | 2016/073770 | A1 | 5/2016 |
| WO | 2016/073774 | A2 | 5/2016 |

OTHER PUBLICATIONS

Brandacher et al., Prognostic value of indoleamine 2, 3-dioxygenase expression in colorectal cancer: effect on tumor-infiltrating T cells, Clinical cancer research, Feb. 15, 2006;12(4):1144-1151.
Bundgaard H. (C) Means to enhance penetration:(1) Prodrugs as a means to improve the delivery of peptide drugs, Advanced Drug Delivery Reviews, Jan. 1, 1992;8(1):1-38.
Bundgaard, H., Chapter 5: "Design and Application of Prodrugs", A Textbook of Drug Design and Development, pp. 113-191, Krogsgaard-Larsen, P., et al., eds., Harwood Academic Publishers, 1991.
Evans et al., Asymmetric alkylation reactions of chiral imide enolates. A practical approach to the enantioselective synthesis of. alpha.-substituted carboxylic acid derivatives, Journal of the American Chemical Society, Mar. 1982;104(6):1737-1739.
Goldstein et al., Biological efficacy of a chimeric antibody to the epidermal growth factor receptor in a human tumor xenograft model. Clinical Cancer Research, Nov. 1, 1995;1(11):1311-1318.
Ishiyama et al., Palladium (0)-catalyzed cross-coupling reaction of alkoxydiboron with haloarenes: a direct procedure for arylboronic esters, The Journal of Organic Chemistry, Nov. 1995;60(23):7508-7510.
Kakeya et al., Studies on Prodrugs of Cephalosporins. I. Synthesis and Biological Properties of Glycyloxybenzoyloxymethyl and Glycylaminobenzoyloxymethyl Esters of 7ß-[2-(2-Aminothiazol-4-yl)-(Z)-2-methoxyiminoacetamido]-3-methyl-3-cephem-4-carboxylic Acid, Chemical and pharmaceutical bulletin, Feb. 25, 1984;32(2):692-698.
Kohl et al., Inhibition of farnesyltransferase induces regression of mammary and salivary carcinomas in ras transgenic mice, Nature medicine. Aug. 1995;1(8):792-797.
Littlejohn et al., Expression and purification of recombinant human indoleamine 2, 3-dioxygenase, Protein expression and purification, Jun. 1, 2000;19(1):22-29.
Nielsen et al., Glycolamide esters as biolabile prodrugs of carboxylic acid agents: synthesis, stability, bioconversion, and physicochemical properties, Journal of Pharmaceutical Sciences, Apr. 1988;77(4):285-298.
Pubchem, Substance Record for SID 111585117. Create Date: Mar. 7, 2011. Retrieved on Jun. 22, 2017. Retrieved from the Internet: https://pubchem.ncbi.nlm.nih.gov/substance/111585117, entire document.
Pubchem, Substance Record for SID 121181436. Create Date: May 5, 2011. Retrieved on Jun. 22, 2017. Retrieved from the Internet: https://pubchem.ncbi.nlm.nih.gov/substance/121181436. entire document.
Sarkar et al., Induction of indoleamine 2, 3-dioxygenase by interferon-? in human islets, Diabetes, Jan. 1, 2007;56(1):72-79.
Sausville et al., Cyclin-dependent kinase modulators studied at the NCI: pre-clinical and clinical studies, Current Medicinal Chemistry-Anti-Cancer Agents, Jan. 1, 2003;3(1):47-56.
Scheller et al., Paclitaxel balloon coating, a novel method for prevention and therapy of restenosis, Circulation, Aug. 17, 2004;110(7):810-814.
Sekulic et al., A direct linkage between the phosphoinositide 3-kinase-AKT signaling pathway and the mammalian target of rapamycin in mitogen-stimulated and transformed cells, Cancer research, Jul. 1, 2000;60(13):3504-3513.
Serafini et al., Myeloid suppressor cells in cancer: recruitment, phenotype, properties, and mechanisms of immune suppression, In Seminars in cancer biology Feb. 1, 2006 (vol. 16, No. 1, pp. 53-65). Academic Press.
Surry et al., "Dialkylbiaryl Phosphines in Pd-Catalyzed Amination: A User's Guide", Chem. Sci., 2011, 2, 27-50.
Vlahos et al., A specific inhibitor of phosphatidylinositol 3-kinase, 2-(4-morpholinyl)-8-phenyl-4H-1-benzopyran-4-one (LY294002), Journal of Biological Chemistry, J. Biol. Chem, 1994, 269, 5241-5248.
Widder, K., et al., eds., Methods of Enzymology, Academic Press, 1985, 112, 309-396.
Zou et al., "Heck-type coupling vs. conjugate addition in phosphine-rhodium catalyzed reactions of aryl boronic acids with a,ß-unsaturated carbonyl compounds: a systematic investigation", Dalton Trans., 2007, 28, 3055-3064.
Vacchelli et al., Trial watch: IDO Inhibitors in cancer therapy, OncoImmunology, 2014, 3(10), e957994-1 to 3957994-10.
Gaspari ot al. "Structure-Activity Study of Brassinin Derivatives as Indoleamlne 2,3-Dioxygenase Inhibitors", J Med Chem. 2006. vol. 49(2), pp. 684-692, entire document, especially: abstract; p. 21, Scheme 1, e.g. products 2, 3, 4 and 7.

INHIBITORS OF INDOLEAMINE 2,3-DIOXYGENASE AND METHODS OF THEIR USE

CROSS-REFERENCE TO RELATED APPLICATION

This application claims the benefit of priority to U.S. provisional patent application No. 62/724,404, filed on Aug. 29, 2018, the entirety of which is incorporated by reference herein.

FIELD OF THE DISCLOSURE

The disclosure relates generally to compounds that modulate or inhibit the enzymatic activity of indoleamine 2,3-dioxygenase (IDO), pharmaceutical compositions containing said compounds and methods of treating proliferative disorders, such as cancer, viral infections and/or autoimmune diseases utilizing the compounds of the disclosure.

BACKGROUND

Indoleamine 2,3-dioxygenase (IDO; also known as IDO1) is an IFN-γ target gene that plays a role in immunomodulation. IDO is an oxidoreductase and one of two enzymes that catalyze the first and rate-limiting step in the conversion of tryptophan to N-formyl-kynurenine. It exists as a 41 kD monomer that is found in several cell populations, including immune cells, endothelial cells, and fibroblasts. IDO is relatively well-conserved between species, with mouse and human sharing 63% sequence identity at the amino acid level. Data derived from its crystal structure and site-directed mutagenesis show that both substrate binding and the relationship between the substrate and iron-bound dioxygenase are necessary for activity. A homolog to IDO (IDO2) has been identified that shares 44% amino acid sequence homology with IDO, but its function is largely distinct from that of IDO. (See, e.g., Serafini, P. et al., *Semin. Cancer Biol.*, 16(1):53-65 (February 2006) and Ball, H. J. et al., *Gene*, 396(1):203-213 (Jul. 1, 2007)).

IDO plays a major role in immune regulation, and its immunosuppressive function manifests in several manners. Importantly, IDO regulates immunity at the T cell level, and a nexus exists between IDO and cytokine production. In addition, tumors frequently manipulate immune function by upregulation of IDO. Thus, modulation of IDO can have a therapeutic impact on a number of diseases, disorders and conditions.

A pathophysiological link exists between IDO and cancer. Disruption of immune homeostasis is intimately involved with tumor growth and progression, and the production of IDO in the tumor microenvironment appears to aid in tumor growth and metastasis. Moreover, increased levels of IDO activity are associated with a variety of different tumors (Brandacher, G. et al., *Clin. Cancer Res.*, 12(4):1144-1151 (Feb. 15, 2006)).

Treatment of cancer commonly entails surgical resection followed by chemotherapy and radiotherapy. The standard treatment regimens show highly variable degrees of long-term success because of the ability of tumor cells to essentially escape by regenerating primary tumor growth and, often more importantly, seeding distant metastasis. Recent advances in the treatment of cancer and cancer-related diseases, disorders and conditions comprise the use of combination therapy incorporating immunotherapy with more traditional chemotherapy and radiotherapy. Under most scenarios, immunotherapy is associated with less toxicity than traditional chemotherapy because it utilizes the patient's own immune system to identify and eliminate tumor cells.

In addition to cancer, IDO has been implicated in, among other conditions, immunosuppression, chronic infections, and autoimmune diseases or disorders (e.g., rheumatoid arthritis). Thus, suppression of tryptophan degradation by inhibition of IDO activity has tremendous therapeutic value. Moreover, inhibitors of IDO can be used to enhance T cell activation when the T cells are suppressed by pregnancy, malignancy, or a virus (e.g., HIV). Although their roles are not as well defined, IDO inhibitors may also find use in the treatment of patients with neurological or neuropsychiatric diseases or disorders (e.g., depression).

Small molecule inhibitors of IDO have been developed to treat or prevent IDO-related diseases. For example, the IDO inhibitors 1-methyl-DL-tryptophan; p-(3-benzofuranyl)-DL-alanine; p-[3-benzo(b)thienyl]-DL-alanine; and 6-nitro-L-tryptophan have been used to modulate T cell-mediated immunity by altering local extracellular concentrations of tryptophan and tryptophan metabolites (WO 99/29310). Compounds having IDO inhibitory activity are further reported in PCT Publication No. WO 2004/094409.

In view of the role played by indoleamine 2,3-dioxygenase in a diverse array of diseases, disorders and conditions, and the limitations (e.g., efficacy) of current IDO inhibitors, new IDO modulators, and compositions and methods associated therewith, are needed.

SUMMARY OF THE DISCLOSURE

The disclosure is directed to compounds of formula I or II:

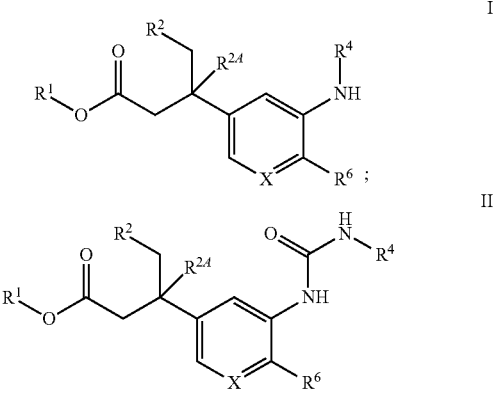

wherein X is CH, C—$V^a$—$R^3$, or N, wherein $V^a$ is $C_1$-$C_6$alkylene optionally substituted with phenyl optionally substituted with halogen; $R^1$ is H or $C_{1-6}$alkyl; $R^2$ is H, $C_{1-6}$alkyl, or $C_{0-6}$alk-$OC_{1-6}$alkyl, $R^{2A}$ is H or $C_{1-6}$alkyl, $R^6$ is H or —$V^b$—$R^3$, such that $R^6$ must be H when X is C—$V^a$—$R^3$, and $R^6$ must be —$V^b$—$R^3$ when X is CH or N; $V^b$ is $C_1$-$C_6$alkylene optionally substituted with one, two, or three substituents independently selected from —OH, $C_{1-6}$alkyl, $C_{1-6}$haloalkyl, and heterocycloalkyl; or $V^b$ is $C_{2-6}$alkenylene optionally substituted with $C_{1-6}$alkyl; $R^3$ is $C_{1-6}$alkyl optionally substituted with one, two or three —OH, or is $OC_{1-6}$alkyl optionally substituted with one, two or three —OH; $R^4$ is phenyl, pyridyl, pyrazinyl, pyridazinyl, pyrimidyl, or benzothiazolyl, each of which is optionally substituted with one, two or three substituents independently selected from halogen, $C_{1-6}$alkyl, $C_{1-6}$haloalkyl, $OC_{1-6}$haloalkyl, $C_{0-6}$alk-O—$C_{1-6}$alkyl, —CN, —COOH, and —COOC$_{1-6}$alkyl; and the pharmaceutically acceptable salt thereof and solvates thereof. Compositions comprising these compounds, as well as methods of using these compounds, are also described.

DETAILED DESCRIPTION

Compounds of the Disclosure

The disclosure is directed to compounds of formula I and formula II:

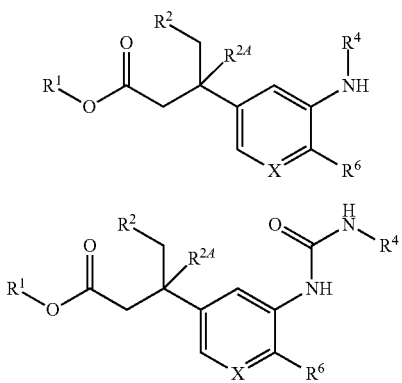

Some embodiments of the disclosure are directed to compounds of formula I. Other embodiments of the disclosure are directed to compounds of formula II.

According to the disclosure, X is CH, N, or C—$V^a$—$R^3$. In some embodiments, X is CH. In other embodiments, X is N. In other embodiments, X is C—$V^a$—$R^3$.

$V^a$ is $C_1$-$C_6$alkylene, for example, $C_1$-$C_5$alkylene, $C_1$-$C_4$alkylene, $C_1$-$C_3$alkylene, $C_1$-$C_2$alkylene, $C_6$alkylene, $C_5$alkylene, $C_4$alkylene, $C_3$alkylene, $C_2$alkylene, or $C_1$alkylene. In some aspects, the $C_1$-$C_6$alkylene is substituted with a phenyl group that is optionally substituted with halogen (e.g., fluoro, chloro, bromo, iodo). For example, in some aspects, the $C_1$-$C_6$alkylene is substituted with 4-fluorophenyl.

According to the disclosure, $R^1$ is H or $C_{1-6}$alkyl. In some aspects, $R^1$ is H. In other aspects, $R^1$ is $C_{1-6}$alkyl, for example, $C_6$alkyl (e.g., hexyl, methylpentanyl), $C_5$alkyl (e.g., pentyl, isopentyl), $C_4$alkyl (e.g., butyl, t-butyl), $C_3$alkyl (e.g., propyl, isopropyl), ethyl ($C_2$alkyl), or methyl ($C_1$alkyl). In preferred embodiments, $R^1$ is H.

According to the disclosure, $R^2$ is H, $C_{1-6}$alkyl, or $C_{0-6}$alk-OC$_{1-6}$alkyl. In some aspects, $R^2$ is H. In other aspects, $R^2$ is $C_{1-6}$alkyl, for example, $C_6$alkyl (e.g., hexyl, methylpentanyl), $C_5$alkyl (e.g., pentyl, isopentyl), $C_4$alkyl (e.g., butyl, t-butyl), $C_3$alkyl (e.g., propyl, isopropyl), ethyl ($C_2$alkyl), or methyl ($C_1$alkyl). In some aspects, $R^2$ is $C_{0-6}$alk-OC$_{1-6}$alkyl, for example, $C_{1-6}$alk-OC$_{1-6}$alkyl, $C_{0-5}$alk-OC$_{1-6}$alkyl, $C_{0-4}$alk-OC$_{1-6}$alkyl, $C_{0-3}$alk-OC$_{1-6}$alkyl, $C_{0-2}$alk-OC$_{1-6}$alkyl, $C_2$alk-OC$_{1-6}$alkyl, $C_1$alk-OC$_{1-6}$alkyl, $C_0$alk-OC$_{1-6}$alkyl, $C_{0-6}$alk-OC$_{1-5}$alkyl, $C_{1-6}$alk-OC$_{1-5}$alkyl, $C_{0-6}$alk-OC$_{1-4}$alkyl, $C_{0-6}$alk-OC$_{1-3}$alkyl, $C_{0-6}$alk-OC$_{1-2}$alkyl, and $C_{0-6}$alk-OC$_1$alkyl.

According to the disclosure, $R^{2A}$ is H or $C_{1-6}$alkyl. In some aspects, $R^{2A}$ is H. Preferably, $R^{2A}$ is H when $R^2$ is $C_{1-6}$alkyl or $C_{0-6}$alk-OC$_{1-6}$alkyl. In other aspects, $R^{2A}$ is $C_{1-6}$alkyl, for example, $C_6$alkyl (e.g., hexyl, methylpentanyl), $C_5$alkyl (e.g., pentyl, isopentyl), $C_4$alkyl (e.g., butyl, t-butyl), $C_3$alkyl (e.g., propyl, isopropyl), ethyl ($C_2$alkyl), or methyl ($C_1$alkyl).

According to the disclosure, $R^6$ is H when X is C—$V^a$—$R^3$, or $R^6$ is —$V^b$—$R^3$ when X is CH or N.

According to the disclosure, $V^b$ is $C_1$-$C_6$alkylene, for example, $C_1$-$C_5$alkylene, $C_1$-$C_4$alkylene, $C_1$-$C_3$alkylene, $C_1$-$C_2$alkylene, $C_6$alkylene, $C_5$alkylene, $C_4$alkylene, $C_3$alkylene, $C_2$alkylene, or $C_1$alkylene. In some aspects, the $C_1$-$C_6$alkylene is substituted with one, two, or three substitutents, preferably one or two, independently selected from OH, $C_{1-6}$alkyl, $C_{1-6}$haloalkyl, and heterocycloalkyl. For example, in some aspects, the $C_1$-$C_6$alkylene is substituted with one, two, or three, preferably one or two, OH. In other aspects, $C_1$-$C_6$alkylene is substituted with one, two, or three, preferably one or two, independently selected $C_{1-6}$alkyl, for example, $C_6$alkyl (e.g., hexyl, methylpentanyl), $C_5$alkyl (e.g., pentyl, isopentyl), $C_4$alkyl (e.g., butyl, t-butyl), $C_3$alkyl (e.g., propyl, isopropyl), ethyl ($C_2$alkyl), or methyl ($C_1$alkyl). In other aspects, the $C_1$-$C_6$alkylene is substituted with one, two, or three, preferably one, independently selected $C_{1-6}$haloalkyl, for example, CF$_3$. In other aspects, the $C_1$-$C_6$alkylene is substituted with one, two, or three, preferably one, independently selected heterocycloalkyl, for example, morpholinyl, tetrahydropyranyl, or piperdinyl.

In other embodiments of the disclosure, $V^b$ is $C_{2-6}$alkenylene, for example, $C_2$alkenylene, $C_3$alkenylene, $C_4$alkenylene, $C_5$alkenylene, or $C_6$alkenylene. In some aspects, the $C_{2-6}$alkenylene is substituted with one, two, or three, preferably one or two, independently selected $C_{1-6}$alkyl, for example $C_6$alkyl (e.g., hexyl, methylpentanyl), $C_5$alkyl (e.g., pentyl, isopentyl), $C_4$alkyl (e.g., butyl, t-butyl), $C_3$alkyl (e.g., propyl, isopropyl), ethyl ($C_2$alkyl), or methyl ($C_1$alkyl).

According to the disclosure, $R^3$ is $C_{1-6}$alkyl optionally substituted with one, two or three —OH, or is OC$_{1-6}$alkyl optionally substituted with one, two or three —OH. The $C_{1-6}$alkyl, whether substituted or not, can be, for example, $C_6$alkyl (e.g., hexyl, methylpentanyl), $C_5$alkyl (e.g., pentyl, isopentyl), $C_4$alkyl (e.g., butyl, t-butyl), $C_3$alkyl (e.g., propyl, isopropyl), ethyl ($C_2$alkyl), or methyl ($C_1$alkyl). In some embodiments, $R^3$ is $C_{1-6}$alkyl optionally substituted with one, two or three —OH. In some aspects, the $C_{1-6}$alkyl is unsubstituted. In some aspects, the $C_{1-6}$alkyl is substituted with one OH. In other aspects, the $C_{1-6}$alkyl is substituted with two OH. In yet other aspects, the $C_{1-6}$alkyl is substituted with three OH.

In some embodiments, $R^3$ is OC$_{1-6}$alkyl optionally substituted with one, two or three —OH. In some embodiments, $R^3$ is OC$_{1-6}$alkyl optionally substituted with one, two or three —OH. The OC$_{1-6}$alkyl, whether substituted or not, can be, for example, methoxy (OC$_1$alkyl), ethoxy (OC$_1$alkyl), OC$_3$alkyl, OC$_4$alkyl, OC$_5$alkyl, or OC$_6$alkyl. In some aspects, the OC$_{1-6}$alkyl is unsubstituted. In some aspects, the OC$_{1-6}$alkyl is substituted with one OH. In other aspects, the OC$_{1-6}$alkyl is substituted with two OH. In yet other aspects, the OC$_{1-6}$alkyl is substituted with three OH. In some aspects, $R^3$ is OC$_{1-6}$alkyl, for example, methoxy (OC$_1$alkyl), ethoxy (OC$_1$alkyl), OC$_3$alkyl, OC$_4$alkyl, OC$_5$alkyl, or OC$_6$alkyl.

According to the disclosure, $R^4$ is phenyl, pyridyl, pyrazinyl, pyridazinyl, pyrimidyl, or benzothiazolyl, each of which is optionally substituted with one, two or three substituents independently selected from halogen, $C_{1-6}$alkyl, $C_{1-6}$haloalkyl, OC$_{1-6}$haloalkyl, $C_{0-6}$alk-O—$C_{1-6}$alkyl, —CN, —COOH, and —COOC$_{1-6}$alkyl.

In some aspects, $R^4$ is phenyl. In other aspects, $R^4$ is phenyl substituted with one, two or three substituents independently selected from halogen, $C_{1-6}$alkyl, $C_{1-6}$haloalkyl, $OC_{1-6}$haloalkyl, $C_{0-6}$alk-O—$C_{1-6}$alkyl, —CN, —COOH, and —COOC$_{1-6}$alkyl. In some aspects, the phenyl is substituted with one substituent that is halogen, $C_{1-6}$alkyl, $C_{1-6}$haloalkyl, $OC_{1-6}$haloalkyl, $C_{0-6}$alk-O—$C_{1-6}$alkyl, —CN, —COOH, and —COOC$_{1-6}$alkyl. In some aspects, the phenyl is substituted with two substituents independently selected from halogen, $C_{1-6}$alkyl, $C_{1-6}$haloalkyl, $OC_{1-6}$haloalkyl, $C_{0-6}$alk-O—$C_{1-6}$alkyl, —CN, —COOH, and —COOC$_{1-6}$alkyl. In some embodiments, the phenyl is 4-cyano-3-fluorophenyl. In other aspects, the phenyl is substituted with three substituents independently selected from halogen, $C_{1-6}$alkyl, $C_{1-6}$haloalkyl, $OC_{1-6}$haloalkyl, $C_{0-6}$alk-O—$C_{1-6}$alkyl, —CN, —COOH, and —COOC$_{1-6}$alkyl. In those embodiments wherein the phenyl is substituted with one or more halogen, the halogen may be independently selected from F, Cl, Br, or I, preferably F, Cl, or Br. In some embodiments, the phenyl is 4-chlorophenyl. In other embodiments, the phenyl is 4-fluorophenyl. In yet other embodiments, the phenyl is 4-chloro-2-fluorophenyl. In those embodiments where the phenyl is substituted with one or more $C_{1-6}$alkyl, the $C_{1-6}$alkyl is independently selected from $C_6$alkyl, $C_5$alkyl, $C_4$alkyl, $C_3$alkyl, ethyl ($C_2$alkyl), or methyl ($C_1$alkyl). In some aspects, the phenyl group is substituted with one methyl group. In some aspects, the phenyl is 4-methyl-phenyl (i.e., p-tolyl). In those embodiments wherein the phenyl is substituted with one or more $C_{1-6}$haloalkyl, the $C_{1-6}$haloalkyl is independently selected from, e.g., $CF_3$ or $CHF_2$, preferably $CF_3$. In those embodiments wherein the phenyl is substituted with one or more $OC_{1-6}$haloalkyl, the $OC_{1-6}$haloalkyl is independently selected from, e.g., $OCF_3$ or $OCHF_2$, preferably $OCF_3$. In those embodiments where the phenyl is substituted with one or more $C_{0-6}$alk-O—$C_{1-6}$alkyl, the $C_{0-6}$alk-O—$C_{1-6}$alkyl, is independently selected from, e.g., $C_{1-6}$alk-OC$_{1-6}$alkyl, $C_{1-5}$alk-OC$_{1-6}$alkyl, $C_{1-4}$alk-OC$_{1-6}$alkyl, $C_{1-3}$alk-OC$_{1-6}$alkyl, $C_{1-2}$alk-OC$_{1-6}$alkyl, $C_2$alk-OC$_{1-6}$alkyl, $C_1$alk-OC$_{1-6}$alkyl, $C_0$alk-OC$_{1-6}$alkyl, $C_{0-6}$alk-OC$_{1-5}$alkyl, $C_{0-6}$alk-OC$_{1-5}$alkyl, $C_{0-6}$alk-OC$_{1-4}$alkyl, $C_{0-6}$alk-OC$_{1-3}$alkyl, $C_{0-6}$alk-OC$_{1-2}$alkyl, or $C_{0-6}$alk-OC$_1$alkyl. In some embodiments, the phenyl is substituted with one or more CN. In some embodiments, the phenyl is 4-cyanophenyl. In other embodiments, the phenyl is substituted with one or more COOH. In those embodiments wherein the phenyl is substituted with one or more —COOC$_{1-6}$alkyl, the —COOC$_{1-6}$alkyl is independently selected from —COOC$_6$alkyl, —COOC$_5$alkyl, —COOC$_4$alkyl, —COOC$_3$alkyl, —COOC$_2$alkyl, and —COOC$_1$alkyl.

In some aspects, $R^4$ is pyridyl. In other aspects, $R^4$ is pyridyl substituted with one, two or three substituents independently selected from halogen, $C_{1-6}$alkyl, $C_{1-6}$haloalkyl, $OC_{1-6}$haloalkyl, $C_{0-6}$alk-O—$C_{1-6}$alkyl, —CN, —COOH, and —COOC$_{1-6}$alkyl. In some aspects, the pyridyl is substituted with one substituent that is halogen, $C_{1-6}$alkyl, $C_{1-6}$haloalkyl, $OC_{1-6}$haloalkyl, $C_{0-6}$alk-O—$C_{1-6}$alkyl, —CN, —COOH, and —COOC$_{1-6}$alkyl. In some aspects, the pyridyl is substituted with two substituents independently selected from halogen, $C_{1-6}$alkyl, $C_{1-6}$haloalkyl, $OC_{1-6}$haloalkyl, $C_{0-6}$alk-O—$C_{1-6}$alkyl, —CN, —COOH, and —COOC$_{1-6}$alkyl. In other aspects, the pyridyl is substituted with three substituents independently selected from halogen, $C_{1-6}$alkyl, $C_{1-6}$haloalkyl, $OC_{1-6}$haloalkyl, $C_{0-6}$alk-O—$C_{1-6}$alkyl, —CN, —COOH, and —COOC$_{1-6}$alkyl. In those embodiments wherein the pyridyl is substituted with one or more halogen, the halogen may be independently selected from F, Cl, Br, or I, preferably F, Cl, or Br. In those embodiments where the pyridyl is substituted with one or more $C_{1-6}$alkyl, the $C_{1-6}$alkyl is independently selected from $C_6$alkyl, $C_5$alkyl, $C_4$alkyl, $C_3$alkyl, ethyl ($C_2$alkyl), or methyl ($C_1$alkyl). In those embodiments wherein the pyridyl is substituted with one or more $C_{1-6}$haloalkyl, the $C_{1-6}$haloalkyl is independently selected from, e.g., $CF_3$ or $CHF_2$, preferably $CF_3$. In those embodiments wherein the pyridyl is substituted with one or more $OC_{1-6}$haloalkyl, the $OC_{1-6}$haloalkyl is independently selected from, e.g., $OCF_3$ or $OCHF_2$, preferably $OCF_3$. In some embodiments, the pyridyl is 5-(difluoromethoxy)pyridin-2-yl. In those embodiments where the pyridyl is substituted with one or more $C_{0-6}$alk-O—$C_{1-6}$alkyl, the $C_{0-6}$alk-O—$C_{1-6}$alkyl, is independently selected from, e.g., $C_{1-6}$alk-OC$_{1-6}$alkyl, $C_{1-5}$alk-OC$_{1-6}$alkyl, $C_{1-4}$alk-OC$_{1-6}$alkyl, $C_{1-3}$alk-OC$_{1-6}$alkyl, $C_{1-2}$alk-OC$_{1-6}$alkyl, $C_2$alk-OC$_{1-6}$alkyl, $C_1$alk-OC$_{1-6}$alkyl, $C_0$alk-OC$_{1-6}$alkyl, $C_{0-6}$alk-OC$_{1-5}$alkyl, $C_{0-6}$alk-OC$_{1-5}$alkyl, $C_{0-6}$alk-OC$_{1-4}$alkyl, $C_{0-6}$alk-OC$_{1-3}$alkyl, $C_{0-6}$alk-OC$_{1-2}$alkyl, or $C_{0-6}$alk-OC$_1$alkyl. In some embodiments, the pyridyl is 6-(methoxymethyl)pyridin-3-yl. In some embodiments, the pyridyl is substituted with one or more CN. In other embodiments, the pyridyl is substituted with one or more COOH. In those embodiments wherein the pyridyl is substituted with one or more —COOC$_{1-6}$alkyl, the —COOC$_{1-6}$alkyl is independently selected from —COOC$_6$alkyl, —COOC$_5$alkyl, —COOC$_4$alkyl, —COOC$_3$alkyl, —COOC$_2$alkyl, and —COOC$_1$alkyl.

In some aspects, $R^4$ is pyrazinyl. In other aspects, $R^4$ is pyrazinyl substituted with one, two or three substituents independently selected from halogen, $C_{1-6}$alkyl, $C_{1-6}$haloalkyl, $OC_{1-6}$haloalkyl, $C_{0-6}$alk-O—$C_{1-6}$alkyl, —CN, —COOH, and —COOC$_{1-6}$alkyl. In some aspects, the pyrazinyl is substituted with one substituent that is halogen, $C_{1-6}$alkyl, $C_{1-6}$haloalkyl, $OC_{1-6}$haloalkyl, $C_{0-6}$alk-O—$C_{1-6}$alkyl, —CN, —COOH, and —COOC$_{1-6}$alkyl. In some aspects, the pyrazinyl is substituted with two substituents independently selected from halogen, $C_{1-6}$alkyl, $C_{1-6}$haloalkyl, $OC_{1-6}$haloalkyl, $C_{0-6}$alk-O—$C_{1-6}$alkyl, —CN, —COOH, and —COOC$_{1-6}$alkyl. In other aspects, the pyrazinyl is substituted with three substituents independently selected from halogen, $C_{1-6}$alkyl, $C_{1-6}$haloalkyl, $OC_{1-6}$haloalkyl, $C_{0-6}$alk-O—$C_{1-6}$alkyl, —CN, —COOH, and —COOC$_{1-6}$alkyl. In those embodiments wherein the pyrazinyl is substituted with one or more halogen, the halogen may be independently selected from F, Cl, Br, or I, preferably F, Cl, or Br. In those embodiments where the pyrazinyl is substituted with one or more $C_{1-6}$alkyl, the $C_{1-6}$alkyl is independently selected from $C_6$alkyl, $C_5$alkyl, $C_4$alkyl, $C_3$alkyl, ethyl ($C_2$alkyl), or methyl ($C_1$alkyl). In those embodiments wherein the pyrazinyl is substituted with one or more $C_{1-6}$haloalkyl, the $C_{1-6}$haloalkyl is independently selected from, e.g., $CF_3$ or $CHF_2$, preferably $CF_3$. In those embodiments wherein the pyrazinyl is substituted with one or more $OC_{1-6}$haloalkyl, the $OC_{1-6}$haloalkyl is independently selected from, e.g., $OCF_3$ or $OCHF_2$, preferably $OCF_3$. In those embodiments where the pyrazinyl is substituted with one or more $C_{0-6}$alk-O—$C_{1-6}$alkyl, the $C_{0-6}$alk-O—$C_{1-6}$alkyl, is independently selected from, e.g., $C_{1-6}$alk-OC$_{1-6}$alkyl, $C_{1-5}$alk-OC$_{1-6}$alkyl, $C_{1-4}$alk-OC$_{1-6}$alkyl, $C_{1-3}$alk-OC$_{1-6}$alkyl, $C_{1-2}$alk-OC$_{1-6}$alkyl, $C_2$alk-OC$_{1-6}$alkyl, $C_1$alk-OC$_{1-6}$alkyl, $C_0$alk-OC$_{1-6}$alkyl, $C_{0-6}$alk-OC$_{1-5}$alkyl, $C_{0-6}$alk-OC$_{1-5}$alkyl, $C_{0-6}$alk-OC$_{1-4}$alkyl, $C_{0-6}$alk-OC$_{1-3}$alkyl, $C_{0-6}$alk-OC$_{1-2}$alkyl, or $C_{0-6}$alk-OC$_1$alkyl. In some embodiments, the pyrazinyl is 5-ethoxypyrazin-2-yl. In other embodiments, the pyrazinyl is 5-methoxypyrazin-2-yl. In some embodiments, the pyrazinyl is substituted with one or more CN. In other embodiments, the pyrazinyl is substituted with one or more COOH. In those embodiments wherein the pyrazinyl is substituted with one or more —COOC$_{1-6}$alkyl, the —COOC$_{1-6}$alkyl is independently selected from —COOC$_6$alkyl, —COOC$_5$alkyl, —COOC$_4$alkyl, —COOC$_3$alkyl, —COOC$_2$alkyl, and —COOC$_1$alkyl.

In some aspects, R$^4$ is pyridazinyl. In other aspects, R$^4$ is pyridazinyl substituted with one, two or three substituents independently selected from halogen, C$_{1-6}$alkyl, C$_{1-6}$haloalkyl, OC$_{1-6}$haloalkyl, C$_{0-6}$alk-O—C$_{1-6}$alkyl, —CN, —COOH, and —COOC$_{1-6}$alkyl. In some aspects, the pyridazinyl is substituted with one substituent that is halogen, C$_{1-6}$alkyl, C$_{1-6}$haloalkyl, OC$_{1-6}$haloalkyl, C$_{0-6}$alk-O—C$_{1-6}$alkyl, —CN, —COOH, and —COOC$_{1-6}$alkyl. In some aspects, the pyridazinyl is substituted with two substituents independently selected from halogen, C$_{1-6}$alkyl, C$_{1-6}$haloalkyl, OC$_{1-6}$haloalkyl, C$_{0-6}$alk-O—C$_{1-6}$alkyl, —CN, —COOH, and —COOC$_{1-6}$alkyl. In other aspects, the pyridazinyl is substituted with three substituents independently selected from halogen, C$_{1-6}$alkyl, C$_{1-6}$haloalkyl, OC$_{1-6}$haloalkyl, C$_{0-6}$alk-O—C$_{1-6}$alkyl, —CN, —COOH, and —COOC$_{1-6}$alkyl. In those embodiments wherein the pyridazinyl is substituted with one or more halogen, the halogen may be independently selected from F, Cl, Br, or I, preferably F, Cl, or Br. In those embodiments where the pyridazinyl is substituted with one or more C$_{1-6}$alkyl, the C$_{1-6}$alkyl is independently selected from C$_6$alkyl, C$_5$alkyl, C$_4$alkyl, C$_3$alkyl, ethyl (C$_2$alkyl), or methyl (C$_1$alkyl). In those embodiments wherein the pyridazinyl is substituted with one or more C$_{1-6}$haloalkyl, the C$_{1-6}$haloalkyl is independently selected from, e.g., CF$_3$ or CHF$_2$, preferably CF$_3$. In those embodiments wherein the pyridazinyl is substituted with one or more OC$_{1-6}$haloalkyl, the OC$_{1-6}$haloalkyl is independently selected from, e.g., OCF$_3$ or OCHF$_2$, preferably OCF$_3$. In those embodiments where the pyridazinyl is substituted with one or more C$_{0-6}$alk-O—C$_{1-6}$alkyl, the C$_{0-6}$alk-O—C$_{1-6}$alkyl, is independently selected from, e.g., C$_{1-6}$alk-OC$_{1-6}$alkyl, C$_{1-5}$alk-OC$_{1-6}$alkyl, C$_{1-4}$alk-OC$_{1-6}$alkyl, C$_{1-3}$alk-OC$_{1-6}$alkyl, C$_{1-2}$alk-OC$_{1-6}$alkyl, C$_2$alk-OC$_{1-6}$alkyl, C$_1$alk-OC$_{1-6}$alkyl, C$_0$alk-OC$_{1-6}$alkyl, C$_{0-6}$alk-OC$_{1-5}$alkyl, C$_{0-6}$alk-OC$_{1-5}$alkyl, C$_{0-6}$alk-OC$_{1-4}$alkyl, C$_{0-6}$alk-OC$_{1-3}$alkyl, C$_{0-6}$alk-OC$_{1-2}$alkyl, or C$_{0-6}$alk-OC$_1$alkyl. In some embodiments, the pyridazinyl is substituted with one or more CN. In other embodiments, the pyridazinyl is substituted with one or more COOH. In those embodiments wherein the pyridazinyl is substituted with one or more —COOC$_{1-6}$alkyl, the —COOC$_{1-6}$alkyl is independently selected from —COOC$_6$alkyl, —COOC$_5$alkyl, —COOC$_4$alkyl, —COOC$_3$alkyl, —COOC$_2$alkyl, and —COOC$_1$alkyl.

In some aspects, R$^4$ is pyrimidyl. In other aspects, R$^4$ is pyrimidyl substituted with one, two or three substituents independently selected from halogen, C$_{1-6}$alkyl, C$_{1-6}$haloalkyl, OC$_{1-6}$haloalkyl, C$_{0-6}$alk-O—C$_{1-6}$alkyl, —CN, —COOH, and —COOC$_{1-6}$alkyl. In some aspects, the pyrimidyl is substituted with one substituent that is halogen, C$_{1-6}$alkyl, C$_{1-6}$haloalkyl, OC$_{1-6}$haloalkyl, C$_{0-6}$alk-O—C$_{1-6}$alkyl, —CN, —COOH, and —COOC$_{1-6}$alkyl. In some aspects, the pyrimidyl is substituted with two substituents independently selected from halogen, C$_{1-6}$alkyl, C$_{1-6}$haloalkyl, OC$_{1-6}$haloalkyl, C$_{0-6}$alk-O—C$_{1-6}$alkyl, —CN, —COOH, and —COOC$_{1-6}$alkyl. In other aspects, the pyrimidyl is substituted with three substituents independently selected from halogen, C$_{1-6}$alkyl, C$_{1-6}$haloalkyl, OC$_{1-6}$haloalkyl, C$_{0-6}$alk-O—C$_{1-6}$alkyl, —CN, —COOH, and —COOC$_{1-6}$alkyl. In those embodiments wherein the pyrimidyl is substituted with one or more halogen, the halogen may be independently selected from F, Cl, Br, or I, preferably F, Cl, or Br. In some embodiments, the pyrimidinyl is 5-fluoropyrimidin-2-yl. In those embodiments where the pyrimidyl is substituted with one or more C$_{1-6}$alkyl, the C$_{1-6}$alkyl is independently selected from C$_6$alkyl, C$_5$alkyl, C$_4$alkyl, C$_3$alkyl, ethyl (C$_2$alkyl), or methyl (C$_1$alkyl). In some embodiments, the pyrimidyl is 2-methylpyrimidin-5-yl. In other embodiments, the pyrimidyl is 2-ethylpyrimidin-5-yl. In those embodiments wherein the pyrimidyl is substituted with one or more C$_{1-6}$haloalkyl, the C$_{1-6}$haloalkyl is independently selected from, e.g., CF$_3$ or CHF$_2$, preferably CF$_3$. In some embodiments, the pyrimidyl is 2-(trifluoromethyl)pyrimidin-5-yl. In those embodiments wherein the pyrimidyl is substituted with one or more OC$_{1-6}$haloalkyl, the OC$_{1-6}$haloalkyl is independently selected from, e.g., OCF$_3$ or OCHF$_2$, preferably OCF$_3$. In those embodiments where the pyrimidyl is substituted with one or more C$_{0-6}$alk-O—C$_{1-6}$alkyl, the C$_{0-6}$alk-O—C$_{1-6}$alkyl, is independently selected from, e.g., C$_{1-6}$alk-OC$_{1-6}$alkyl, C$_{1-5}$alk-OC$_{1-6}$alkyl, C$_{1-4}$alk-OC$_{1-6}$alkyl, C$_{1-3}$alk-OC$_{1-6}$alkyl, C$_{1-2}$alk-OC$_{1-6}$alkyl, C$_2$alk-OC$_{1-6}$alkyl, C$_1$alk-OC$_{1-6}$alkyl, C$_0$alk-OC$_{1-6}$alkyl, C$_{0-6}$alk-OC$_{1-5}$alkyl, C$_{0-6}$alk-OC$_{1-5}$alkyl, C$_{0-6}$alk-OC$_{1-4}$alkyl, C$_{0-6}$alk-OC$_{1-3}$alkyl, C$_{0-6}$alk-OC$_{1-2}$alkyl, or C$_{0-6}$alk-OC$_1$alkyl. In some embodiments, the pyrimidyl is 2-ethoxypyrimidin-5-yl. In other embodiments, the pyrimidyl is 2-methoxypyrimidin-5-yl. In yet other embodiments, the pyrimidyl is 2-(methoxymethyl)pyrimidin-5-yl). In some embodiments, the pyrimidyl is substituted with one or more CN. In other embodiments, the pyrimidyl is substituted with one or more COOH. In those embodiments wherein the pyrimidyl is substituted with one or more —COOC$_{1-6}$alkyl, the —COOC$_{1-6}$alkyl is independently selected from —COOC$_6$alkyl, —COOC$_5$alkyl, —COOC$_4$alkyl, —COOC$_3$alkyl, —COOC$_2$alkyl, and —COOC$_1$alkyl.

In some aspects, R$^4$ is benzothiazolyl. In other aspects, R$^4$ is benzothiazolyl substituted with one, two or three substituents independently selected from halogen, C$_{1-6}$alkyl, C$_{1-6}$haloalkyl, OC$_{1-6}$haloalkyl, C$_{0-6}$alk-O—C$_{1-6}$alkyl, —CN, —COOH, and —COOC$_{1-6}$alkyl. In some aspects, the benzothiazolyl is substituted with one substituent that is halogen, C$_{1-6}$alkyl, C$_{1-6}$haloalkyl, OC$_{1-6}$haloalkyl, C$_{0-6}$alk-O—C$_{1-6}$alkyl, —CN, —COOH, and —COOC$_{1-6}$alkyl. In some aspects, the benzothiazolyl is substituted with two substituents independently selected from halogen, C$_{1-6}$alkyl, C$_{1-6}$haloalkyl, OC$_{1-6}$haloalkyl, C$_{0-6}$alk-O—C$_{1-6}$alkyl, —CN, —COOH, and —COOC$_{1-6}$alkyl. In other aspects, the benzothiazolyl is substituted with three substituents independently selected from halogen, C$_{1-6}$alkyl, C$_{1-6}$haloalkyl, OC$_{1-6}$haloalkyl, C$_{0-6}$alk-O—C$_{1-6}$alkyl, —CN, —COOH, and —COOC$_{1-6}$alkyl. In those embodiments wherein the benzothiazolyl is substituted with one or more halogen, the halogen may be independently selected from F, Cl, Br, or I, preferably F, Cl, or Br. In those embodiments where the benzothiazolyl is substituted with one or more C$_{1-6}$alkyl, the C$_{1-6}$alkyl is independently selected from C$_6$alkyl, C$_5$alkyl, C$_4$alkyl, C$_3$alkyl, ethyl (C$_2$alkyl), or methyl (C$_1$alkyl). In some embodiments, the benzothiazolyl is 2-methylbenzo[d]thiazol-6-yl. In those embodiments wherein the benzothiazolyl is substituted with one or more C$_{1-6}$haloalkyl, the C$_{1-6}$haloalkyl is independently selected from, e.g., CF$_3$ or CHF$_2$, preferably CF$_3$. In those embodiments wherein the benzothiazolyl is substituted with one or more OC$_{1-6}$haloalkyl, the OC$_{1-6}$haloalkyl is independently selected from, e.g., OCF$_3$ or OCHF$_2$, preferably OCF$_3$. In those embodiments where the benzothiazolyl is substituted with one or more C$_{0-6}$alk-O—C$_{1-6}$alkyl, the C$_{0-6}$alk-O—C$_{1-6}$alkyl, is independently selected from, e.g., $C_{1-6}$alk-$OC_{1-6}$alkyl, $C_{1-5}$alk-$OC_{1-6}$alkyl, $C_{1-4}$alk-$OC_{1-6}$alkyl, $C_{1-3}$alk-$OC_{1-6}$alkyl, $C_{1-2}$alk-$OC_{1-6}$alkyl, $C_2$alk-$OC_{1-6}$alkyl, $C_1$alk-$OC_{1-6}$alkyl, $C_0$alk-$OC_{1-6}$alkyl, $C_{0-6}$alk-$OC_{1-5}$alkyl, $C_{0-6}$alk-$OC_{1-5}$alkyl, $C_{0-6}$alk-$OC_{1-4}$alkyl, $C_{0-6}$alk-$OC_{1-3}$alkyl, $C_{0-6}$alk-$OC_{1-2}$alkyl, or $C_{0-6}$alk-$OC_1$alkyl. In some embodiments, the benzothiazolyl is substituted with one or more CN. In other embodiments, the benzothiazolyl is substituted with one or more COOH. In those embodiments wherein the benzothiazolyl is substituted with one or more —$COOC_{1-6}$alkyl, the —$COOC_{1-6}$alkyl is independently selected from —$COOC_6$alkyl, —$COOC_5$alkyl, —$COOC_4$alkyl, —$COOC_3$alkyl, —$COOC_2$alkyl, and —$COOC_1$alkyl.

Sub-formulas of formula I include formulas wherein X is CH, $V^b$ is $C_1$alk substituted with one R that is $CF_3$ or heterocycloalkyl, and $R^{2A}$ is H, for example:

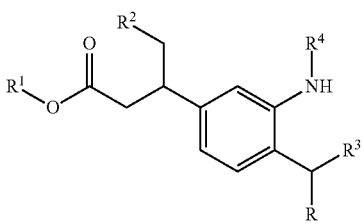

I-A wherein $R^1$ is H or $C_{1-6}$alkyl, $R^2$ is $C_{1-6}$alkyl or $C_0$alk-$OC_{1-6}$alkyl ($OC_{1-6}$alkyl); $R^3$ is $C_{1-6}$alkyl optionally substituted with one, two or three —OH, or is $OC_{1-6}$alkyl optionally substituted with one, two or three —OH; and $R^4$ is phenyl, pyridyl, pyrazinyl, pyridazinyl, pyrimidyl, or benzothiazolyl, each of which is optionally substituted with one, two or three substituents independently selected from halogen, $C_{1-6}$alkyl, $C_{1-6}$haloalkyl, $OC_{1-6}$haloalkyl, $C_{0-6}$alk-O—$C_{1-6}$alkyl, —CN, —COOH, and —$COOC_{1-6}$alkyl. Preferably, in the compounds of formula I-A, $R^4$ is substituted with one or two, preferably one substituent, that is halogen, $C_{1-6}$alkyl, $C_{1-6}$haloalkyl, $OC_{1-6}$haloalkyl, $C_{0-6}$alk-O—$C_{1-6}$alkyl, —CN, —COOH, and —$COOC_{1-6}$alkyl. In some preferred embodiments of the compounds of formula I-A, $R^4$ is 4-cyano-3-fluorophenyl, 4-chlorophenyl, 4-fluorophenyl, 4-chloro-2-fluorophenyl, 4-methyl-phenyl, 4-cyanophenyl, 5-(difluoromethoxy)pyridin-2-yl, 6-(methoxymethyl)pyridin-3-yl, 5-ethoxypyrazin-2-yl, 5-methoxypyrazin-2-yl, 5-fluoropyrimidin-2-yl, 2-methylpyrimidin-5-yl, 2-ethylpyrimidin-5-yl, 2-(trifluoromethyl)pyrimidin-5-yl, 2-ethoxypyrimidin-5-yl, 2-methoxypyrimidin-5-yl, 2-(methoxymethyl)pyrimidin-5-yl), or 2-methylbenzo[d]thiazol-6-yl. In preferred embodiments of compounds of formula I-A, $R^1$ is H, R is $CF_3$ and $R^3$ is $OC_{1-6}$alkyl. In other preferred embodiments of compounds of formula I-A, $R^1$ is H, R is $C_{1-6}$alkyl and $R^3$ is $OC_{1-6}$alkyl. In other preferred embodiments of compounds of formula I-A, $R^1$ is H, R is $C_{1-6}$alkyl and $R^3$ is $C_{1-6}$alkyl. In other preferred embodiments of compounds of formula I-A, $R^1$ is H, R is heterocycloalkyl (e.g., morpholinyl or tetrahydropyranyl) and $R^3$ is $C_{1-6}$alkyl. The disclosure also encompasses enantiomers or diastereomers of formula I-A. The disclosure also encompasses the pharmaceutically acceptable salts of compounds of formula I-A. The disclosure also encompasses solvates of compounds of formula I-A.

Sub-formulas of formula I include formulas wherein X is N, $V^b$ is $C_1$alk substituted with one R that is $CF_3$ or heterocycloalkyl, and $R^{2A}$ is H, for example:

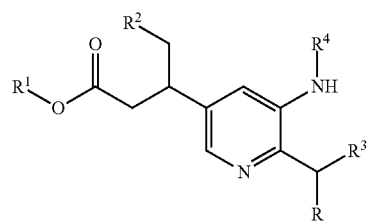

I-B wherein $R^1$ is H or $C_{1-6}$alkyl, $R^2$ is $C_{1-6}$alkyl or $C_0$alk-$OC_{1-6}$alkyl ($OC_{1-6}$alkyl); $R^3$ is $C_{1-6}$alkyl optionally substituted with one, two or three —OH, or is $OC_{1-6}$alkyl optionally substituted with one, two or three —OH; and $R^4$ is phenyl, pyridyl, pyrazinyl, pyridazinyl, pyrimidyl, or benzothiazolyl, each of which is optionally substituted with one, two or three substituents independently selected from halogen, $C_{1-6}$alkyl, $C_{1-6}$haloalkyl, $OC_{1-6}$haloalkyl, $C_{0-6}$alk-O—$C_{1-6}$alkyl, —CN, —COOH, and —$COOC_{1-6}$alkyl. Preferably, in the compounds of formula I-B, $R^4$ is substituted with one or two, preferably one substituent, that is halogen, $C_{1-6}$alkyl, $C_{1-6}$haloalkyl, $OC_{1-6}$haloalkyl, $C_{0-6}$alk-O—$C_{1-6}$alkyl, —CN, —COOH, and —$COOC_{1-6}$alkyl. In some preferred embodiments of the compounds of formula I-B, $R^4$ is 4-cyano-3-fluorophenyl, 4-chlorophenyl, 4-fluorophenyl, 4-chloro-2-fluorophenyl, 4-methyl-phenyl, 4-cyanophenyl, 5-(difluoromethoxy)pyridin-2-yl, 6-(methoxymethyl)pyridin-3-yl, 5-ethoxypyrazin-2-yl, 5-methoxypyrazin-2-yl, 5-fluoropyrimidin-2-yl, 2-methylpyrimidin-5-yl, 2-ethylpyrimidin-5-yl, 2-(trifluoromethyl)pyrimidin-5-yl, 2-ethoxypyrimidin-5-yl, 2-methoxypyrimidin-5-yl, 2-(methoxymethyl)pyrimidin-5-yl), or 2-methylbenzo[d]thiazol-6-yl. In preferred embodiments of compounds of formula I-B, $R^1$ is H, R is $CF_3$ and $R^3$ is $OC_{1-6}$alkyl. In other preferred embodiments of compounds of formula I-B, $R^1$ is H, R is $C_{1-6}$alkyl and $R^3$ is $OC_{1-6}$alkyl. In other preferred embodiments of compounds of formula I-B, $R^1$ is H, R is $C_{1-6}$alkyl and $R^3$ is $C_{1-6}$alkyl. In other preferred embodiments of compounds of formula I-B, $R^1$ is H, R is heterocycloalkyl (e.g., morpholinyl or tetrahydropyranyl) and $R^3$ is $C_{1-6}$alkyl. The disclosure also encompasses enantiomers or diastereomers of formula I-B. The disclosure also encompasses the pharmaceutically acceptable salts of compounds of formula I-B. The disclosure also encompasses solvates of compounds of formula I-B.

Sub-formulas of formula I include formulas wherein X is C—$V^a$—$R^3$, $V^a$ is $C_1$alk substituted with one R that is phenyl, and $R^{2A}$ is H, for example:

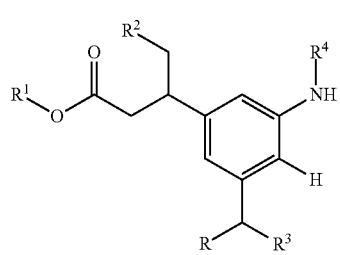

I-C wherein $R^1$ is H or $C_{1-6}$alkyl, $R^2$ is $C_{1-6}$alkyl or $C_0$alk-$OC_{1-6}$alkyl ($OC_{1-6}$alkyl); $R^3$ is $C_{1-6}$alkyl optionally substituted with one, two or three —OH, or is $OC_{1-6}$alkyl optionally substituted with one, two or three —OH; and $R^4$ is phenyl, pyridyl, pyrazinyl, pyridazinyl, pyrimidyl, or benzothiazolyl, each of which is optionally substituted with one, two or three substituents independently selected from halogen, $C_{1-6}$alkyl, $C_{1-6}$haloalkyl, $OC_{1-6}$haloalkyl, $C_{0-6}$alk-O—$C_{1-6}$alkyl, —CN, —COOH, and —COO$C_{1-6}$alkyl. Preferably, in the compounds of formula I-C, $R^4$ is substituted with one or two, preferably one substituent, that is halogen, $C_{1-6}$alkyl, $C_{1-6}$haloalkyl, $OC_{1-6}$haloalkyl, $C_{0-6}$alk-O—$C_{1-6}$alkyl, —CN, —COOH, and —COO$C_{1-6}$alkyl. In some preferred embodiments of the compounds of formula I-C, $R^4$ is 4-cyano-3-fluorophenyl, 4-chlorophenyl, 4-fluorophenyl, 4-chloro-2-fluorophenyl, 4-methyl-phenyl, 4-cyanophenyl, 5-(difluoromethoxy)pyridin-2-yl, 6-(methoxymethyl)pyridin-3-yl, 5-ethoxypyrazin-2-yl, 5-methoxypyrazin-2-yl, 5-fluoropyrimidin-2-yl, 2-methylpyrimidin-5-yl, 2-ethylpyrimidin-5-yl, 2-(trifluoromethyl)pyrimidin-5-yl, 2-ethoxypyrimidin-5-yl, 2-methoxypyrimidin-5-yl, 2-(methoxymethyl)pyrimidin-5-yl), or 2-methylbenzo[d]thiazol-6-yl. In preferred embodiments of compounds of formula I-C, $R^1$ is H, R is phenyl substituted with halogen, and $R^3$ is $OC_{1-6}$alkyl. In other preferred embodiments of formula I-C, $R^1$ is H, R is 4-fluorophenyl, and $R^3$ is $OC_{1-6}$alkyl. In other preferred embodiments of formula I-C, $R^1$ is H, R is 4-fluorophenyl, and $R^3$ is $C_{1-6}$alkyl. The disclosure also encompasses enantiomers or diastereomers of formula I-C. The disclosure also encompasses the pharmaceutically acceptable salts of compounds of formula I-C. The disclosure also encompasses solvates of compounds of formula I-C.

Sub-formulas of formula II include formulas wherein X is CH, $V^b$ is $C_1$alk substituted with one R that is $CF_3$ or heterocycloalkyl, and $R^{2A}$ is H, for example:

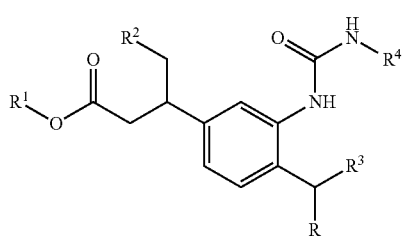

II-A wherein $R^1$ is H or $C_{1-6}$alkyl, $R^2$ is $C_{1-6}$alkyl or $C_0$alk-O$C_{1-6}$alkyl (O$C_{1-6}$alkyl); $R^3$ is $C_{1-6}$alkyl optionally substituted with one, two or three —OH, or is $OC_{1-6}$alkyl optionally substituted with one, two or three —OH; and $R^4$ is phenyl, pyridyl, pyrazinyl, pyridazinyl, pyrimidyl, or benzothiazolyl, each of which is optionally substituted with one, two or three substituents independently selected from halogen, $C_{1-5}$alkyl, $C_{1-6}$haloalkyl, $OC_{1-6}$haloalkyl, $C_{0-6}$alk-O—$C_{1-6}$alkyl, —CN, —COOH, and —COO$C_{1-6}$alkyl. Preferably, in the compounds of formula II-A, $R^4$ is substituted with one or two, preferably one substituent, that is halogen, $C_{1-6}$alkyl, $C_{1-6}$haloalkyl, $OC_{1-6}$haloalkyl, $C_{0-6}$alk-O—$C_{1-6}$alkyl, —CN, —COOH, and —COO$C_{1-6}$alkyl. In some preferred embodiments of the compounds of formula II-A, $R^4$ is 4-cyano-3-fluorophenyl, 4-chlorophenyl, 4-fluorophenyl, 4-chloro-2-fluorophenyl, 4-methyl-phenyl, 4-cyanophenyl, 5-(difluoromethoxy)pyridin-2-yl, 6-(methoxymethyl)pyridin-3-yl, 5-ethoxypyrazin-2-yl, 5-methoxypyrazin-2-yl, 5-fluoropyrimidin-2-yl, 2-methylpyrimidin-5-yl, 2-ethylpyrimidin-5-yl, 2-(trifluoromethyl)pyrimidin-5-yl, 2-ethoxypyrimidin-5-yl, 2-methoxypyrimidin-5-yl, 2-(methoxymethyl)pyrimidin-5-yl), or 2-methylbenzo[d]thiazol-6-yl. In preferred embodiments of compounds of formula II-A, $R^1$ is H, R is $CF_3$ and $R^3$ is $OC_{1-6}$alkyl. In other preferred embodiments of compounds of formula II-A, $R^1$ is H, R is $C_{1-6}$alkyl and $R^3$ is $OC_{1-6}$alkyl. In other preferred embodiments of compounds of formula II-A, $R^1$ is H, R is $C_{1-6}$alkyl and $R^3$ is $C_{1-6}$alkyl. In other preferred embodiments of compounds of formula II-A, $R^1$ is H, R is heterocycloalkyl (e.g., morpholinyl or tetrahydropyranyl) and $R^3$ is $C_{1-6}$alkyl. The disclosure also encompasses enantiomers or diastereomers of formula II-A. The disclosure also encompasses the pharmaceutically acceptable salts of compounds of formula II-A. The disclosure also encompasses solvates of compounds of formula II-A.

Sub-formulas of formula II include formulas wherein X is N, $V^b$ is $C_1$alk substituted with one R that is $CF_3$ or heterocycloalkyl, and $R^{2A}$ is H, for example:

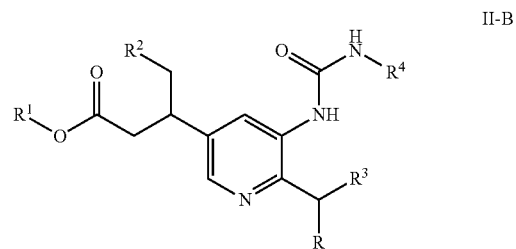

II-B wherein $R^1$ is H or $C_{1-6}$alkyl, $R^2$ is $C_{1-6}$alkyl or $C_0$alk-O$C_{1-6}$alkyl (O$C_{1-6}$alkyl); $R^3$ is $C_{1-6}$alkyl optionally substituted with one, two or three —OH, or is $OC_{1-6}$alkyl optionally substituted with one, two or three —OH; and $R^4$ is phenyl, pyridyl, pyrazinyl, pyridazinyl, pyrimidyl, or benzothiazolyl, each of which is optionally substituted with one, two or three substituents independently selected from halogen, $C_{1-6}$alkyl, $C_{1-6}$haloalkyl, $OC_{1-6}$haloalkyl, $C_{0-6}$alk-O—$C_{1-6}$alkyl, —CN, —COOH, and —COO$C_{1-6}$alkyl. Preferably, in the compounds of formula II-B, $R^4$ is substituted with one or two, preferably one substituent, that is halogen, $C_{1-6}$alkyl, $C_{1-6}$haloalkyl, $OC_{1-6}$haloalkyl, $C_{0-6}$alk-O—$C_{1-6}$alkyl, —CN, —COOH, and —COO$C_{1-6}$alkyl. In some preferred embodiments of the compounds of formula II-B, $R^4$ is 4-cyano-3-fluorophenyl, 4-chlorophenyl, 4-fluorophenyl, 4-chloro-2-fluorophenyl, 4-methyl-phenyl, 4-cyanophenyl, 5-(difluoromethoxy)pyridin-2-yl, 6-(methoxymethyl)pyridin-3-yl, 5-ethoxypyrazin-2-yl, 5-methoxypyrazin-2-yl, 5-fluoropyrimidin-2-yl, 2-methylpyrimidin-5-yl, 2-ethylpyrimidin-5-yl, 2-(trifluoromethyl)pyrimidin-5-yl, 2-ethoxypyrimidin-5-yl, 2-methoxypyrimidin-5-yl, 2-(methoxymethyl)pyrimidin-5-yl), or 2-methylbenzo[d]thiazol-6-yl. In preferred embodiments of compounds of formula II-B, $R^1$ is H, R is $CF_3$ and $R^3$ is $OC_{1-6}$alkyl. In other preferred embodiments of compounds of formula II-B, $R^1$ is H, R is $C_{1-6}$alkyl and $R^3$ is $OC_{1-6}$alkyl. In other preferred embodiments of compounds of formula II-B, $R^1$ is H, R is $C_{1-6}$alkyl and $R^3$ is $C_{1-6}$alkyl. In other preferred embodiments of compounds of formula II-B, $R^1$ is H, R is heterocycloalkyl (e.g., morpholinyl or tetrahydropyranyl) and $R^3$ is $C_{1-6}$alkyl. The disclosure also encompasses enantiomers or diastereomers of formula II-B. The disclosure also encompasses the pharmaceutically acceptable salts of compounds of formula II-B. The disclosure also encompasses solvates of compounds of formula II-B.

Sub-formulas of formula II include formulas wherein X is C—$V^a$—$R^3$, $V^a$ is $C_1$alk substituted with one R that is phenyl, and $R^{2A}$ is H, for example:

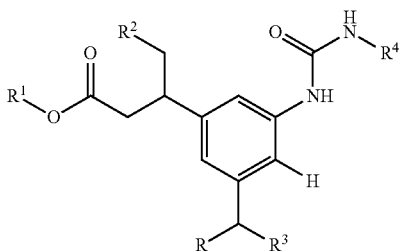

II-C wherein $R^1$ is H or $C_{1-6}$alkyl, $R^2$ is $C_{1-6}$alkyl or $C_0$alk-O$C_{1-6}$alkyl (O$C_{1-6}$alkyl); $R^3$ is $C_{1-6}$alkyl optionally substituted with one, two or three —OH, or is O$C_{1-6}$alkyl optionally substituted with one, two or three —OH; and $R^4$ is phenyl, pyridyl, pyrazinyl, pyridazinyl, pyrimidyl, or benzothiazolyl, each of which is optionally substituted with one, two or three substituents independently selected from halogen, $C_{1-5}$alkyl, $C_{1-6}$haloalkyl, O$C_{1-6}$haloalkyl, $C_{0-6}$alk-O—$C_{1-6}$alkyl, —CN, —COOH, and —COO$C_{1-6}$alkyl. Preferably, in the compounds of formula II-C, $R^4$ is substituted with one or two, preferably one substituent, that is halogen, $C_{1-6}$alkyl, $C_{1-6}$haloalkyl, O$C_{1-6}$haloalkyl, $C_{0-6}$alk-O—$C_{1-6}$alkyl, —CN, —COOH, and —COO$C_{1-6}$alkyl. In some preferred embodiments of the compounds of formula II-C, $R^4$ is 4-cyano-3-fluorophenyl, 4-chlorophenyl, 4-fluorophenyl, 4-chloro-2-fluorophenyl, 4-methyl-phenyl, 4-cyanophenyl, 5-(difluoromethoxy)pyridin-2-yl, 6-(methoxymethyl)pyridin-3-yl, 5-ethoxypyrazin-2-yl, 5-methoxypyrazin-2-yl, 5-fluoropyrimidin-2-yl, 2-methylpyrimidin-5-yl, 2-ethylpyrimidin-5-yl, 2-(trifluoromethyl)pyrimidin-5-yl, 2-ethoxypyrimidin-5-yl, 2-methoxypyrimidin-5-yl, 2-(methoxymethyl)pyrimidin-5-yl), or 2-methylbenzo[d]thiazol-6-yl). In preferred embodiments of compounds of formula II-C, $R^1$ is H, R is phenyl substituted with halogen, and $R^3$ is O$C_{1-6}$alkyl. In other preferred embodiments of compounds of formula II-C, $R^1$ is H, R is 4-fluorophenyl and $R^3$ is O$C_{1-6}$alkyl. In other preferred embodiments of compounds of formula II-C, $R^1$ is H, R is 4-fluorophenyl and $R^3$ is $C_{1-6}$alkyl. The disclosure also encompasses enantiomers or diastereomers of formula II-C. The disclosure also encompasses the pharmaceutically acceptable salts of compounds of formula II-C. The disclosure also encompasses solvates of compounds of formula II-C.

OTHER EMBODIMENTS OF THE DISCLOSURE

In another embodiment, the present disclosure provides a composition comprising one or more compounds of the present disclosure and/or a pharmaceutically acceptable salt thereof, a stereoisomer thereof, a tautomer thereof, or a solvate thereof.

In another embodiment, the present disclosure provides a pharmaceutical composition comprising a pharmaceutically acceptable carrier and at least one of the compounds of the present disclosure and/or a pharmaceutically acceptable salt thereof, a stereoisomer thereof, a tautomer thereof, or a solvate thereof.

In another embodiment, the present disclosure provides a pharmaceutical composition, comprising a pharmaceutically acceptable carrier and a therapeutically effective amount of at least one of the compounds of the present disclosure and/or a pharmaceutically acceptable salt thereof, a stereoisomer thereof, a tautomer thereof, or a solvate thereof.

In another embodiment, the present disclosure provides a process for making a compound of the present disclosure and/or a pharmaceutically acceptable salt thereof, a stereoisomer thereof, a tautomer thereof, or a solvate thereof.

In another embodiment, the present disclosure provides an intermediate for making a compound of the present disclosure and/or a pharmaceutically acceptable salt thereof, a stereoisomer thereof, a tautomer thereof, or a solvate thereof.

In another embodiment, the present disclosure provides a method for the treatment and/or prophylaxis of various types of cancer, viral infections and/or autoimmune diseases, comprising administering to a patient in need of such treatment and/or prophylaxis a therapeutically effective amount of one or more compounds of the present disclosure and/or a pharmaceutically acceptable salt thereof, a stereoisomer thereof or a tautomer thereof, alone, or, optionally, in combination with another compound of the present disclosure and/or at least one other type of therapeutic agent, such as a chemotherapeutic agent or a signal transductor inhibitor.

In another embodiment, the present disclosure provides a compound of the present disclosure, and/or a pharmaceutically acceptable salt thereof, a stereoisomer thereof or a tautomer thereof, for use in therapy.

In another embodiment, the present disclosure provides a combined preparation of a compound of the present disclosure, and/or a pharmaceutically acceptable salt thereof, a stereoisomer thereof or a tautomer thereof, and additional therapeutic agent(s) for simultaneous, separate or sequential use in therapy.

In another embodiment, the present disclosure provides a combined preparation of a compound of the present disclosure, and/or a pharmaceutically acceptable salt thereof, a stereoisomer thereof or a tautomer thereof, and additional therapeutic agent(s) for simultaneous, separate or sequential use in the treatment and/or prophylaxis of multiple diseases or disorders associated with the enzymatic activity of IDO.

In another aspect, the disclosure provides a method of treating a patient suffering from or susceptible to a medical condition that is sensitive to enzymatic activity of IDO. A number of medical conditions can be treated. The method comprises administering to the patient a therapeutically effective amount of a composition comprising a compound described herein and/or a pharmaceutically acceptable salt thereof, a stereoisomer thereof or a tautomer thereof. For example, the compounds described herein may be used to treat or prevent viral infections, proliferative diseases (e.g., cancer), and autoimmune diseases.

THERAPEUTIC APPLICATIONS

The compounds and pharmaceutical compositions of the present disclosure are useful in treating or preventing any disease or conditions that are sensitive to enzymatic activity of IDO. These include viral and other infections (e.g., skin infections, GI infection, urinary tract infections, genitourinary infections, systemic infections), proliferative diseases (e.g., cancer), and autoimmune diseases (e.g., rheumatoid arthritis, lupus). The compounds and pharmaceutical compositions may be administered to animals, preferably mammals (e.g., domesticated animals, cats, dogs, mice, rats), and more preferably humans. Any method of administration may be used to deliver the compound or pharmaceutical composition to the patient. In certain embodiments, the compound or pharmaceutical composition is administered orally. In other embodiments, the compound or pharmaceutical composition is administered parenterally.

Compounds of the disclosure can modulate activity of the enzyme indoleamine-2,3-dioxygenase (IDO). The term "modulate" is meant to refer to an ability to increase or decrease activity of an enzyme or receptor. Accordingly, compounds of the disclosure can be used in methods of modulating IDO by contacting the enzyme with any one or more of the compounds or compositions described herein. In some embodiments, compounds of the present disclosure can act as inhibitors of IDO. In further embodiments, the compounds of the disclosure can be used to modulate activity of IDO in cell or in an individual in need of modulation of the enzyme by administering a modulating (e.g., inhibiting) amount of a compound of the disclosure.

Compounds of the disclosure can inhibit activity of the enzyme indoleamine-2,3-dioxygenase (IDO). For example, the compounds of the disclosure can be used to inhibit activity of IDO in cell or in an individual in need of modulation of the enzyme by administering an inhibiting amount of a compound of the disclosure.

The present disclosure further provides methods of inhibiting the degradation of tryptophan in a system containing cells expressing IDO such as a tissue, living organism, or cell culture. In some embodiments, the present disclosure provides methods of altering (e.g., increasing) extracellular tryptophan levels in a mammal by administering an effective amount of a compound of composition provided herein. Methods of measuring tryptophan levels and tryptophan degradation are routine in the art.

The present disclosure further provides methods of inhibiting immunosuppression such as IDO-mediated immunosuppression in a patient by administering to the patient an effective amount of a compound or composition recited herein. IDO-mediated immunosuppression has been associated with, for example, cancers, tumor growth, metastasis, viral infection, and viral replication.

The present disclosure further provides methods of treating diseases associated with activity or expression, including abnormal activity and/or overexpression, of IDO in an individual (e.g., patient) by administering to the individual in need of such treatment a therapeutically effective amount or dose of a compound of the present disclosure or a pharmaceutical composition thereof. Example diseases can include any disease, disorder or condition that is directly or indirectly linked to expression or activity of the IDO enzyme, such as over expression or abnormal activity. An IDO-associated disease can also include any disease, disorder or condition that can be prevented, ameliorated, or cured by modulating enzyme activity. Examples of IDO-associated diseases include cancer, viral infection such as HIV infection, HCV infection, depression, neurodegenerative disorders such as Alzheimer's disease and Huntington's disease, trauma, age-related cataracts, organ transplantation (e.g., organ transplant rejection), and autoimmune diseases including asthma, rheumatoid arthritis, multiple sclerosis, allergic inflammation, inflammatory bowel disease, psoriasis and systemic lupus erythematosus.

As used herein, the term "cell" is meant to refer to a cell that is in vitro, ex vivo or in vivo. In some embodiments, an ex vivo cell can be part of a tissue sample excised from an organism such as a mammal. In some embodiments, an in vitro cell can be a cell in a cell culture. In some embodiments, an in vivo cell is a cell living in an organism such as a mammal.

As used herein, the term "contacting" refers to the bringing together of indicated moieties in an in vitro system or an in vivo system. For example, "contacting" the IDO enzyme with a compound of the disclosure includes the administration of a compound of the present disclosure to an individual or patient, such as a human, having IDO, as well as, for example, introducing a compound of the disclosure into a sample containing a cellular or purified preparation containing the IDO enzyme.

The term "IDO inhibitor" refers to an agent capable of inhibiting the activity of indoleamine 2,3-dioxygenase (IDO) and thereby reversing IDO-mediated immunosuppression. The IDO inhibitor may inhibit IDO1 and/or IDO2 (INDOL1). An IDO inhibitor may be a reversible or irreversible IDO inhibitor. "A reversible IDO inhibitor" is a compound that reversibly inhibits IDO enzyme activity either at the catalytic site or at a non-catalytic site and "an irreversible IDO inhibitor" is a compound that irreversibly destroys IDO enzyme activity.

Types of cancers that may be treated with the compounds of this disclosure include, but are not limited to, brain cancers, skin cancers, bladder cancers, ovarian cancers, breast cancers, gastric cancers, pancreatic cancers, prostate cancers, colon cancers, blood cancers, lung cancers and bone cancers. Examples of such cancer types include neuroblastoma, intestine carcinoma such as rectum carcinoma, colon carcinoma, familiar adenomatous polyposis carcinoma and hereditary non-polyposis colorectal cancer, esophageal carcinoma, labial carcinoma, larynx carcinoma, hypopharynx carcinoma, tongue carcinoma, salivary gland carcinoma, gastric carcinoma, adenocarcinoma, medullary thyroid carcinoma, papillary thyroid carcinoma, renal carcinoma, kidney parenchymal carcinoma, ovarian carcinoma, cervix carcinoma, uterine corpus carcinoma, endometrium carcinoma, chorion carcinoma, pancreatic carcinoma, prostate carcinoma, testis carcinoma, breast carcinoma, urinary carcinoma, melanoma, brain tumors such as glioblastoma, astrocytoma, meningioma, medulloblastoma and peripheral neuroectodermal tumors, Hodgkin lymphoma, non-Hodgkin lymphoma, Burkitt lymphoma, acute lymphatic leukemia (ALL), chronic lymphatic leukemia (CLL), acute myeloid leukemia (AML), chronic myeloid leukemia (CML), adult T-cell leukemia lymphoma, diffuse large B-cell lymphoma (DLBCL), hepatocellular carcinoma, gall bladder carcinoma, bronchial carcinoma, small cell lung carcinoma, non-small cell lung carcinoma, multiple myeloma, basalioma, teratoma, retinoblastoma, choroid melanoma, seminoma, rhabdomyosarcoma, craniopharyngioma, osteosarcoma, chondrosarcoma, myosarcoma, liposarcoma, fibrosarcoma, Ewing sarcoma and plasmacytoma.

Thus, according to another embodiment, the disclosure provides a method of treating an autoimmune disease by providing to a patient in need thereof a compound or composition of the present disclosure. Examples of such autoimmune diseases include, but are not limited to, collagen diseases such as rheumatoid arthritis, systemic lupus erythematosus, Sharp's syndrome, CREST syndrome (calcinosis, Raynaud's syndrome, esophageal dysmotility, telangiectasia), dermatomyositis, vasculitis (Morbus Wegener's) and Sjögren's syndrome, renal diseases such as Goodpasture's syndrome, rapidly-progressing glomerulonephritis and membranoproliferative glomerulonephritis type II, endocrine diseases such as type-I diabetes, autoimmune polyendocrinopathy-candidiasis-ectodermal dystrophy (APECED), autoimmune parathyroidism, pernicious anemia, gonad insufficiency, idiopathic Morbus Addison's, hyperthyreosis, Hashimoto's thyroiditis and primary myxedema, skin diseases such as pemphigus vulgaris, bullous pemphigoid, herpes gestationis, epidermolysis bullosa and erythema multiforme major, liver diseases such as primary biliary cirrhosis, autoimmune cholangitis, autoimmune hepatitis type-1, autoimmune hepatitis type-2, primary sclerosing cholangitis, neuronal diseases such as multiple sclerosis, myasthenia gravis, myasthenic Lambert-Eaton syndrome, acquired neuromyotomy, Guillain-Barré syndrome (Muller-Fischer syndrome), stiff-man syndrome, cerebellar degeneration, ataxia, opsoclonus, sensoric neuropathy and achalasia, blood diseases such as autoimmune hemolytic anemia, idiopathic thrombocytopenic purpura (Morbus Werlhof), infectious diseases with associated autoimmune reactions such as AIDS, malaria and Chagas disease.

One or more additional pharmaceutical agents or treatment methods such as, for example, anti-viral agents, chemotherapeutics or other anticancer agents, immune enhancers, immunosuppressants, radiation, anti-tumor and anti-viral vaccines, cytokine therapy (e.g., IL2 and GM-CSF), and/or tyrosine kinase inhibitors can be optionally used in combination with the compounds of the present disclosure for treatment of IDO-associated diseases, disorders or conditions. The agents can be combined with the present compounds in a single dosage form, or the agents can be administered simultaneously or sequentially as separate dosage forms.

Suitable chemotherapeutic or other anticancer agents include, for example, alkylating agents (including, without limitation, nitrogen mustards, ethylenimine derivatives, alkyl sulfonates, nitrosoureas and triazenes) such as uracil mustard, chlormethine, cyclophosphamide (CYTOXAN®), ifosfamide, melphalan, chlorambucil, pipobroman, triethylene-melamine, triethylenethiophosphoramine, busulfan, carmustine, lomustine, streptozocin, dacarbazine, and temozolomide.

In the treatment of melanoma, suitable agents for use in combination with the compounds of the present disclosure include: dacarbazine (DTIC), optionally, along with other chemotherapy drugs such as carmustine (BCNU) and cisplatin; the "Dartmouth regimen", which consists of DTIC, BCNU, cisplatin and tamoxifen; a combination of cisplatin, vinblastine, and DTIC, temozolomide or YERVOY®. Compounds according to the disclosure may also be combined with immunotherapy drugs, including cytokines such as interferon alpha, interleukin 2, and tumor necrosis factor (TNF) in the treatment of melanoma.

Compounds of the disclosure may also be used in combination with vaccine therapy in the treatment of melanoma. Anti-melanoma vaccines are, in some ways, similar to the anti-virus vaccines which are used to prevent diseases caused by viruses such as polio, measles, and mumps. Weakened melanoma cells or parts of melanoma cells called antigens may be injected into a patient to stimulate the body's immune system to destroy melanoma cells.

Melanomas that are confined to the arms or legs may also be treated with a combination of agents including one or more compounds of the disclosure, using a hyperthermic isolated limb perfusion technique. This treatment protocol temporarily separates the circulation of the involved limb from the rest of the body and injects high doses of chemotherapy into the artery feeding the limb, thus providing high doses to the area of the tumor without exposing internal organs to these doses that might otherwise cause severe side effects. Usually the fluid is warmed to 102° to 104° F. Melphalan is the drug most often used in this chemotherapy procedure. This can be given with another agent called tumor necrosis factor (TNF).

Suitable chemotherapeutic or other anticancer agents include, for example, antimetabolites (including, without limitation, folic acid antagonists, pyrimidine analogs, purine analogs and adenosine deaminase inhibitors) such as methotrexate, 5-fluorouracil, floxuridine, cytarabine, 6-mercaptopurine, 6-thioguanine, fludarabine phosphate, pentostatine, and gemcitabine.

Suitable chemotherapeutic or other anticancer agents further include, for example, certain natural products and their derivatives (for example, vinca alkaloids, antitumor antibiotics, enzymes, lymphokines and epipodophyllotoxins) such as vinblastine, vincristine, vindesine, bleomycin, dactinomycin, daunorubicin, doxorubicin, epirubicin, idarubicin, ara-C, paclitaxel (Taxol), mithramycin, deoxycoformycin, mitomycin-C, L-asparaginase, interferons (especially IFN-a), etoposide, and teniposide.

Other cytotoxic agents include navelbene, CPT-11, anastrazole, letrazole, capecitabine, reloxafine, and droloxafine.

Also suitable are cytotoxic agents such as epidophyllotoxin; an antineoplastic enzyme; a topoisomerase inhibitor; procarbazine; mitoxantrone; platinum coordination complexes such as cisplatin and carboplatin; biological response modifiers; growth inhibitors; antihormonal therapeutic agents; leucovorin; tegafur; and haematopoietic growth factors.

Other anticancer agent(s) include antibody therapeutics such as trastuzumab (HERCEPTIN®), antibodies to costimulatory molecules such as CTLA-4, 4-1BB and PD-1, or antibodies to cytokines (IL-1O or TGF-β).

Other anticancer agents also include those that block immune cell migration such as antagonists to chemokine receptors, including CCR2 and CCR4.

Other anticancer agents also include those that augment the immune system such as adjuvants or adoptive T cell transfer.

Anticancer vaccines include dendritic cells, synthetic peptides, DNA vaccines and recombinant viruses.

The pharmaceutical composition of the disclosure may optionally include at least one signal transduction inhibitor (STI). A "signal transduction inhibitor" is an agent that selectively inhibits one or more vital steps in signaling pathways, in the normal function of cancer cells, thereby leading to apoptosis. Suitable STIs include, but are not limited to: (i) bcr/abl kinase inhibitors such as, for example, STI 571 (GLEEVEC®); (ii) epidermal growth factor (EGF) receptor inhibitors such as, for example, kinase inhibitors (IRESSA®, SSI-774) and antibodies (Imclone: C225 [Goldstein et al., *Clin. Cancer Res.*, 1:1311-1318 (1995)], and Abgenix: ABX-EGF); (iii) her-2/neu receptor inhibitors such as farnesyl transferase inhibitors (FTI) such as, for example, L-744,832 (Kohl et al., *Nat. Med.*, 1(8):792-797 (1995)); (iv) inhibitors of Akt family kinases or the Akt pathway, such as, for example, rapamycin (see, for example, Sekulic et al., *Cancer Res.*, 60:3504-3513 (2000)); (v) cell cycle kinase inhibitors such as, for example, flavopiridol and UCN-O1 (see, for example, Sausville, *Curr. Med. Chem. Anti-Canc. Agents*, 3:47-56 (2003)); and (vi) phosphatidyl inositol kinase inhibitors such as, for example, LY294002 (see, for example, Vlahos et al., *J. Biol. Chem.*, 269:5241-5248 (1994)). Alternatively, at least one STI and at least one IDO inhibitor may be in separate pharmaceutical compositions. In a specific embodiment of the present disclosure, at least one IDO inhibitor and at least one STI may be administered to the patient concurrently or sequentially. In other words, at least one IDO inhibitor may be administered first, at least one STI may be administered first, or at least one IDO inhibitor and at least one STI may be administered at the same time. Additionally, when more than one IDO inhibitor and/or STI is used, the compounds may be administered in any order.

The present disclosure further provides a pharmaceutical composition for the treatment of a chronic viral infection in a patient comprising at least one IDO inhibitor, optionally, at least one chemotherapeutic drug, and, optionally, at least one antiviral agent, in a pharmaceutically acceptable carrier. The pharmaceutical compositions may include at least one IDO inhibitor of the instant disclosure in addition to at least one established (known) IDO inhibitor. In a specific embodiment, at least one of the IDO inhibitors of the pharmaceutical composition is selected from the group consisting of compounds of formulas I and II, and sub-formulae thereof.

Also provided is a method for treating a chronic viral infection in a patient by administering an effective amount of the above pharmaceutical composition.

In a specific embodiment of the present disclosure, at least one IDO inhibitor and at least one chemotherapeutic agent may be administered to the patient concurrently or sequentially. In other words, at least one IDO inhibitor may be administered first, at least one chemotherapeutic agent may be administered first, or at least one IDO inhibitor and the at least one STI may be administered at the same time. Additionally, when more than one IDO inhibitor and/or chemotherapeutic agent is used, the compounds may be administered in any order. Similarly, any antiviral agent or STI may also be administered at any point in comparison to the administration of an IDO inhibitor.

Chronic viral infections that may be treated using the present combinatorial treatment include, but are not limited to, diseases caused by: hepatitis C virus (HCV), human papilloma virus (HPV), cytomegalovirus (CMV), herpes simplex virus (HSV), Epstein-Barr virus (EBV), varicella zoster virus, Coxsackie virus, human immunodeficiency virus (HIV). Notably, parasitic infections (e.g., malaria) may also be treated by the above methods wherein compounds known to treat the parasitic conditions are optionally added in place of the antiviral agents.

In yet another embodiment, the pharmaceutical compositions comprising at least one IDO inhibitor of the instant disclosure may be administered to a patient to prevent arterial restenosis, such as after balloon endoscopy or stent placement. In a particular embodiment, the pharmaceutical composition further comprises at least one taxane (e.g., paclitaxel (Taxol); see, e.g., Scheller et al., Circulation, 110:810-814 (2004)).

Suitable antiviral agents contemplated for use in combination with the compounds of the present disclosure can comprise nucleoside and nucleotide reverse transcriptase inhibitors (NRTIs), non-nucleoside reverse transcriptase inhibitors (NNRTIs), protease inhibitors and other antiviral drugs.

Examples of suitable NRTIs include zidovudine (AZT); didanosine (ddl); zalcitabine (ddC); stavudine (d4T); lamivudine (3TC); abacavir (1592U89); adefovir dipivoxil [bis(POM)-PMEA]; lobucavir (BMS-180194); BCH-10652; emtricitabine [(−)-FTC]; beta-L-FD4 (also called beta-L-D4C and named beta-L-2',3'-dicleoxy-5-fluoro-cytidene); DAPD, ((−)-beta-D-2,6-diamino-purine dioxolane); and lodenosine (FddA). Typical suitable NNRTIs include nevirapine (BI-RG-587); delaviradine (BHAP, U-90152); efavirenz (DMP-266); PNU-142721; AG-1549; MKC-442 (1-(ethoxy-methyl)-5-(1-methylethyl)-6-(phenylmethyl)-(2,4 (1H,3H)-pyrimidinedione); and (+)-calanolide A (NSC-675451) and B. Typical suitable protease inhibitors include saquinavir (Ro 31-8959); ritonavir (ABT-538); indinavir (MK-639); nelfinavir (AG-1343); amprenavir (141W94); lasinavir (BMS-234475); DMP-450; BMS-2322623; ABT-378; and AG-1549. Other antiviral agents include hydroxyurea, ribavirin, IL-2, IL-12, pentafuside and Yissum Project No. 11607.

Combination with an Immuno-Oncology Agent

Further provided herein are methods of treatment wherein a compound of Formula I or formula II (or a sub-formula thereof) is administered with one or more immuno-oncology agents. The immuno-oncology agents used herein, also known as cancer immunotherapies, are effective to enhance, stimulate, and/or upregulate immune responses in a subject.

In one aspect, the Compound of Formula I or formula II (or sub-formula thereof) is sequentially administered prior to administration of the immuno-oncology agent. In another aspect, the Compound of Formula I or formula II is administered concurrently with the immunology-oncology agent. In yet another aspect, the Compound of Formula I or formula II (or sub-formula thereof) is sequentially administered after administration of the immuno-oncology agent.

In another aspect, the Compound of Formula I or formula II (or sub-formula thereof) may be co-formulated with an immuno-oncology agent.

Immuno-oncology agents include, for example, a small molecule drug, antibody, or other biologic or small molecule. Examples of biologic immuno-oncology agents include, but are not limited to, cancer vaccines, antibodies, and cytokines. In one aspect, the antibody is a monoclonal antibody. In another aspect, the monoclonal antibody is humanized or human.

In one aspect, the immuno-oncology agent is (i) an agonist of a stimulatory (including a co-stimulatory) receptor or (ii) an antagonist of an inhibitory (including a co-inhibitory) signal on T cells, both of which result in amplifying antigen-specific T cell responses (often referred to as immune checkpoint regulators).

Certain of the stimulatory and inhibitory molecules are members of the immunoglobulin super family (IgSF). One important family of membrane-bound ligands that bind to co-stimulatory or co-inhibitory receptors is the B7 family, which includes B7-1, B7-2, B7-H1 (PD-L1), B7-DC (PD-L2), B7-H2 (ICOS-L), B7-H3, B7-H4, B7-H5 (VISTA), and B7-H6. Another family of membrane bound ligands that bind to co-stimulatory or co-inhibitory receptors is the TNF family of molecules that bind to cognate TNF receptor family members, which includes CD40 and CD40L, OX-40, OX-40L, CD70, CD27L, CD30, CD30L, 4-1BBL, CD137 (4-1BB), TRAIL/Apo2-L, TRAILR1/DR4, TRAILR2/DR5, TRAILR3, TRAILR4, OPG, RANK, RANKL, TWEAKR/Fn14, TWEAK, BAFFR, EDAR, XEDAR, TACI, APRIL, BCMA, LTβR, LIGHT, DcR3, HVEM, VEGI/TL1A, TRAMP/DR3, EDAR, EDA1, XEDAR, EDA2, TNFR1, Lymphotoxin α/TNFβ, TNFR2, TNFα, LTβR, Lymphotoxin α 1β2, FAS, FASL, RELT, DR6, TROY, NGFR.

In another aspect, the immuno-oncology agent is a cytokine that inhibits T cell activation (e.g., IL-6, IL-10, TGF-ß, VEGF, and other immunosuppressive cytokines) or a cytokine that stimulates T cell activation, for stimulating an immune response.

In one aspect, T cell responses can be stimulated by a combination of the Compound of Formula I or formula II (or sub-formula thereof) and one or more of (i) an antagonist of a protein that inhibits T cell activation (e.g., immune checkpoint inhibitors) such as CTLA-4, PD-1, PD-L1, PD-L2, LAG-3, TIM-3, Galectin 9, CEACAM-1, BTLA, CD69, Galectin-1, TIGIT, CD113, GPR56, VISTA, 2B4, CD48, GARP, PD1H, LAIR1, TIM-1, and TIM-4, and (ii) an agonist of a protein that stimulates T cell activation such as B7-1, B7-2, CD28, 4-1BB (CD137), 4-1BBL, ICOS, ICOS-L, OX40, OX40L, GITR, GITRL, CD70, CD27, CD40, DR3 and CD28H.

Other agents that can be combined with the Compound of Formula I or formula II (or sub-formula thereof) for the treatment of cancer include antagonists of inhibitory receptors on NK cells or agonists of activating receptors on NK cells. For example, the Compound of Formula I or formula II (or sub-formula thereof) can be combined with antagonists of KIR, such as lirilumab.

Yet other agents for combination therapies include agents that inhibit or deplete macrophages or monocytes, including but not limited to CSF-1R antagonists such as CSF-1R antagonist antibodies including RG7155 (WO 11/70024, WO 11/107553, WO 11/131407, WO 13/87699, WO 13/119716, WO 13/132044) or FPA-008 (WO 11/140249, WO 13/169264, WO 14/036357).

In another aspect, the Compound of Formula I or formula II (or sub-formula thereof) can be used with one or more of agonistic agents that ligate positive costimulatory receptors, blocking agents that attenuate signaling through inhibitory receptors, antagonists, and one or more agents that increase systemically the frequency of anti-tumor T cells, agents that overcome distinct immune suppressive pathways within the tumor microenvironment (e.g., block inhibitory receptor engagement (e.g., PD-L1/PD-1 interactions), deplete or inhibit Tregs (e.g., using an anti-CD25 monoclonal antibody (e.g., daclizumab) or by ex vivo anti-CD25 bead depletion), inhibit metabolic enzymes such as IDO, or reverse/prevent T cell anergy or exhaustion) and agents that trigger innate immune activation and/or inflammation at tumor sites.

In one aspect, the immuno-oncology agent is a CTLA-4 antagonist, such as an antagonistic CTLA-4 antibody. Suitable CTLA-4 antibodies include, for example, YERVOY® (ipilimumab) or tremelimumab.

In another aspect, the immuno-oncology agent is a PD-1 antagonist, such as an antagonistic PD-1 antibody. Suitable PD-1 antibodies include, for example, OPDIVO® (nivolumab), KEYTRUDA® (pembrolizumab), or MEDI-0680 (AMP-514; WO 2012/145493). The immuno-oncology agent may also include pidilizumab (CT-011), though its specificity for PD-1 binding has been questioned. Another approach to target the PD-1 receptor is the recombinant protein composed of the extracellular domain of PD-L2 (B7-DC) fused to the Fc portion of IgG1, called AMP-224.

In another aspect, the immuno-oncology agent is a PD-L1 antagonist, such as an antagonistic PD-L1 antibody. Suitable PD-L1 antibodies include, for example, MPDL3280A (RG7446; WO 2010/077634), durvalumab (MEDI4736), BMS-936559 (WO 2007/005874), and MSB0010718C (WO 2013/79174).

In another aspect, the immuno-oncology agent is a LAG-3 antagonist, such as an antagonistic LAG-3 antibody. Suitable LAG3 antibodies include, for example, BMS-986016 (WO 10/19570, WO 14/08218), or IMP-731 or IMP-321 (WO 08/132601, WO 09/44273).

In another aspect, the immuno-oncology agent is a CD137 (4-1BB) agonist, such as an agonistic CD137 antibody. Suitable CD137 antibodies include, for example, urelumab and PF-05082566 (WO 12/32433).

In another aspect, the immuno-oncology agent is a GITR agonist, such as an agonistic GITR antibody. Suitable GITR antibodies include, for example, BMS-986153, BMS-986156, TRX-518 (WO 06/105021, WO 09/009116) and MK-4166 (WO 11/028683).

In another aspect, the immuno-oncology agent is an IDO antagonist. Suitable IDO antagonists include, for example, INCB-024360 (WO 2006/122150, WO 07/75598, WO 08/36653, WO 08/36642), indoximod, or NLG-919 (WO 09/73620, WO 09/1156652, WO 11/56652, WO 12/142237).

In another aspect, the immuno-oncology agent is an OX40 agonist, such as an agonistic OX40 antibody. Suitable OX40 antibodies include, for example, MEDI-6383 or MEDI-6469.

In another aspect, the immuno-oncology agent is an OX40L antagonist, such as an antagonistic OX40 antibody. Suitable OX40L antagonists include, for example, RG-7888 (WO 06/029879).

In another aspect, the immuno-oncology agent is a CD40 agonist, such as an agonistic CD40 antibody. In yet another embodiment, the immuno-oncology agent is a CD40 antagonist, such as an antagonistic CD40 antibody. Suitable CD40 antibodies include, for example, lucatumumab or dacetuzumab.

In another aspect, the immuno-oncology agent is a CD27 agonist, such as an agonistic CD27 antibody. Suitable CD27 antibodies include, for example, varlilumab.

In another aspect, the immuno-oncology agent is MGA271 (to B7H3) (WO 11/109400).

The present disclosure also includes pharmaceutical kits useful, for example, in the treatment or prevention of IDO-associated diseases or disorders, obesity, diabetes and other diseases referred to herein which include one or more containers containing a pharmaceutical composition comprising a therapeutically effective amount of a compound of the disclosure. Such kits can further include, if desired, one or more of various conventional pharmaceutical kit components, such as, for example, containers with one or more pharmaceutically acceptable carriers, additional containers, as will be readily apparent to those skilled in the art. Instructions, either as inserts or as labels, indicating quantities of the components to be administered, guidelines for administration, and/or guidelines for mixing the components, can also be included in the kit.

The combination therapy is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single dosage form having a fixed ratio of each therapeutic agent or in multiple, single dosage forms for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. Combination therapy also can embrace the administration of the therapeutic agents as described above in further combination with other biologically active ingredients and non-drug therapies (e.g., surgery or radiation treatment). Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

PHARMACEUTICAL COMPOSITIONS AND DOSING

The disclosure also provides pharmaceutically acceptable compositions which comprise a therapeutically effective amount of one or more of the compounds of Formula I and/or Formula II (or sub-formula thereof), formulated together with one or more pharmaceutically acceptable carriers (additives) and/or diluents, and optionally, one or more additional therapeutic agents described above.

The compounds of this disclosure can be administered for any of the uses described herein by any suitable means, for example, orally, such as tablets, capsules (each of which includes sustained release or timed release formulations), pills, powders, granules, elixirs, tinctures, suspensions (including nanosuspensions, microsuspensions, spray-dried dispersions), syrups, and emulsions; sublingually; buccally; parenterally, such as by subcutaneous, intravenous, intramuscular, or intrasternal injection, or infusion techniques (e.g., as sterile injectable aqueous or non-aqueous solutions or suspensions); nasally, including administration to the nasal membranes, such as by inhalation spray; topically, such as in the form of a cream or ointment; or rectally such as in the form of suppositories. They can be administered alone, but generally will be administered with a pharmaceutical carrier selected on the basis of the chosen route of administration and standard pharmaceutical practice.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient.

The term "pharmaceutical composition" means a composition comprising a compound of the disclosure in combination with at least one additional pharmaceutically acceptable carrier. A "pharmaceutically acceptable carrier" refers to media generally accepted in the art for the delivery of biologically active agents to animals, in particular, mammals, including, i.e., adjuvant, excipient or vehicle, such as diluents, preserving agents, fillers, flow regulating agents, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms.

Pharmaceutically acceptable carriers are formulated according to a number of factors well within the purview of those of ordinary skill in the art. These include, without limitation: the type and nature of the active agent being formulated; the subject to which the agent-containing composition is to be administered; the intended route of administration of the composition; and the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, Allen, Jr., L. V. et al., *Remington: The Science and Practice of Pharmacy* (2 Volumes), 22nd Edition, Pharmaceutical Press (2012).

The dosage regimen for the compounds of the present disclosure will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired.

By way of general guidance, the daily oral dosage of each active ingredient, when used for the indicated effects, will range between about 0.001 to about 5000 mg per day, preferably between about 0.01 to about 1000 mg per day, and most preferably between about 0.1 to about 250 mg per day. Intravenously, the most preferred doses will range from about 0.01 to about 10 mg/kg/minute during a constant rate infusion. Compounds of this disclosure may be administered in a single daily dose, or the total daily dosage may be administered in divided doses of two, three, or four times daily.

The compounds are typically administered in admixture with suitable pharmaceutical diluents, excipients, or carriers (collectively referred to herein as pharmaceutical carriers) suitably selected with respect to the intended form of administration, e.g., oral tablets, capsules, elixirs, and syrups, and consistent with conventional pharmaceutical practices.

Dosage forms (pharmaceutical compositions) suitable for administration may contain from about 1 milligram to about 2000 milligrams of active ingredient per dosage unit. In these pharmaceutical compositions the active ingredient will ordinarily be present in an amount of about 0.1-95% by weight based on the total weight of the composition.

A typical capsule for oral administration contains at least one of the compounds of the present disclosure (250 mg), lactose (75 mg), and magnesium stearate (15 mg). The mixture is passed through a 60 mesh sieve and packed into a No. 1 gelatin capsule.

A typical injectable preparation is produced by aseptically placing at least one of the compounds of the present disclosure (250 mg) into a vial, aseptically freeze-drying and sealing. For use, the contents of the vial are mixed with 2 mL of physiological saline, to produce an injectable preparation.

The present disclosure includes within its scope pharmaceutical compositions comprising, as an active ingredient, a therapeutically effective amount of at least one of the compounds of the present disclosure, alone or in combination with a pharmaceutical carrier. Optionally, compounds of the present disclosure can be used alone, in combination with other compounds of the disclosure, or in combination with one or more other therapeutic agent(s), e.g., an anticancer agent or other pharmaceutically active material.

Regardless of the route of administration selected, the compounds of the present disclosure, which may be used in a suitable hydrated form, and/or the pharmaceutical compositions of the present disclosure, are formulated into pharmaceutically acceptable dosage forms by conventional methods known to those of skill in the art.

Actual dosage levels of the active ingredients in the pharmaceutical compositions of this disclosure may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present disclosure employed, or the ester, salt or amide thereof, the route of administration, the time of administration, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the disclosure employed in the pharmaceutical composition at levels lower than that required in order to achieve the desired therapeutic effect and gradually increase the dosage until the desired effect is achieved.

In general, a suitable daily dose of a compound of the disclosure will be that amount of the compound which is the lowest dose effective to produce a therapeutic effect. Such an effective dose will generally depend upon the factors described above.

If desired, the effective daily dose of the active compound may be administered as two, three, four, five, six or more sub-doses administered separately at appropriate intervals throughout the day, optionally, in unit dosage forms. In certain aspects of the disclosure, dosing is one administration per day.

While it is possible for a compound of the present disclosure to be administered alone, it is preferable to administer the compound as a pharmaceutical formulation (composition).

Definitions

Unless specifically stated otherwise herein, references made in the singular may also include the plural. For example, "a" and "an" may refer to either one, or one or more.

Unless otherwise indicated, any heteroatom with unsatisfied valences is assumed to have hydrogen atoms sufficient to satisfy the valences.

Throughout the specification and the appended claims, a given chemical formula or name shall encompass all stereo and optical isomers and racemates thereof where such isomers exist. Unless otherwise indicated, all chiral (enantiomeric and diastereomeric) and racemic forms are within the scope of the disclosure. Many geometric isomers of C=C double bonds, C=N double bonds, ring systems, and the like can also be present in the compounds, and all such stable isomers are contemplated in the present disclosure. Cis- and trans- (or E- and Z-) geometric isomers of the compounds of the present disclosure are described and may be isolated as a mixture of isomers or as separated isomeric forms. The present compounds can be isolated in optically active or racemic forms. Optically active forms may be prepared by resolution of racemic forms or by synthesis from optically active starting materials. All processes used to prepare compounds of the present disclosure and intermediates made therein are considered to be part of the present disclosure. When enantiomeric or diastereomeric products are prepared, they may be separated by conventional methods, for example, by chromatography or fractional crystallization. Depending on the process conditions the end products of the present disclosure are obtained either in free (neutral) or salt form. Both the free form and the salts of these end products are within the scope of the disclosure. If so desired, one form of a compound may be converted into another form. A free base or acid may be converted into a salt; a salt may be converted into the free compound or another salt; a mixture of isomeric compounds of the present disclosure may be separated into the individual isomers. Compounds of the present disclosure, free form and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the disclosure.

For purposes of clarity and in accordance with standard convention in the art, the symbol ⊢ is used in formulas and tables to show the bond that is the point of attachment of the moiety or substituent to the core/nucleus of the structure.

Additionally, for purposes of clarity, where a substituent has a dash (-) that is not between two letters or symbols; this is used to indicate a point of attachment for a substituent. For example, —$CONH_2$ is attached through the carbon atom.

Additionally, for purposes of clarity, when there is no substituent shown at the end of a solid line, this indicates that there is a methyl ($CH_3$) group connected to the bond.

As used herein, the terms "alkyl" and "alkylene" (also referred to as "alk") are intended to include both branched and straight-chain saturated aliphatic hydrocarbon groups having the specified number of carbon atoms. For example, "$C_1$-$C_6$ alkyl" or "$C_{1-6}$ alkyl" denotes alkyl having 1 to 6 carbon atoms. Example alkyl groups include, but are not limited to, methyl ($C_1$, Me), ethyl ($C_2$, Et), propyl ($C_3$, e.g., n-propyl and isopropyl), butyl ($C_4$, e.g., n-butyl, isobutyl, t-butyl), pentyl ($C_5$, e.g., n-pentyl, isopentyl, neopentyl), and hexyl variants ($C_6$). "$C_1$-$C_6$alkylene" denotes alkylene having 1 to 6 carbon atoms. Example alkylene groups include, but are not limited to, methylene (—$CH_2$—), ethylene (—$CH_2CH_2$—), and the like.

As used herein, "$C_{2-6}$alkenylene" is intended to include both branched and straight-chain hydrocarbon groups having the specified number of carbon atoms and at least one double bond. Example alkenylene groups include ethenyl, propenyl, butenyl, methylbutenyl, methylpenentyl, and the like.

As used herein, "aryl" refers to an aromatic ring system which includes, but not limited to phenyl, biphenyl, indanyl, 1-naphthyl, 2-naphthyl and terahydronaphthyl.

As used herein, the term "heteroaryl" is intended to mean stable monocyclic and polycyclic aromatic hydrocarbons that include at least one heteroatom ring member such as sulfur, oxygen, or nitrogen. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrroyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, benzodioxolanyl and benzodioxane. Heteroaryl groups are substituted or unsubstituted. The nitrogen atom is substituted or unsubstituted (i.e., N or NR wherein R is H or another substituent, if defined). The nitrogen and sulfur heteroatoms may optionally be oxidized (i.e., N→O and $S(O)_p$, wherein p is 0, 1 or 2).

"Halo" or "halogen" includes fluoro, chloro, bromo, and iodo.

"Haloalkyl" is intended to include both branched and straight-chain saturated aliphatic hydrocarbon groups having the specified number of carbon atoms, substituted with 1 or more halogens. Examples of haloalkyl include, but are not limited to, fluoromethyl, difluoromethyl, trifluoromethyl, trichloromethyl, pentafluoroethyl, pentachloroethyl, 2,2,2-trifluoroethyl, heptafluoropropyl, and heptachloropropyl. Examples of haloalkyl also include "fluoroalkyl" that is intended to include both branched and straight-chain saturated aliphatic hydrocarbon groups having the specified number of carbon atoms, substituted with 1 or more fluorine atoms.

The term "heterocycloalkyl" refers to any five to ten membered monocyclic or bicyclic, saturated ring structure containing at least one heteroatom selected from the group consisting of O, N and S. The heterocycloalkyl group may be attached at any heteroatom or carbon atom of the ring such that the result is a stable structure. Examples of suitable heterocycloalkyl groups include, but are not limited to, azepanyl, aziridinyl, azetidinyl, pyrrolidinyl, dioxolanyl, imidazolidinyl, pyrazolidinyl, piperazinyl, piperidinyl, dioxanyl, morpholinyl, dithianyl, thiomorpholinyl, oxazepanyl, oxiranyl, oxetanyl, quinuclidinyl, tetrahyofuranyl, tetrahydropyranyl, piperazinyl, hexahydro-5H-[1,4]dioxino[2,3-c]pyrrolyl, benzo[d][1,3]dioxolyl, and the like.

As referred to herein, the term "substituted" means that at least one hydrogen atom is replaced with a non-hydrogen group, provided that normal valencies are maintained and that the substitution results in a stable compound.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like.

The pharmaceutically acceptable salts of the present disclosure can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Allen, Jr., L. V., ed., *Remington: The Science and Practice of Pharmacy,* 22nd Edition, Pharmaceutical Press, London, UK (2012). The disclosure of which is hereby incorporated by reference.

In addition, compounds of formula I and formula II (or sub-formula thereof) may have prodrug forms. Any compound that will be converted in vivo to provide the bioactive agent (i.e., a compound of formula I or II (or sub-formula thereof)) is a prodrug within the scope and spirit of the disclosure. Various forms of prodrugs are well known in the art. For examples of such prodrug derivatives, see:

a) Bundgaard, H., ed., *Design of Prodrugs,* Elsevier (1985), and Widder, K. et al., eds., *Methods in Enzymology,* 112:309-396, Academic Press (1985);

b) Bundgaard, H., Chapter 5: "Design and Application of Prodrugs", *A Textbook of Drug Design and Development,* pp. 113-191, Krogsgaard-Larsen, P. et al., eds., Harwood Academic Publishers (1991);

c) Bundgaard, H., *Adv. Drug Deliv. Rev.,* 8:1-38 (1992);

d) Nielsen, N. M. et al., *J. Pharm. Sci.,* 77:285 (1988);

e) Kakeya, N. et al., *Chem. Pharm. Bull.,* 32:692 (1984); and g) Rautio, J., ed., *Prodrugs and Targeted Delivery* (*Methods and Principles in Medicinal Chemistry*), Vol. 47, Wiley-VCH (2011).

Compounds containing a carboxy group can form physiologically hydrolyzable esters that serve as prodrugs by being hydrolyzed in the body to yield formula I or formula II compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of formula I or formula II (or sub-formula thereof) include $C_{1-6}$alkyl, $C_{1-6}$alkylbenzyl, 4-methoxybenzyl, indanyl, phthalyl, methoxymethyl, $C_{1-6}$ alkanoyloxy-$C_{1-6}$alkyl (e.g., acetoxymethyl, pivaloyloxymethyl or propionyloxymethyl), $C_{1-6}$alkoxycarbonyloxy-$C_{1-6}$alkyl (e.g., methoxycarbonyl-oxymethyl or ethoxycarbonyloxymethyl, glycyloxymethyl, phenylglycyloxymethyl, (5-methyl-2-oxo-1,3-dioxolen-4-yl)-methyl), and other well-known physiologically hydrolyzable esters used, for example, in the penicillin and cephalosporin arts. Such esters may be prepared by conventional techniques known in the art.

Preparation of prodrugs is well known in the art and described in, for example, King, F. D., ed., *Medicinal Chemistry: Principles and Practice,* The Royal Society of Chemistry, Cambridge, UK (Second Edition, reproduced, 2006); Testa, B. et al., *Hydrolysis in Drug and Prodrug Metabolism. Chemistry, Biochemistry and Enzymology,* VCHA and Wiley-VCH, Zurich, Switzerland (2003); Wermuth, C. G., ed., *The Practice of Medicinal Chemistry,* Third Edition, Academic Press, San Diego, Calif. (2008).

The present disclosure is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the disclosure can generally be prepared by conventional techniques known to those skilled in the art or by processes analogous to those described herein, using an appropriate isotopically-labeled reagent in place of the non-labeled reagent otherwise employed.

The term "solvate" means a physical association of a compound of this disclosure with one or more solvent molecules, whether organic or inorganic. This physical association includes hydrogen bonding. In certain instances the solvate will be capable of isolation, for example, when one or more solvent molecules are incorporated in the crystal lattice of the crystalline solid. The solvent molecules in the solvate may be present in a regular arrangement and/or a non-ordered arrangement. The solvate may comprise either a stoichiometric or nonstoichiometric amount of the solvent molecules. "Solvate" encompasses both solution-phase and isolable solvates. Exemplary solvates include, but are not limited to, hydrates, ethanolates, methanolates, and isopropanolates. Methods of solvation are generally known in the art.

As used herein, the term "patient" refers to organisms to be treated by the methods of the present disclosure. Such organisms preferably include, but are not limited to, mammals (e.g., murines, simians, equines, bovines, porcines, canines, felines, and the like), and most preferably refers to humans.

As used herein, the term "effective amount" means that amount of a drug or pharmaceutical agent, i.e., a compound of the disclosure, that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. An effective amount can be administered in one or more administrations, applications or dosages and is not intended to be limited to a particular formulation or administration route. The term also includes within its scope amounts effective to enhance normal physiological function As used herein, the term "treating" includes any effect, e.g., lessening, reducing, modulating, ameliorating or eliminating, that results in the improvement of the condition, disease, disorder, and the like, or ameliorating a symptom thereof.

For therapeutic use, salts of the compounds of the present disclosure are contemplated as being pharmaceutically acceptable. However, salts of acids and bases that are non-pharmaceutically acceptable may also find use, for example, in the preparation or purification of a pharmaceutically acceptable compound.

METHODS OF PREPARATION

The compounds of the present disclosure may be prepared from starting materials which are known in the chemical literature or are commercially available by methods such as those illustrated in the following Schemes utilizing chemical transformations known to one of ordinary skill in the art. Solvents, temperatures, pressures, and other reaction conditions may readily be selected by one of ordinary skill in the art. These Schemes are illustrative and are not meant to limit the possible techniques one skilled in the art may use to manufacture compounds disclosed herein. Different methods may be evident to those skilled in the art. Additionally, the various steps in the synthesis may be performed in an alternate sequence or order to give the desired compound(s).

Further, the representation of the reactions in these Schemes as discrete steps does not preclude their being performed in tandem, either by telescoping multiple steps in the same reaction vessel or by performing multiple steps without purifying or characterizing the intermediate(s). In addition, many of the compounds prepared by the methods below can be further modified using conventional chemistry well known to those skilled in the art. All documents cited herein are incorporated herein by reference in their entirety.

Reference can also be made to International Publication Nos. WO2016/073738, WO2016/073770, and WO2016/073774.

References to many of these chemical transformations employed herein can be found in Smith, M. B. et al., *March's Advanced Organic Chemistry Reactions, Mechanisms, and Structure*, Fifth Edition, Wiley-Interscience, New York (2001), or other standard texts on the topic of synthetic organic chemistry. Certain transformations may require that reactive functional groups be masked by protecting group(s). A convenient reference which provides conditions for introduction, removal, and relative susceptibility to reaction conditions of these groups is Greene, T. W. et al., *Protective Groups in Organic Synthesis*, Third Edition, Wiley-Interscience, New York (1999).

Schemes 1-5 depict methods for preparing compounds of formula I and II.

Aryl halides III are common reagents in organic synthesis and are commercially available. Treatment of III with a reducing metal, such as Zinc in acidic media, such as acetic acid, will result in reduction of the nitro group affording the aniline IV. Treatment of the ester IV with an excess of alkyl lithium, such as methyllithium, will result in the formation of the carbinol of general structure V. The carbinol V can be treated with a strong base, such as sodium hydride, to give the resulting alkoxide, which can then be treated with an alkyl halide, such as ethyl iodide, to give the ether of general structure VI. The boronate (VII) can be prepared from the previously discussed aryl halide (VI) under standard condition utilizing a Pd catalyst such as $Pd(PPh_3)_4$ or 1,1'-bis(diphenylphosphino)ferrocenedichloro palladium(II). Rhodium catalyzed 1,4-conjugate addition of the boronic ester (VII) and an unsaturated ester (VIII) are well known (Zou, G. et al., *Dalton Trans.*, 28:3055 (2007)) and can be accomplished using a rhodium[1] catalyst, for example, $[Rh(COD)Cl]_2$ in the presence of a strong base such as NaOH to afford saturated esters of the general structure (IX). Amines of general structure IX can undergo a palladium catalyzed coupling to both aryl and heteroaryl halides X to afford N-arylated compounds of general structure XI. Coupling can be accomplished by utilizing conditions established by Buchwald and Hartwig (i.e., $Pd_2(dba)_3$, Xantphos and base) that are well-known to one skilled in the art (Surry, D. S. et al., *Chem. Sci.*, 2:27-50 (2011)). Compounds of general structure XI can then be converted to compounds of formula (I) of the present disclosure via hydrolysis of the ester by treatment under basic aqueous conditions, such as but not limited to, treatment with LiOH, water and THF. Amines of general structure IX can also be treated with an isocyanate XII to afford compounds of general structure XIII, which can also then be converted to compounds of formula (II) of the present disclosure by treatment with an aqueous base as described previously.

Scheme 1.

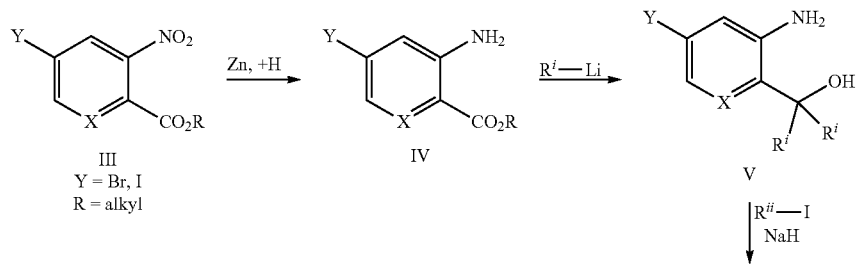

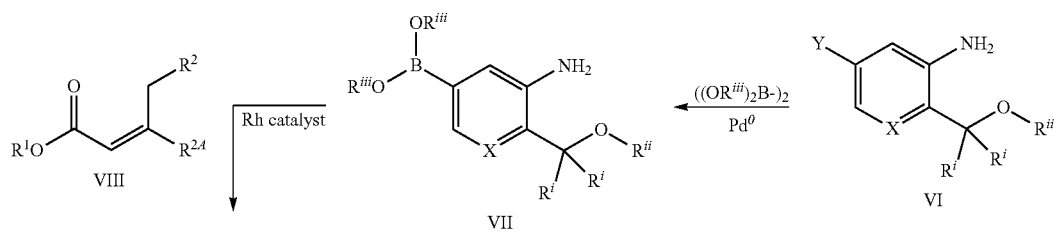

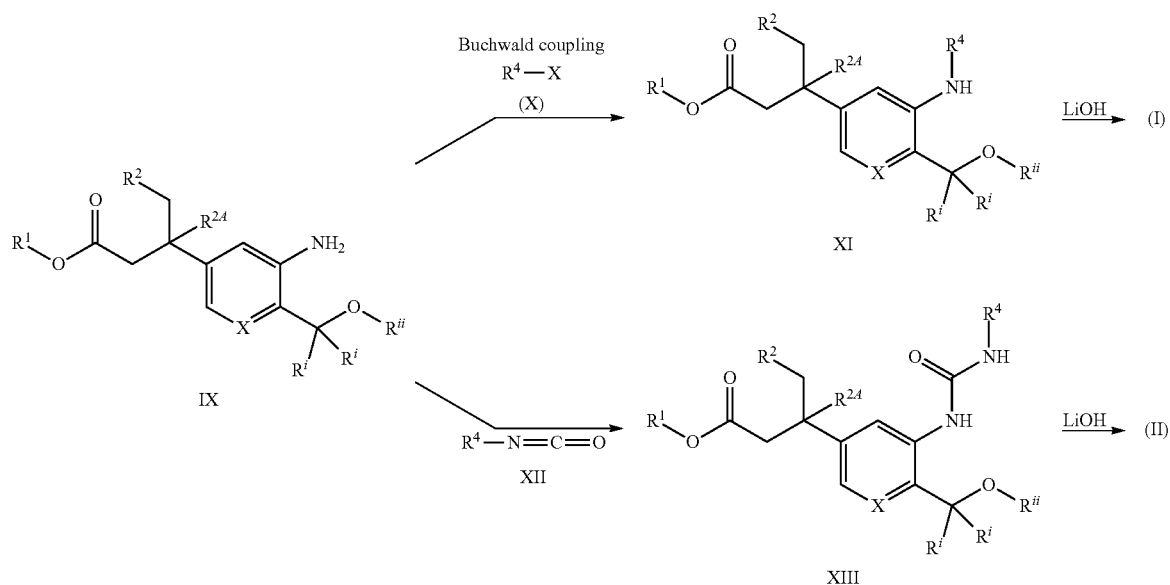

In another embodiment, the conjugate addition of boronates of general structure VII, where $R^x$ is hydrogen, to the unsaturated ester VIII can be accomplished with a chiral catalyst to give products of general structure XIV and XV with enhanced optical purity at the benzylic position (see Scheme 2 below). One can accomplish this transformation using the conditions developed by Hayashi whereby chlorobis(ethylene)rhodium(I)dimer is combined with (R)- or (S)-BINAP as the chiral ligand (Hayashi et al., *J. Am. Chem. Sci.*, 124:5052 (2002)). The desired stereochemistry at the benzylic position of compounds of general structure XIV and XV can be obtained by the appropriate choice of (R)- or (S)-BINAP used in the conjugate addition. Compounds of general structure XIV and XV with enhanced stereochemical purity can then be converted to compounds of formula (I) and formula (II) of the present disclosure by methods previously discussed.

Scheme 2.

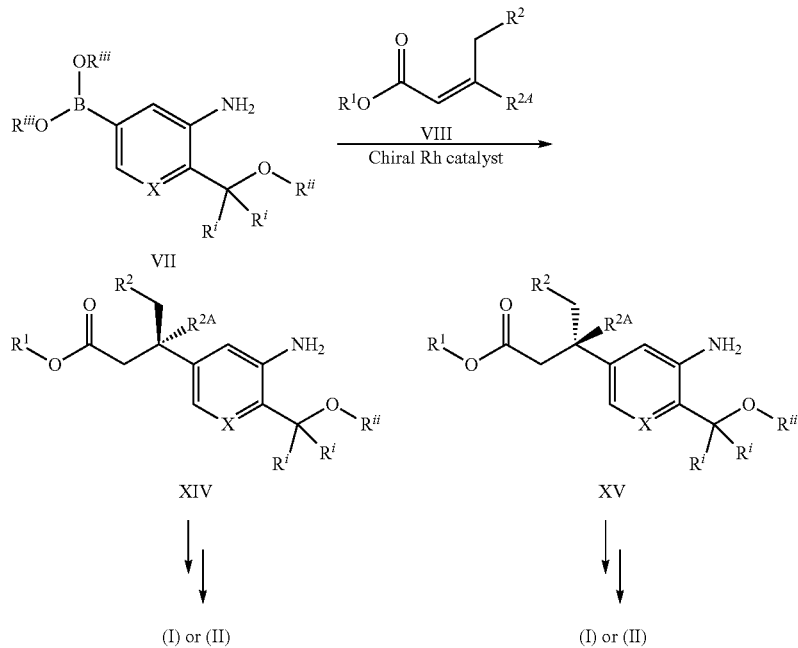

Aryl halides of general structure XVI are widely available and can be treated with an organometallic reagent, such as methyllithium, at low temperatures, such as 0 or −78 degrees Celsius, to afford a carbinol of general structure XVII. Carbinols of general structure XVII can be converted to ethers of general structure XVIII by methods well known to one of ordinary skill in the art, such as by treatment with an alkyl iodide and strong base such as NaH. Compounds of general structure XVIII can be converted to the aniline of general structure XIX by treatment under reductive conditions with a metal such as Zinc in the presence of a strong acid, such as acetic acid. Compounds of general structure XIX can then be converted to compounds formula (I) or formula (II) of the present disclosure by methods previously discussed.

In another embodiment, compounds of general structure XVII can be converted to compounds of general structure XX by treatment with methanesulfonyl chloride in the presence of an oranic base, such as diisopropylethylamine. Treatment of compounds of general structure XX with an amine of general structure XXI with or without heating, will result in a nucleophilic displacement to afford compounds of general structure XXII. Compounds of general structure XXII can be converted to compounds of formula (I) or formula (II) of the present disclosure by methods previously discussed.

Scheme 3.

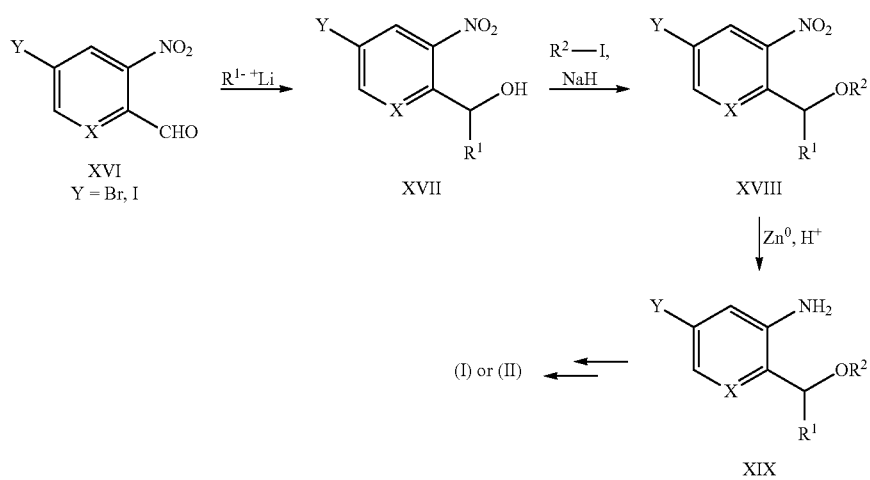

Scheme 4.

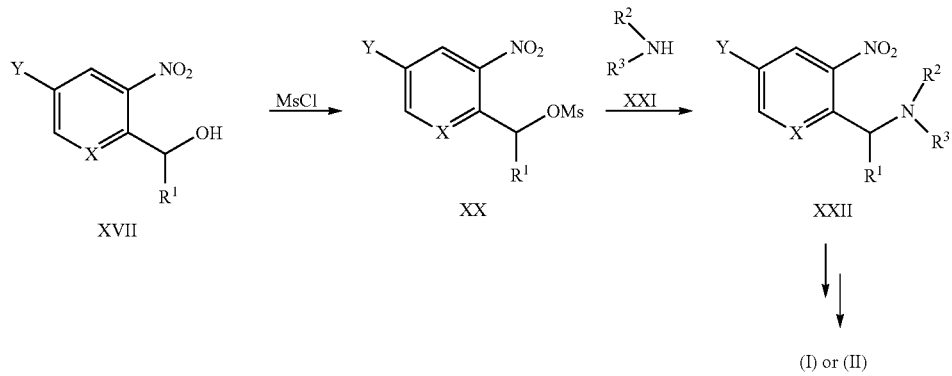

In another embodiment, the boronate XXIV can be prepared from the halide XXIII under standard condition utilizing a Pd catalyst such as Pd(PPh$_3$)$_4$ or 1,1'-bis(diphenylphosphino)ferrocenedichloro palladium(II). Rhodium catalyzed 1,4-conjugate addition of the boronic ester XXIV and an unsaturated ester VIII are well known (Zou, G. et al., Dalton Trans., 28:3055 (2007)) and can be accomplished using a rhodium[1] catalyst, for example, [Rh(COD)Cl]$_2$ in the presence of a strong base such as NaOH to afford saturated esters of the general structure XXV. Compounds of general structure XXV can be deprotected by methods well known to one of ordinary skill in the art, to afford the corresponding phenol. The phenol can be activated by treatment with triflic anhydride in the presence of an organic base such as diisopropylethylamine to afford a compound of general structure XXVI. Boronic esters of general structure XXVII can be prepared from the triflate XXVI by methods already described herein. Suzuki coupling of the vinyl triflate XXVIII with the boronic ester of general structure XXVII will afford compounds of general structure XXIX. Compounds of general structure XXX can be prepared by simultaneous reduction of the olefin and nitro functionality in compounds of general structure XXIX by treatment with a catalyst such as Pd on carbon under an atmosphere of hydrogen. Compounds of general structure XXX can be transformed to compounds of formula (I) and formula (II) of the present disclosure by methods previously described herein.

Scheme 5.

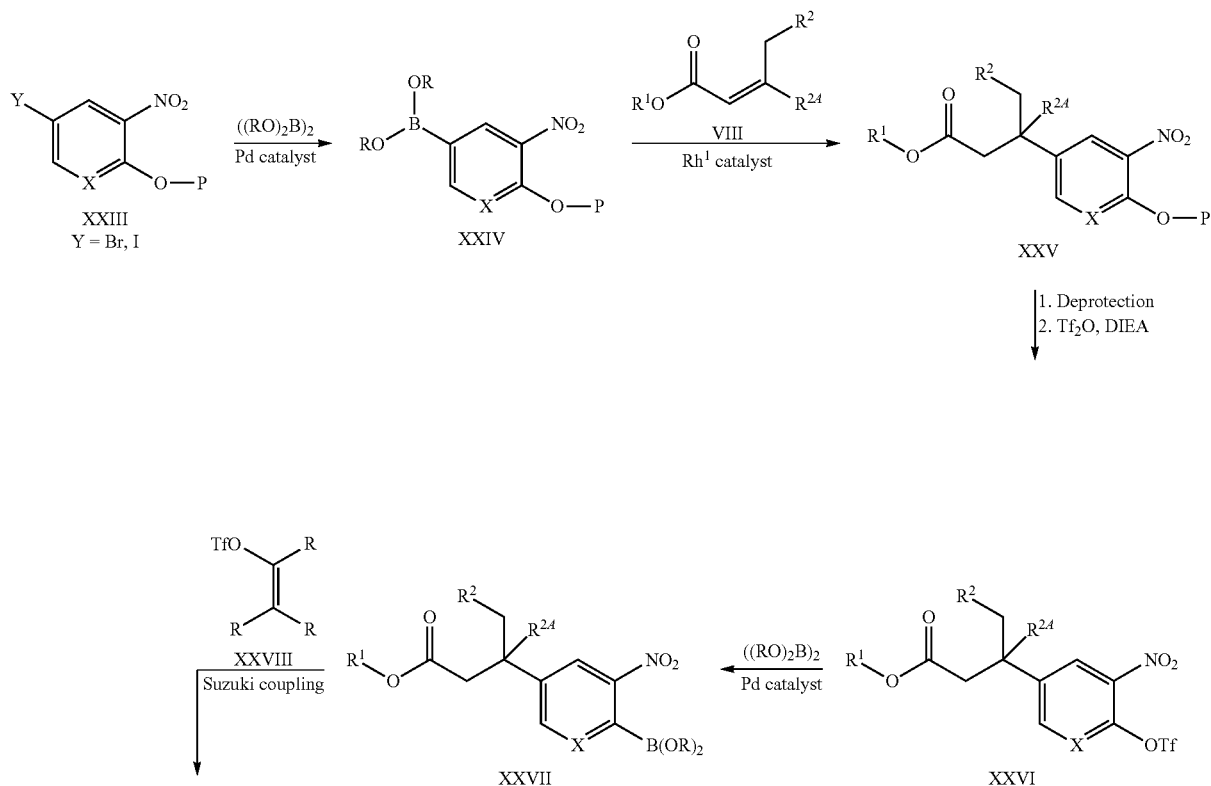

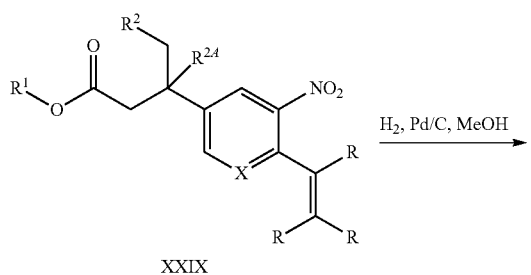 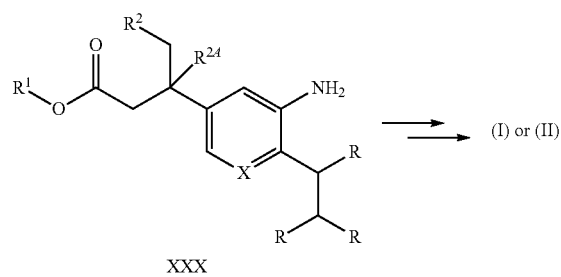

Compounds of formula I-C and II-C, in which the central aromatic ring is 1,3,5-substituted, are made using analogous procedures.

EXAMPLES

The following Examples are put forth so as to provide those of ordinary skill in the art with a complete disclosure and description of how to make and use the compounds of the present disclosure, and are not intended to limit the scope of the disclosure, nor are they intended to represent that the experiments below were performed or that they are all of the experiments that may be performed. It is to be understood that exemplary descriptions written in the present tense were not necessarily performed, but rather that the descriptions can be performed to generate data and the like of a nature described therein. Efforts have been made to ensure accuracy with respect to numbers used (e.g., amounts, temperature, etc.), but some experimental errors and deviations should be accounted for.

Unless indicated otherwise, parts are parts by weight, molecular weight is weight average molecular weight, temperature is in degrees Celsius (° C.), and pressure is at or near atmospheric. Standard abbreviations are used, including the following: wt=wildtype; bp=base pair(s); kb=kilobase(s); nt=nucleotides(s); aa=amino acid(s); s or sec=second(s); min=minute(s); h or hr=hour(s); ng=nanogram; μg=microgram; mg=milligram; g=gram; kg=kilogram; dl or dL=deciliter; μl or μL=microliter; ml or mL=milliliter; l or L=liter; μM=micromolar; mM=millimolar; M=molar; kDa=kilodalton; i.m.=intramuscular(ly); i.p.=intraperitoneal(ly); SC or SQ=subcutaneous(ly); QD=daily; BID=twice daily; QW=weekly; QM=monthly; HPLC=high performance liquid chromatography; BW=body weight; U=unit; ns=not statistically significant; PBS=phosphate-buffered saline; IHC=immunohistochemistry; DMEM=Dulbecco's Modification of Eagle's Medium; EDTA=ethylenediaminetetraacetic acid.

Analytical HPLC/MS was Performed Using the Following Methods:

Method N: Kinetex XB-C18 (75×3) mm, 2.6 μm; Mobile P Chiralcel hase A: 10 mM $NH_4OAc$ in Water: Acetonitrile (98:02); Mobile Phase B: 10 mM $NH_4OAc$ in Water: Acetonitrile (02:98); Gradient: 20-100% B over 4 minutes, flow rate 1 mL/min, then a 0.6 minute hold at 100% B flow rate 1.5 mL/min; then Gradient: 100-20% B over 0.1 minutes, flow rate 1.5 mL/min.

Method O: Column: Ascentis Express C18 (50×2.1) mm, 2.7 μm; flow rate 1.1 mL/min; gradient time 3 min; Temperature: 50° C., 0% Solvent B to 100% Solvent B; monitoring at 220 nm (Solvent A: 95% Water: 5% Acetonitrile; 10 mM $NH_4OAc$; Solvent B: 5% Water: 95% Acetonitrile; 10 mM $NH_4OAc$).

Method P: Column: Ascentis Express C18 (50×4.6) mm, 2.7 μm, flow rate 4 mL/min; gradient: 0 to 100% solvent B over 4 min; Temperature: 50° C. Monitoring at 220 nm (Solvent A: 95:05 water: $CH_3CN$ with 10 mM $NH_4OAc$ and Solvent B: 05:95 water: $CH_3CN$ with 10 mM $NH_4OAc$)

Method Q: Column: Ascentis Express C18 (50×4.6) mm, 2.7 μm, flow rate 4 mL/min; gradient: 0 to 100% solvent B over 4 min; Temperature: 50° C.; monitoring at 220 nm (Solvent A: 95:05 water: $CH_3CN$ with 0.1% TFA and Solvent B: 05:95 water: $CH_3CN$ with 0.1% TFA)

Method R: Column: Ascentis Express C18 (50×2.1) mm, 2.7 μm, flow rate 1.1 mL/min; gradient: 0 to 100% solvent B over 3 min; Temperature: 50° C.; monitoring at 220 nm (Solvent A: 95:05 water: $CH_3CN$ with 0.1% TFA and Solvent B: 05:95 water: $CH_3CN$ with 0.1% TFA)

Method S: Column: Chiralpak ASH (250×4.6) mm, 5.0 μm; Isocratic Mode, $CO_2$: Co-Solvent (85:15), Co-Solvent: 0.2% DEA in Methanol; Co-Solvent percentage: 15%, Column Temperature: 22.1° C.; Back Pressure: 100 bars; Total Flow: 3 g/min; $CO_2$ flow: 2.55 g/min; Co-Solvent flow: 0.45 g/min.

Method T: Column: Acquity BEH C18 (2.1×50 mm) 1.7 um; Mobile phase A: Buffer:ACN (95:5); Mobile phase B:Buffer:ACN (5:95), Buffer:5 mM Ammonium Acetate; Gradient: 20-90% B over 1.1 minutes, then a 0.6 minute hold at 90% B, flow rate 0.5 mL/min.

Method U: Column: Kinetex XB-C18 (75×3) mm, 2.6 μm; Mobile Phase A: 10 mM $NH_4COOH$ in Water: Acetonitrile (98:02; Mobile Phase B: 10 mM $NH_4COOH$ in Water: Acetonitrile (02:98); Gradient: 20-100% B over 4 minutes, flow rate 1 mL/min, then a 0.6 minute hold at 100% B flow rate 1.5 mL/min; then Gradient: 100-20% B over 0.1 minutes, flow rate 1.5 mL/min.

Method V: Column: Chiralpak ASH (250×4.6) mm, 5.0 μm; Isocratic Mode, Co-Solvent: 0.2% DEA in Methanol; Co-Solvent percentage: 20%, Column Temperature: 20.2° C.; Back Pressure: 100 bars; Total Flow: 3 g/min; $CO_2$ flow: 2.4 g/min; Co-Solvent flow: 0.6 g/min.

Method W: Column: Chiralpak ASH (250×4.6) mm, 5.0 μm; Isocratic Mode, Co-Solvent: 0.2% DEA in Methanol; Co-Solvent percentage: 30%, Column Temperature: 20.2° C.; Back Pressure: 100 bars; Total Flow: 3 g/min; $CO_2$ flow: 2.1 g/min; Co-Solvent flow: 0.9 g/min.

Method X: Column: Chiralpak ASH (250×4.6) mm, 5.0 μm; Isocratic Mode, Co-Solvent: 0.2% DEA in Methanol; Co-Solvent percentage: 25%, Column Temperature: 24.3° C.; Back Pressure: 100 bars; Total Flow: 3 g/min; $CO_2$ flow: 2.5 g/min; Co-Solvent flow: 0.75 g/min.

Method Y: Column: Chiralpak ASH (250×4.6) mm, 5.0 μm; Isocratic Mode, Co-Solvent: 0.2% DEA in Methanol;

Co-Solvent percentage: 25%, Column Temperature: 27.1° C.; Back Pressure: 100 bars; Total Flow: 3 g/min; $CO_2$ flow: 2.25 g/min; Co-Solvent flow: 0.75 g/min.

Method Z: Column: Chiralcel-OJH (250×4.6) mm, 5.0 μm; Isocratic Mode, Co-Solvent: 0.2% DEA in Methanol; Co-Solvent percentage: 30%, Column Temperature: 26° C.; Back Pressure: 100 bars; Total Flow: 3 g/min; $CO_2$ flow: 2.1 g/min; Co-Solvent flow: 0.9 g/min.

Method AA: Column: Acquity BEH C18 (2.1×50 mm) 1.7 um; Mobile phase A: 0.1% TFA in water; Mobile phase B: Acetonitrile; Gradient: 2-98% B over 1 minutes, then a 0.6 minute hold at 98% B.

Method AB: Column: Lux Cellulose-4 (250×4.6) mm, 5.0 μm; Isocratic Mode, Co-Solvent: 0.2% DEA in Methanol; Co-Solvent percentage: 30%, Column Temperature: 24.2° C.; Back Pressure: 100 bars; Total Flow: 3 g/min; $CO_2$ flow: 2.1 g/min; Co-Solvent flow: 0.9 g/min.

Method AC: Column: Chiralcel-ASH (250×4.6) mm, 5.0 μm; Isocratic Mode, Co-Solvent: 0.2% DEA in Methanol; Co-Solvent percentage: 30%, Column Temperature: 26° C.; Back Pressure: 100 bars; Total Flow: 3 g/min; $CO_2$ flow: 2.1 g/min; Co-Solvent flow: 0.9 g/min.

Method AD: Column: Kinetex XB-C18 (75×3) mm, 2.6 m; Mobile Phase A: 0.1% HCOOH in Water; Mobile Phase B: 100% Acetonitrile Gradient: 20-100% B over 4 minutes, flow rate 1 mL/min, then a 0.6 minute hold at 100% B flow rate 1.5 mL/min; flow rate 1.5 mL/min.

Method AE: Column: HP-5MS (Part Number: Agilent 19091S-433); (250×30) mm; 0.25 μm; Injection volume 3 μl, runtime 17 min (GCMS).

Method AF: Column: Chiralpak AD-H (250×4.6) mm, 5.0 μm; Isocratic Mode, Co-Solvent: 0.25% DEA in Methanol; Co-Solvent percentage: 30%, Column Temperature: 25° C.; Back Pressure: 100 bars; Total Flow: 3 g/min; $CO_2$ flow: 2.1 g/min; Co-Solvent flow: 0.9 g/min.

Method AG: Column: Chiralcel-ASH (250×2.1) mm, 5.0 μm; Isocratic Mode, Co-Solvent: 0.25% DEA in Methanol; Co-Solvent percentage: 45%, Column Temperature: 25° C.; Back Pressure: 100 bars; Total Flow: 75 g/min.

Method AH: Column: Chiralcel-ASH (250×4.6) mm, 5.0 μm; Isocratic Mode, Co-Solvent: 0.2% DEA in Methanol; Co-Solvent percentage: 40%, Column Temperature: 25° C.; Back Pressure: 100 bars; Total Flow: 4 g/min.

Method AI: Column: Chiralcel-ASH (250×4.6) mm, 5.0 μm; Isocratic Mode, Co-Solvent: 0.2% DEA in Methanol; Co-Solvent percentage: 30%, Column Temperature: 24.7° C.; Back Pressure: 95 bars; Total Flow: 4 g/min; $CO_2$ flow: 2.4 g/min; Co-Solvent flow: 1.6 g/min.

Method AJ: Column: Chiralpak AD-H (250×30) mm, 5.0 μm; Isocratic Mode, Co-Solvent: 0.25% DEA in Methanol; Co-Solvent percentage: 30%, Column Temperature: 25° C.; Back Pressure: 100 bars; Total Flow: 120 g/min.

Method AK: Column: Chiralpak AD-H (250×4.6) mm, 5.0 μm; Isocratic Mode, Co-Solvent: 0.25% DEA in Methanol; Co-Solvent percentage: 40%, Column Temperature: 25° C.; Back Pressure: 100 bars; Total Flow: 4 g/min; $CO_2$ flow: 2.4 g/min; Co-Solvent flow: 1.6 g/min.

Method AM: Column: Chiralpak IA (250×4.6) mm, 5.0 μm; Isocratic Mode, Co-Solvent: 0.2% DEA in Methanol; Co-Solvent percentage: 30%, Column Temperature: 21° C.; Back Pressure: 100 bars; Total Flow: 3 g/min; $CO_2$ flow: 2.1 g/min; Co-Solvent flow: 0.9 g/min.

Method AN: Column: Chiralpak IA (250×4.6) mm, 5.0 μm; Isocratic Mode, Co-Solvent: 0.2% DEA in Methanol; Co-Solvent percentage: 20%, Column Temperature: 21° C.; Back Pressure: 100 bars; Total Flow: 3 g/min; $CO_2$ flow: 2.4 g/min; Co-Solvent flow: 0.6 g/min.

Method AU: Column: Xbridge C18 (50×3.0) mm, 1.7 μm; flow rate 1.0 mL/min; gradient time 0 min 0% Solvent B to 2 min 100% Solvent B, then a 1.0 minute hold at 100% B, monitoring at 220 nm (Solvent A: 10 mM 98% Ammonium formate, 2% Acetonitrile; Solvent B: 10 mM 2% Ammonium formate, 98% Acetonitrile).

Method AV: Column: Acquity BEH C8 (2.1×50 mm) 1.7 um; Mobile phase A: Buffer:ACN (95:5); Mobile phase B:Buffer:ACN (5:95), Buffer:5 mM Ammonium Acetate; Gradient: 20-90% B over 1.1 minutes, then a 0.6 minute hold at 90% B, flow rate 0.5 mL/min.

Method AQ: Column: Chiralpak OD-H (250×4.6) mm, 5.0 μm, Co-Solvent: 0.2% DEA in Methanol; Co-Solvent percentage: 40%, Column Temperature: 30° C.; Back Pressure: 100 bars; Total Flow: 3 g/min;

Method AR: Column: Lux Cellulose-2 (250×4.6) mm, 5.0 μm; Isocratic Mode, Co-Solvent: 0.2% DEA in Methanol; Co-Solvent percentage: 10%, Column Temperature: 30° C.; Back Pressure: 100 bars; Total Flow: 3 g/min.

Method AS: Column: Whelk-01(R,R) (4.6×250)mm, 5u; Co-Solvent: 0.2% DEA in IPA; Co-Solvent percentage: 15%, Column Temperature: 20.6° C.; Back Pressure: 100 bars; Total Flow: 3 g/min.

Method AT: Column: Acentis Express C18 (50×2.1) mm, 1.7 μm; flow rate 1.0 mL/min; gradient time 0 min 20% Solvent B to 4 min 100% Solvent B, then a 0.6 minute hold at 100% B, monitoring at 220 nm (Solvent A: 10 mM 98% Ammonium formate, 2% Acetonitrile; Solvent B: 10 mM 2% Ammonium formate, 98% Acetonitrile).

Method AU: Column: Waters XBridge C18, 19×150 mm, 5 μm particles; Mobile Phase A: 10-mM ammonium acetate; Mobile Phase B: acetonitrile; gradient: 5-45% B over 25 minutes, then a 5-minute hold at 100% B; Flow: 15 mL/min.

Method AV: Column: Lux Cellulose-2 (250×4.6) mm, 5.0 μm; Isocratic Mode, Co-Solvent: 25% (0.2% DEA in Methanol; Co-Solvent percentage: 75%, Column Temperature: 30° C.; Back Pressure: 100 bars; Total Flow: 3 g/min; $CO_2$ flow: 2.1 g/min; Co-Solvent flow: 0.9 g/min.

Method AW: Column: YMC Amylose SA (250×4.6) mm, 5.0 μm; Isocratic Mode, Co-Solvent: (0.2% DEA in Ethanol; Co-Solvent percentage: 20%, Column Temperature: 30° C.; Back Pressure: 100 bars; Total Flow: 3 g/min; $CO_2$ flow: 2.1 g/min; Co-Solvent flow: 0.9 g/min.

Method AX: Column: Chiralpak IC (250×4.6) mm, 5.0 μm; Isocratic Mode, Co-Solvent: 0.25% DEA in Ethanol; Co-Solvent percentage: 30%, Column Temperature: 30° C.; Back Pressure: 100 bars; Total Flow: 3 g/min; $CO_2$ flow: 2.1 g/min; Co-Solvent flow: 0.9 g/min.

Method AY: Column: Acquity BEH C18 (3.0×50 mm) 1.7 um; Mobile phase A: Buffer:ACN (95:5); Mobile phase B:Buffer:ACN (5:95), Buffer:5 mM Ammonium Acetate; Gradient: 20-90% B over 1.1 minutes, then 1.7 minute hold at 90% B, flow rate 0.7 mL/min.

Method AZ: Column: Chiralpak AD-H (250×30) mm, 5.0 μm; Isocratic Mode, Co-Solvent: 0.2% DEA in Methanol; Co-Solvent percentage: 30%, Column Temperature: 25° C.; Back Pressure: 100 bars; Total Flow: 120 g/min.

Method BA: Column: Acquity UPLC BEH C18 (3×50 mm) 1.7 um; Mobile phase A: Buffer:ACN (95:5); Mobile phase B:Buffer:ACN (5:95), Buffer:5 mM Ammonium Acetate; Gradient: 20-90% B over 1.1 minutes, then a 0.6 minute hold at 90% B, flow rate 0.7 mL/min.

Method BB: Column: ZORBAX SBC18 (4.6×50) mm, 5 m; Mobile Phase A: 10 mM $NH_4COOH$ in Water: Acetonitrile (98:02; Mobile Phase B: 10 mM $NH_4COOH$ in Water: Acetonitrile (02:98); Gradient: 0-100% B over 4 minutes, flow rate 1.5 mL/min, then a 0.6 minute hold at 100% B flow rate 1.5 mL/min; then Gradient: 100-30% B over 0.1 minutes, flow rate 1.5 mL/min.

Method BC: Column: Acquity BEH C18 (2.1×50 mm) 1.7 um; Mobile phase A: 0.1% TFA in water; Mobile phase B: 0.1% TFA in Acetonitrile; Gradient: 10-90% B over 1.0 minutes, then a 0.6 minute hold at 90% B, flow rate 0.7 mL/min.

Method BD: Column-Kinetex SBC18 (4.6×50 mm-5 µm), M.phase A: 10 mM $NH_4COOH$ IN WATER:ACN(98:02), M.phase B: 10 mM $NH_4COOH$ IN WATER:ACN(02:98), Buffer: 10 mM Ammonium Acetate; Gradient: 30-100% B over 4.0 minutes, then a 0.6 minute hold at 100% B, flow rate 1.5 mL/min.

Method BE: Gemini-Kinetex nx-C18 (4.6×50 mm-5 µm), M.phase A: 10 mM $NH_4COOH$ IN WATER:ACN(98:02), M.phase B: 10 mM $NH_4COOH$ IN WATER:ACN(02:98), Buffer: 10 mM Ammonium Acetate; Gradient: 30-100% B over 4.0 minutes, then a 0.6 minute hold at 100% B, flow rate 1.5 mL/min.

Method BF: Column: Chiralcel-OJH (250×4.6) mm, 5.0 µm; Co-Solvent: 0.2% DEA in Methanol; Co-Solvent percentage: 20%, Column Temperature: 30° C.; Back Pressure: 100 bars; Total Flow: 3 g/min.

Method BG: Column: Whelk-01(R,R) (4.6×250)mm, 5u; Co-Solvent: 0.2% DEA in Ethanol; Co-Solvent percentage: 5%, Column Temperature: 22.2° C.; Back Pressure: 100 bars; Total Flow: 3 g/min Method BH: Column: Chiralpak AD-H (250×4.6) mm, 5.0 µm; Co-Solvent: 0.2% DEA in IPA; Co-Solvent percentage: 15%, Column Temperature: 30° C.; Back Pressure: 100 bars; Total Flow: 3 g/min.

Method BI: Column: Chiralpak AD-H (250×3.0) mm, 5.0 µm; Isocratic Mode, Co-Solvent: 0.2% DEA in Methanol; Co-Solvent percentage: 30%, Column Temperature: 25° C.; Back Pressure: 100 bars.

Method BJ: Column: Chiralpak AD-H (250×4.6) mm, 5.0 µm; Co-Solvent: 0.2% DEA in Methanol+IPA (1:1); Co-Solvent percentage: 10%, Column Temperature: 30° C.; Back Pressure: 100 bars; Total Flow: 3 g/min.

Method BK: Column: Chiralpak AD-H (250×4.6) mm, 5.0 µm; Co-Solvent: 0.2% DEA in Methanol; Co-Solvent percentage: 10%, Column Temperature: 30° C.; Back Pressure: 100 bars; Total Flow: 3 g/min.

Method BL: Column: Chiralpak OD-H (250×2.1) mm, 5.0 µm, Co-Solvent: 0.2% DEA in IPA; Co-Solvent percentage: 15%, Column Temperature: 30° C.

Method BM: Column: Chiralpak AD-H (250×4.6) mm, 5.0 µm; Co-Solvent: 0.2% DEA in Methanol; Co-Solvent percentage: 25%, Column Temperature: 30° C.; Back Pressure: 100 bars; Total Flow: 3 g/min Method BN: Column: Chiralpak AD-H (250×4.6) mm, 5.0 µm; Co-Solvent: 0.1% $NH_4OH$ in IPA; Co-Solvent percentage: 10%, Column Temperature: 30° C.; Back Pressure: 100 bars; Total Flow: 3 g/min.

Method BO: Column-Ascentis Express C18 (50×2.1 mm) 2.7 m, M.phase A: 10 mM $NH_4COOH$ IN WATER:ACN(98:02), M.phase B: 10 mM $NH_4COOH$ IN WATER:ACN(02:98); Gradient: 0-100% B over 1.5 minutes, then a 1.7 minute hold at 100% B, flow rate 1.0 mL/min.

Method BP: Column: Whelk-01(R,R) (4.6×250)mm, 5u; Co-Solvent: 0.2% DEA in IPA; Co-Solvent percentage: 10%, Column Temperature: 30° C.; Back Pressure: 100 bars; Total Flow: 3 g/min.

Method BQ: Column: Chiralpak IC (250×4.6) mm, 5.0 µm; Isocratic Mode, Co-Solvent: 0.2% DEA in Mehanol: IPA (1:1); Co-Solvent percentage: 10%, Column Temperature: 30° C.; Back Pressure: 100 bars; Total Flow: 3 g/min.

Method BR: Column: Chiralpak OJ-H (250×4.6 mm), 5 micron; MOBILE PHASE: 0.2% TEA in n-Hexane:EtOH (70:30), FLOW:1.0 mL\min.

Method BS: Column: Chiralcel-OJH (250×4.6) mm, 5.0 µm; Co-Solvent: 0.2% DEA in Methanol; Co-Solvent percentage: 25%, Column Temperature: 28° C.; Back Pressure: 100 bars; Total Flow: 3 g/min.

Method BT: Column: Chiralcel-OJH (250×4.6) mm, 5.0 µm; Co-Solvent: 0.2% DEA in Methanol; Co-Solvent percentage: 15%, Column Temperature: 30° C.; Back Pressure: 100 bars; Total Flow: 60 g/min.

Method BU: Column: Chiralpak AD-H (250×4.6) mm, 5.0 µm; Isocratic Mode, Co-Solvent: 0.2% DEA in IPA+ACN; Co-Solvent percentage: 10%, Column Temperature: 25° C.; Back Pressure: 100 bars; Total Flow: 3 g/min.

Method BV: Column: lux amylose 2 (250×21.2) mm, Mobile Phase A: 0.2% DEA in Hexane; Mobile Phase B: EtOH; Flow: 25 mL/min.

Method BW: Column: Lux Cellulose-2 (250×4.6) mm, 5.0 µm; Isocratic Mode, Co-Solvent: 25% (0.1% $NH_4OH$ in Methanol); Co-Solvent percentage: 75%, Column Temperature: 30° C.; Back Pressure: 100 bars; Total Flow: 3 g/min;

Method BX: Column: Lux Cellulose-2 (250×4.6) mm, 5.0 µm; Isocratic Mode, Co-Solvent: 0.2% DEA in Ethanol; Co-Solvent percentage: 20%, Column Temperature: 30° C.; Back Pressure: 100 bars; Total Flow: 3 g/min.

Method BY: Column: Chiralpak AD-H (250×4.6) mm, 5.0 µm; Isocratic Mode, Co-Solvent: 0.2% DEA in Ethanol; Co-Solvent percentage: 25%, Column Temperature: 25.7° C.; Back Pressure: 100 bars; $CO_2$ flow rate: 2.25 g/min; Co solvent flow rate: 0.75 g/min; Total Flow: 3 g/min.

Method BZ: Column: Chiralcel-OJH (250×4.6) mm, 5.0 µm; Co-Solvent: 0.2% DEA in Methanol; Co-Solvent percentage: 10%, Column Temperature: 30° C.; Back Pressure: 100 bars; Total Flow: 3 mL/min.

Method CA: Column: YMC Amylose SA (250×4.6) mm, 5.0 µm; Isocratic Mode, Co-Solvent: 0.2% DEA in IPA; Co-Solvent percentage: 15%, Column Temperature: 35° C.; Back Pressure: 100 bars; Total Flow: 60.0 g/min Method CB: Column: Chiralpak ASH (250×4.6) mm, 5.0 µm; Isocratic Mode, Co-Solvent: 0.2% DEA in Hexane: IPA (98:02); Total Flow: 1.0 mL/min.

Method CC: Column: Lux Cellulose-4 (250×4.6) mm, 5.0 µm; Isocratic Mode, Co-Solvent: 30% (0.1% $NH_4OH$ in Methanol); Co-Solvent percentage: 30%, Column Temperature: 30° C.; Back Pressure: 100 bars; Total Flow: 60 g/min.

Method CD: Column: Chiralcel-OJH (250×4.6) mm, 5.0 µm; Co-Solvent: 0.2% DEA in Methanol; Co-Solvent percentage: 30%, Column Temperature: 30° C.; Back Pressure: 100 bars; Total Flow: 3 mL/min.

Method CE: Column: Chiralcel-OJH (250×2.1) mm, 5.0 µm; Co-Solvent: 0.2% DEA in Methanol; Co-Solvent percentage: 20%, Column Temperature: 30° C.; Back Pressure: 100 bars; Total Flow: 60 mL/min.

Method CF: Column: Chiralcel-OJH (250×4.6) mm, 5.0 µm; Co-Solvent: 0.2% DEA in IPA:ACN (1:1); Co-Solvent percentage: 20%, Column Temperature: 30° C.; Back Pressure: 100 bars; Total Flow: 3 mL/min.

Method CG: Column: Chiralpak IC (250×3.0) mm, 5.0 µm; Co-Solvent: 0.2% DEA in Methanol: IPA (1:1); Co-Solvent percentage: 10%, Column Temperature: 30° C.; Back Pressure: 100 bars; Total Flow: 110 g/min.

Method CH: Column: lux amylose 2 (250×4.6) mm, 5.0 µm; Mobile Phase A: 0.2% DEA in Hexane; Mobile Phase B: EtOH; Flow: 1 mL/min.

Method CI: Column-KINETICSX 2.6 u EVO c18 100 Au. M.phase A; 5 mM NH$_4$C0AC IN WATER:ACN (95:05), M.phase B: 5 mM NH$_4$C0AC IN WATER:ACN(05:95), Buffer:5 mM Ammonium Acetate; flow rate 0.7 mL/min Method CJ: Column: Chiralcel-OJH (250×4.6) mm, 5.0 µm; Co-Solvent: 0.2% DEA in n-Hexane:EtOH(98:2Total Flow: 1 mL/min.

Method CK: Column: Lux Cellulose-4 (250×4.6) mm, 5.0 µm; Isocratic Mode, Co-Solvent: 0.2% DEA in IPA; Co-Solvent percentage: 15%, Column Temperature: 30° C.; Back Pressure: 100 bars; Total Flow: 3 g/min.

Method CL: Column: Chiralpak AD-H (250×4.6) mm, 5.0 µm; Isocratic Mode, Co-Solvent: 0.2% DEA in Methanol; Co-Solvent percentage: 30%, Column Temperature: 30° C.; Back Pressure: 100 bars; Total Flow: 4 g/min.

Method CM: Column: Chiralpak AD-H (250×4.6) mm, 5.0 µm; Co-Solvent: 0.2% DEA in IPA; Co-Solvent percentage: 30%, Column Temperature: 30° C.; Back Pressure: 100 bars; Total Flow: 4 g/min.

Method CN: Column: Chiralpak IC (250×4.6) mm, 5.0 µm; Isocratic Mode, Co-Solvent: 0.2% DEA in Mehanol:ACN (1:1); Co-Solvent percentage: 25%, Column Temperature: 30° C.; Back Pressure: 100 bars; Total Flow: 3 g/min.

Method CO: Column: Lux Cellulose-4 (250×4.6) mm, 5.0 µm; Co-Solvent: 0.2% DEA in Methanol; Co-Solvent percentage: 10%, Column Temperature: 30° C.; Back Pressure: 100 bars; Total Flow: 3 g/min.

Method CP: Column: ZORBAX AQ (4.6×50) mm, 5 m; Mobile Phase A: 10 mM NH$_4$COOH in Water: Acetonitrile (98:02; Mobile Phase B: 10 mM NH$_4$COOH in Water: Acetonitrile (02:98); Gradient: 30-100% B over 4 minutes, flow rate 1.5 mL/min, then a 0.6 minute hold at 100% B flow rate 1.5 mL/min; then Gradient: 100-30% B over 0.1 minutes, flow rate 1.5 mL/min.

Method CQ: Column: Gemini nx-C18 (50×4.6) mm, 5 µm; Mobile Phase A: 10 mM NH$_4$COOH in Water: Acetonitrile (98:02; Mobile Phase B: 10 mM NH$_4$COOH in Water: Acetonitrile (02:98); Gradient: 30-100% B over 4 minutes, flow rate 1.5 mL/min, then a 0.6 minute hold at 100% B flow rate 1.5 mL/min; then Gradient: 100-30% B over 0.1 minutes, flow rate 1.5 mL/min.

Method CR: Column: Chiralpak AD-H (250×4.6) mm, 5.0 µm; Co-Solvent: 0.2% DEA in Methanol; Co-Solvent percentage: 20%, Column Temperature: 30° C.; Back Pressure: 100 bars; Total Flow: 3 g/min.

Method CS: Column: Xbridge C18 (50×4.6) mm, 5 µm, flow rate 4.0 mL/min; gradient: 0 to 100% solvent B over 3 min; Temperature: 35° C.; monitoring at 220 nm (Solvent A: 95:05 water: CH$_3$CN with 0.1% TFA and Solvent B: 05:95 water: CH$_3$CN with 0.1% TFA)

Method CT: Column: Chiralpak IA (250×4.6) mm, 5.0 µm; Co-Solvent: 0.2% DEA in Methanol; Co-Solvent percentage: 15%, Column Temperature: 21.7° C.; Back Pressure: 96 bars; Total Flow: 3 g/min; CO$_2$ flow: 2.55 g/min; Co-Solvent flow: 0.45 g/min.

Method CU: Column: Chiralpak ASH (250×4.6) mm, 5.0 µm; Co-Solvent: 0.2% DEA in IPA; Co-Solvent percentage: 20%, Column Temperature: 30° C.; Back Pressure: 100 bars; Total Flow: 3 mL/min.

Method CV: Column: Lux Cellulose-4 (250×4.6) mm, 5.0 µm; Co-Solvent: 0.2% DEA in IPA: Methanol, (1:1); Co-Solvent percentage: 10%, Column Temperature: 30° C.; Back Pressure: 100 bars; Total Flow: 3 g/min.

Method CW: Column: Chiralpak AD-H (250×30) mm, 5.0 µm; Isocratic Mode, Co-Solvent: 0.2% DEA in Methanol; Co-Solvent percentage: 30%, Column Temperature: 21.6° C.; Back Pressure: 104 bars; Total Flow: 3 g/min. CO$_2$ flow rate: 2.1; Co solvent flow rate: 0.9

Method CX: Column: Lux Amylose-2 (250×4.6) mm, 5.0 µm; Isocratic Mode, Co-Solvent: 15% (0.2% DEA in IPA; Column Temperature: 30° C.; Back Pressure: 101 bars; Total Flow: 3 g/min; CO$_2$ flow: 2.55 g/min; Co-Solvent flow: 0.45 g/min.

Method CY: Column: Lux Cellulose-4 (250×4.6) mm, 5.0 µm; Mobile Phase: 0.2% TFA in n-Hexane:Methanol:Ethanol (97:03), flow rate 1.0 mL/min.

Method CZ: Column: Xbridge C18 (50×4.6) mm, 5.0 µm; Mobile Phase A: 0.1% TFA in Water; Mobile Phase B: Acetonitrile; Gradient: 5-95% B over 4 minutes, Temp: 35° C.; Flow Rate: 4.0 mL/min.

Method DA: Column: R,R-WHELK (250×4.6) mm, 5 µm, MOBILE PHASE: 0.2% EA in n-Hexane:IPA (99:01), FLOW: 1.0 mL/min Method DB: Column Lux Cellulose-4 (4.6×250) mm, 5 um, Co-Solvent 0.2% DEA in Methanol, Column Temperature 19.4° C., CO2 Flow Rate 1.8 g/min, Co-Solvent Flow Rate 1.2 g/min, Co-Solvent 40%, Total Flow 3 g/min, Back Pressure 104 bars.

Method DC: Column: Xbridge C18 (50×4.6)mm, 5 m, Solvent A: 10 mM NH4OAC, Solvent B: Acetonitrile, Temp: 35° C., Gradient: 5-95% B over 4 minutes, Flow Rate: 4.0 ml/min.

Method DD: Column CHIRALPAK ADH (250×4.6) mm, 5 um, Co-Solvent 0.2% DEA in Methanol, Column Temperature 19.5° C., CO$_2$ Flow Rate 2.25 g/min, Co-Solvent Flow Rate 0.75 g/min, Co-Solvent 25%; Total Flow 3 g/min; Back Pressure 100 bars.

Method DE: Column Chiralpak AD-H (250×4.6)mm, 5 um, Column Temperature 27° C., Co-Solvent 0.2% DEA in Methanol, CO$_2$ Flow Rate 2.25 g/min, Co-Solvent Flow Rate 0.75 g/min, Co-Solvent 25%, Total Flow 3 g/min, Back Pressure 98 bars.

Method DF: Column Chiralpak IA (250×4.6) mm, 5u, Co-Solvent 0.1% NH$_4$OH IN IPA, Column Temperature 19.3° C., CO$_2$ Flow Rate 1.8 g/min, Co-Solvent Flow Rate 1.2 g/min, Co-Solvent 40%, Total Flow 3 g/min, Back Pressure 100 bars.

Method DG: Column: Chiralpak AD-H (250×4.6) mm, 5 um, Co-Solvent; 0.2% DEA in IPA, Column Temperature: 15.3° C., CO2 Flow Rate: 2.4 g/min, Co-Solvent Flow Rate: 3 g/min, Co-Solvent: 99%, Back Pressure 100 bars.

Method DH: Column: Chiralpak AD-H (250×4.6) mm, 5 um, Co-Solvent: 0.2% DEA in IPA, Column Temperature: 27.7° C., CO2 Flow Rate: 2.4 g/min, Co-Solvent Flow Rate: 0.6 g/min, Co-Solvent: 20%, Total Flow; 3 g/min, Back Pressure; 100 bars.

Method DI: Column: Chiralpak AD-H (250×4.6) mm, 5 um, Co-Solvent: 0.10% NH$_4$OH IN IPA, Column Temperature: 21.4° C., CO2 Flow Rate: 2.25 g/min, Co-Solvent Flow Rate: 0.75 g/min, Co-Solvent: 25%, Total Flow: 3 g/min, Back Pressure: 102 bars.

Method DJ: Column: Chiralpak AD-H (250×4.6) mm, 5 um, Co-Solvent: IPA, Column Temperature: 20.6° C., CO2 Flow Rate: 2.7 g/min, Co-Solvent Flow Rate: 0.3 g/min, Co-Solvent: 10%, Total Flow: 3, Back Pressure: 100

Method DK: Column: CHIRALPAK-IA (250×4.6), 5 um, MOBILE PHASE: 0.2% DEA in n-Hexane:EtOH (60:40), FLOW: 1.0 mL/min.

Method DL: Column: Chiralpak AD-H (250×4.6) mm, 5.0 µm; Isocratic Mode, Co-Solvent: 0.2% DEA in IPA+ACN; Co-Solvent percentage: 10%, Column Temperature: 30° C.; Back Pressure: 100 bars; Total Flow: 3 g/min.

Method DM: Column: Xbridge BEH C8 (2.1×50 mm) 2.5 um; Mobile phase A: Buffer:ACN (95:5); Mobile phase B:Buffer:ACN (5:95), Buffer:5 mM Ammonium Acetate; Gradient: 20-90% B over 1.1 minutes, then a 1.7 minute hold at 90% B, flow rate 0.5 mL/min.

Method DN: Column: Chiralcel-OJH (250×4.6) mm, 5.0 μm; Isocratic Mode, Co-Solvent: 0.2% DEA in Ethanol; Co-Solvent percentage: 10%, Column Temperature: 25.8° C.; Back Pressure: 100 bars; Total Flow: 3 g/min; $CO_2$ flow: 2.7 g/min; Co-Solvent flow: 0.3 g/min.

Method DO: Column: Acquity BEH C18 (2.1×50 mm) 1.7 um; Mobile phase A: Buffer:ACN (95:5); Mobile phase B:Buffer:ACN (5:95), Buffer:5 mM Ammonium Acetate; Gradient: 20-90% B over 1.1 minutes, then a 0.6 minute hold at 90% B, flow rate 0.7 mL/min.

Method DP: Column:Chiralcel OD-H (250×4.6)mm, 5 μm; Co-Solvent: 0.2% DEA in MeOH; $CO_2$ Flow Rate: 2.4 g/min; Co-Solvent Flow Rate: 0.6; Co-Solvent 20%; Total Flow: 3; Back Pressure: 100

Method DQ: Column:Chiralcel IE (250×4.6)mm, 5 μm; Mobile Phase: 0.2% DEA in Hexane:Ethanol:Methanol (1:1) (95:05) Flow: 1.0 ml/min Method DR: Kinetex C18 (75×3) mm, 2.6 μm; Mobile Phase A: 10 mM $NH_4OAc$ in Water: Acetonitrile (98:02); Mobile Phase B: 10 mM $NH_4OAc$ in Water: Acetonitrile (02:98); Gradient: 80-98% B over 2.5 minutes, flow rate 1 mL/min, then a 1.0 minute hold at 98% B flow rate 1.0 mL/min; then Gradient: 100-20% B over 0.1 minutes, flow rate 1.0 mL/min.

Method DS: Column: Chiralpak AD-H (250×4.6) mm, 5.0 μm; Co-Solvent: 0.2% DEA in Methanol; Co-Solvent percentage: 15%, Column Temperature: 30° C.; Back Pressure: 100 bars; Total Flow: 3 g/min.

Method DT: Column: Chiralcel-OJ-H (250×30) mm, 5.0 μm; Mobile Phase-A: 0.2% TEA in n-HEPTANE; Mobile Phase-B: ETHANOL; Flow: 25 ml/min; Mode: Isocratic:A:B=90:10, Run time: 15 min.

Method DU: Column: Chiralpak AD-H (250×30) mm, 5 μm; Co-Solvent: 15% (0.2% DEA in Methanol); Co-Solvent percentage: 15%, Column Temperature: 30° C.; Back Pressure: 100 bars; Total Flow: 80 g/min.

Method DV: Column: Chiralcel OJ-H (250×30) mm, 5 μm; Mobile Phase-A: 0.2% DEA in n-Hexane; Mobile Phase-B: EtOH; Flow: 27 ml/min; Mode: Isocratic:A:B=95:05, Run time 40.0 min.

Method DW: Column: Chiralcel AS-H (250×30 mm) mm, 5.0 μm; Mobile Phase-A: 0.2% DEA in n-Hexane; Mobile Phase-B: EtOH; Flow: 27 ml/min; Mode:Isocratic:A:B=95:05.

Method DX: Column: Chiralcel OJ-H (250×30) mm, 5 μm; Mobile Phase-A: 0.2% DEA in n-Hexane; Mobile Phase-B: EtOH; Flow: 25 ml/min; Mode:Isocratic:A:B=95:05.

Method DY: Column: Chiralcel-OJH (250×4.6) mm, 5.0 μm; Co-Solvent: 0.2% DEA in n-Hexane:EtOH(90:10)Total Flow: 1 mL/min.

Method DZ: Column: Chiralpak-OJH (250×4.6) mm, 5.0 μm; Co-Solvent: 0.2% DEA in n-Hexane:EtOH(70:30)Total Flow: 1 mL/min Method EA: Column: Chiralpak AD-H (250×4.6) mm, 5.0 μm; Isocratic Mode, Co-Solvent: 0.2% DEA in Methanol; Co-Solvent percentage: 25%, Column Temperature: 25° C.; Back Pressure: 100 bars; Total Flow: 3 g/min; $CO_2$ flow: 2.25 g/min; Co-Solvent flow: 0.75 g/min.

Method EB: Column: Chiralpak AD-H (250×4.6) mm, 5.0 μm; Isocratic Mode, Co-Solvent: 0.2% DEA in IPA; Co-Solvent percentage: 10%, Column Temperature: 24.9° C.; Back Pressure: 100 bars; Total Flow: 3 g/min; $CO_2$ flow: 2.7 g/min; Co-Solvent flow: 0.3 g/min.

Method EC: Column: Chiralpak IC (250×4.6) mm, 5.0 μm; Isocratic Mode, Co-Solvent: 0.2% DEA in Methanol; Co-Solvent percentage: 30%, Column Temperature: 30° C.; Back Pressure: 100 bars; Total Flow: 3 g/min; $CO_2$ flow: 2.1 g/min.

Method ED: Column: Lux Cellulose-4 (250×4.6) mm, 5.0 μm; Co-Solvent: 0.2% DEA in Methanol:Methanol, (1:1); Co-Solvent percentage: 20%, Column Temperature: 25° C.; Back Pressure: 101 bars; Total Flow: 3 g/min.

Method EE: Column: Chiralcel OD-H (250×30) mm, 5.0 μm; Co-Solvent: 0.2% DEA in Methanol; Co-Solvent: 20%; Total Flow: 120.0 g/min; Back Pressure: 100 bars.

Method EF: Column: Chiralpak AS-H (250×21) mm, 5 μm; Mobile Phase A: 0.2% DEA in n-Hexane; Mobile Phase B: IPA; Flow: 20 ml/min; Mode:Isocratic:A:B=90:10.

Method EG: Column ChiralCel ODH (250×4.6) mm, 5 μm; Co-Solvent IPA:ACN(1+1); Column Temperature 24.7; Total Flow 3 g/min; $CO_2$ Flow Rate 2.7 g/min; Co-Solvent Flow Rate 0.3 g/min; Co-Solvent percentage 10%; Back Pressure: 100 bars.

Method EH: Waters Acquity SDS using the following method: Linear Gradient of 2% to 98% solvent B over 1.00 min; UV visualization at 220 or 254 nm; Column: BEH C18 2.1 mm×50 mm; 1.7 um particle (Heated to Temp. 50° C.); Flow rate: 0.8 ml/min; Mobile phase A: 100% Water, 0.05% TFA; Mobile phase B: 100% Acetonitrile, 0.05% TFA.

Method EI: Column: Waters Acquity UPLC BEH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: UV at 220 nm.

Example 1, Example 2

(Enantiomer 1, Enantiomer 2) (R)-3-(4-(2-ethoxypropan-2-yl)-3-(3-(p-tolyl)ureido)phenyl)pentanoic Acid (S)-3-(4-(2-ethoxypropan-2-yl)-3-(3-(p-tolyl)ureido)phenyl)pentanoic Acid (Absolute Stereochemistry not Determined)

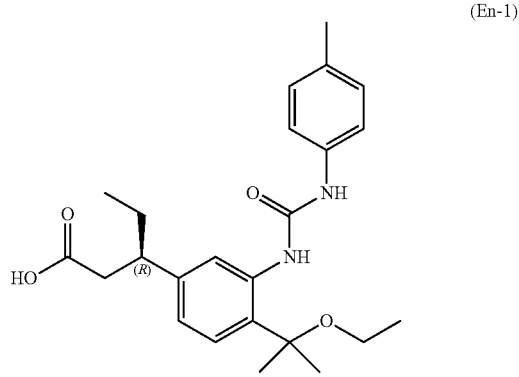

(En-1)

47

-continued

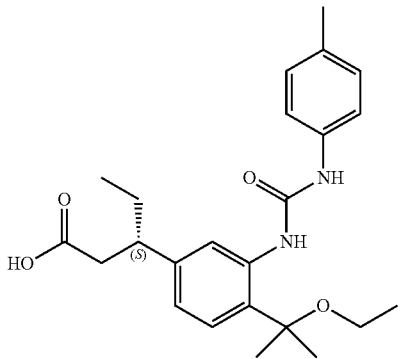

(En-2)

The synthesis of these enantiomers is described below:

1A. Methyl 4-bromo-2-nitrobenzoate

To a solution of 4-bromo-2-nitrobenzoic acid (10 g, 40.6 mmol) in DMF (100 mL) was added potassium carbonate (11.24 g, 81 mmol) followed by methyl iodide (3.30 mL, 52.8 mmol) dropwise. The mixture was stirred at 80° C. for 3 h. After cooling to room temperature, the mixture was filtered and residue was dissolved in ethyl acetate (2×200 mL). The organic layer was washed with water (200 mL) followed by brine (100 mL), dried over anhydrous sodium sulfate and concentrated under reduced pressure. The crude sample was purified by flash chromatography (5% Ethyl acetate: Pet ether; 80 g silica gel column) to afford 1A (off white solid, 8.2 g, 31.5 mmol, 78% yield). $^1$H NMR (400 MHz, DMSO-$d_6$) δ 8.35 (d, J=2.0 Hz, 1H), 8.07 (dd, J=8.0, 1.6 Hz, 1H), 7.84 (d, J=8.0 Hz, 1H), 3.85 (s, 3H).

1B. Methyl 2-amino-4-bromobenzoate

To a solution of 1A (1.0 g, 3.85 mmol) in Acetic Acid (5 mL) was added iron powder (0.430 g, 7.69 mmol) and allowed to stir for 2 h at room temperature. Then reaction mixture was basified using 10% sodium carbonate (30 mL) and extracted with ethyl acetate (2×200 mL). The combined organic layer was dried over sodium sulfate and concentrated under reduced pressure. The crude sample was purified by flash chromatography (5% Ethyl acetate: Pet ether; 12 g silica gel column) to afford 1B (off white solid 0.75 g, 3.26 mmol, 85% yield). LC-MS Anal. Calc'd for $C_8H_8BrNO_2$ 228.9, found [M+H] 230.3, Tr=0.98 min (Method DM)

1C. 2-(2-amino-4-bromophenyl) propan-2-ol

A solution of 1B (0.2 g, 0.869 mmol) in Tetrahydrofuran (4 mL) was cooled to −78° C. Then 3 M methylmagnesium bromide (1.188 mL, 3.56 mmol) was added drop wise over 15 min and stirred at 0° C. for 3 h. Reaction mixture was carefully quenched with aqueous saturated ammonium chloride solution (20 mL) and extracted with ethyl acetate (2×20 mL). The separated organic layer was washed with brine (20 mL), dried over sodium sulfate, filtered and concentrated under reduced pressure. The crude sample was purified by flash chromatography (20% Ethyl acetate: Pet ether; 12 g silica gel column) to afford 1C (Gummy brown oil, 0.12 g, 0.522 mmol, 60.0%). $^1$H NMR (400 MHz, DMSO-$d_6$) δ 6.91 (d, J=8.8 Hz, 1H), 6.78 (d, J=2.0 Hz, 1H), 6.61-6.55 (m, 1H), 5.66 (s, 2H), 5.26 (s, 1H), 1.46 (s, 6H).

1D. 5-bromo-2-(2-ethoxypropan-2-yl)aniline

To a solution of 1C (0.08 g, 0.348 mmol) in Ethanol (2 mL) was added p-toluenesulfonic acid (0.012 g, 0.070 mmol) and stirred for 12 h at 40° C. Then reaction mixture was quenched with 10% sodium bicarbonate solution, extracted with ethyl acetate (2×50 mL). The separated organic layer was washed with brine (20 mL), dried over sodium sulfate, filtered and concentrated under reduced pressure. The crude sample was purified by flash chromatography (10% Ethyl acetate: Pet ether; 4 g silica gel column) to afford 1D (colorless oil, 0.070 g, 0.271 mmol, 78% yield). $^1$H NMR (400 MHz, Chloroform-d) δ 6.90 (d, J=8.0 Hz, 1H), 6.79-6.73 (m, 2H), 4.77 (br. s., 2H), 3.24 (q, J=7.2 Hz, 2H), 1.56 (s, 6H), 1.17 (t, J=7.2 Hz, 3H).

1E. 5-(5,5-dimethyl-1,3,2-dioxaborinan-2-yl)-2-(2-ethoxypropan-2-yl)aniline

The compound 1D (0.5 g, 1.937 mmol) was dissolved in DMSO (5 mL). Then bis(neopentyl glycolato)diboron (0.569 g, 2.52 mmol) and potassium acetate (0.570 g, 5.81 mmol) were added and allowed to stir for 15 min under argon purging. Then the 1,1'-bis(diphenylphosphino)ferrocene-palladium(ii)dichloride dichloromethane complex (0.047 g, 0.058 mmol) was added and the reaction mixture was stirred overnight at 80° C. Then reaction mixture quenched with water (50 mL), extracted with ethyl acetate (2×100 mL). The organic layer was isolated, washed with brine (50 mL) and dried over sodium sulfate. The crude sample was purified by flash chromatography (10% Ethyl acetate: Pet ether; 12 g silica gel column) to afford 1E (pale yellow oil, 0.48 g, 1.648 mmol, 85% yield). $^1$H NMR (400 MHz, DMSO-$d_6$) δ 7.01 (d, J=1.2 Hz, 1H), 6.95 (d, J=7.6 Hz, 1H), 6.89-6.82 (m, 1H), 5.22 (s, 2H), 3.71 (s, 4H), 3.11 (q, J=7.2 Hz, 2H), 1.50 (s, 6H), 1.08 (t, J=7.2 Hz, 3H), 0.94 (s, 6H).

1F. methyl 3-(3-amino-4-(2-ethoxypropan-2-yl)phenyl)pentanoate (Absolute Stereochemistry not Determined)

To nitrogen flushed seal tube was added Dioxane (5 mL) which was purged with nitrogen for 15 mins. To this was added (R)-(+)-2,2'-bis(diphenylphosphino)-1,1'-binaphthyl (0.020 g, 0.032 mmol) and chlorobis(ethylene)rhodium(i) dimer (8.41 mg, 0.022 mmol). After stirring for 30 mins at room temperature, 1E (0.420 g, 1.442 mmol), methyl 2-pentenoate (0.494 g, 4.33 mmol) and sodium hydroxide (1.298 mL, 1.298 mmol) was added. Then the mixture was purged for another 10 mins and heated to 50° C. for 1 h. The reaction mixture was quenched with acetic acid (0.074 mL, 1.298 mmol), diluted with water 50 mL and extracted using ethyl acetate (2×100 mL). The separated organic layer was washed with 50 mL brine solution and dried over sodium sulfate, filtered and concentrated under reduced pressure. The crude sample was purified by flash chromatography (10% Ethyl acetate: Pet ether; 12 g silica gel column) to afford 1F (Enantiomeric mixture). $^1$H NMR (400 MHz, DMSO-d$_6$) δ 6.88 (d, J=8.0 Hz, 1H), 6.44 (d, J=2.0 Hz, 1H), 6.35 (dd, J=7.6, 1.2 Hz, 1H), 5.20 (s, 2H), 3.52 (s, 3H), 3.11 (q, J=7.2 Hz, 2H), 2.77-2.68 (m, 1H), 2.61-2.53 (m, 1H), 1.62-1.53 (m, 1H), 1.51-1.42 (m, 7H), 1.08 (t, J=7.6 Hz, 3H), 0.71 (t, J=7.2 Hz, 3H), (Note: One proton is buried under the solvent peak).

Chiral separation of Enantiomeric mixture 1F yielded 1F Enantiomer 1, Tr=8.05 min, and 1F Enantiomer 2, Tr=10.14 min (Method DT)

1F Enantiomer 1 (Colorless oil, 0.22 g, 0.750 mmol, 52.0% yield): $^1$H NMR (400 MHz, DMSO-d$_6$) δ=6.88 (d, J=8.0 Hz, 1H), 6.44 (d, J=2.0 Hz, 1H), 6.35 (d, J=7.2 Hz, 1H), 5.20 (m, 2H), 3.52 (s, 3H), 3.11 (q, J=6.8 Hz, 2H), 2.77-2.69 (m, 1H), 2.62-2.54 (m, 1H), 1.62-1.53 (m, 1H), 1.52-1.43 (m, 7H), 1.08 (t, J=7.2 Hz, 3H), 0.71 (t, J=7.3 Hz, 3H), (Note: One proton is buried under the solvent peak).

1F Enantiomer 2 (Colorless oil, 0.120 g, 0.409 mmol, 28.4% yield): $^1$H NMR (400 MHz, DMSO-d$_6$) δ 6.88 (d, J=7.2 Hz, 1H), 6.44 (d, J=2.0 Hz, 1H), 6.35 (dd, J=8.0, 2.0 Hz, 1H), 5.20 (s, 2H), 3.52 (s, 3H), 3.11 (q, J=7.2 Hz, 2H), 2.78-2.68 (m, 1H), 2.61-2.53 (m, 1H), 1.62-1.44 (m, 8H), 1.08 (t, J=6.8 Hz, 3H), 0.71 (t, J=7.2 Hz, 3H), (Note: One proton is buried under the solvent peak).

1G. methyl 3-(4-(2-ethoxypropan-2-yl)-3-(3-(p-tolyl)ureido)phenyl)pentanoate (Absolute Stereochemistry not Determined)

The compound 1F Enantiomer 1 was dissolved in tetrahydrofuran (3 mL). To this solution was added TEA (0.171 mL, 1.227 mmol), followed by 1-isocyanato-4-methylbenzene (0.155 mL, 1.227 mmol) and stirred at RT for 2 h. The reaction mixture was diluted with water (20 mL), extracted with ethyl acetate (2×30 mL). Separated organic layer were washed with 10% Sodium bicarbonate (20 mL), dried over sodium sulfate, and concentrated under reduced pressure to afford 1G (Gummy yellow solid, 0.33 g, 0.774 mmol, 76% yield). LC-MS Anal. Calc'd for C$_{25}$H$_{34}$N$_2$O$_4$ 426.2, found [M+H] 427.2, Tr=3.64 min (Method U)

Example 1. (R)-3-(4-(2-ethoxypropan-2-yl)-3-(3-(p-tolyl)ureido)phenyl)pentanoic Acid (Absolute Stereochemistry not Determined)

To the solution of 1G (0.025 g, 0.059 mmol) in tetrahydrofuran (1 mL), MeOH (0.5 mL), H$_2$O (0.5 mL) was added lithium hydroxide (4.21 mg, 0.176 mmol) and allowed to stir for 2 h at room temperature. Then the reaction mixture was concentrated under reduced pressure, diluted with 5 mL of water and acidified with saturated solution of citric acid till pH ~4. Then the reaction mixture was extracted with ethyl acetate (25 mL), washed with brine (10 mL), dried over sodium sulfate and concentrated under reduced pressure. The crude material was purified using preparative HPLC to afford Example 1 (off white solid, 0.0067 g, 0.016 mmol, 27% yield). LC-MS Anal. Calc'd for C$_{24}$H$_{32}$N$_2$O$_4$ 412.23, found [M+H] 413.4, Tr=2.02 min (Method U). $^1$H NMR (400 MHz, methanol-d$_4$) δ 7.89 (d, J=1.5 Hz, 1H), 7.36-7.30 (m, 2H), 7.19 (d, J=8.0 Hz, 1H), 7.14 (d, J=8.0 Hz, 2H), 6.90 (dd, J=8.0, 2.0 Hz, 1H), 3.23 (q, J=7.2 Hz, 2H), 3.03-2.94 (m, 1H), 2.66-2.51 (m, 2H), 2.32 (s, 3H), 1.82-1.72 (m, 1H), 1.59 (m, 7H), 1.12 (t, J=7.2 Hz, 3H), 0.84 (t, J=7.2 Hz, 3H).

Example 2

(S)-3-(4-(2-ethoxypropan-2-yl)-3-(3-(p-tolyl)ureido)phenyl)pentanoic Acid (Absolute Stereochemistry not Determined)

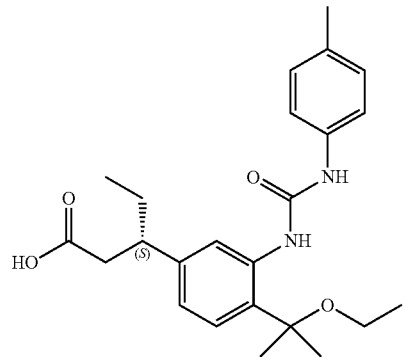

2A. methyl 3-(3-amino-4-(2-ethoxypropan-2-yl)phenyl)pentanoate (Absolute Stereochemistry not Determined)

2A (Enantiomeric mixture) was prepared from 1E and (S)-(-)-2,2'-bis(diphenylphosphino)-1,1'-binaphthyl following the procedure described for the synthesis of 1F. LC-MS Anal. Calc'd for C$_{17}$H$_{27}$NO$_3$ 293.19. $^1$H NMR (400 MHz, DMSO-d$_6$) δ 6.88 (d, J=8.0 Hz, 1H), 6.44 (d, J=2.0 Hz, 1H), 6.35 (d, J=7.6 Hz, 1H), 5.20 (m, 2H), 3.52 (s, 3H), 3.11 (q, J=7.2 Hz, 2H), 2.72 (s, 1H), 2.58 (m, 1H), 2.47 (m, 1H), 1.56 (d, J=6.0 Hz, 1H), 1.48 (s, 7H), 1.08 (t, J=7.2 Hz, 3H), 0.71 (t, J=7.2 Hz, 3H).

Chiral purification of 2A (Enantiomeric mixture) was yielded 2A Enantiomer 1, Tr=7.94 min and 2A Enantiomer 2, Tr=10.30 min (Method DT).

2A Enantiomer 1 (Colorless oil, 0.030 g, 0.102 mmol, 7.09% yield): $^1$H NMR (400 MHz, DMSO-d$_6$) δ 6.88 (d, J=8.0 Hz, 1H), 6.44 (d, J=2.0 Hz, 1H), 6.35 (d, J=7.5 Hz, 1H), 5.20 (s, 2H), 3.52 (s, 3H), 3.11 (q, J=7.2 Hz, 2H), 2.72 (d, J=7.6 Hz, 1H), 2.61-2.53 (m, 1H), 1.61-1.52 (m, 1H), 1.48 (s, 7H), 1.08 (t, J=7.2 Hz, 3H), 0.71 (t, J=7.2 Hz, 3H), (Note: One proton is buried under the solvent peak).

2A Enantiomer 2 (Colorless oil, 0.070 g, 0.239 mmol, 16.54% yield): $^1$H NMR (400 MHz, DMSO-d$_6$) δ 6.88 (d, J=8.0 Hz, 1H), 6.44 (d, J=1.6 Hz, 1H), 6.35 (dd, J=7.6, 1.6 Hz, 1H), 5.20 (s, 2H), 3.52 (s, 3H), 3.11 (q, J=6.8 Hz, 2H), 2.79-2.68 (m, 1H), 2.62-2.53 (m, 1H), 1.51 (m, 8H), 1.08 (t, J=7.2 Hz, 3H), 0.71 (t, J=7.6 Hz, 3H), (Note: One proton is buried under the solvent peak).

2B. methyl 3-(4-(2-ethoxypropan-2-yl)-3-(3-(p-tolyl)ureido)phenyl)pentanoate (Absolute Stereochemistry not Determined)

2B was prepared from 2A Enantiomer 2 and 1-isocyanato-4-methylbenzene following the procedure described for the synthesis of 1G. LC-MS Anal. Calc'd for $C_{25}H_{34}N_2O_4$ 426.25, found [M+H] 427.2, Tr=3.62 min (Method U).

Example 2. (S)-3-(4-(2-ethoxypropan-2-yl)-3-(3-(p-tolyl)ureido)phenyl)pentanoic Acid (Absolute Stereochemistry not Determined)

Example 2 was prepared from 2B following the procedure described for the synthesis of Example 1. LC-MS Anal. Calc'd for $C_{24}H_{32}N_2O_4$ 412.23, found [M+H] 413.2, Tr=2.02 min (Method U). $^1$H NMR (400 MHz, methanol-$d_4$) δ 7.88 (d, J=1.6 Hz, 1H), 7.36-7.30 (m, 2H), 7.20 (s, 1H), 7.13 (s, 2H), 6.90 (dd, J=8.0, 1.6 Hz, 1H), 3.23 (q, J=7.2 Hz, 2H), 3.03-2.94 (m, 1H), 2.64-2.50 (m, 2H), 2.32 (s, 3H), 1.83-1.72 (m, 1H), 1.70-1.64 (m, 1H), 1.62 (s, 6H), 1.12 (t, J=7.2 Hz, 3H), 0.84 (t, J=7.6 Hz, 3H).

Example 3, Example 4

(R)-3-(4-(2-ethoxypropan-2-yl)-3-((2-methylbenzo[d]thiazol-6-yl)amino)phenyl)pentanoic Acid (S)-3-(4-(2-ethoxypropan-2-yl)-3-((2-methylbenzo[d]thiazol-6-yl)amino)phenyl)pentanoic Acid (Absolute Stereochemistry not Determined)

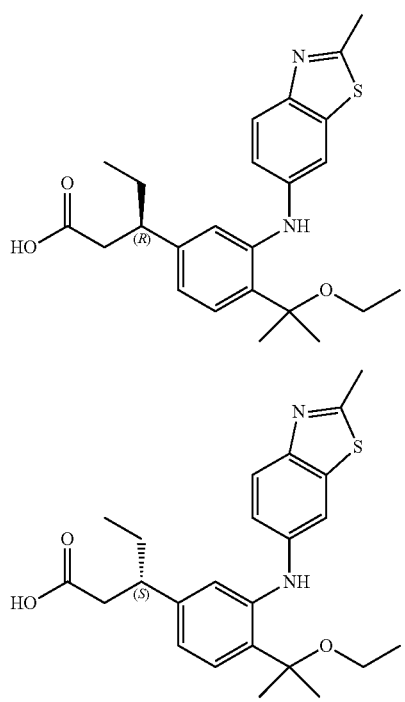

The synthesis of these enantiomers is described below:

3A. methyl 3-(4-(2-ethoxypropan-2-yl)-3-((2-methylbenzo[d]thiazol-6-yl)amino)phenyl)pentanoate (Absolute Stereochemistry not Determined)

To a well degassed solution of 1F Enantiomer 1 (0.05 g, 0.170 mmol), 6-bromo-2-methylbenzo[d]thiazole (0.043 g, 0.187 mmol), $Cs_2CO_3$ (0.167 g, 0.511 mmol) in Dioxane (3 mL) was added Xantphos (0.030 g, 0.051 mmol) and bis(dibenzylideneacetone)palladium (9.80 mg, 0.017 mmol). The resulting reaction mixture was allowed to stir at 110° C. in sealed vessel for 12 h. Then the reaction mixture was diluted with water (50 mL), extracted with ethyl acetate (2×100 mL). Then the organic layer was washed with brine, dried over sodium sulfate, filtered and concentrated under reduced pressure. The crude sample was purified by flash chromatography (10% Ethyl acetate: Pet ether; 4 g silica gel column) to afford 3A (gummy brown solid, 0.030 g, 0.068 mmol, 40.0% yield). LC-MS Anal. Calc'd for $C_{25}H_{32}N_2O_3S$ 440.21, found [M+H] 441.2, Tr=4.09 min (Method U).

Example 3. 3-(4-(2-ethoxypropan-2-yl)-3-((2-methylbenzo[d]thiazol-6-yl)amino)phenyl)pentanoic Acid (Absolute Stereochemistry not Determined)

Example 3 was prepared from 3A following the procedure described for the synthesis of Example 2. LC-MS Anal. Calc'd for $C_{24}H_{30}N_2O_3S$ 426.19, found [M+H] 427.2, Tr=2.06 min (Method O). $^1$H NMR (400 MHz, methanol-$d_4$) δ 7.76 (d, J=8.0 Hz, 1H), 7.58 (d, J=2.8 Hz, 1H), 7.28-7.19 (m, 2H), 7.19-7.14 (m, 1H), 6.79 (dd, J=8.0, 1.6 Hz, 1H), 3.39-3.35 (m, 2H), 2.97-2.88 (m, 1H), 2.79 (s, 3H), 2.65-2.47 (m, 2H), 1.78-1.66 (m, 1H), 1.65-1.57 (m, 7H), 1.27 (t, J=7.2 Hz, 3H), 0.84 (t, J=7.2 Hz, 3H).

Example 4

(S)-3-(4-(2-ethoxypropan-2-yl)-3-((2-methylbenzo[d]thiazol-6-yl)amino)phenyl)pentanoic Acid (Absolute Stereochemistry not Determined)

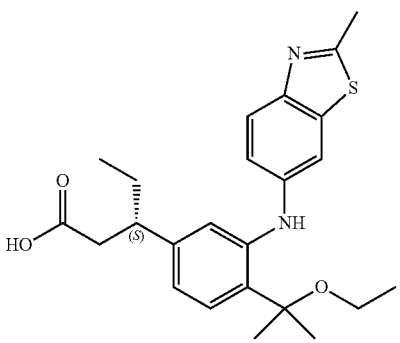

Example 4 was prepared from 1F Enantiomer 2 and 6-bromo-2-methylbenzo[d]thiazole (0.051 g, 0.225 mmol) following the procedure described for the synthesis of Example 3. LC-MS Anal. Calc'd for $C_{24}H_{30}N_2O_3S$ 426.19, found [M+H] 427.2, Tr=2.07 min (Method O). $^1$H NMR (400 MHz, methanol-$d_4$) δ 7.76 (d, J=8.4 Hz, 1H), 7.58 (d, J=2.0 Hz, 1H), 7.25-7.20 (m, 2H), 7.19-7.14 (m, 1H), 6.82-6.72 (m, 1H), 3.38-3.35 (m, 2H), 2.98-2.86 (m, 1H), 2.79 (s, 3H), 2.64-2.47 (m, 2H), 1.78-1.66 (m, 1H), 1.64-1.55 (m, 7H), 1.27 (t, J=7.2 Hz, 3H), 0.84 (t, J=7.2 Hz, 3H).

Example 5

(S)-3-(3-((4-chlorophenyl)amino)-4-(2-ethoxypropan-2-yl)phenyl)pentanoic Acid (Absolute Stereochemistry not Determined)

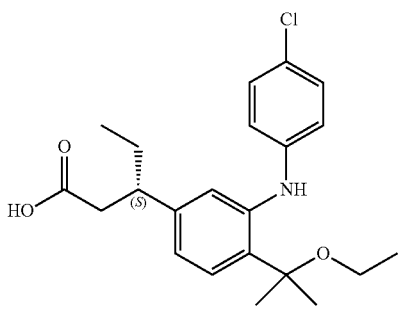

Example 5 was prepared from 1F Enantiomer 2 and 1-bromo-4-chlorobenzene following the procedure described for the synthesis of Example 3. LC-MS Anal. Calc'd for C$_{22}$H$_{28}$C$_1$NO$_3$ 389.17, found [M−H] 388.0, Tr=2.89 min (Method O). $^1$H NMR (400 MHz, DMSO-d$_6$) δ 7.93 (s, 1H), 7.26 (s, 2H), 7.16 (d, J=7.2 Hz, 1H), 7.05 (s, 1H), 7.00 (d, J=8.8 Hz, 2H), 6.75 (d, J=6.0 Hz, 1H), 3.24-3.17 (m, 2H), 2.86-2.76 (m, 1H), 2.46 (d, J=6.8 Hz, 1H), 2.40-2.31 (m, 1H), 1.67-1.56 (m, 1H), 1.50 (s, 6H), 1.47-1.41 (m, 1H), 1.15 (t, J=7.2 Hz, 3H), 0.72 (t, J=7.2 Hz, 3H).

Example 6

(S)-3-(4-(2-ethoxypropan-2-yl)-3-((2-ethoxypyrimidin-5-yl)amino)phenyl)pentanoic Acid (Absolute Stereochemistry not Determined)

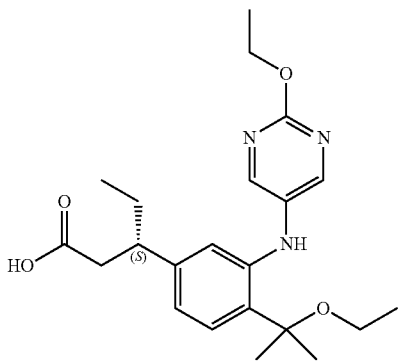

Example 6 was prepared from 1F Enantiomer 2 and 5-bromo-2-ethoxypyrimidine following the procedure described for the synthesis of Example 3. LC-MS Anal. Calc'd for C$_{22}$H$_{31}$N$_3$O$_4$ 401.23, found [M+H] 402.2, Tr=2.11 min (Method O). $^1$H NMR (400 MHz, DMSO-d$_6$) δ 8.37 (s, 1H), 7.65 (s, 1H), 7.12 (d, J=8.4 Hz, 1H), 6.81 (d, J=1.6 Hz, 1H), 6.68 (dd, J=8.0, 1.6 Hz, 1H), 4.31 (q, J=7.2 Hz, 2H), 3.26-3.19 (m, 2H), 2.82-2.70 (m, 2H), 2.46-2.38 (m, 2H), 1.55 (s, 7H), 1.48-1.38 (m, 1H), 1.33 (t, J=7.2 Hz, 3H), 1.15 (t, J=7.2 Hz, 3H), 0.69 (t, J=7.2 Hz, 3H).

Example 7, Example 19, Example 31, Example 41

(Diastereomer 1, Diastereomer 2, Diastereomer 3, Diastereomer 4) (R)-3-(4-((R)-1-ethoxy-2,2,2-trifluoroethyl)-3-(3-(p-tolyl)ureido)phenyl)pentanoic Acid (S)-3-(4-((R)-1-ethoxy-2,2,2-trifluoroethyl)-3-(3-(p-tolyl)ureido)phenyl)pentanoic Acid (R)-3-(4-((S)-1-ethoxy-2,2,2-trifluoroethyl)-3-(3-(p-tolyl)ureido)phenyl)pentanoic Acid (S)-3-(4-((S)-1-ethoxy-2,2,2-trifluoroethyl)-3-(3-(p-tolyl)ureido)phenyl)pentanoic Acid (Absolute and Relative Stereochemistry not Determined)

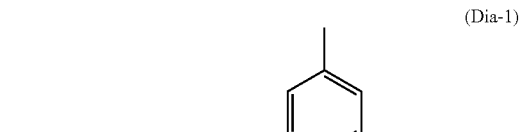

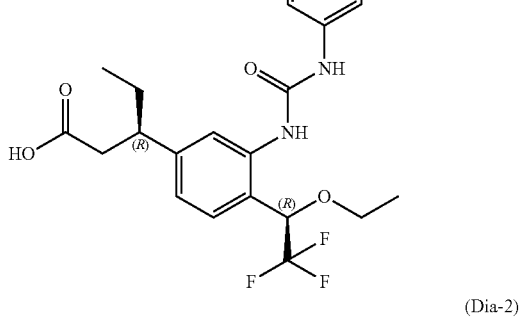

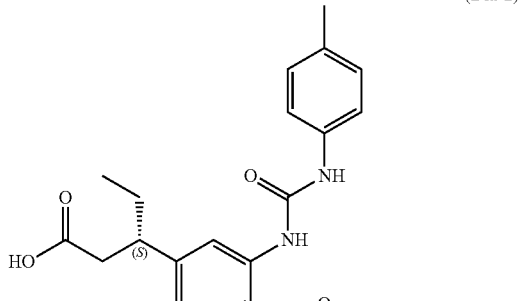

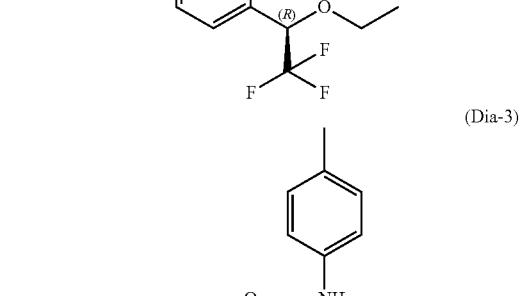

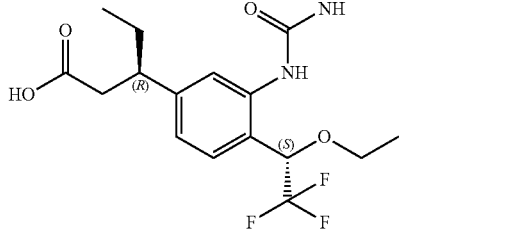

(Dia-4)

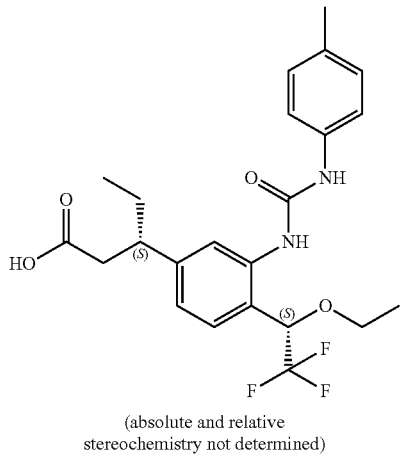

(absolute and relative stereochemistry not determined)

The synthesis of these four diastereomers and their analogs are described below:

Example 7

Diastereomer 1 (R)-3-(4-((R)-1-ethoxy-2,2,2-trifluoroethyl)-3-(3-(p-tolyl)ureidophenyl)pentanoic Acid

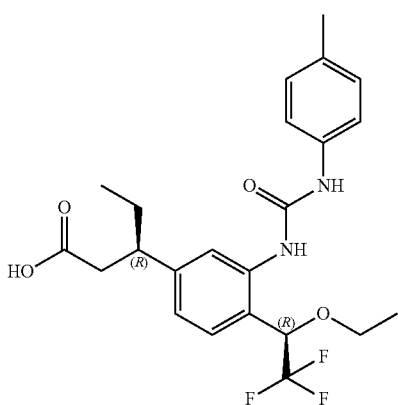

7A.
1-(4-bromo-2-nitrophenyl)-2,2,2-trifluoroethanol

To a solution of 4-bromo-2-nitrobenzaldehyde (8.7 g, 37.8 mmol) at 0° C. in Tetrahydrofuran (120 mL) was added Tetrabutylammonium fluoride (3.78 mL, 3.78 mmol) and allowed to stir for 5 min. Then (trifluoromethyl) trimethylsilane (8.40 mL, 56.7 mmol) was added drop wise and reaction mixture was allowed to stir for 12 h at room temperature. Then the reaction mixture was quenched with 1.5 N HCl (100 mL), stirred for 15 min, and then extracted with Ethyl acetate (2×200 mL). The separated organic layer washed with brine, dried over sodium sulfate, filtered and concentrated under reduced pressure. The crude sample was purified by flash chromatography (20% Ethyl acetate: Pet ether; 80 g silica gel column) to afford 7A (pale yellow oil, 6.2 g, 20.66 mmol, 54.6% yield). $^1$H NMR (400 MHz, DMSO-d$_6$) δ 8.29 (d, J=2.0 Hz, 1H), 8.07 (dd, J=8.4, 2.0 Hz, 1H), 7.84 (d, J=8.4 Hz, 1H), 7.42 (d, J=6.4 Hz, 1H), 5.79 (t, J=6.4 Hz, 1H).

7B. 4-bromo-1-(1-ethoxy-2,2,2-trifluoroethyl)-2-nitrobenzene

To a solution of 7A (13 g, 43.3 mmol) in THF (150 mL) was added cesium carbonate (28.2 g, 87 mmol) and stirred for 15 min. Then ethyl iodide (14.01 mL, 173 mmol) was added and allowed to stir for 12 h. Then reaction mixture was diluted with water (200 mL), extracted with ethyl acetate (2×200 mL). Separated organic layer was washed with brine (200 mL), dried over sodium sulfate and concentrated under reduced pressure. The crude sample was purified by flash chromatography (10% Ethyl acetate: Pet ether; 80 g silica gel column) to afford 7B (Pale yellow oil, 6.2 g, 18.90 mmol, 43.6% yield). $^1$H NMR (400 MHz, DMSO-d$_6$) δ 8.37-8.34 (m, 1H), 8.12-8.07 (m, 1H), 7.75 (d, J=8.0 Hz, 1H), 5.71 (m, 1H), 3.71 (m, 1H), 3.57 (m, 1H), 1.16 (t, J=6.8 Hz, 3H).

7C. 5-bromo-2-(1-ethoxy-2,2,2-trifluoroethyl)aniline (Absolute and Relative Stereochemistry not Determined)

To a solution of 7B (4.4 g, 13.41 mmol) in Acetic Acid (50 mL) was added iron (3.00 g, 53.6 mmol) and allowed to stir for 4 h at 27° C. Reaction mixture was diluted with water (100 mL), basified with sat. solution of sodium carbonate and extracted with Ethyl acetate (2×200 mL). The organic layer was washed with brine (100 mL). Then organic layer was dried over sodium sulfate, filtered and concentrated under reduced presser. The crude sample was purified by flash chromatography (10% Ethyl acetate: Pet ether; 40 g silica gel column) to afford 7C racemate. $^1$H NMR (400 MHz, DMSO-d$_6$) δ 7.07 (d, J=8.0 Hz, 1H), 6.86 (d, J=2.4 Hz, 1H), 6.71 (dd, J=8.0, 2.0 Hz, 1H), 5.61 (s, 2H), 5.22 (m, 1H), 3.52-3.42 (m, 2H), 1.13 (t, J=7.2 Hz, 3H).

The chiral separation of 7C racemate yielded 7C Enantiomer 1, Tr=3.50 min, 7C Enantiomer 2, Tr=4.50 min (Method DU).

7C Enantiomer 1: LC-MS Anal. Calc'd for $C_{10}H_{11}BrF_3NO$ 296.99, found [M+H]298.0, Tr=2.20 min (Method BB).

7C Enantiomer 2: LC-MS Anal. Calc'd for $C_{10}H_{11}BrF_3NO$ 296.99, found [M+H]298.0 Tr=2.12 min (Method BB)

7D. 5-(5,5-dimethyl-1,3,2-dioxaborinan-2-yl)-2-(1-ethoxy-2,2,2-trifluoroethyl)aniline (Absolute and Relative Stereochemistry not Determined)

The compound 7C Enantiomer 1 (2.3 g, 7.72 mmol) was dissolved in Dioxane (45 mL) and to that bis(neopentyl glycolato)diboron (2.266 g, 10.03 mmol) and potassium acetate (2.272 g, 23.15 mmol) was added and argon gas was purged for 15 min. Then 1,1'-bis(diphenylphosphino)ferrocene-palladium(ii)dichloride dichloromethane complex (0.189 g, 0.231 mmol) was added and the reaction mixture was heated at 80° C. and stirred for overnight. Then the Reaction mixture was quenched with water (50 mL), extracted with ethyl acetate (2×100 mL). The organic layer was washed with brine and dried over sodium sulfate. Then it was filtered and concentrated under reduced pressure. The crude sample was purified by flash chromatography (10% Ethyl acetate: Pet ether; 24 g silica gel column) to afford 7D (Pale yellow oil, 2.2 g, 6.64 mmol, 86% yield). LC-MS Anal. Calc'd for $C_{15}H_{21}BF_3NO_3$ 331.15, found [M+H] 264.2.0 (for parent Boronic acid), Tr=1.13 min (Method BB).

7E. methyl 3-(3-amino-4-(1-ethoxy-2,2,2-trifluoroethyl)phenyl)pentanoate (Absolute and Relative Stereochemistry not Determined)

To a well degassed mixture of Dioxane (20 mL) 7D (2.0 g, 6.04 mmol), methyl 2-pentenoate (2.068 g, 18.12 mmol), sodium hydroxide (5.44 mL, 5.44 mmol) was added chloro (1,5-cyclooctadiene)rhodium(i) dimer (0.149 g, 0.302 mmol) and allowed to stir for 12 h at 50° C. Then the reaction mixture was quenched with acetic acid (0.311 mL, 5.44 mmol), diluted with water 100 mL and extracted twice using ethyl acetate (2×100 mL). Then the separated organic layer was washed with 50 mL brine solution and dried over sodium sulfate, filtered and concentrated under reduced pressure. The crude sample was purified by flash chromatography (15% Ethyl acetate: Pet ether; 24 g silica gel column) to afford 7E Diastereomeric mixture (Brown oil, 1.4 g, 4.20 mmol, 69.5% yield). LC-MS Anal. Calc'd for $C_{16}H_{22}F_3NO_3$ 333.15, found [M+H] 334.2, Tr=2.83 min (Method BB).

Chiral Separation of 7E diastereomeric mixture was yielded 7E Diastereomer 1, Tr=25.65 min and 7E Diastereomer 2, Tr=31.75 min (Method DV).

7E Diastereomer 1 (Brown oil, 0.45 g, 1.350 mmol, 22.35% yield): $^1$H NMR (400 MHz, DMSO-$d_6$) δ 7.05 (d, J=7.2 Hz, 1H), 6.48 (d, J=2.0 Hz, 1H), 6.42 (dd, J=8.0, 1.6 Hz, 1H), 5.24-5.12 (m, 3H), 3.51 (s, 3H), 3.48-3.39 (m, 2H), 2.78-2.69 (m, 1H), 2.62-2.54 (m, 1H), 1.63-1.52 (m, 1H), 1.51-1.41 (m, 1H), 1.16-1.06 (m, 3H), 0.71 (t, J=7.2 Hz, 3H), (Note: One proton is buried under the solvent peak).

7E Diastereomer 2 (Brown oil, 0.56 g, 1.680 mmol, 27.8% yield). LC-MS Anal. Calc'd for $C_{16}H22F_3NO_3$ 333.15, found [M+H] 334.0 Tr=2.30 min (Method BB).

7F. methyl 3-(4-(1-ethoxy-2,2,2-trifluoroethyl)-3-(3-(p-tolyl)ureido)phenyl)pentanoate (Absolute and Relative Stereochemistry not Determined)

To a solution of 7E Diastereomer 1 (0.020 g, 0.060 mmol) in THF (2 mL) was added 1-isocyanato-4-methylbenzene (7.99 mg, 0.060 mmol) and allowed to stir for 12 h at room temperature. Then the Reaction mixture was concentrated under reduced pressure to afford 7F (Off white gummy solid, 0.050 g, 0.039 mmol, 64.8% yield) and was taken forward as such for the next step without any further purification. LC-MS Anal. Calc'd for $C_{24}H_{29}F_3N_2O_4$ 466.20, found [M+H] 467.3, Tr=1.57 min (Method AV).

Example 7. (R)-3-(4-((R)-1-ethoxy-2,2,2-trifluoroethyl)-3-(3-(p-tolyl)ureido)phenyl)pentanoic Acid (Absolute and Relative Stereochemistry not Determined)

To the solution of 7F (0.035 g, 0.075 mmol) in Tetrahydrofuran (1 mL), methanol (0.5 mL), $H_2O$ (0.5 mL) was added lithium hydroxide monohydrate (5.39 mg, 0.225 mmol) and allowed to stir for the 12 h at room temperature. Then the reaction mixture was concentrated under reduced pressure, diluted with 5 mL of water and acidified with sat. solution of citric acid till pH ~4. Then the aqueous layer was extracted with DCM (5 mL), washed with brine (5 mL), dried over sodium sulfate, filtered and concentrated under reduced pressure. The crude was purified using preparative HPLC to afford Example 7 Diastereomer 1 (white solid, 0.0046 g, 10.17 μmol, 13.55% yield). LC-MS Anal. Calc'd for $C_{23}H27F_3N_2O_4$ 452.19, found [M+H] 453.2, Tr=2.24 min (Method R). $^1$H NMR (400 MHz, DMSO-$d_6$) δ 11.88 (br. s., 1H), 8.90 (s, 1H), 8.05 (s, 1H), 7.61 (s, 1H), 7.40-7.27 (m, 3H), 7.13-6.97 (m, 3H), 5.24 (q, J=7.2 Hz, 1H), 3.56 (m, 2H), 2.97-2.82 (m, 1H), 2.65-2.53 (m, 1H), 2.49-2.42 (m, 1H), 2.24 (s, 3H), 1.71-1.45 (m, 2H), 1.16 (t, J=7.2 Hz, 3H), 0.74 (t, J=7.2 Hz, 3H).

Example 8

(R)-3-(3-(3-(4-cyanophenyl)ureido)-4-((R)-1-ethoxy-2,2,2-trifluoroethyl)phenyl)pentanoic Acid (Absolute and Relative Stereochemistry not Determined)

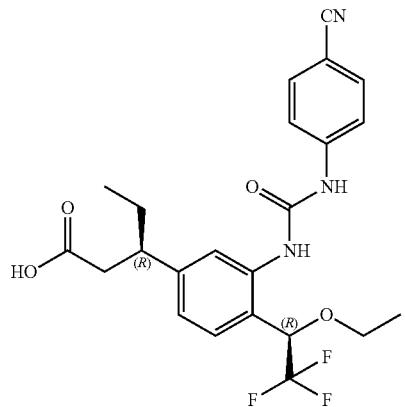

8A. methyl 3-(3-(3-(4-cyanophenyl)ureido)-4-(1-ethoxy-2,2,2-trifluoroethyl)phenyl)pentanoate (Absolute and Relative Stereochemistry not Determined)

8A was prepared from 7E Diastereomer 1 and corresponding aryl isocyanates following the procedure described for the synthesis of 7F. LC-MS Anal. Calc'd for $C_{24}H_{26}F_3N_3O_4$ 477.18, found [M+H] 478.3, Tr=1.48 min (Method AV).

Example 8. (R)-3-(3-(3-(4-cyanophenyl)ureido)-4-((R)-1-ethoxy-2,2,2-trifluoroethyl)phenyl)pentanoic Acid (Absolute and Relative Stereochemistry not Determined)

To the solution of 8A (0.04 g, 0.048 mmol) in Tetrahydrofuran (2 ml), MeOH (2 mL) was added lithium hydroxide monohydrate (0.020 g, 0.478 mmol) and allowed to stir for the 12 h at room temperature. The reaction mixture was concentrated under reduced pressure, diluted with 5 ml of water and acidified with sat. solution of citric acid, till pH is ~4. The reaction mixture was extracted with DCM (5 ml), washed with brine (5 mL), dried over sodium sulfate, filtered and concentrated under reduced pressure. The isolated crude was purified using preparative HPLC to afford Example 8. LC-MS Anal. Calc'd for $C_{23}H_{24}F_3N_3O_4$ 463.1, found [M+H] 464.1, Tr=2.1 min (Method R). $^1$H NMR (400 MHz, DMSO-$d_6$) δ 12.05 (br. s., 1H), 9.54 (s, 1H), 8.28 (s, 1H), 7.77-7.70 (m, 2H), 7.68-7.62 (m, 2H), 7.55 (s, 1H), 7.39 (d, J=8.4 Hz, 1H), 7.10 (d, J=7.2 Hz, 1H), 5.29-5.19 (m, 1H), 3.64-3.47 (m, 2H), 2.98-2.84 (m, 1H), 2.64-2.54 (m, 1H), 2.46 (d, J=7.6 Hz, 1H), 1.72-1.59 (m, 1H), 1.58-1.46 (m, 1H), 1.16 (t, J=7.2 Hz, 3H), 0.74 (t, J=7.2 Hz, 3H).

Example 9

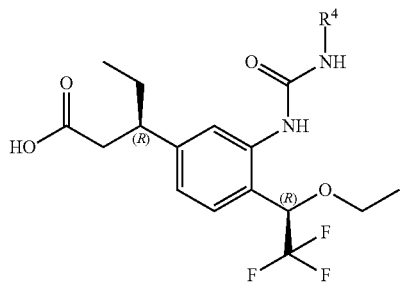

Examples 9 was prepared from 7E Diastereomer 1 and corresponding aryl isocyanates following the procedure described for the synthesis of Example 7.

| Ex. No. | Name | R⁴ | Tr min | Method | (M + H) |
|---|---|---|---|---|---|
| 9 | (R)-3-(3-(3-(4-chloro-2-fluorophenyl)ureido)-4-((R)-1-ethoxy-2,2,2-trifluoroethyl)phenyl) pentanoic acid (absolute and relative stereochemistry not determined) | Cl, F (4-chloro-2-fluorophenyl) | 2.36 | R | 491.1 |

Example 10

(R)-3-(4-((R)-1-ethoxy-2,2,2-trifluoroethyl)-3-((2-methoxypyrimidin-5-yl)amino)phenyl)pentanoic Acid (Absolute and Relative Stereochemistry not Determined)

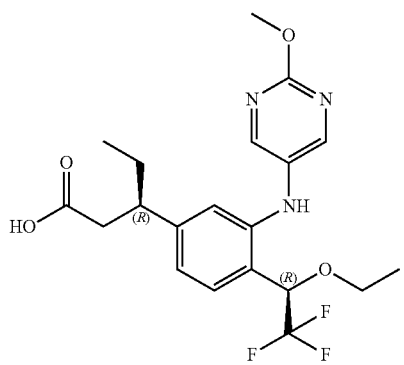

Example 10 was prepared from 7E Diastereomer 1 and 5-bromo-2-methoxypyrimidine following the procedure described for the synthesis of Example 3. LC-MS Anal. Calc'd for $C_{20}H_{24}F_3N_3O_4$ 427.17, found [M+H] 428.2, Tr=2.00 min (Method R). $^1$H NMR (400 MHz, DMSO-d$_6$) δ 8.24 (s, 1H), 7.50 (s, 1H), 7.37 (d, J=7.6 Hz, 1H), 6.91 (s, 2H), 5.44-5.36 (m, 1H), 3.86 (s, 3H), 3.59-3.47 (m, 3H), 2.86-2.76 (m, 1H), 2.56 (d, J=6.4 Hz, 1H), 2.49-2.37 (m, 1H), 1.59 (m, 1H), 1.53-1.41 (m, 1H), 1.14 (t, J=7.2 Hz, 3H), 0.70 (t, J=7.2 Hz, 3H).

Example 11-14

Diastereomer 1

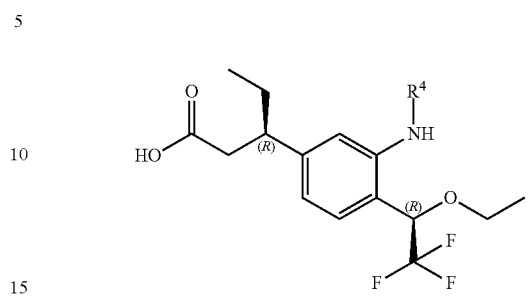

Examples 11-14 was prepared from 7E Diastereomer 1 and corresponding aryl halides following the procedure described for the synthesis of Example 3.

| Ex. No. | Name | R⁴ | Tr min | Method | (M + H) |
|---|---|---|---|---|---|
| 11 | (R)-3-(3-((4-chlorophenyl)amino)-4-((R)-1-ethoxy-2,2,2-trifluoroethyl)phenyl)pentanoic acid (absolute and relative stereochemistry not determined) | 4-chlorophenyl | 2.32 | R | 430.2 |
| 12 | (R)-3-(4-((R)-1-ethoxy-2,2,2-trifluoroethyl)-3-((2-ethoxypyrimidin-5-yl)amino)phenyl) pentanoic acid (absolute and relative stereochemistry not determined) | 2-ethoxypyrimidin-5-yl | 1.77 | O | 442.2 |
| 13 | (R)-3-(4-((R)-1-ethoxy-2,2,2-trifluoroethyl)-3-((5-ethoxypyrazin-2-yl)amino)phenyl) pentanoic acid (absolute and relative stereochemistry not determined) | 5-ethoxypyrazin-2-yl | 2.31 | R | 442.1 |
| 14 | (R)-3-(4-((R)-1-ethoxy-2,2,2-trifluoroethyl)-3-((5-methoxypyrazin-2-yl)amino)phenyl) pentanoic acid (absolute and relative stereochemistry not determined) | 5-methoxypyrazin-2-yl | 2.22 | R | 428.1 |

Example 15

(R)-3-(3-((4-cyanophenyl)amino)-4-((R)-1-ethoxy-2,2,2-trifluoroethyl)phenyl)pentanoic Acid (Absolute and Relative Stereochemistry not Determined)

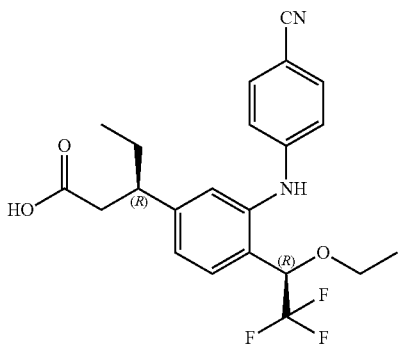

15A. Methyl 3-(3-((4-cyanophenyl)amino)-4-(1-ethoxy-2,2,2-trifluoroethyl)phenyl)pentanoate (Absolute and Relative Stereochemistry not Determined)

15A was prepared from 7E Diastereomer 1 and 4-bromobenzonitrile following the procedure described for the synthesis of 3A. LC-MS Anal. Calc'd for $C_{23}H_{25}F_3N_2O_3$ 434.18, found [M+H] 435.5, Tr=1.58 min (Method AV).

Example 15. (R)-3-(3-((4-cyanophenyl)amino)-4-((R)-1-ethoxy-2,2,2-trifluoroethyl)phenyl)pentanoic Acid (Absolute and Relative Stereochemistry not Determined)

To the solution 15A (0.06 g, 0.138 mmol) in Tetrahydrofuran (2 ml), MeOH (2 mL) was added lithium hydroxide monohydrate (0.058 g, 1.381 mmol) and allowed to stir for the 12 h at room temperature. The reaction mixture was concentrated under reduced pressure, diluted with water (5 mL) and acidified with sat. solution of citric acid till pH ~4. Then the reaction mixture extracted with DCM (5 mL), washed with brine (5 mL), dried over sodium sulfate, filtered and concentrated under reduced pressure. The isolated crude material was purified using preparative HPLC to afford Example 15 (off white solid, 0.028 g, 0.067 mmol, 48.2% yield). LC-MS Anal. Calc'd for $C_{22}H_{23}F_3N_2O_3$ 420.1, found [M+H] 421.1, Tr=2.25 min (Method R). $^1$H NMR (400 MHz, DMSO-$d_6$) δ 8.41 (s, 1H), 7.57-7.43 (m, 3H), 7.22-7.10 (m, 2H), 6.77 (d, J=8.8 Hz, 2H), 5.25 (q, J=6.8 Hz, 1H), 3.55-3.45 (m, 2H), 2.94-2.84 (m, 1H), 2.63-2.55 (m, 1H), 2.48-2.41 (m, 1H), 1.70-1.45 (m, 2H), 1.11 (t, J=7.2 Hz, 3H), 0.72 (t, J=7.2 Hz, 3H).

Example 16

(R)-3-(4-((R)-1-ethoxy-2,2,2-trifluoroethyl)-3-((2-(methoxymethyl)pyrimidin-5-yl)amino)phenyl)pentanoic Acid (Absolute and Relative Stereochemistry not Determined)

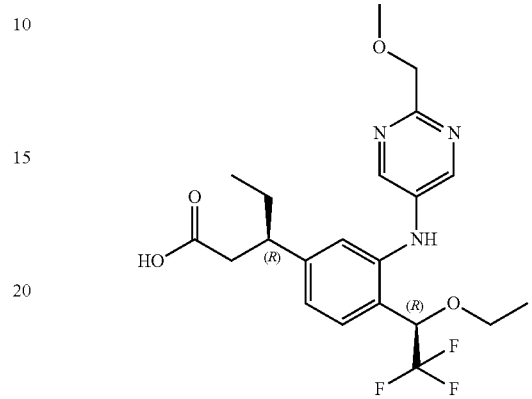

To a solution of 7E Diastereomer 1 (0.03 g, 0.090 mmol), 5-bromo-2-(methoxymethyl)pyrimidine (0.018 g, 0.090 mmol), sodium tert-butoxide (8.65 mg, 0.090 mmol) in Dioxane (2 mL) in a sealed vessel, Argon gas was purged for 10 min. Then xantphos (0.016 g, 0.027 mmol) and bis(dibenzylideneacetone)palladium (5.17 mg, 9.00 μmol) were added and Argon was purged for another 5 min. Then the reaction mixture was placed in a preheated oil bath at 110° C. and stirred for 3 h. Then the reaction mixture was concentrated under reduced pressure. Then diluted with 5 mL of water and acidified with sat. solution of citric acid till pH 4. Reaction mixture was extracted with DCM (30 mL). The organic layer was washed with brine (20 mL), dried over sodium sulfate and concentrated under reduced pressure. The isolated crude was purified using preparative HPLC to afford Example 16 Diastereomer 1 (white solid, 0.007 g, 0.015 mmol, 16.91% yield). LC-MS Anal. Calc'd for $C_{21}H_{26}F_3N_3O_4$ 441.18, found [M+H]442.1, Tr=1.85 min (Method R). $^1$H NMR (400 MHz, DMSO-$d_6$) δ 8.29 (s, 2H), 7.96 (s, 1H), 7.45 (d, J=8.4 Hz, 1H), 7.19-7.06 (m, 2H), 5.38 (q, J=6.8 Hz, 1H), 4.46-4.38 (m, 2H), 3.57-3.50 (m, 2H), 3.32 (s, 3H), 2.92-2.83 (m, 1H), 2.63-2.54 (m, 1H), 2.49-2.43 (m, 1H), 1.68-1.58 (m, 1H), 1.56-1.44 (m, 1H), 1.16-1.08 (t, J=8 Hz, 3H), 0.72 (t, J=7.2 Hz, 3H).

Example 17-18

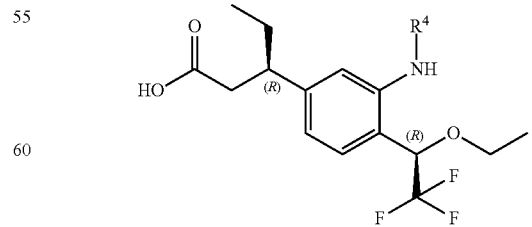

Examples 17-18 was prepared from 7E Diastereomer 1 and corresponding aryl halides following the procedure described for the synthesis of Example 16.

| Ex. No. | Name | R⁴ | Tr min | Method | (M + H) |
|---|---|---|---|---|---|
| 17 | (R)-3-(4-((R)-1-ethoxy-2,2,2-trifluoroethyl)-3-((2-methylpyrimidin-5-yl)amino)phenyl)pentanoic acid (absolute and relative stereochemistry not determined) | 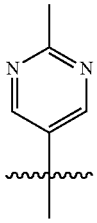 [SMILES: *c1cnc(C)nc1] | 1.74 | R | 412.1 |
| 18 | (R)-3-(4-((R)-1-ethoxy-2,2,2-trifluoroethyl)-3-((2-ethylpyrimidin-5-yl)amino)phenyl)pentanoic acid (absolute and relative stereochemistry not determined) | 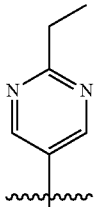 | 1.88 | R | 426.2 |

Example 19

(Diastereomer 2) (S)-3-(4-((R)-1-ethoxy-2,2,2-trifluoroethyl)-3-(3-(p-tolyl)ureido)phenyl)pentanoic Acid (Absolute and Relative Stereochemistry not Determined)

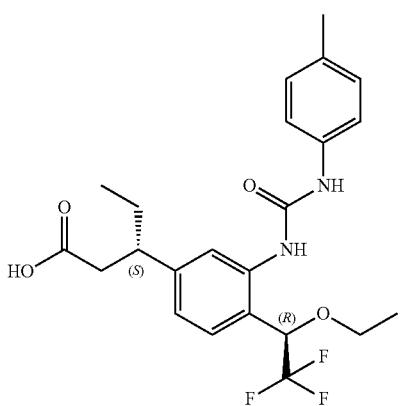

Example 19 was prepared from 7E Diastereomer 2 and 1-isocyanato-4-methylbenzene following the procedure described for the synthesis of Example 7. LC-MS Anal. Calc'd for $C_{23}H_{27}F_3N_2O_4$ 452.19, found [M+H] 453.2, Tr=2.24 min (Method R). ¹H NMR (400 MHz, DMSO-d₆) δ 12.01 (br.s., 1H), 8.89 (s, 1H), 8.04 (s, 1H), 7.61 (s, 1H), 7.42-7.28 (m, 3H), 7.13-7.00 (m, 3H), 5.24 (q, J=6.8 Hz, 1H), 3.64-3.48 (m, 2H), 2.97-2.83 (m, 1H), 2.63-2.54 (m, 1H), 2.45 (d, J=7.6 Hz, 1H), 2.24 (s, 3H), 1.71-1.45 (m, 2H), 1.16 (t, J=7.2 Hz, 3H), 0.74 (t, J=7.2 Hz, 3H).

Example 20-21

Diastereomer 2

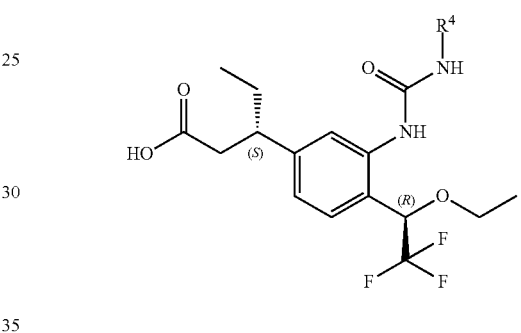

Examples 20 was prepared from 7E Diastereomer 2 and corresponding aryl isocyanates following the procedure described for the synthesis of Example 7.

Examples 21 was prepared from 7E Diastereomer 2 and corresponding aryl isocyanates following the procedure described for the synthesis of Example 8.

| Ex. No. | Name | R⁴ | Tr min | Method | (M + H) |
|---|---|---|---|---|---|
| 20 | (S)-3-(3-(3-(4-chloro-2-fluorophenyl)ureido)-4-((R)-1-ethoxy-2,2,2-trifluoroethyl)phenyl)pentanoic acid (absolute and relative stereochemistry not determined) | 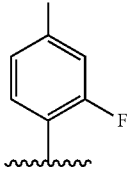 | 2.37 | R | 491.1 |
| 21 | (S)-3-(3-(3-(4-cyanophenyl)ureido)-4-((R)-1-ethoxy-2,2,2-trifluoroethyl)phenyl)pentanoic acid (absolute and relative stereochemistry not determined) | 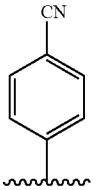 | 2.10 | R | 464.1 |

Example 22

(S)-3-(4-((R)-1-ethoxy-2,2,2-trifluoroethyl)-3-((2-methoxypyrimidin-5-yl)amino)phenyl)pentanoic Acid (Absolute and Relative Stereochemistry not Determined)

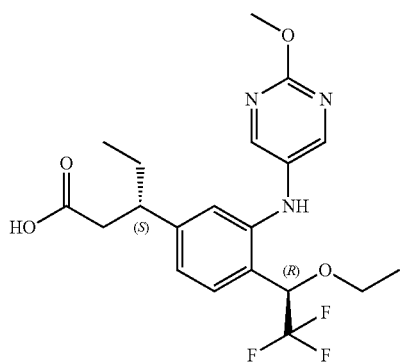

Example 22 was prepared from 7E Diastereomer 2 and 5-bromo-2-methoxypyrimidine following the procedure described for the synthesis of Example 3. LC-MS Anal. Calc'd for $C_{20}H_{24}F_3N_3O_4$ 427.17, found [M+H] 428.1

Tr=2.01 min (Method R). $^1$H NMR (400 MHz, DMSO-$d_6$) δ 8.24 (s, 2H), 7.50 (s, 1H), 7.37 (d, J=8.4 Hz, 1H), 6.96-6.89 (m, 2H), 5.45-5.35 (m, 1H), 3.86 (s, 3H), 3.57-3.48 (m, 2H), 2.80 (d, J=6.4 Hz, 1H), 2.55 (d, J=6.4 Hz, 1H), 2.47-2.37 (m, 1H), 1.59 (m, 1H), 1.53-1.41 (m, 1H), 1.14 (t, J=7.2 Hz, 3H), 0.70 (t, J=7.2 Hz, 3H).

Example 23-26

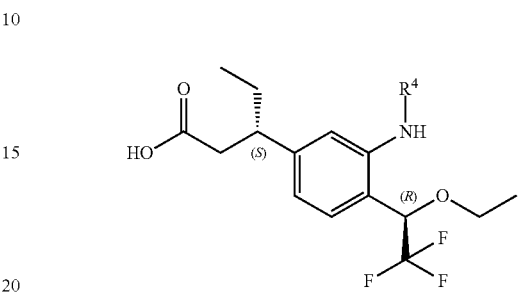

Examples 23-25 were prepared from 7E Diastereomer 2 and corresponding aryl halides following the procedure described for the synthesis of Example 3.

Examples 26 was prepared from 7E Diastereomer 2 and corresponding aryl halides following the procedure described for the synthesis of Example 15.

| Ex. No. | Name | R$^4$ | Tr min | Method | (M + H) |
|---|---|---|---|---|---|
| 23 | (S)-3-(3-((4-chlorophenyl)amino)-4-((R)-1-ethoxy-2,2,2-trifluoroethyl)phenyl)pentanoic acid (absolute and relative stereochemistry not determined) | 4-chlorophenyl | 2.32 | R | 430.2 |
| 24 | (S)-3-(4-((R)-1-ethoxy-2,2,2-trifluoroethyl)-3-((2-ethoxypyrimidin-5-yl)amino)phenyl)pentanoic acid (absolute and relative stereochemistry not determined) | 2-ethoxypyrimidin-5-yl | 1.78 | O | 442.2 |
| 25 | (S)-3-(4-((R)-1-ethoxy-2,2,2-trifluoroethyl)-3-((5-methoxypyrazin-2-yl)amino)phenyl)pentanoic acid (absolute and relative stereochemistry not determined) | 5-methoxypyrazin-2-yl | 2.22 | R | 428.4 |

| Ex. No. | Name | R⁴ | Tr min | Method | (M + H) |
|---|---|---|---|---|---|
| 26 | (S)-3-(3-((4-cyanophenyl)amino)-4-((R)-1-ethoxy-2,2,2-trifluoroethyl)phenyl)pentanoic acid (absolute and relative stereochemistry not determined) | 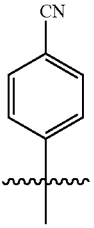 | 2.25 | R | 421.1 |

Example 27

(S)-3-(4-((R)-1-ethoxy-2,2,2-trifluoroethyl)-3-((2-(methoxymethyl)pyrimidin-5-yl)amino)phenyl)pentanoic Acid (Absolute and Relative Stereochemistry not Determined)

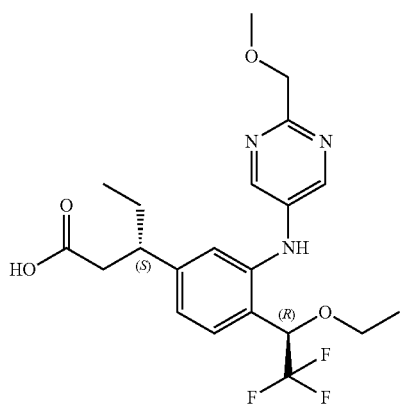

Example 27 was prepared from 7E Diastereomer 2 and 5-bromo-2-(methoxymethyl)pyrimidine following the procedure described for the synthesis of Example 16. LC-MS Anal. Calc'd for $C_{21}H26F_3N_3O_4$ 441.18, found [M+H] 442.1, Tr=1.87 min (Method R). ¹H NMR (400 MHz, DMSO-d₆) δ 8.40-8.19 (m, 2H), 7.96 (s, 1H), 7.45 (d, J=8.4 Hz, 1H), 7.26-6.95 (m, 2H), 5.38 (q, J=6.8 Hz, 1H), 4.43 (s, 2H), 3.59-3.46 (m, 2H), 3.33-3.30 (S, 3H), 2.93-2.83 (m, 1H), 2.63-2.53 (m, 1H), 2.49-2.42 (m, 1H), 1.69-1.57 (m, 1H), 1.56-1.44 (m, 1H), 1.17-1.09 (t, J=8 Hz, 3H), 0.72 (t, J=7.2 Hz, 3H).

Example 28-30

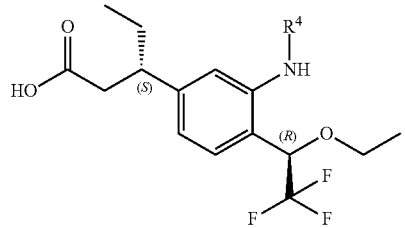

Examples 28-30 were prepared from 7E Diastereomer 2 and corresponding aryl halides following the procedure described for the synthesis of Example 16.

| Ex. No. | Name | R⁴ | Tr min | Method | (M + H) |
|---|---|---|---|---|---|
| 28 | (S)-3-(4-((R)-1-ethoxy-2,2,2-trifluoroethyl)-3-((2-methylpyrimidin-5-yl)amino)phenyl)pentanoic acid (absolute and relative stereochemistry not determined) | 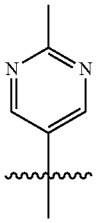 | 1.76 | R | 412.2 |
| 29 | (S)-3-(4-((R)-1-ethoxy-2,2,2-trifluoroethyl)-3-((2-ethylpyrimidin-5-yl)amino)phenyl)pentanoic acid absolute and relative stereochemistry not determined) | 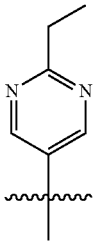 [SMILES: *c1cnc(CC)nc1] | 1.90 | R | 426.2 |

-continued

| Ex. No. | Name | $R^4$ | Tr min | Method | (M + H) |
|---|---|---|---|---|---|
| 30 | (S)-3-(4-((R)-1-ethoxy-2,2,2-trifluoroethyl)-3-((4-fluorophenyl)amino)phenyl)pentanoic acid (absolute and relative stereochemistry not determined) | 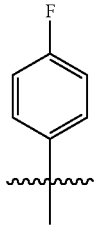 | 2.46 | R | 414.1 |

Example 31

(R)-3-(4-((S)-1-ethoxy-2,2,2-trifluoroethyl)-3-(3-(p-tolyl)ureido)phenyl)pentanoic Acid (Absolute and Relative Stereochemistry not Determined)

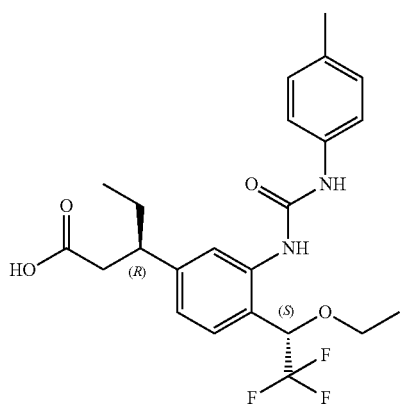

31A. 5-(5,5-dimethyl-1,3,2-dioxaborinan-2-yl)-2-(1-ethoxy-2,2,2-trifluoroethyl)aniline (Absolute and Relative Stereochemistry not Determined)

31A was prepared from 7C Enantiomer 2 following the procedure described for the synthesis of 7D. LC-MS Anal. Calc'd for $C_{15}H_{21}BF_3NO_3$ 331.15, found 264.2 (for parent Boronic acid), Tr=1.24 min (Method BB).

31B. methyl 3-(3-amino-4-(1-ethoxy-2,2,2-trifluoroethyl)phenyl)pentanoate (Absolute and Relative Stereochemistry not Determined)

31B Diastereomeric mixture was prepared from 31A following the procedure described for the synthesis of 7E. LC-MS Anal. Calc'd for $C_{16}H_{22}F_3NO_3$ 333.15, found 334.2, Tr=2.28 min (Method BB).

Chiral separation of 31B diastereomeric mixture was afforded 31B Diastereomer 3, Tr=20.53 min; 31B Diastereomer 4 Tr=27.61 min (Method DV).

31B Diastereomer 3 (Brown oil, 0.6 g, 1.800 mmol, 27.1% yield). LC-MS Anal. Calc'd for $C_{16}H_{22}F_3NO_3$ 333.15, found [M+H] 334.2, Tr=2.21 min (Method BB)

31B Diastereomer 4 (Brown oil, 0.6 g, 1.800 mmol, 27.1% yield). LC-MS Anal. Calc'd for $C_{16}H_{22}F_3NO_3$ 333.15, found [M+H] 334.2, Tr=2.21 min (Method BB).

Example 31. (R)-3-(4-((S)-1-ethoxy-2,2,2-trifluoroethyl)-3-(3-(p-tolyl)ureido)phenyl)pentanoic Acid (Absolute and Relative Stereochemistry not Determined)

To a solution of 31B Diastereomer 3 (0.020 g, 0.060 mmol) in THF (2 mL) was added 1-isocyanato-4-methylbenzene (7.99 mg, 0.060 mmol) and allowed to stir for 12 h at room temperature. Then MeOH (2 mL), Water (2 mL) and lithium hydroxide monohydrate (10.07 mg, 0.240 mmol) was added and allowed to stir for another 12 h. Then reaction mixture was concentrated under reduced pressure, diluted with water and acidified to pH ~4 with 1.5 N HCl. The aqueous layer was extracted with DCM (20 mL), dried over sodium sulfate, filtered and concentrated under educed pressure. The preparative HPLC purification was afforded Example 31 (Off white solid, 0.016 g, 0.035 mmol, 58.9% yield). LC-MS Anal. Calc'd for $C_{23}H_{27}F_3N_2O_4$ 452.19, found [M+H] 453.1, Tr=2.20 min (Method R). $^1$H NMR (400 MHz, DMSO-$d_6$) δ 8.91 (s, 1H), 8.06 (s, 1H), 7.62 (d, J=1.6 Hz, 1H), 7.40-7.30 (m, 3H), 7.12-6.98 (m, 3H), 5.25 (q, J=7.2 Hz, 1H), 3.64-3.47 (m, 2H), 2.98-2.82 (m, 1H), 2.62-2.51 (m, 1H), 2.49-2.37 (m, 1H), 2.25 (s, 3H), 1.75-1.40 (m, 2H), 1.22-1.08 (t, J=8 Hz, 3H), 0.75 (t, J=7.2 Hz, 3H).

Example 32

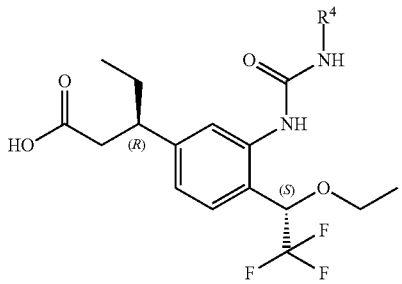

Examples 32 was prepared from 31B Diastereomer 3 and corresponding aryl isocyanates following the procedure described for the synthesis of Example 31.

| Ex. No. | Name | R⁴ | Tr min | Method | (M + H) |
|---|---|---|---|---|---|
| 32 | (R)-3-(3-(3-(4-chloro-2-fluorophenyl)ureido)-4-((S)-1-ethoxy-2,2,2-trifluoroethyl)phenyl)pentanoic acid (absolute and relative stereochemistry not determined) | 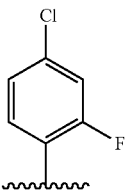 | 2.32 | R | 491.1 |

Example 33

(R)-3-(4-((S)-1-ethoxy-2,2,2-trifluoroethyl)-3-((2-methoxypyrimidin-5-yl)amino)phenyl)pentanoic Acid (Absolute and Relative Stereochemistry not Determined)

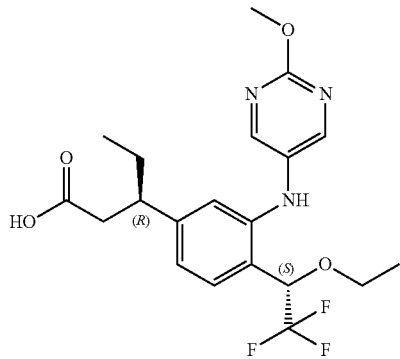

Example 33 was prepared from 31B Diastereomer 3 and 5-bromo-2-methoxypyrimidine following the procedure described for the synthesis of Example 3. LC-MS Anal. Calc'd for $C_{20}H_{24}F_3N_3O_4$ 427.17, found [M+H] 428.2, Tr=2.08 min (Method R). $^1$H NMR (400 MHz, DMSO-$d_6$) δ 8.25 (s, 2H), 7.51 (s, 1H), 7.38 (s, 1H), 6.96-6.87 (m, 2H), 5.42 (q, J=6.8 Hz, 1H), 3.87 (s, 3H), 3.58-3.47 (m, 2H), 2.81 (m, 1H), 2.58-2.52 (m, 1H), 2.46-2.36 (m, 1H), 1.68-1.41 (m, 2H), 1.15 (t, J=7.2 Hz, 3H), 0.71 (t, J=7.2 Hz, 3H).

Example 34-37

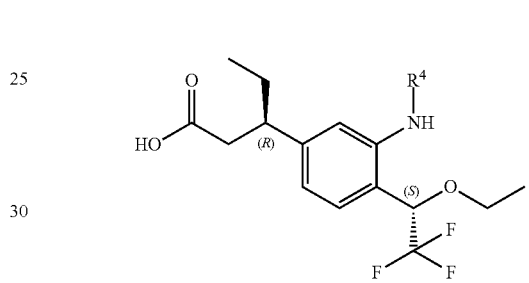

Examples 34-36 were prepared from 31B Diastereomer 3 and corresponding aryl halides following the procedure described for the synthesis of Example 3.

Examples 37 was prepared from 31B Diastereomer 3 and corresponding aryl halides following the procedure described for the synthesis of Example 15.

| Ex. No. | Name | R⁴ | Tr min | Method | (M + H) |
|---|---|---|---|---|---|
| 34 | (R)-3-(3-((4-chlorophenyl)amino)-4-((S)-1-ethoxy-2,2,2-trifluoroethyl)phenyl)pentanoic acid (absolute and relative stereochemistry not determined) | 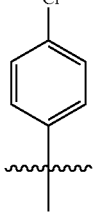 | 2.32 | R | 430.2 |
| 35 | (R)-3-(4-((S)-1-ethoxy-2,2,2-trifluoroethyl)-3-((2-ethoxypyrimidin-5-yl)amino)phenyl)pentanoic acid (absolute and relative stereochemistry not determined) | 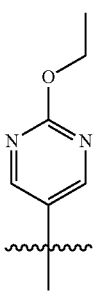 | 2.18 | R | 442.2 |

| Ex. No. | Name | R⁴ | Tr min | Method | (M + H) |
|---|---|---|---|---|---|
| 36 | (R)-3-(4-((S)-1-ethoxy-2,2,2-trifluoroethyl)-3-((5-methoxypyrazin-2-yl)amino)phenyl)pentanoic acid (absolute and relative stereochemistry not determined) | 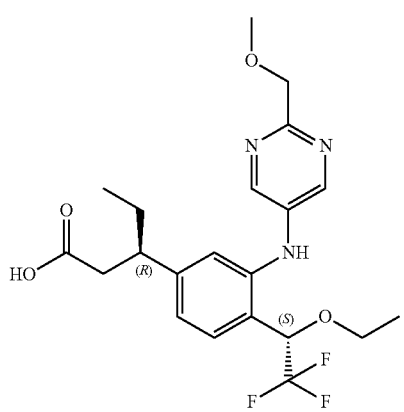 | 2.22 | R | 428.1 |
| 37 | (R)-3-(3-((4-cyanophenyl)amino)-4-((S)-1-ethoxy-2,2,2-trifluoroethyl)phenyl)pentanoic acid (absolute and relative stereochemistry not determined) | | 2.24 | R | 421.2 |

Example 38

(R)-3-(4-((S)-1-ethoxy-2,2,2-trifluoroethyl)-3-((2-(methoxymethyl)pyrimidin-5-yl)amino)phenyl)pentanoic Acid (Absolute and Relative Stereochemistry not Determined)

Example 38 was prepared from 31B Diastereomer 3 and 5-bromo-2-(methoxymethyl)pyrimidine following the procedure described for the synthesis of Example 16. LC-MS Anal. Calc'd for $C_{21}H_{26}F_3N_3O_4$ 441.18, found [M+H] 442.1, Tr=1.85 min (Method R). ¹H NMR (400 MHz, DMSO-$d_6$) δ 8.28 (s, 2H), 7.95 (s, 1H), 7.45 (d, J=8.4 Hz, 1H), 7.17 (d, J=1.6 Hz, 1H), 7.10 (dd, J=8.4, 1.6 Hz, 1H), 5.38 (q, J=7.2 Hz, 1H), 4.42 (s, 2H), 3.57-3.46 (m, 2H), 3.32 (s, 3H), 2.94-2.81 (m, 1H), 2.56-2.54 (m, 1H), 2.50-2.47 (m, 1H), 1.71-1.58 (m, 1H), 1.56-1.44 (m, 1H), 1.13 (t, J=7.2 Hz, 3H), 0.71 (t, J=7.2 Hz, 3H).

Example 39-40

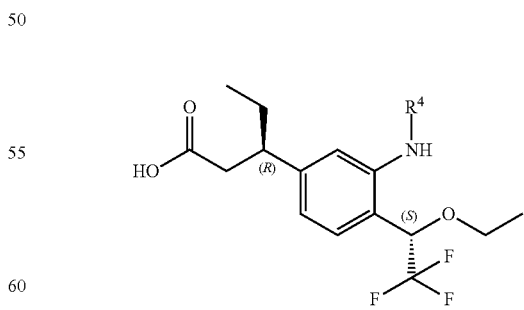

Examples 39-40 were prepared from 31B Diastereomer 3 and corresponding aryl halides following the procedure described for the synthesis of Example 16.

| Ex. No. | Name | R⁴ | Tr min | Method | (M + H) |
|---|---|---|---|---|---|
| 39 | (R)-3-(4-((S)-1-ethoxy-2,2,2-trifluoroethyl)-3-((2-methylpyrimidin-5-yl)amino)phenyl)pentanoic acid (absolute and relative stereochemistry not determined) | 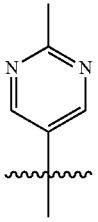 [SMILES: *c1cnc(C)nc1] | 1.75 | R | 412.1 |
| 40 | (R)-3-(4-((S)-1-ethoxy-2,2,2-trifluoroethyl)-3-((2-ethylpyrimidin-5-yl)amino)phenyl)pentanoic acid (absolute and relative stereochemistry not determined) | 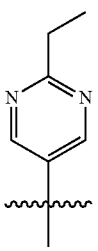 [SMILES: *c1cnc(CC)nc1] | 1.91 | R | 426.2 |

Example 41

(S)-3-(4-((S)-1-ethoxy-2,2,2-trifluoroethyl)-3-(3-(p-tolyl)ureido)phenyl)pentanoic Acid (Absolute and Relative Stereochemistry not Determined)

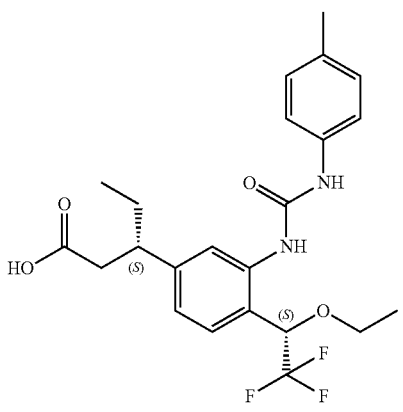

Example 41 was prepared from 31B Diastereomer 4 and 1-isocyanato-4-methylbenzene following the procedure described for the synthesis of Example 31. LC-MS Anal. Calc'd for $C_{23}H_{27}F_3N_2O_4$ 452.19, found [M+H] 453.2, Tr=2.20 min (Method R). $^1$H NMR (400 MHz, DMSO-d$_6$) δ 8.91 (s, 1H), 8.06 (s, 1H), 7.61 (d, J=1.6 Hz, 1H), 7.41-7.32 (m, 3H), 7.12-7.01 (m, 3H), 5.24 (q, J=6.8 Hz, 1H), 3.63-3.49 (m, 2H), 2.96-2.84 (m, 1H), 2.63-2.53 (m, 1H), 2.48-2.40 (m, 1H), 2.24 (s, 3H), 1.70-1.59 (m, 1H), 1.58-1.42 (m, 1H), 1.16 (t, J=7.2 Hz, 3H), 0.74 (t, J=7.2 Hz, 3H).

Example 42

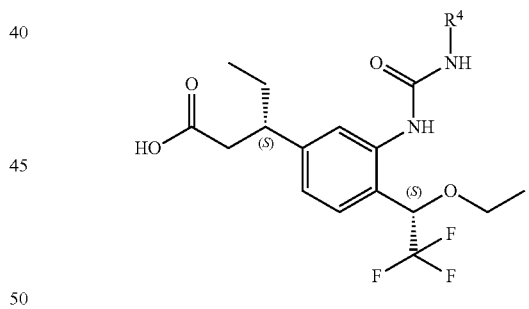

Examples 42 was prepared from 31B Diastereomer 4 and corresponding aryl isocyanates following the procedure described for the synthesis of Example 31.

| Ex. No. | Name | R⁴ | Tr min | Method | (M + H) |
|---|---|---|---|---|---|
| 42 | (S)-3-(3-(3-(4-chloro-2-fluorophenyl)ureido)-4-((S)-1-ethoxy-2,2,2-trifluoroethyl)phenyl)pentanoic acid (absolute and relative stereochemistry not determined) | 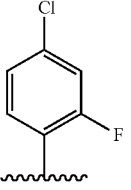 [SMILES: *c1ccc(Cl)cc1F] | 2.32 | R | 491.1 |

Example 43

(S)-3-(4-((S)-1-ethoxy-2,2,2-trifluoroethyl)-3-((2-methoxypyrimidin-5-yl)amino)phenyl)pentanoic Acid (Absolute and Relative Stereochemistry not Determined)

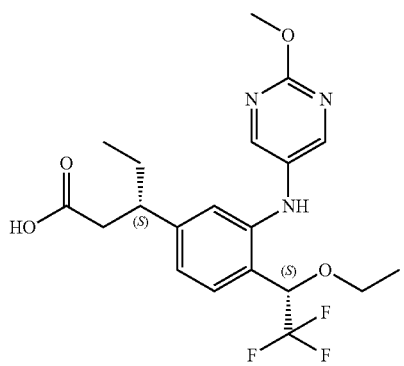

Example 43 was prepared from 31B Diastereomer 4 and 5-bromo-2-methoxypyrimidine following the procedure described for the synthesis of Example 3. LC-MS Anal. Calc'd for $C_{20}H_{24}F_3N_3O_4$ 427.17, found [M+H] 428.1, Tr=2.06 min (Method R). $^1$H NMR (400 MHz, DMSO-$d_6$) δ 8.25 (s, 2H), 7.50 (s, 1H), 7.37 (d, J=8.4 Hz, 1H), 6.96-6.86 (m, 2H), 5.47-5.32 (m, 1H), 3.87 (s, 3H), 3.58-3.45 (m, 2H), 2.87-2.74 (m, 1H), 2.57-2.51 (m, 1H), 2.46-2.38 (m, 1H), 1.67-1.38 (m, 2H), 1.15 (t, J=7.6 Hz, 3H), 0.70 (t, J=7.2 Hz, 3H)

Example 44-48

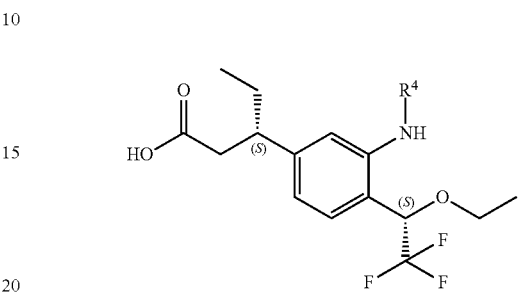

Examples 44-47 were prepared from 31B Diastereomer 4 and corresponding aryl halides following the procedure described for the synthesis of Example 3.

Examples 48 was prepared from 31B Diastereomer 4 and corresponding aryl halides following the procedure described for the synthesis of Example 15.

| Ex. No. | Name | $R^4$ | Tr min | Method | (M + H) |
|---|---|---|---|---|---|
| 44 | (S)-3-(3-((4-chlorophenyl)amino)-4-((S)-1-ethoxy-2,2,2-trifluoroethyl)phenyl)pentanoic acid (absolute and relative stereochemistry not determined) | 4-chlorophenyl | 2.64 | R | 430.1 |
| 45 | (S)-3-(4-((S)-1-ethoxy-2,2,2-trifluoroethyl)-3-((2-ethoxypyrimidin-5-yl)amino)phenyl)pentanoic acid (absolute and relative stereochemistry not determined) | 2-ethoxypyrimidin-5-yl | 2.19 | R | 442.2 |
| 46 | (S)-3-(4-((S)-1-ethoxy-2,2,2-trifluoroethyl)-3-((5-methoxypyrazin-2-yl)amino)phenyl)pentanoic acid (absolute and relative stereochemistry not determined) | 5-methoxypyrazin-2-yl | 2.23 | R | 428.2 |

-continued

| Ex. No. | Name | R⁴ | Tr min | Method | (M + H) |
|---|---|---|---|---|---|
| 47 | (S)-3-(4-((S)-1-ethoxy-2,2,2-trifluoroethyl)-3-((4-fluorophenyl)amino)phenyl)pentanoic acid (absolute and relative stereochemistry not determined) | 4-F-C₆H₄- | 2.06 | O | 414.1 |
| 48 | (S)-3-(4-((S)-1-ethoxy-2,2,2-trifluoroethyl)-3-((4-fluorophenyl)amino)phenyl)pentanoic acid (absolute and relative stereochemistry not determined) | 4-CN-C₆H₄- | 2.05 | R | 421.3 |

Example 49

(S)-3-(4-((S)-1-ethoxy-2,2,2-trifluoroethyl)-3-((2-(methoxymethyl)pyrimidin-5-yl)amino)phenyl)pentanoic Acid (Absolute and Relative Stereochemistry not Determined)

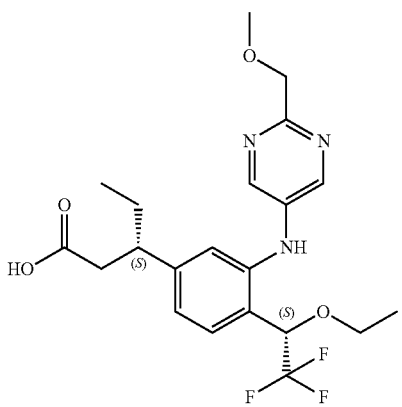

Example 49 was prepared from 31B Diastereomer 4 and 5-bromo-2-(methoxymethyl)pyrimidine following the procedure described for the synthesis of Example 16. LC-MS Anal. Calc'd for $C_{21}H_{26}F_3N_3O_4$ 441.18, found [M+H] 442.1, Tr=1.87 min (Method R). ¹H NMR (400 MHz, DMSO-d₆) δ 8.29 (s, 2H), 7.96 (s, 1H), 7.46 (d, J=7.8 Hz, 1H), 7.18 (d, J=1.6 Hz, 1H), 7.14-7.08 (m, 1H), 5.39 (q, J=7.2 Hz, 1H), 4.43 (s, 2H), 3.60-3.46 (m, 2H), 3.33 (s, 3H), 2.88-2.85 (m, 1H), 2.63-2.54 (m, 1H), 2.50-2.42 (m, 1H), 1.70-1.58 (m, 1H), 1.57-1.45 (m, 1H), 1.14 (t, J=7.2 Hz, 3H), 0.73 (t, J=7.2 Hz, 3H).

Example 50-51

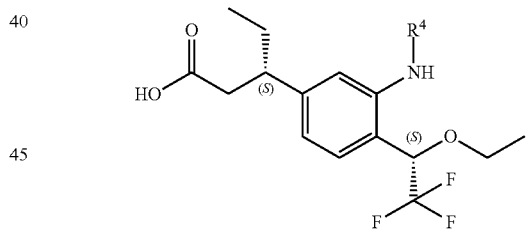

Examples 50-51 were prepared from 31B Diastereomer 4 and corresponding aryl halides following the procedure described for the synthesis of Example 16.

| Ex. No. | Name | R⁴ | Tr min | Method | (M + H) |
|---|---|---|---|---|---|
| 50 | (S)-3-(4-((S)-1-ethoxy-2,2,2-trifluoroethyl)-3-((4-fluorophenyl)amino)phenyl)pentanoic acid (absolute and relative stereochemistry not determined) | pyrimidin-2-yl | 1.52 | R | 412.2 |

-continued

| Ex. No. | Name | R⁴ | Tr min | Method | (M + H) |
|---|---|---|---|---|---|
| 51 | (S)-3-(4-((S)-1-ethoxy-2,2,2-trifluoroethyl)-3-((4-fluorophenyl)amino)phenyl)pentanoic acid (absolute and relative stereochemistry not determined) |  | 1.93 | R | 426.2 |

Example 52, Example 60

(R)-3-(4-((R)-1-ethoxy-2,2,2-trifluoroethyl)-3-(3-(p-tolyl)ureido)phenyl)-4-methoxybutanoic Acid (S)-3-(4-((R)-1-ethoxy-2,2,2-trifluoroethyl)-3-(3-(p-tolyl)ureido)phenyl)-4-methoxybutanoic Acid (Absolute and Relative Stereochemistry not Determined)

(Dia-1)
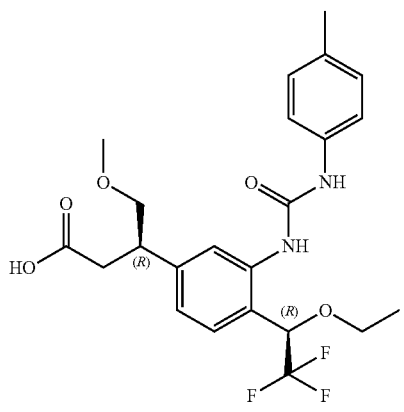

(Dia-2)
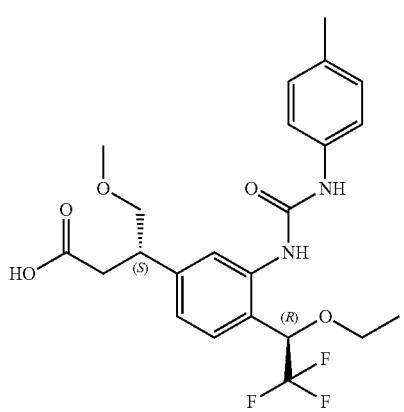

52A. methyl 3-(3-amino-4-(1-ethoxy-2,2,2-trifluoroethyl)phenyl)-4-methoxybutanoate (Absolute and Relative Stereochemistry not Determined)

Example 52A Diastereomeric mixture was prepared from 7D and (E)-methyl 4-methoxybut-2-enoate following the procedure described for the synthesis of 7E. LC-MS Anal. Calc'd for $C_{16}H_{22}F_3NO_4$ 349.15, found [M+H] 350.2, Tr=1.94 min (Method BB).

Chiral separation of 52A diastereomeric mixture was yielded 52A Diastereomer 1, Tr=23.17 min. and 52A Diastereomer 2, Tr=29.16 min (Method DW).

52A Diastereomer 1 (pale yellow oil, 0.05 g, 0.143 mmol, 18.96% yield). LC-MS Anal. Calc'd for $C_{16}H_{22}F_3NO_4$ 349.15, found [M+H] 350.2, Tr=2.10 min (Method BB)

52A Diastereomer 2 (pale yellow oil, 0.05 g, 0.143 mmol, 18.96% yield). ¹H NMR (400 MHz, DMSO-d₆) δ 7.06 (d, J=7.2 Hz, 1H), 6.55-6.44 (m, 2H), 5.26-5.14 (m, 3H), 3.53 (s, 3H), 3.51-3.34 (m, 4H), 3.22 (s, 3H), 3.19-3.10 (m, 1H), 2.71 (m, 1H), 2.54 (m, 1H), 1.14 (t, J=7.2 Hz, 3H).

Example 52. (R)-3-(4-((R)-1-ethoxy-2,2,2-trifluoroethyl)-3-(3-(p-tolyl)ureido)phenyl)-4-methoxybutanoic Acid (Absolute and Relative Stereochemistry not Determined)

Example 52 was prepared from 52A Diastereomer 1 and 1-isocyanato-4-methylbenzene following the procedure described for the synthesis of Example 31. LC-MS Anal. Calc'd for $C_{23}H_{27}F_3N_2O_5$ 468.18, found [M+H] 469.2, Tr=2.07 min (Method R). ¹H NMR (400 MHz, DMSO-d₆) δ 12.10 (br. s., 1H), 8.90 (s, 1H), 8.05 (s, 1H), 7.64 (d, J=1.6 Hz, 1H), 7.39-7.32 (m, 3H), 7.09 (d, J=8.4 Hz, 3H), 5.29-5.19 (m, 1H), 3.56 (t, J=7.2 Hz, 2H), 3.51-3.40 (m, 2H), 3.31-3.25 (m, 1H), 3.22 (s, 3H), 2.72-2.63 (m, 1H), 2.24 (s, 3H), 1.16 (t, J=7.2 Hz, 3H), (Note: one proton buried under solvent peak).

Example 53

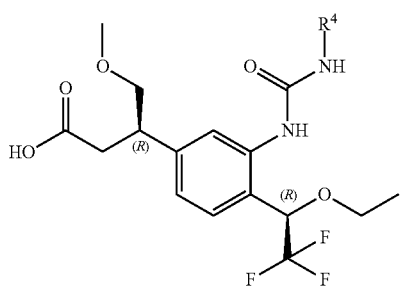

Examples 53 was prepared from 52A Diastereomer 1 and 4-chloro-2-fluoro-1-isocyanatobenzene following the procedure described for the synthesis of Example 52.

| Ex. No. | Name | R⁴ | Tr min | Method | (M + H) |
|---|---|---|---|---|---|
| 53 | (R)-3-(3-(4-chloro-2-fluorophenyl)ureido)-4-((R)-1-ethoxy-2,2,2-trifluoroethyl)phenyl)-4-methoxybutanoic acid (absolute and relative stereochemistry not determined) | 4-chloro-2-fluorophenyl | 2.19 | R | 507.1 |

Example 54

3-(4-(1-ethoxy-2,2,2-trifluoroethyl)-3-((2-methoxy-pyrimidin-5-yl)amino)phenyl)-4-methoxybutanoic Acid (Absolute and Relative Stereochemistry not Determined)

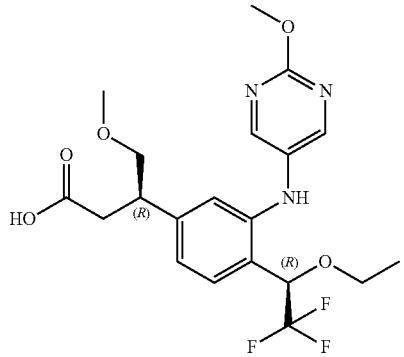

Example 54 was prepared from 52A Diastereomer 1 and 5-bromo-2-methoxypyrimidine following the procedure described for the synthesis of Example 3. LC-MS Anal. Calc'd for $C_{20}H_{24}F_3N_3O_5$ 443.16, found [M+H] 444.1, Tr=1.83 min (Method R). ¹H NMR (400 MHz, DMSO-$d_6$) δ 8.27 (s, 2H), 7.51 (s, 1H), 7.36 (d, J=8.0 Hz, 1H), 7.00-6.91 (m, 2H), 5.41 (m, 1H), 3.87 (s, 3H), 3.59-3.48 (m, 2H), 3.46-3.40 (m, 2H), 3.22-3.16 (m, 4H), 2.61 (m, 1H), 2.48-2.39 (m, 1H), 1.15 (t, J=7.2 Hz, 3H).

Example 55-57

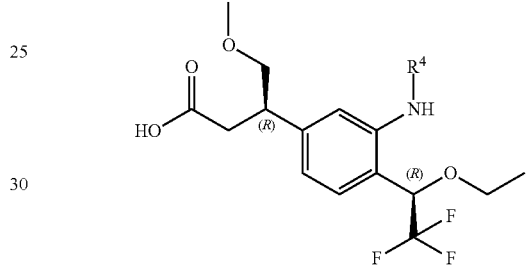

Examples 55-56 were prepared from 52A Diastereomer 1 and corresponding aryl halides following the procedure described for the synthesis of Example 3.

Examples 57 was prepared from 52A Diastereomer 1 and corresponding aryl halides following the procedure described for the synthesis of Example 15.

| Ex. No. | Name | R⁴ | Tr min | Method | (M + H) |
|---|---|---|---|---|---|
| 55 | (R)-3-(3-((4-cyano-3-fluorophenyl)amino)-4-((R)-1-ethoxy-2,2,2-trifluoroethyl)phenyl)-4-methoxybutanoic acid (absolute and relative stereochemistry not determined) | 4-cyano-3-fluorophenyl | 2.11 | R | 455.1 |
| 56 | (R)-3-(4-((R)-1-ethoxy-2,2,2-trifluoroethyl)-3-((5-fluoropyrimidin-2-yl)amino)phenyl)-4-methoxybutanoic acid (absolute and relative stereochemistry not determined) | 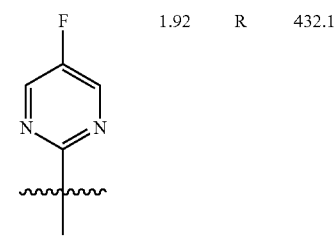 | 1.92 | R | 432.1 |

| Ex. No. | Name | R⁴ | Tr min | Method | (M + H) |
|---|---|---|---|---|---|
| 57 | (R)-3-(3-((4-cyanophenyl)amino)-4-((R)-1-ethoxy-2,2,2-trifluoroethyl)phenyl)-4-methoxybutanoic acid (absolute and relative stereochemistry not determined) | CN-C₆H₄- | 2.09 | R | 437.1 |

Example 58

(R)-3-(3-((4-chlorophenyl)amino)-4-((R)-1-ethoxy-2,2,2-trifluoroethyl)phenyl)-4-methoxybutanoic Acid (Absolute and Relative Stereochemistry not Determined)

Tr=2.39 min (Method R). ¹H NMR (400 MHz, DMSO-d₆) δ 7.72 (s, 1H), 7.40 (d, J=8.0 Hz, 1H), 7.22-7.17 (m, 2H), 7.13 (d, J=1.6 Hz, 1H), 7.05 (dd, J=8.4, 1.2 Hz, 1H), 6.86-6.81 (m, 2H), 5.36 (q, J=6.8 Hz, 1H), 3.57-3.47 (m, 2H), 3.47-3.42 (m, 2H), 3.24 (d, J=8.8 Hz, 1H), 3.21 (s, 3H), 2.63 (m, 1H), 2.45 (m, 1H), 1.13 (t, J=7.2 Hz, 3H).

Example 59

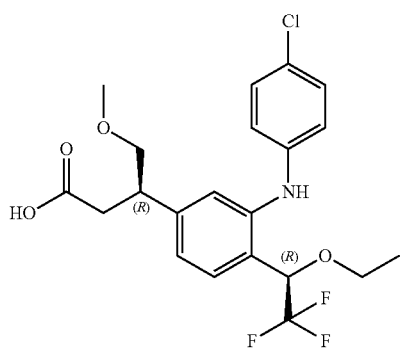

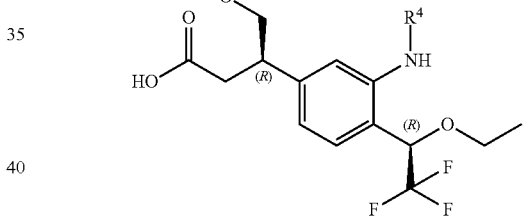

Example 58 was prepared from 52A Diastereomer 1 and 1-bromo-4-chlorobenzene following the procedure described for the synthesis of Example 16. LC-MS Anal. Calc'd for C₂₁H₂₃ClF₃NO₄ 445.12, found [M+H] 446.1, Examples 59 was prepared from 52A Diastereomer 1 and corresponding aryl halides following the procedure described for the synthesis of Example 16.

| Ex. No. | Name | R⁴ | Tr min | Method | (M + H) |
|---|---|---|---|---|---|
| 59 | (R)-3-(4-((R)-1-ethoxy-2,2,2-trifluoroethyl)-3-((2-methylpyrimidin-5-yl)amino)phenyl)-4-methoxybutanoic acid (absolute and relative stereochemistry not determined) | 2-methylpyrimidin-5-yl | 1.50 | R | 428.2 |

Example 60

(S)-3-(4-((R)-1-ethoxy-2,2,2-trifluoroethyl)-3-(3-(p-tolyl)ureido)phenyl)-4-methoxybutanoic Acid (Absolute and Relative Stereochemistry not Determined)

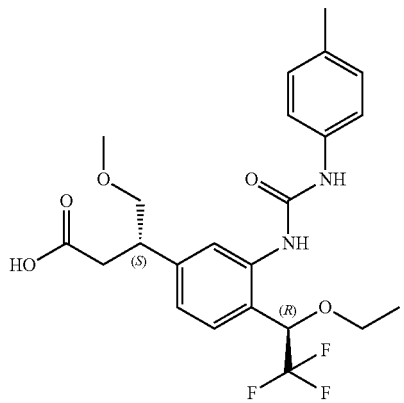

Example 60 was prepared from 52A Diastereomer 2 and 1-isocyanato-4-methylbenzene following the procedure described for the synthesis of Example 52. LC-MS Anal. Calc'd for $C_{23}H_{27}F_3N_2O_5$ 468.18, found [M+H] 469.2, Tr=2.08 min (Method R). $^1$H NMR (400 MHz, DMSO-$d_6$) δ 12.10 (br. s., 1H), 8.89 (s, 1H), 8.05 (s, 1H), 7.64 (d, J=1.6 Hz, 1H), 7.40-7.31 (m, 3H), 7.09 (d, J=8.4 Hz, 3H), 5.24 (m, 1H), 3.63-3.39 (m, 4H), 3.30-3.24 (m, 1H), 3.22 (s, 3H), 2.75-2.61 (m, 1H), 2.24 (s, 3H), 1.16 (t, J=7.2 Hz, 3H) (Note: one proton buried under solvent peak).

Example 61

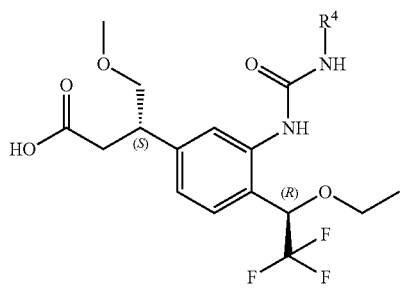

Examples 61 was prepared from 52A Diastereomer 2 and 4-chloro-2-fluoro-1-isocyanatobenzene following the procedure described for the synthesis of Example 52.

Example 62

(S)-3-(4-((R)-1-ethoxy-2,2,2-trifluoroethyl)-3-((2-methoxypyrimidin-5-yl)amino)phenyl)-4-methoxybutanoic Acid (Absolute and Relative Stereochemistry not Determined)

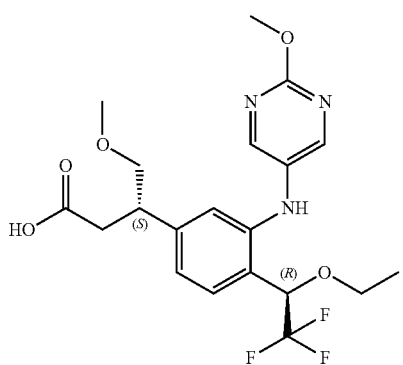

Example 62 was prepared from 52A Diastereomer 2 and 5-bromo-2-methoxypyrimidine following the procedure described for the synthesis of Example 3. LC-MS Anal. Calc'd for $C_{20}H_{24}F_3N_3O_5$ 443.16, found [M+H] 444.1, Tr=1.82 min (Method R). $^1$H NMR (400 MHz, DMSO-$d_6$) δ 12.55 (br. s., 1H), 8.36-8.17 (m, 2H), 7.51 (s, 1H), 7.36 (d, J=8.0 Hz, 1H), 7.01-6.91 (m, 2H), 5.42 (q, J=6.4 Hz, 1H), 3.87 (s, 3H), 3.61-3.48 (m, 2H), 3.47-3.38 (m, 2H), 3.22-3.16 (m, 4H), 2.61 (m, 1H), 2.48-2.40 (m, 1H), 1.15 (t, J=7.2 Hz, 3H).

Example 63-65

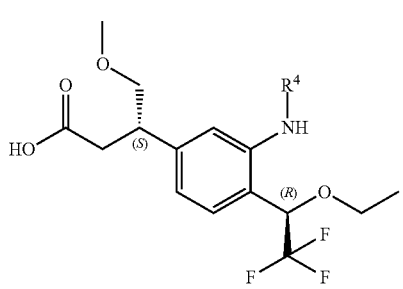

Examples 63-64 were prepared from 52A Diastereomer 2 and corresponding aryl halides following the procedure described for the synthesis of Example 3.

| Ex. No. | Name | $R^4$ | Tr min | Method | (M + H) |
|---|---|---|---|---|---|
| 61 | (S)-3-(3-(3-(4-chloro-2-fluorophenyl)ureido)-4-((R)-1-ethoxy-2,2,2-trifluoroethyl)phenyl)-4-methoxybutanoic acid (absolute and relative stereochemistry not determined) | 4-chloro-2-fluorophenyl | 2.20 | R | 507.1 |

Examples 65 was prepared from 52A Diastereomer 2 and corresponding aryl halides following the procedure described for the synthesis of Example 15.

| Ex. No. | Name | R⁴ | Tr min | Method | (M + H) |
|---|---|---|---|---|---|
| 63 | (S)-3-(3-(4-cyano-3-fluorophenyl)ureido)-4-((R)-1-ethoxy-2,2,2-trifluoroethyl)phenyl)-4-methoxybutanoic acid (absolute and relative stereochemistry not determined) | CN, F (3-cyano-4-fluorophenyl group) | 2.11 | R | 455.1 |
| 64 | (S)-3-(4-((R)-1-ethoxy-2,2,2-trifluoroethyl)-3-((5-fluoropyrimidin-2-yl)amino)phenyl)-4-methoxybutanoic acid (absolute and relative stereochemistry not determined) | 5-fluoropyrimidin-2-yl | 1.92 | R | 432.1 |
| 65 | (S)-3-(3-((4-cyanophenyl)amino)-4-((R)-1-ethoxy-2,2,2-trifluoroethyl)phenyl)-4-methoxybutanoic acid (absolute and relative stereochemistry not determined) | 4-cyanophenyl | 2.09 | R | 437.1 |

Example 66

(S)-3-(3-((4-chlorophenyl)amino)-4-((R)-1-ethoxy-2,2,2-trifluoroethyl)phenyl)-4-methoxybutanoic Acid (Absolute and Relative Stereochemistry not Determined)

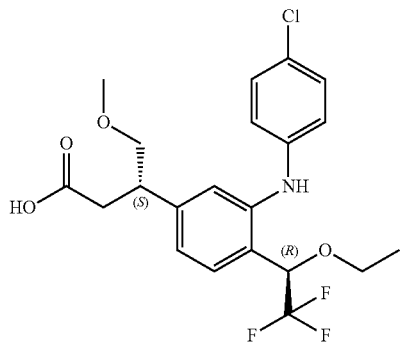

Example 66 was prepared from 52A Diastereomer 2 and 1-bromo-4-chlorobenzene following the procedure described for the synthesis of Example 16. LC-MS Anal. Calc'd for $C_{21}H_{23}ClF_3NO_4$ 445.12, found [M+H] 446.1, Tr=2.39 min (Method R). $^1$H NMR (400 MHz, DMSO-$d_6$) δ 12.06 (br. s., 1H), 7.71 (s, 1H), 7.39 (d, J=7.2 Hz, 1H), 7.19 (d, J=8.8 Hz, 2H), 7.12 (s, 1H), 7.04 (d, J=8.4 Hz, 1H), 6.83 (d, J=8.8 Hz, 2H), 5.35 (q, J=7.2 Hz, 1H), 3.58-3.39 (m, 4H), 3.28-3.18 (m, 4H), 2.65-2.58 (m, 1H), 2.48-2.41 (m, 1H), 1.12 (t, J=7.2 Hz, 3H).

Example 67

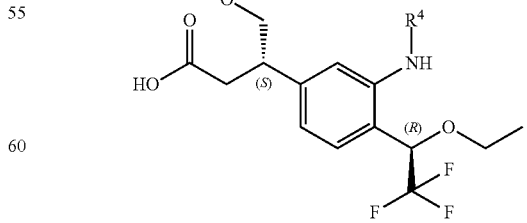

Examples 67 was prepared from 52A Diastereomer 2 and corresponding aryl halides following the procedure described for the synthesis of Example 66.

| Ex. No. | Name | R⁴ | Tr min | Method | (M + H) |
|---|---|---|---|---|---|
| 67 | (S)-3-(4-((R)-1-ethoxy-2,2,2-trifluoroethyl)-3-((2-methylpyrimidin-5-yl)amino)phenyl)-4-methoxybutanoic acid (absolute and relative stereochemistry not determined) | 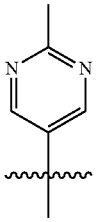 [SMILES: *c1cnc(C)nc1] | 1.50 | R | 428.1 |

Example 68

(R)-3-(3-(3-(4-chloro-2-fluorophenyl)ureido)-4-((S)-1-ethoxy-2,2,2-trifluoroethyl)phenyl)-4-methoxybutanoic Acid (Absolute and Relative Stereochemistry not Determined)

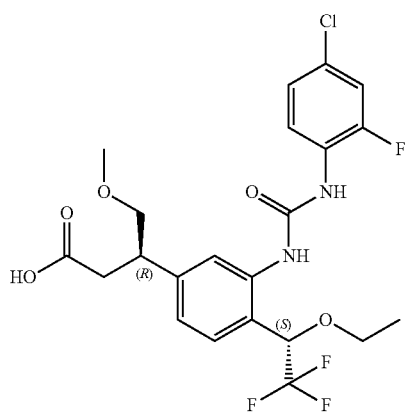

68A. methyl 3-(3-amino-4-(1-ethoxy-2,2,2-trifluoroethyl)phenyl)-4-methoxybutanoate (absolute and relative stereochemistry not determined)

68A Diastereomeric mixture was prepared from 31A and (E)-methyl 4-methoxybut-2-enoate following the procedure described for the synthesis of 31B. LC-MS Anal. Calc'd for $C_{16}H_{22}F_3NO_4$ 349.15, found [M+H] 350.2, Tr=1.94 min (Method BB).

Chiral purification of 68A diastereomeric mixture was yielded 68A Diastereomer 3, Tr=38.06 min and 68A Diastereomer 4, Tr=47.38 min (Method DX).

68A Diastereomer 3 (Pale Yellow oil, 0.1 g, 0.286 mmol, 23.70% yield) LC-MS Anal. Calc'd for $C_{16}H_{22}F_3NO_4$ 349.15, found [M+H] 350.2, Tr=1.86 min (Method BB)

68A Diastereomer 4 (Pale yellow oil, 0.12 g, 0.343 mmol, 28.4% yield). LC-MS Anal. Calc'd for $C_{16}H_{22}F_3NO_4$ 349.15, found [M+H] 350.2, Tr=1.88 min (Method BB)

Example 68. (R)-3-(3-(3-(4-chloro-2-fluorophenyl)ureido)-4-((S)-1-ethoxy-2,2,2-trifluoroethyl)phenyl)-4-methoxybutanoic Acid (Absolute and Relative Stereochemistry not Determined)

Example 68 was prepared from 68A Diastereomer 3 and 4-chloro-2-fluoro-1-isocyanatobenzene following the procedure described for the synthesis of Example 31. LC-MS Anal. Calc'd for $C_{22}H_{23}ClF_4N_2O_5$ 506.12, found [M+H] 507.1, Tr=2.15 min (Method R). ¹H NMR (400 MHz, DMSO-$d_6$) δ 8.99 (d, J=2.0 Hz, 1H), 8.46 (s, 1H), 8.15 (t, J=8.8 Hz, 1H), 7.59 (d, J=1.6 Hz, 1H), 7.48 (m, 1H), 7.40 (d, J=8.0 Hz, 1H), 7.23 (d, J=9.2 Hz, 1H), 7.15 (dd, J=8.0, 1.2 Hz, 1H), 5.24 (q, J=6.8 Hz, 1H), 3.62-3.44 (m, 3H), 3.34-3.26 (m, 2H), 3.23 (s, 3H), 2.67 (dt, J=10.0, 6.0 Hz, 1H), 2.49-2.45 (m, 1H), 1.16 (t, J=7.2 Hz, 3H).

Example 69

(R)-3-(4-((S)-1-ethoxy-2,2,2-trifluoroethyl)-3-((2-methoxypyrimidin-5-yl)amino)phenyl)-4-methoxybutanoic Acid (Absolute and Relative Stereochemistry not Determined)

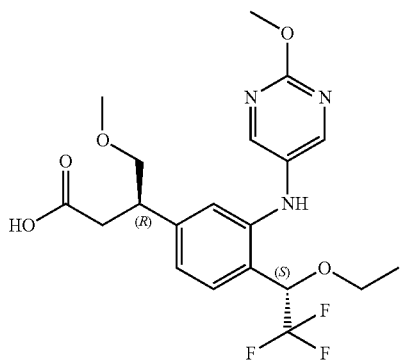

Example 69 was prepared from 68A Diastereomer 3 and 5-bromo-2-methoxypyrimidine following the procedure described for the synthesis of Example 3. LC-MS Anal. Calc'd for $C_{20}H_{24}F_3N_3O_5$ 443.16, found [M+H] 444.1, Tr=1.82 min (Method R). ¹H NMR (400 MHz, DMSO-$d_6$) δ 12.01 (br. s., 1H), 8.26 (s, 2H), 7.51 (s, 1H), 7.36 (d, J=8.4 Hz, 1H), 6.99-6.91 (m, 2H), 5.46-5.36 (m, 1H), 3.87 (s, 3H), 3.58-3.48 (m, 2H), 3.43-3.38 (m, 2H), 3.23-3.15 (m, 4H), 2.65-2.56 (m, 1H), 2.48-2.39 (m, 1H), 1.15 (t, J=7.2 Hz, 3H).

Example 70-73

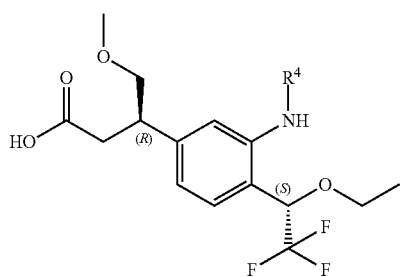

Example 74

(R)-3-(4-((S)-1-ethoxy-2,2,2-trifluoroethyl)-3-((2-methylpyrimidin-5-yl)amino)phenyl)-4-methoxybutanoic Acid (Absolute and Relative Stereochemistry not Determined)

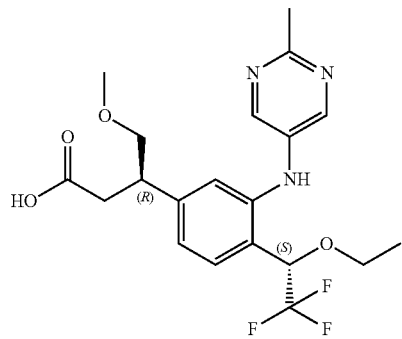

Examples 70-72 were prepared from 68A Diastereomer 3 and corresponding aryl halides following the procedure described for the synthesis of Example 3.

Examples 73 was prepared from 68A Diastereomer 3 and corresponding aryl halides following the procedure described for the synthesis of Example 15.

| Ex. No. | Name | R⁴ | Tr min | Method | (M + H) |
|---|---|---|---|---|---|
| 70 | (R)-3-(3-((4-cyano-3-fluorophenyl)amino)-4-((S)-1-ethoxy-2,2,2-trifluoroethyl)phenyl)-4-methoxybutanoic acid (absolute and relative stereochemistry not determined) | CN, F-phenyl | 2.12 | R | 455.1 |
| 71 | (R)-3-(4-((S)-1-ethoxy-2,2,2-trifluoroethyl)-3-((5-fluoropyrimidin-2-yl)amino)phenyl)-4-methoxybutanoic acid (absolute and relative stereochemistry not determined) | F-pyrimidine | 1.16 | R | 432.1 |
| 72 | (R)-3-(3-((4-chlorophenyl)amino)-4-((S)-1-ethoxy-2,2,2-trifluoroethyl)phenyl)-4-methoxybutanoic acid (absolute and relative stereochemistry not determined) | Cl-phenyl | 2.39 | R | 446.1 |
| 73 | (R)-3-(3-((4-cyanophenyl)amino)-4-((S)-1-ethoxy-2,2,2-trifluoroethyl)phenyl)-4-methoxybutanoic acid (absolute and relative stereochemistry not determined) | CN-phenyl | 2.03 | R | 437.1 |

Example 74 was prepared from 68A Diastereomer 3 and 5-bromo-2-methylpyrimidine following the procedure described for the synthesis of Example 16. LC-MS Anal. Calc'd for $C_{20}H_{24}F_3N_3O_4$ 427.17, found [M+H] 428.1, Tr=1.50 min (Method R). $^1$H NMR (400 MHz, DMSO-$d_6$) δ 8.27 (s, 2H), 7.77 (s, 1H), 7.42 (d, J=8.4 Hz, 1H), 7.16 (d, J=1.6 Hz, 1H), 7.07 (dd, J=8.0, 1.6 Hz, 1H), 5.46-5.35 (m, 1H), 3.58-3.46 (m, 5H), 3.29-3.14 (m, 5H), 2.65-2.56 (m, 1H), 2.49-2.40 (m, 1H), 1.14 (t, J=7.2 Hz, 3H), (Note: one proton is buried under the solvent peak).

Example 75

(S)-3-(3-(3-(4-chloro-2-fluorophenyl)ureido)-4-((S)-1-ethoxy-2,2,2-trifluoroethyl)phenyl)-4-methoxybutanoic Acid (Absolute and Relative Stereochemistry not Determined)

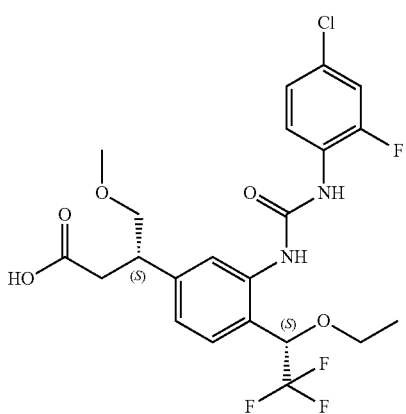

Example 75 was prepared from 68A Diastereomer 4 and 4-chloro-2-fluoro-1-isocyanatobenzene following the procedure described for the synthesis of Example 31. LC-MS Anal. Calc'd for $C_{22}H_{23}ClF_4N_2O_5$ 506.12, found [M+H] 507.1, Tr=2.15 min (Method R). $^1$H NMR (400 MHz, DMSO-$d_6$) δ 8.97 (s, 1H), 8.46 (s, 1H), 8.14 (t, J=8.8 Hz, 1H), 7.58 (d, J=1.6 Hz, 1H), 7.46 (dd, J=11.2, 2.4 Hz, 1H), 7.40 (d, J=8.0 Hz, 1H), 7.22 (d, J=9.2 Hz, 1H), 7.14 (dd, J=8.4, 1.6 Hz, 1H), 5.27-5.17 (m, 1H), 3.62-3.48 (m, 3H), 3.32-3.25 (m, 1H), 3.21 (s, 3H), 2.71-2.60 (m, 1H), 2.49-2.44 (m, 1H), 1.15 (t, J=7.2 Hz, 3H), (Note: One proton is buried under the solvent peak).

Example 76

(S)-3-(4-((S)-1-ethoxy-2,2,2-trifluoroethyl)-3-((2-methoxypyrimidin-5-yl)amino)phenyl)-4-methoxybutanoic Acid (Absolute and Relative Stereochemistry not Determined)

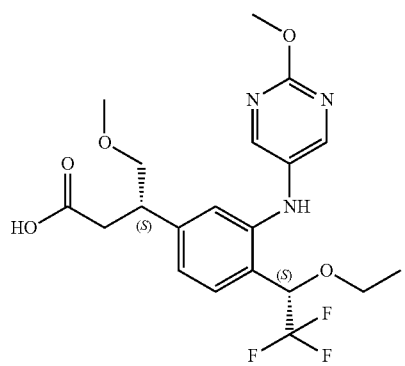

Example 76 was prepared from 68A Diastereomer 4 and 5-bromo-2-methoxypyrimidine following the procedure described for the synthesis of Example 3. LC-MS Anal. Calc'd for $C_{20}H_{24}F_3N_3O_5$ 443.16, found [M+H] 444.1, Tr=1.83 min (Method R). $^1$H NMR (400 MHz, DMSO-$d_6$) δ 12.25-11.73 (br. s., 1H), 8.26 (s, 2H), 7.52 (s, 1H), 7.36 (d, J=8.0 Hz, 1H), 7.00-6.90 (m, 2H), 5.41 (q, J=7.2 Hz, 1H), 3.87 (s, 3H), 3.58-3.48 (m, 2H), 3.46-3.39 (m, 3H), 3.23-3.15 (s, 3H), 2.61 (dd, J=16.0, 6.0 Hz, 1H), 2.44 (dd, J=16.0, 8.0 Hz, 1H), 1.15 (t, J=7.2 Hz, 3H).

Example 77-80

Diastereomer 4

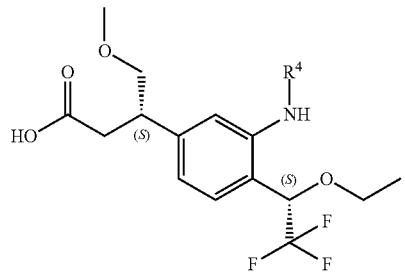

Examples 77-79 were prepared from 68A Diastereomer 4 and corresponding aryl halides following the procedure described for the synthesis of Example 3.

Examples 80 was prepared from 68A Diastereomer 4 and corresponding aryl halides following the procedure described for the synthesis of Example 15.

| Ex. No. | Name | R⁴ | Tr min | Method | (M + H) |
|---|---|---|---|---|---|
| 77 | (S)-3-(3-((4-cyano-3-fluorophenyl)amino)-4-((S)-1-ethoxy-2,2,2-trifluoroethyl)phenyl)-4-methoxybutanoic acid (absolute and relative stereochemistry not determined) | CN, F (3-fluoro-4-cyanophenyl) | 2.12 | R | 455.1 |
| 78 | (S)-3-(4-((S)-1-ethoxy-2,2,2-trifluoroethyl)-3-((5-fluoropyrimidin-2-yl)amino)phenyl)-4-methoxybutanoic acid (absolute and relative stereochemistry not determined) | 5-fluoropyrimidin-2-yl | 1.91 | R | 432.1 |
| 79 | (S)-3-(3-((4-chlorophenyl)amino)-4-((S)-1-ethoxy-2,2,2-trifluoroethyl)phenyl)-4-methoxybutanoic acid (absolute and relative stereochemistry not determined | 4-chlorophenyl | 2.40 | R | 446.1 |
| 80 | (S)-3-(3-((4-cyanophenyl)amino)-4-((S)-1-ethoxy-2,2,2-trifluoroethyl)phenyl)-4-methoxybutanoic acid (absolute and relative stereochemistry not determined) | 4-cyanophenyl | 2.03 | R | 437.1 |

Example 81

(S)-3-(4-((S)-1-ethoxy-2,2,2-trifluoroethyl)-3-((2-methylpyrimidin-5-yl)amino)phenyl)-4-methoxybutanoic Acid

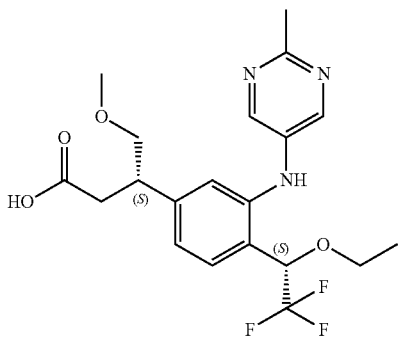

Example 81 was prepared from 68A Diastereomer 4 and 5-bromo-2-methylpyrimidine following the procedure described for the synthesis of Example 16. LC-MS Anal. Calc'd for $C_{20}H_{24}F_3N_3O_4$ 427.17, found [M+H] 428.1, Tr=1.51 min (Method R). ¹H NMR (400 MHz, DMSO-d₆) δ 8.27 (s, 2H), 7.77 (s, 1H), 7.42 (d, J=7.6 Hz, 1H), 7.16 (s, 1H), 7.08 (d, J=8.1 Hz, 1H), 5.46-5.35 (m, 1H), 3.60-3.41 (m, 5H), 3.32-3.19 (m, 5H), 2.66-2.59 (m, 1H), 2.46 (d, J=8.0 Hz, 1H), 1.14 (t, J=7.2 Hz, 3H), (Note: one proton is buried under the solvent peak).

Example 83

(S)-3-(3-((4-chlorophenyl)amino)-4-((R)-2,2,2-trifluoro-1-methoxyethyl)phenyl)pentanoic acid (R)-3-(3-((4-chlorophenyl)amino)-4-((R)-2,2,2-trifluoro-1-methoxyethyl)phenyl)pentanoic Acid (Absolute and Relative Stereochemistry not Determined)

(Dia-1)

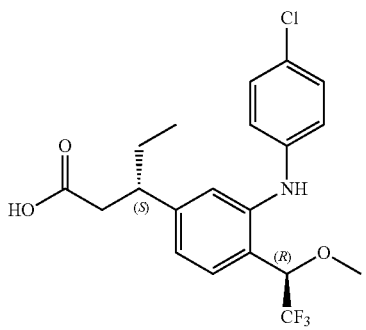

-continued

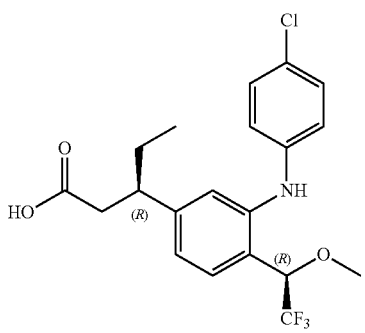

(Dia-2)

83A.
1-(4-bromo-2-nitrophenyl)-2,2,2-trifluoroethanol

To a stirred solution of 4-bromo-2-nitrobenzaldehyde (20 g, 87 mmol) in Tetrahydrofuran (200 mL) under nitrogen atmosphere at 0° C. was added tetrabutylammonium fluoride (8.70 mL, 8.70 mmol) and it was stirred for 5 min. After that (trifluoromethyl) trimethylsilane (19.32 mL, 130 mmol) was added dropwise manner. The reaction mixture was stirred at room temperature for 12 h. Reaction mixture was diluted with 1.5 N HCl (100 mL) and it was stirred for 1 h. It was extracted with ethyl acetate (2×150 mL). The combined organic layer was washed with brine (10 mL), dried over anhydrous sodium sulfate, concentrated under reduced pressure to get crude compound. Purification via flash chromatography gave 83A (Gummy solid, 17 g, 41.9 mmol, 48% yield). LC-MS Anal. Calc'd for $C_8H_5BrF_3NO_3$ 298.9, found [M+H] 299.8, $T_r$=1.30 min (Method AY).

83B. 4-bromo-2-nitro-1-(2,2,2-trifluoro-1-methoxyethyl)benzene

To a stirred solution of 83A (10.3 g, 34.3 mmol) in DMF (100 mL) under nitrogen atmosphere at 0° C. was added cesium carbonate (22.37 g, 68.7 mmol), followed by iodomethane (8.59 mL, 137 mmol). The reaction mixture was stirred at room temperature for 15 h. Reaction mixture was quenched with water (300 mL) and it was extracted with ethyl acetate (3×150 mL). The combined organic layer was washed with brine (100 mL), dried over anhydrous sodium sulfate, concentrated under reduced pressure to get crude compound. Purification via flash chromatography gave 83B (Gummy solid, 8.7 g, 27.7 mmol, 81% yield). $^1$H NMR (400 MHz, DMSO-$d_6$) δ 8.19 (s, 1H), 7.86-7.73 (m, 2H), 5.67-5.61 (q, J=5.90 Hz, 1H), 3.60-3.52 (s, 3H).

83C. 5-bromo-2-(2,2,2-trifluoro-1-methoxyethyl)aniline (Absolute Stereochemistry not Determined)

To a stirred solution of 83B (8.7 g, 27.7 mmol) in Acetic Acid (87 mL) under nitrogen atmosphere at 0° C. was added iron (6.19 g, 111 mmol). The reaction mixture was stirred at room temperature for 4 h. Reaction mixture was quenched with water (200 mL) and it was extracted with ethyl acetate (2×200 mL). The combined organic layer was washed with 10% sodium bicarbonate (4×150 mL) and brine (150 mL), dried over anhydrous sodium sulfate, concentrated under reduced pressure to get crude compound 83C (Racemate) Chiral separation of Racemate 83C (Method DL) gave Enantiomer 1 and Enantiomer 2 as single enantiomers. Enantiomer 1, Tr=2.61 min (Method DL) and Enantiomer 2, Tr=3.29 min (Method DL).

83C Enantiomer 1 (Gummy solid, 1.9 g, 6.69 mmol, 24% yield): LC-MS Anal. Calc'd for $C_9H_9BrF_3NO$ 282.9, found [M+2] 285.0, Tr=1.99 min (Method BB).

83C Enantiomer 2 (Gummy solid, 1.9 g, 6.62 mmol, 23% yield): LC-MS Anal. Calc'd for $C_9H_9BrF_3NO$ 282.9, found [M+2] 285.0, Tr=2.92 min (Method BB).

83D. 5-(5,5-dimethyl-1,3,2-dioxaborinan-2-yl)-2-(2,2,2-trifluoro-1-methoxyethyl)aniline (Absolute Stereochemistry not Determined)

In a sealed tube 83C Enantiomer 1 (1.7 g, 5.98 mmol), bis(neopentyl glycolato)diboron (1.487 g, 6.58 mmol) and potassium acetate (1.762 g, 17.95 mmol) in 1,4-Dioxane (28 mL) purged with Argon for 10 min. To this $PdCl_2$(dppf)-$CH_2Cl_2$Adduct (0.244 g, 0.299 mmol) was added and purged with Argon for 5 min. The reaction mixture was heated at 90° C. for 4 h. Reaction mixture was cooled to room temperature and quenched with water (50 mL). Aqueous layer was extracted with ethyl acetate (3×50 mL). The combined organic layer was washed with brine (40 mL), dried over anhydrous sodium sulfate, concentrated under reduced pressure to get crude compound. Purification via flash chromatography gave 83D (yellow solid, 1.7 g, 5.36 mmol, 89% yield). LC-MS Anal. Calc'd for $C_{14}H_{19}BF_3NO_3$ 317.1, found MS (ES): m/z=250.0 [M+H] for parent boronic acid, $T_r$=1.28 min (Method U).

83E. methyl 3-(3-amino-4-(2,2,2-trifluoro-1-methoxyethyl)phenyl)pentanoate (Absolute and Relative Stereochemistry not Determined)

In a sealed tube 83D (1 g, 3.15 mmol), (E)-methyl pent-2-enoate (0.540 g, 4.73 mmol) and sodium hydroxide (2.84 mL, 2.84 mmol) in 1,4-Dioxane (10 mL) was purged with Argon for 10 min. To this chloro(1,5-cyclooctadiene)rhodium(i) dimer (0.016 g, 0.032 mmol) was added and purged with Argon for 5 min. The reaction mixture was heated at 50° C. for 2 h. LCMS indicated completion of reaction. Reaction mixture was cooled to room temperature and quenched with acetic acid (0.181 mL) and it was stirred for 5 minutes before it was partitioned between ethyl acetate (40 mL) and water (20 mL). Aqueous layer was extracted with ethyl acetate (30 mL). The combined organic layer was washed with brine (30 mL), dried over anhydrous sodium sulfate, concentrated under reduced pressure to get crude compound. Purification via flash chromatography gave 83E (diastereomer mixture).

Chiral separation of diastereomer mixture 83E by Preparative HPLC (Method DY) gave Diastereomer 1 and Diastereomer 2 as single diastereomers. Diastereomer 1, Tr=18.71 min (Method DY) and Diastereomer 2, Tr=22.02 min (Method DY).

83E Diastereomer 1 (yellow liquid, 240 mg, 0.741 mmol, 23% yield): LC-MS Anal. Calc'd for $C_{15}H_{20}F_3NO_3$ 319.1, found [M+H] 320.0, Tr=2.31 min (Method BB).

83E Diastereomer 2 (yellow liquid, 220 mg, 0.684 mmol, 21% yield): LC-MS Anal. Calc'd for $C_{15}H_{20}F_3NO_3$ 319.1, found [M+H] 320.0, Tr=2.31 min (Method BB).

83F. methyl 3-(3-((4-chlorophenyl)amino)-4-(2,2,2-trifluoro-1-methoxyethyl)phenyl)pentanoate (Absolute and Relative Stereochemistry not Determined)

The mixture of 83E Diastereomer 1 (0.040 g, 0.125 mmol), 1-bromo-4-chlorobenzene (0.029 g, 0.150 mmol), 4,5-bis(diphenylphosphino)-9,9-dimethylxanthene (7.25 g, 0.013 mmol) and Cs$_2$CO$_3$ (0.061 g, 0.188 mmol) in 1,4-Dioxane (2 mL) was stirred at room temperature. Argon gas was bubbled through the mixture for 5 min. Bis(dibenzylideneacetone)palladium (3.60 mg, 6.26 µmol) was added and argon gas was bubbled through the mixture for 5 min. The reaction mixture was sealed and placed in preheated oil bath at 110° C. for 5 h. The reaction mixture was cooled to room temperature and concentrated under reduced pressure to afford a residue. The residue was reconstituted in a mixture of ethyl acetate (15 mL) and water (15 mL). The organic layer was separated and aqueous layer was extracted with ethyl acetate (2×10 mL). Combined organic layer was washed with water (10 mL), brine (10 mL), dried over anhydrous sodium sulfate and concentrated under reduced pressure to afford a residue. The residue was purified via flash silica gel column chromatography to afford 83F (yellow liquid, 50 mg, 0.058 mmol, 46% yield). LC-MS Anal. Calc'd for C$_{21}$H$_{23}$ClF$_3$NO$_3$ 429.1, found [M+H] 430.0, T$_r$=3.92 min (Method U).

Example 83 Diastereomer 1. (S)-3-(3-((4-chlorophenyl)amino)-4-((R)-2,2,2-trifluoro-1-methoxyethyl)phenyl)pentanoic Acid (Absolute and Relative Stereochemistry not Determined)

To a stirred solution of 83F (0.050 g, 0.116 mmol) in a mixture of THF (0.7 mL), Methanol (0.7 mL) and water (0.1 mL) was added LiOH.H$_2$O (0.020 g, 0.465 mmol). The reaction mixture was stirred at room temperature for 12 h. The reaction mixture was concentrated under reduced pressure. The aqueous residue so obtained was acidified with aqueous citric acid. The aqueous layer was diluted with water (10 mL) and extracted with ethyl acetate (2×10 mL). Combined organic layer was washed with water (10 mL), brine (10 mL), dried over anhydrous sodium sulfate and concentrated under reduced pressure to afford a residue. The residue was purified via preparative LC/MS to afford Example 83 Diastereomer 1 (19 mg, 0.045 mmol, 39% yield). LC-MS Anal. Calc'd for C$_{20}$H$_{21}$ClF$_3$NO$_3$ 415.1, found [M+H] 416.1, Tr=1.77 min (Method O). $^1$H NMR (400 MHz, DMSO-d$_6$) δ 7.71 (s, 1H) 7.36-7.38 (d, J=8.07 Hz, 1H) 7.19-7.21 (d, J=8.4 Hz, 2H) 7.01-7.06 (m, 2H) 6.79-6.83 (d, J=8.80 Hz, 2H) 5.23-5.28 (q, J=6.83 Hz, 1H) 3.17 (s, 3H) 2.86-2.82 (m, 1H) 2.67 (m, 1H) 2.46 (m, 1H) 1.47-1.64 (m, 2H) 0.72 (t, J=7.2 Hz, 3H).

Example 83 Diastereomer 2. (R)-3-(3-((4-chlorophenyl)amino)-4-((R)-2,2,2-trifluoro-1-methoxyethyl)phenyl)pentanoic Acid (Absolute and Relative Stereochemistry not Determined)

Example 83 Diastereomer 2 was prepared from 83E Diastereomer 2 by following the procedure described for the synthesis of Example 83 Diastereomer 1. LC-MS Anal. Calc'd for C$_{20}$H$_{21}$ClF$_3$NO$_3$ 415.1, found [M+H] 416.1, T$_r$=1.99 min (Method O). $^1$H NMR (400 MHz, DMSO-d$_6$) δ 7.71 (s, 1H), 7.37 (d, J=8.07 Hz, 1H), 7.20 (d, J=8.4 Hz, 2H), 7.06-7.01 (m, 2H), 6.81 (d, J=8.80 Hz, 2H), 5.28-5.23 (q, J=6.83 Hz, 1H), 2.86-2.82 (m, 1H), 2.62-2.52 (m, 1H), 2.45-2.42 (m, 1H), 1.65-1.45 (m, 2H), 0.72 (t, J=7.20 Hz, 3H). Note: (three protons buried under solvent peak)

Example 84

(R)-3-(3-((4-chlorophenyl)amino)-4-((S)-2,2,2-trifluoro-1-methoxyethyl)phenyl)pentanoic acid (S)-3-(3-((4-chlorophenyl)amino)-4-((S)-2,2,2-trifluoro-1-methoxyethyl)phenyl)pentanoic Acid

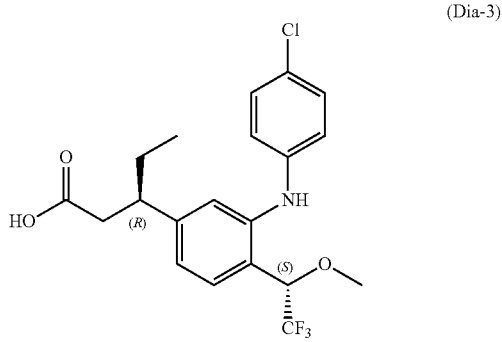

(Dia-3)

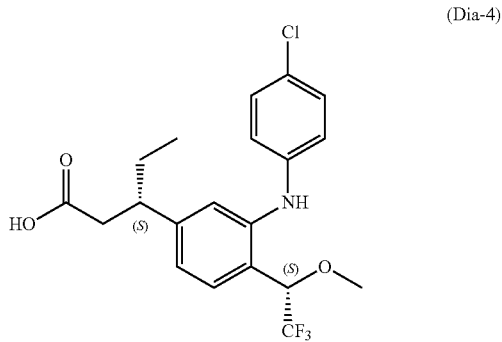

(Dia-4)

84A. 5-(5,5-dimethyl-1,3,2-dioxaborinan-2-yl)-2-(2,2,2-trifluoro-1-methoxyethyl)aniline (Absolute Stereochemistry not Determined)

In a sealed 83C Enantiomer 2 (1.9 g, 6.69 mmol), bis (neopentyl glycolato)diboron (1.662 g, 7.36 mmol) and potassium acetate (1.969 g, 20.07 mmol) in 1,4-Dioxane (19 mL) purged with Argon for 10 min. To this PdCl$_2$(dppf)-CH$_2$Cl$_2$Adduct (0.273 g, 0.334 mmol) was added and purged with Argon for 5 min. The reaction mixture was heated at 90° C. for 4 h. Reaction mixture was cooled to room temperature and quenched with water (50 mL). Aqueous layer was extracted with ethyl acetate (3×50 mL). The combined organic layer was washed with brine (40 mL), dried over anhydrous sodium sulfate, concentrated under reduced pressure to get crude compound. Purification via flash chromatography gave 84A (yellow solid, 1.9 g, 5.69 mmol, 85% yield). LC-MS Anal. Calc'd for C$_{14}$H$_{19}$BF$_3$NO$_3$ 317.1, found MS (ES): m/z=250.0 [M+H] for parent boronic acid, T$_r$=1.26 min (Method U).

84B. methyl 3-(3-amino-4-(2,2,2-trifluoro-1-methoxyethyl)phenyl)pentanoate (Absolute and Relative Stereochemistry not Determined)

In a sealed tube 84A (1 g, 3.15 mmol), (E)-methyl pent-2-enoate (0.540 g, 4.73 mmol) and sodium hydroxide (2.84 mL, 2.84 mmol) in 1,4-Dioxane (10 mL) was purged with Argon for 10 min. To this chloro(1,5-cyclooctadiene)

rhodium(i) dimer (0.016 g, 0.032 mmol) was added and purged with Argon for 5 min. The reaction mixture was heated at 50° C. for 2 h. LCMS indicated completion of reaction. Reaction mixture was cooled to room temperature and quenched with acetic acid (0.181 mL) and it was stirred for 5 minutes before it was partitioned between ethyl acetate (40 mL) and water (20 mL). Aqueous layer was extracted with ethyl acetate (30 mL). The combined organic layer was washed with brine (30 mL), dried over anhydrous sodium sulfate, concentrated under reduced pressure to get crude compound. Purification via flash chromatography gave 84B (diastereomer mixture).

Chiral separation of diastereomer mixture 84B by Preparative HPLC (Method DZ) gave Diastereomer 3 and Diastereomer 4 as single diastereomers. Diastereomer 3, Tr=18.71 min (Method DZ) and Diastereomer 4, Tr=22.02 min (Method DZ).

84B Diastereomer 3 (yellow liquid, 250 mg, 0.783 mmol, 24% yield): LC-MS Anal. Calc'd for $C_{15}H_{20}F_3NO_3$ 319.1, found [M+H] 320.0, Tr=2.31 min (Method BB).

84B Diastereomer 4 (yellow liquid, 250 mg, 0.770 mmol, 24% yield): LC-MS Anal. Calc'd for $C_{15}H_{20}F_3NO_3$ 319.1, found [M+H] 320.2, Tr=2.06 min (Method BB).

84C. methyl 3-(3-((4-chlorophenyl)amino)-4-(2,2,2-trifluoro-1-methoxyethyl)phenyl)pentanoate (Absolute and Relative Stereochemistry not Determined)

84C was prepared from 84B Diastereomer 3 by following the same procedure described for the synthesis of 83F. LC-MS Anal. Calc'd for $C_{21}H_{23}ClF_3NO_3$ 429.1, found [M+H]430.2, $T_r$=3.50 min (Method DC).

Example 84 Diastereomer 3. (R)-3-(3-((4-chlorophenyl)amino)-4-((S)-2,2,2-trifluoro-1-methoxyethyl)phenyl)pentanoic Acid (Absolute and Relative Stereochemistry not Determined)

Example 84 Diastereomer 3 was prepared from 84C by following the procedure described for the synthesis of Example 83 Diastereomer 1. LC-MS Anal. Calc'd for $C_{20}H_{21}ClF_3NO_3$ 415.1, found [M+H] 416.2, $T_r$=1.76 min (Method O). $^1$H NMR (400 MHz, DMSO-$d_6$) δ 7.70 (s, 1H), 7.38 (d, J=7.97 Hz, 1H), 7.20 (d, J=8.78 Hz, 2H), 7.03 (m, 2H), 6.80 (d, J=8.85 Hz, 2H), 5.23-5.28 (q, J=6.82 Hz, 1H), 2.86-2.84 (m, 1H), 2.67-2.52 (m, 1H), 2.46-2.42 (m, 1H), 1.65-1.49 (m, 2H), 0.73 (t, J=7.20 Hz, 3H), (Note. three protons buried under solvent peak).

Example 84 Diastereomer 4. (S)-3-(3-((4-chlorophenyl)amino)-4-((S)-2,2,2-trifluoro-1-methoxyethyl)phenyl)pentanoic Acid (Absolute and Relative Stereochemistry not Determined)

Example 84 Diastereomer 4 was prepared from 84B Diastereomer 4 by following the procedure described for the synthesis of Example 83 Diastereomer 1. LC-MS Anal. Calc'd for $C_{20}H_{21}ClF_3NO_3$ 415.1, found [M+H] 416.2, $T_r$=1.76 min (Method O). $^1$H NMR (400 MHz, DMSO-$d_6$) δ 7.71 (s, 1H), 7.37 (d, J=8.03 Hz, 1H), 7.20 (m, 2H), 7.04 (d, J=1.51 Hz, 2H), 6.81(d, J=8.85 Hz, 2H), 5.26-5.28 (q, J=6.82 Hz, 1H), 2.86-2.84 (m, 1H), 2.67-2.52 (m, 1H), 2.45-2.42 (m, 1H), 1.63-1.49 (m, 2H), 0.73 (t, J=7.20 Hz, 3H), (Note. Three protons buried under solvent peak).

Examples 85-88

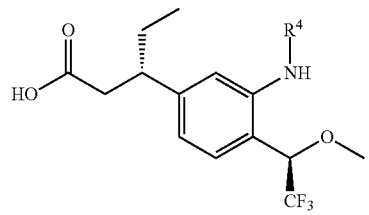

Examples 85-88 were prepared from 83E Diastereomer 1 and the corresponding halides by following the procedure described for the synthesis of Example 83 Diastereomer 1.

| Ex. No. | Name | $R^4$ | Tr (min) Method O | $[M + H]^+$ |
|---|---|---|---|---|
| 85 | (S)-3-(3-((4-cyanophenyl)amino)-4-((R)-2,2,2-trifluoro-1-methoxyethyl)phenyl)pentanoic acid (absolute and relative stereochemistry not determined) | CN-C6H4- | 1.43 | 407.2 |
| 86 | (S)-3-(3-((2-methylpyrimidin-5-yl)amino)-4-((R)-2,2,2-trifluoro-1-methoxyethyl)phenyl)pentanoic acid (absolute and relative stereochemistry not determined) | 2-methylpyrimidin-5-yl | 1.07 | 398.2 |
| 87 | (S)-3-(3-((2-ethoxypyrimidin-5-yl)amino)-4-((R)-2,2,2-trifluoro-1-methoxyethyl)phenyl)pentanoic acid (absolute and relative stereochemistry not determined) | 2-ethoxypyrimidin-5-yl | 1.33 | 428.2 |
| 88 | (S)-3-(4-((R)-2,2,2-trifluoro-1-methoxyethyl)-3-((2-(trifluoromethyl)pyrimidin-5-yl)amino)phenyl)pentanoic acid (absolute and relative stereochemistry not determined) | 2-(CF3)pyrimidin-5-yl | 1.43 | 452.2 |

Examples 89-92

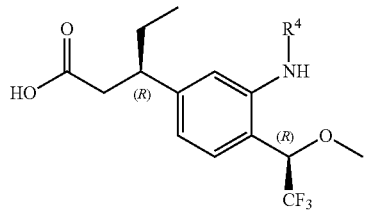

Examples 89-92 were prepared from 83E Diastereomer 2 and the corresponding halides by following the procedure described for the synthesis of Example 83 Diastereomer 1.

| Ex. No. | Name | R⁴ | Tr (min) Method O | [M + H]⁺ |
|---|---|---|---|---|
| 89 | (R)-3-(3-((4-cyanophenyl)amino)-4-((R)-2,2,2-trifluoro-1-methoxyethyl)phenyl)pentanoic acid (absolute and relative stereochemistry not determined) | CN | 1.64 | 407.1 |
| 90 | (R)-3-(3-((2-methylpyrimidin-5-yl)amino)-4-((R)-2,2,2-trifluoro-1-methoxyethyl)phenyl)pentanoic acid (absolute and relative stereochemistry not determined) | | 1.28 | 398.1 |
| 91 | (R)-3-(3-((2-ethoxypyrimidin-5-yl)amino)-4-((R)-2,2,2-trifluoro-1-methoxyethyl)phenyl)pentanoic acid (absolute and relative stereochemistry not determined) | | 1.54 | 428.1 |
| 92 | (R)-3-(4-((R)-2,2,2-trifluoro-1-methoxyethyl)-3-((2-(trifluoromethyl)pyrimidin-5-yl)amino)phenyl)pentanoic acid (absolute and relative stereochemistry not determined) | CF₃ | 1.64 | 452.0 |

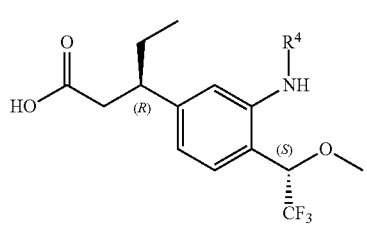

Examples 93-96 were prepared from 84B Diastereomer 3 and the corresponding halides by following the procedure described for the synthesis of Example 83 Diastereomer 1.

| Ex. No. | Name | R⁴ | Tr (min) Method O | [M + H]⁺ |
|---|---|---|---|---|
| 93 | (R)-3-(3-((4-cyanophenyl)amino)-4-((S)-2,2,2-trifluoro-1-methoxyethyl)phenyl)pentanoic acid (absolute and relative stereochemistry not determined) | CN | 1.43 | 407.2 |
| 94 | (R)-3-(3-((2-methylpyrimidin-5-yl)amino)-4-((S)-2,2,2-trifluoro-1-methoxyethyl)phenyl)pentanoic acid (absolute and relative stereochemistry not determined) | | 1.06 | 398.2 |
| 95 | (R)-3-(3-((2-ethoxypyrimidin-5-yl)amino)-4-((S)-2,2,2-trifluoro-1-methoxyethyl)phenyl)pentanoic acid (absolute and relative stereochemistry not determined) | | 1.32 | 428.2 |
| 96 | (R)-3-(4-((S)-2,2,2-trifluoro-1-methoxyethyl)-3-((2-(trifluoromethyl)pyrimidin-5-yl)amino)phenyl)pentanoic acid (absolute and relative stereochemistry not determined) | CF₃ | 1.42 | 452.2 |

Examples 97-100

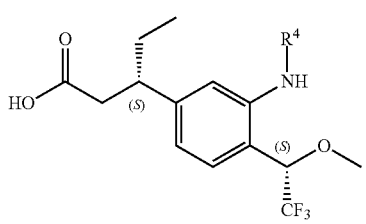

Examples 97-100 were prepared from 84B Diastereomer 4 and the corresponding halides by following the procedure described for the synthesis of Example 83 Diastereomer 1.

| Ex. No. | Name | R⁴ | Tr (min) Method O | [M + H]⁺ |
|---|---|---|---|---|
| 97 | (S)-3-(3-((4-cyanophenyl)amino)-4-((S)-2,2,2-trifluoro-1-methoxyethyl)phenyl)pentanoic acid (absolute and relative stereochemistry not determined) | *(4-cyanophenyl)* | 1.42 | 407.2 |
| 98 | (S)-3-(3-((2-methylpyrimidin-5-yl)amino)-4-((S)-2,2,2-trifluoro-1-methoxyethyl)phenyl)pentanoic acid (absolute and relative stereochemistry not determined) | *(2-methylpyrimidin-5-yl)* | 1.07 | 398.2 |
| 99 | (S)-3-(3-((2-ethoxypyrimidin-5-yl)amino)-4-((S)-2,2,2-trifluoro-1-methoxyethyl)phenyl)pentanoic acid (absolute and relative stereochemistry not determined) | *(2-ethoxypyrimidin-5-yl)* | 1.43 | 428.2 |
| 100 | (S)-3-(4-((S)-2,2,2-trifluoro-1-methoxyethyl)-3-((2-(trifluoromethyl)pyrimidin-5-yl)amino)phenyl)pentanoic acid (absolute and relative stereochemistry not determined) | CF₃ *(2-(trifluoromethyl)pyrimidin-5-yl)* | 1.42 | 452.2 |

Example 101

(S)-3-(3-((4-cyanophenyl)amino)-4-((S)-1-morpholinopropyl)phenyl)-4-methoxybutanoic Acid
(S)-3-(3-((4-cyanophenyl)amino)-4-((R)-1-morpholinopropyl)phenyl)-4-methoxybutanoic Acid
(Absolute and Relative Stereochemistry not Determined)

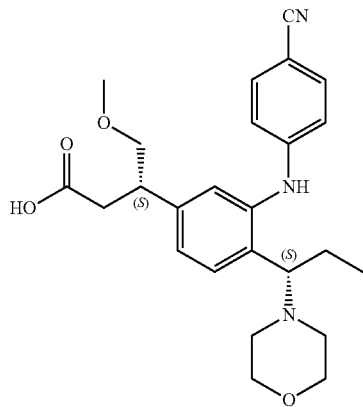
(Dia-1)

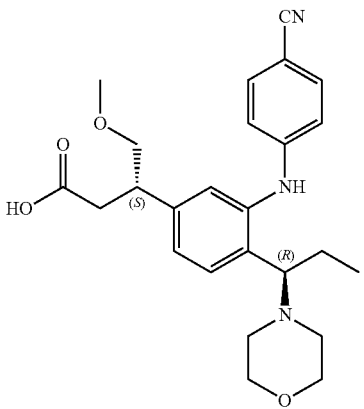
(Dia-2)

124A. methyl 3-(3-((tert-butoxycarbonyl)amino)-4-(1-morpholinopropyl)phenyl)-4-methoxybutanoate (Absolute and Relative Stereochemistry not Determined)

1,4-Dioxane (30 mL) was purged with argon for 10 minute. Then Chlorobis(Ethylene)Rhodium(I)Dimer (0.020 g, 0.052 mmol), (R)-BINAP (0.048 g, 0.076 mmol) were added and purged with argon for another 10 minutes. To the above reaction mixture (1.5 g, 3.47 mmol), (E)-methyl 4-methoxybut-2-enoate (0.677 g, 5.20 mmol), sodium hydroxide (3.12 mL, 3.12 mmol) were added respectively and purged with argon for 10 minutes. The reaction mixture was heated at 50° C. for 3 h in a sealed tube. Reaction mixture was cooled to room temperature and quenched with acetic acid (0.179 mL, 3.12 mmol). The reaction mixture was stirred for 5 minutes. Then the reaction mixture was partitioned between ethyl acetate (25 ml) and water (25 mL). Aqueous layer was extracted with ethyl acetate (2×15 mL). The combined organic layer was washed with brine (25 mL), dried over anhydrous sodium sulfate, filtered and concentrated under reduced pressure to give the crude sample which was purified by flash column chromatography to afford 101A (pale yellow liquid, 1.3 g, 2.452 mmol, 58% yield). LCMS Anal. Calc'd $C_{24}H_{38}N_2O_6$ 450.56, found [M+H] 451.2, Tr=1.75 min (Method BB).

101B. methyl 3-(3-amino-4-(1-morpholinopropyl)phenyl)-4-methoxybutanoate (Absolute and Relative Stereochemistry not Determined)

101A (1.5 g, 3.33 mmol) was taken in HCl in 1,4-Dioxane (8.32 ml, 33.3 mmol) under inert atmosphere. Then the reaction mixture was stirred for 1 h. The reaction mixture was concentrated under reduced pressure and the crude was dissolved in 50 mL of DCM, washed with 10% $NaHCO_3$ solution (10 mL). The organic layer was dried over anhydrous sodium sulfate, filtered and concentrated under reduced pressure to afford 101B.

Chiral separation of 101B Diastereomeric mixture (diastereomeric ratio=53:47) gave 101B Diastereomer 1, Tr=2.58 min and 101B Diastereomer 2, Tr=5.06 min (Method BM).

101B Diastereomer 1 (pale yellow liquid, 300 mg, 0.779 mmol, 23% yield): SFC chiral purity showed 100% de, $T_r$=2.58 min (Method BM). LC-MS Analysis Calc'd for $C_{19}H_{30}N_2O_4$ 350.4, found [M+H] 351.2, $T_r$=1.98 min (Method BD).

101B Diastereomer 2 (pale yellow liquid, 300 mg, 0.770 mmol, 23% yield): SFC chiral purity shows 100% de, $T_r$=5.06 min (Method BM). LC-MS Analysis Calc'd for $C_{19}H_{30}N_2O_4$ 350.4, found [M+H] 351.2, $T_r$=2.16 min (Method AD).

101C. methyl 3-(3-((4-cyanophenyl)amino)-4-(1-morpholinopropyl)phenyl)-4-methoxybutanoate (Absolute and Relative Stereochemistry not Determined)

To a stirred solution of 101B Diastereomer 1 (30 mg, 0.086 mmol) in 1,4-Dioxane (2 mL) was added 4-bromobenzonitrile (18.70 mg, 0.103 mmol), cesium carbonate (41.8 mg, 0.128 mmol) and purged with argon for 10 min. To the above reaction mixture 4,5-Bis(Diphenylphosphino)-9,9-Dimethylxanthene (4.95 mg, 8.56 µmol), Bis(Dibenzylideneacetone)Palladium (2.461 mg, 4.28 µmol) was added and purged with argon for another 10 min. Then the reaction mixture was heated to 110° C. and stirred for 12 h in a sealed vial. The reaction mixture was cooled to room temperature and concentrated under reduced pressure. The residue was diluted with ethyl acetate (10 mL). Then the organic layer was washed with water (2×5 mL), brine solution (1×5 mL), dried over $Na_2SO_4$, filtered and concentrated under reduced pressure to afford the crude product 101C (brown liquid, 30 mg, 0.066 mmol, 78% yield). LCMS Anal. Calc'd $C_{26}H_{33}N_3O_4$ 451.5, found [M−H] 450.5, Tr=1.49 min (Method AY). The crude product was taken to next step without further purification.

Example 101 Diastereomer 1. (S)-3-(3-((4-cyanophenyl)amino)-4-((S)-1-morpholinopropyl)phenyl)-4-methoxybutanoic Acid (Absolute and Relative Stereochemistry not Determined)

To a stirred solution of 101C (30 mg, 0.066 mmol) in a mixture of THF (1 mL), MeOH (1 mL) and $H_2O$ (0.5 mL) was added lithium hydroxide (12.73 mg, 0.531 mmol) and stirred at room temperature for 12 h. The reaction mixture was concentrated to dryness. The residue was dissolved in water (4 mL), acidified with citric acid solution and extracted with ethyl acetate (2×10 mL). The combined organic layer was dried over sodium sulfate, filtered and concentrated under reduced pressure. The crude material was purified via preparative LC/MS to give Example 101 Diastereomer 1 (pale yellow solid, 25 mg, 0.057 mmol, 86%). LC-MS Anal. Calc'd for $C_{25}H_{31}N_3O_4$ 437.5, found [M+H] 438.1, $T_r$=1.46 min (Method O). $^1$H NMR (400 MHz, MeOD) δ 7.53 (d, J=8.80 Hz, 2H), 7.30 (s, 1H), 7.19 (d, J=8.00 Hz, 1H), 7.05 (d, J=8.80 Hz, 2H), 7.00 (d, J=8.00 Hz, 1H), 3.37-3.36 (m, 1H), 3.54-3.59 (m, 2H), 3.34-3.37 (m, 4H), 2.77-2.82 (m, 1H), 2.57-2.60 (m, 3H), 2.43-2.45 (m, 2H), 1.99-2.01 (m, 1H), 1.63-1.67 (m, 1H), 0.67 (t, J=7.20 Hz, 3H), (4 proton is buried under the solvent residual peak).

Example 101 Diastereomer 2. (S)-3-(3-((4-cyanophenyl)amino)-4-((R)-1-morpholinopropyl)phenyl)-4-methoxybutanoic Acid (Absolute and Relative Stereochemistry not Determined)

Example 101 Diastereomer 2 was prepared from 101B Diastereomer 2 following the procedure described for the synthesis of Example 101 Diastereomer 1. LC-MS Anal. Calc'd for $C_{25}H_{31}N_3O_4$ 437.5, found [M+H] 438.1, $T_r$=1.46 min (Method O). $^1$H NMR (400 MHz, MeOD) δ 7.53 (d, J=8.80 Hz, 2H), 7.30 (s, 1H), 7.19 (d, J=8.00 Hz, 1H), 7.05 (d, J=8.80 Hz, 2H), 7.00 (d, J=8.00 Hz, 1H), 3.74-3.80 (m, 4H), 3.54-3.59 (m, 2H), 3.34-3.37 (m, 4H), 2.77-2.82 (m, 1H), 2.57-2.60 (m, 3H), 2.43-2.45 (m, 2H), 1.99-2.01 (m, 1H), 1.63-1.67 (m, 1H), 0.67 (t, J=7.20 Hz, 3H), (one proton is buried under the solvent residual peak).

Example 102-106

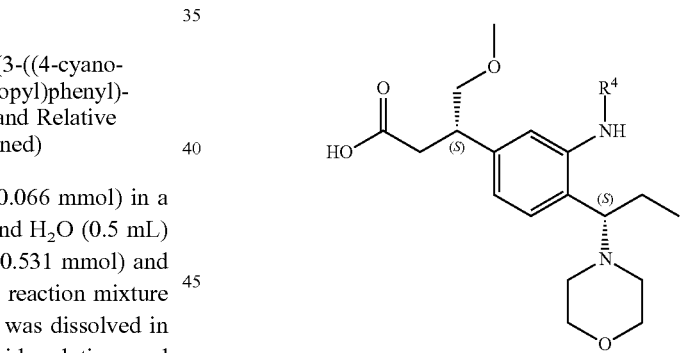

Examples 102-106 were prepared from 101B Diastereomer 1 and corresponding aryl halides following the procedure described for the synthesis of Example 101 Diastereomer 1.

| Ex. No. | Name | $R^4$ | Tr min | Method | (M + H) |
|---|---|---|---|---|---|
| 102 | (S)-3-(3-((2-ethylpyrimidin-5-yl)amino)-4-((S)-1-morpholinopropyl)phenyl)-4-methoxybutanoic acid (absolute and relative stereochemistry not determined) | 2-ethylpyrimidin-5-yl | 1.25 | O | 443.1 |

-continued

| Ex. No. | Name | R⁴ | Tr min | Method | (M + H) |
|---|---|---|---|---|---|
| 103 | (S)-3-(3-((2-ethoxypyrimidin-5-yl)amino)-4-((S)-1-morpholinopropyl)phenyl)-4-methoxybutanoic acid (absolute and relative stereochemistry not determined) | 2-ethoxypyrimidin-5-yl | 1.37 | O | 459.1 |
| 104 | (S)-4-methoxy-3-(3-((6-(methoxymethyl)pyridin-3-yl)amino)-4-((S)-1-morpholinopropyl)phenyl)butanoic acid (absolute and relative stereochemistry not determined) | 6-(methoxymethyl)pyridin-3-yl | 1.25 | O | 458.1 |
| 105 | (S)-3-(3-((4-chlorophenyl)amino)-4-((S)-1-morpholinopropyl)phenyl)-4-methoxybutanoic acid (absolute and relative stereochemistry not determined) | 4-chlorophenyl | 1.58 | O | 447.2 |
| 106 | (S)-3-(3-((4-fluorophenyl)amino)-4-((S)-1-morpholinopropyl)phenyl)-4-methoxybutanoic acid (absolute and relative stereochemistry not determined) | 4-fluorophenyl | 1.70 | O | 344.1 |

Example 107-111

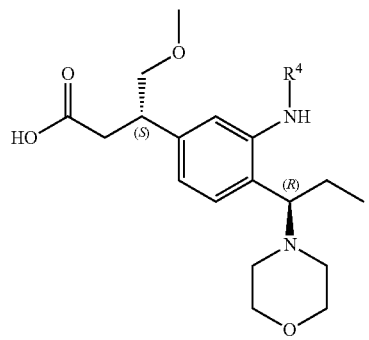

Examples 107-111 were prepared from 101B Diastereomer 2 and corresponding aryl halides following the procedure described for the synthesis of Example 101 Diastereomer 1.

| Ex. NO | Name | R⁴ | Tr min | Method | (M + H) |
|---|---|---|---|---|---|
| 107 | (S)-3-(3-((2-ethylpyrimidin-5-yl)amino)-4-((R)-1-morpholinopropyl)phenyl)-4-methoxybutanoic acid (absolute and relative stereochemistry not determined) | 2-ethylpyrimidin-5-yl | 1.23 | O | 443.1 |
| 108 | (S)-3-(3-((2-ethoxypyrimidin-5-yl)amino)-4-((R)-1-morpholinopropyl)phenyl)-4-methoxybutanoic acid (absolute and relative stereochemistry not determined) | 2-ethoxypyrimidin-5-yl | 1.36 | O | 459.1 |

-continued

| Ex. NO | Name | R⁴ | Tr min | Method | (M + H) |
|---|---|---|---|---|---|
| 109 | (S)-4-methoxy-3-(3-((6-(methoxymethyl)pyridin-3-yl)amino)-4-((R)-1-morpholinopropyl)phenyl) butanoic acid (absolute and relative stereochemistry not determined) | 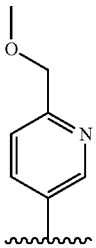 [SMILES: *c1ccc(COC)nc1] | 1.25 | O | 458.1 |
| 110 | (S)-3-(3-((4-chlorophenyl)amino)-4-((R)-1-morpholinopropyl)phenyl)-4-methoxybutanoic acid (absolute and relative stereochemistry not determined) | 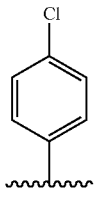 | 1.58 | O | 447.2 |
| 111 | (S)-3-(3-((4-fluorophenyl)amino)-4-((R)-1-morpholinopropyl)phenyl)-4-methoxybutanoic acid (absolute and relative stereochemistry not determined) | 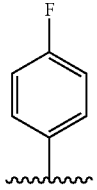 | 1.69 | O | 344.1 |

Example 112

(R)-3-(3-((4-chlorophenyl)amino)-5-((S)-ethoxy(4-fluorophenyl)methyl)phenyl)pentanoic Acid (S)-3-(3-((4-chlorophenyl)amino)-5-((S)-ethoxy(4-fluorophenyl)methyl)phenyl)pentanoic Acid (Absolute and Relative Stereochemistry not Determined)

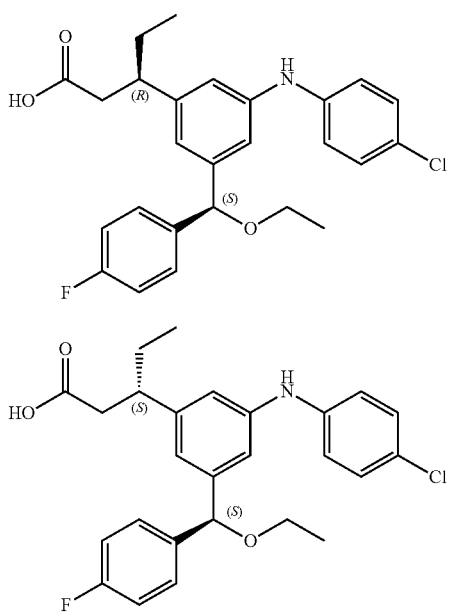

112A. (3-bromo-5-nitrophenyl)(4-fluorophenyl)methanol

To a stirred solution of 3-bromo-5-nitrobenzaldehyde (5 g, 21.74 mmol) in dry THF (50 mL), 4-fluorophenylmagnesium bromide (1 molar THF solution) (26.1 mL, 26.1 mmol) was added slowly in 15 min at −78° C. Reaction was stirred for 60 minutes at same temperature, then quenched with satd. aq. NH₄Cl solution at −78° C. Aqueous layer was extracted with EtOAc (2×100 mL). The combined organic layer was dried over anhydrous sodium sulfate, filtered and concentrated under reduced pressure to give the crude sample which was purified via flash chromatography to afford 112A (pale yellow oil, 4 g, 11.65 mmol, 53.6% yield). ¹H NMR (400 MHz, DMSO-$d_6$) δ 8.25-8.23 (m, 2H), 8.03-8.02 (m, 1H), 7.49-7.46 (m, 2H), 7.19-7.15 (m, 2H), 6.40 (d, J=4.00 Hz, 1H), 5.92 (d, J=4.00 Hz, 1H).

112B. 1-bromo-3-(ethoxy(4-fluorophenyl)methyl)-5-nitrobenzene

To a stirred solution of 60% w/w NaH in mineral oil (0.368 g, 9.20 mmol) in dry DMF (15 mL) was added 112A (2 g, 6.13 mmol) at 0° C. and stirred for 5 min. The reaction mixture was cooled to 0° C. Ethyl iodide (0.743 mL, 9.20 mmol) was added slowly and stirred for another 30 minutes at room temperature. The reaction mixture was quenched with ice water at 0° C. and diluted with EtOAc (50 mL). The organic layer separated and the aqueous layer was extracted with EtOAc (50 mL). The combined organic layer was dried over anhydrous sodium sulfate, filtered and concentrated under reduced pressure to give the crude sample which was purified via flash chromatography to afford 112B (pale yellow oil, 1.65 g, 4.43 mmol, 72.2% yield). ¹H NMR (400 MHz, DMSO-$d_6$) δ 8.27-8.26 (m, 1H), 8.19-8.18 (m, 1H), 8.05-8.01 (m, 1H), 7.49-7.45 (m, 2H), 7.22-7.15 (m, 2H), 5.70 (s, 1H), 3.46 (q, J=6.80 Hz, 2H), 5.20 (t, J=6.80 Hz, 3H).

112C. 3-bromo-5-(ethoxy(4-fluorophenyl)methyl)aniline (Absolute Stereochemistry not Determined)

To a stirred solution of 112B (0.85 g, 2.40 mmol) in AcOH (15 mL), Iron (0.670 g, 12.00 mmol) powder was added at 0° C. The reaction mixture was stirred at room temperature for 2 h. Reaction mixture was concentrated under reduced pressure and the crude material was poured into satd. Na₂CO₃ solution which was extracted with EtOAc (2×50 mL). The combined organic layer was dried over anhydrous sodium sulfate, filtered and concentrated under reduced pressure to give the crude sample which was purified via flash chromatography to give 112C (Racemate).

Chiral separation of Racemate 112C gave Enantiomer 1 and Enatiomer 2 as single Enantiomer (Method BT). Enantiomer 1, Tr=7.7 min and Enantiomer 2, Tr=9.44 min.

112C Enantiomer 1. (pale yellow oil, 0.4 g, 1.172 mmol, 48.8% yield) LC-MS Analysis Calc'd for $C_{15}H_{15}BrFNO$ 324.1, found [M+2] 326.3, $T_r$=1.05 min (Method BC).

112C Enantiomer 2. (pale yellow oil, 0.4 g, 1.172 mmol, 48.8% yield) LC-MS Analysis Calc'd for $C_{15}H_{15}BrFNO$ 324.1, found [M+2] 326.3, $T_r$=1.05 min (Method BC).

112D. (E)-methyl 3-(3-amino-5-(ethoxy(4-fluorophenyl)methyl)phenyl)pent-2-enoate (Absolute and Relative Stereochemistry not Determined)

To a stirring solution of 112C Enantiomer 1 (0.2 g, 0.617 mmol) in DMF (2 mL) were added (E)-methyl pent-2-enoate (0.176 g, 1.542 mmol), tetrabutylammonium bromide (0.040 g, 0.123 mmol) and TEA (0.258 mL, 1.851 mmol). Argon gas was purged through the solution for 20 min. Then dichlorobis(tri-o-tolylphosphine)palladium(II) (0.024 g, 0.031 mmol) was added and the reaction mixture was heated at 120° C. for 16 h in a sealed vessel. The reaction mixture was filtered through Celite pad and rinsed with EtOAc (50 mL). The organic layer was washed with water (20 mL) followed by brine solution (20 mL), dried over anhydrous sodium sulfate, filtered and concentrated under reduced pressure to give the crude sample which was purified via flash chromatography to afford 112D (pale yellow oil, 0.14 g, 0.313 mmol, 50.8% yield). LC-MS Analysis Calc'd for $C_{21}H_{24}FNO_3$ 357.1, found [M+H] 358.2, $T_r$=1.48 min (Method BA).

112E. methyl 3-(3-amino-5-(ethoxy(4-fluorophenyl) methyl)phenyl)pentanoate (Absolute and Relative Stereochemistry not Determined)

To a solution of 112D (0.12 g, 0.336 mmol) in MeOH (2 mL) was added Pd/C (10%) (0.014 g, 0.013 mmol). Then the reaction mixture was subjected to 15 psi of hydrogen pressure for 1 h at RT. The reaction mixture was filtered through Celite pad and the residue on the pad was thoroughly rinsed with MeOH (3×10 mL). The combined filtrate was concentrated under reduced pressure to afford 112E (solid, 0.09 g, 0.225 mmol, 67.1% yield). LC-MS Analysis Calc'd for $C_{21}H_{26}FNO_3$ 359.1, found [M+H] 360.5, $T_r$=1.61 min (Method T).

Example 112. 3-(3-((4-chlorophenyl)amino)-5-(ethoxy(4-fluorophenyl)methyl)phenyl)pentanoic Acid (Absolute and Relative Stereochemistry not Determined)

To a stirring solution of 112E (0.09 g, 0.250 mmol) in 1,4-Dioxane (2 mL) was added 1-bromo-4-chlorobenzene (0.072 g, 0.376 mmol), 4,5-bis(diphenylphosphino)-9,9-dimethylxanthene (0.029 g, 0.050 mmol), sodium tert-butoxide (0.072 g, 0.751 mmol). Argon was purged through reaction mixture for 10 min. Then bis(dibenzylideneacetone)palladium (7.20 mg, 0.013 mmol) was added and heated at 110° C. for 16 h in a sealed tube. The reaction mixture was poured into water (20 mL), extracted with EtOAc (2×25 mL). The combined organic layer was washed with brine solution (25 mL), dried over anhydrous sodium sulfate, filtered and concentrated under reduced pressure to afford Example 112 (Diastereomeric mixture).

Chiral separation of Example 112 Diastereomeric mixture gave Diastereomer 1, Tr=6.29 min and Diastereomer 2, Tr=7.39 min. as single diastereomers (Method BT). Example 112 Diastereomer 1 (off-white solid, 0.015 g, 0.033 mmol, 13% yield). LC-MS Analysis Calc'd for $C_{26}H_{27}C_1FNO_3$ 455.1, found [M+H] 456.1, $T_r$=2.340 min (Method O). $^1$H NMR (400 MHz, DMSO-$d_6$) δ 8.86 (s, 1H), 8.34 (s, 1H), 7.90 (s, 1H), 7.37-7.35 (m, 2H), 7.23-7.16 (m, 2H), 7.14-7.08 (m, 2H), 7.00-6.97 (m, 1H), 6.78-6.74 (m, 2H), 4.55 (s, 1H), 2.86-2.82 (m, 2H), 2.60-2.58 (m, 1H), 2.42-2.40 (m, 1H), 1.53-1.48 (m, 2H), 1.17 (t, J=7.20 Hz, 3H), 0.82-0.81 (m, 1H), 0.70 (t, J=7.60 Hz, 3H).

Example 112 Diastereomer 2 (off-white solid, 0.015 g, 0.033 mmol, 13% yield). LC-MS Analysis Calc'd for $C_{26}H_{27}C_1FNO_3$ 455.1, found [M+H] 456.1, $T_r$=2.349 min (Method O). $^1$H NMR (400 MHz, DMSO-$d_6$) δ 8.17 (s, 1H), 7.36-7.34 (m, 1H), 7.25-7.16 (m, 4H), 7.04-6.98 (m, 4H), 6.72-6.70 (m, 1H), 4.74 (s, 1H), 2.82-2.78 (m, 2H), 2.55-2.52 (m, 1H), 2.42-2.40 (m, 1H), 1.61-1.38 (m, 3H), 1.09-1.06 (m, 3H), 0.76-0.75 (m, 1H), 0.72 (t, J=7.20 Hz, 3H).

Example 113

(R)-3-(3-((4-chlorophenyl)amino)-5-((R)-ethoxy(4-fluorophenyl)methyl)phenyl)pentanoic Acid (S)-3-(3-((4-chlorophenyl)amino)-5-((R)-ethoxy(4-fluorophenyl)methyl)phenyl)pentanoic Acid (Absolute and Relative Stereochemistry not Determined)

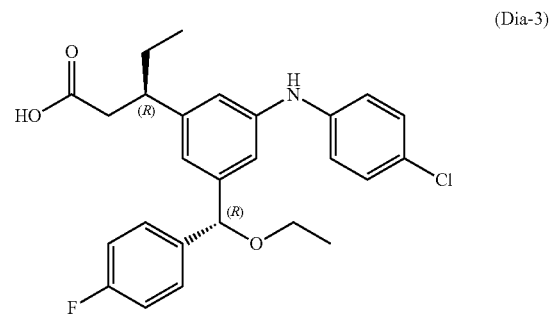

(Dia-3)

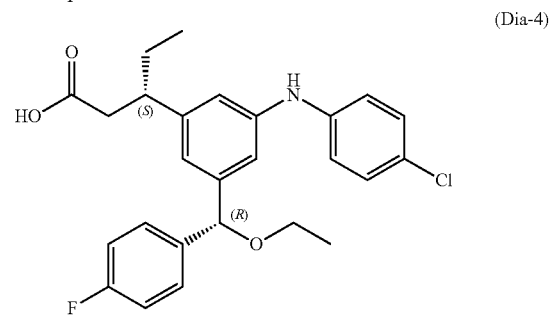

(Dia-4)

113A. (E)-methyl 3-(3-amino-5-(ethoxy(4-fluorophenyl)methyl)phenyl)pent-2-enoate (Absolute and Relative Stereochemistry not Determined)

To a stirring solution of 113C Enantiomer 2 (0.4 g, 1.234 mmol) in DMF (5 mL) were added (E)-methyl pent-2-enoate (0.176 g, 1.542 mmol), tetrabutylammonium bromide (0.040 g, 0.123 mmol) and TEA (0.352 mL, 3.08 mmol). Argon gas was purged through the solution for 20 min. Then dichlorobis(tri-o-tolylphosphine)palladium(II) (0.048 g, 0.062 mmol) was added and heated at 120° C. for 16 h in a sealed vessel. The reaction mixture was filtered through Celite pad and rinsed with EtOAc (50 mL). The organic layer was washed with water (20 mL) followed by brine solution (20 mL), dried over anhydrous sodium sulfate, filtered and concentrated under reduced pressure to give the crude sample which was purified via flash chromatography to afford 113A (pale yellow oil, 0.25 g, 0.63 mmol, 51.0% yield). LC-MS Analysis Calc'd for $C_{21}H_{24}FNO_3$ 357.1, found [M+H] 358.2, $T_r$=0.83 min (Method BC).

113B. methyl 3-(3-amino-5-(ethoxy(4-fluorophenyl) methyl)phenyl)pentanoate (Absolute and Relative Stereochemistry not Determined)

To a solution of 113A (0.25 g, 0.699 mmol) in MeOH (2 mL) was added Pd/C (10%) (0.003 g, 0.028 mmol). Then the reaction mixture was subjected to 15 psi of hydrogen pressure for 1 h at RT. The reaction mixture was filtered through Celite pad and the residue on the pad was thoroughly rinsed with MeOH (3×10 mL). The combined filtrate was concentrated under reduced pressure to afford 113B (solid, 0.18 g, 0.416 mmol, 68.0% yield). LC-MS Analysis Calc'd for $C_{21}H_{26}FNO_3$ 359.1, found [M+H] 360.5, $T_r$=0.84 min (Method BC).

Example 113. 3-(3-((4-chlorophenyl)amino)-5-(ethoxy(4-fluorophenyl)methyl)phenyl)pentanoic Acid (Absolute and Relative Stereochemistry not Determined)

To a stirring solution of 136B (0.075 g, 0.209 mmol) in 1,4-Dioxane (2 mL) was added 1-bromo-4-chlorobenzene (0.060 g, 0.313 mmol), 4,5-bis(diphenylphosphino)-9,9-dimethylxanthene (0.024 g, 0.042 mmol), sodium tert-butoxide (0.060 g, 0.626 mmol). Argon was purged through reaction mixture for 10 min. Then bis(dibenzylideneacetone)palladium (12 mg, 0.021 mmol) was added and the reaction mixture was heated at 110° C. for 16 h in a sealed tube. The reaction mixture was poured into water (20 mL), extracted with EtOAc (2×25 mL). The combined organic layer was washed with brine solution (25 mL), dried over anhydrous sodium sulfate, filtered and concentrated under reduced pressure to afford Example 113 (Diastereomeric mixture).

Chiral separation of Example 113 (Diastereomeric mixture) gave Diastereomer 3, Tr=5.32 min and Diastereomer 4, Tr=6.38 min as single diastereomers (Method BS).

Example 113 Diastereomer 3 (off-white solid, 0.015 g, 0.033 mmol, 13% yield). LC-MS Analysis Calc'd for $C_{26}H_{27}C_1FNO_3$ 455.1, found [M+H] 456.2, $T_r$=2.244 min (Method O). $^1$H NMR (400 MHz, DMSO-$d_6$) δ 8.27 (s, 1H), 7.38-7.36 (m, 2H), 7.22 (d, J=8.40 Hz, 2H), 7.16-7.12 (m, 2H), 6.98 (d, J=8.80 Hz, 2H), 6.83 (s, 1H), 6.78 (s, 1H), 6.73 (s, 1H), 5.35 (s, 1H), 2.85-2.75 (m, 1H), 2.60-2.55 (m, 2H), 2.40-2.36 (m, 1H), 1.67-1.55 (m, 1H), 1.51-1.41 (m, 1H), 1.17 (t, J=6.80 Hz, 3H), 1.01 (t, J=7.20 Hz, 1H), 0.70 (t, J=7.20 Hz, 3H).

Example 113 Diastereomer 4 (off-white solid, 0.015 g, 0.033 mmol, 13% yield). LC-MS Analysis Calc'd for $C_{26}H_{27}C_1FNO_3$ 455.1, found [M+H] 456.2, $T_r$=2.242 min (Method O). $^1$H NMR (400 MHz, DMSO-$d_6$) δ 8.27 (s, 1H), 7.35-7.34 (m, 2H), 7.22 (d, J=8.80 Hz, 2H), 7.17-7.12 (m, 2H), 7.98 (d, J=8.80 Hz, 2H), 6.83 (s, 1H), 6.78 (s, 1H), 6.73 (s, 1H), 5.35 (s, 1H), 2.82-2.82 (m, 2H), 2.62-2.55 (m, 1H), 2.41-2.35 (m, 1H), 1.66-1.55 (m, 1H), 1.51-1.42 (m, 1H), 1.16 (t, J=6.80 Hz, 3H), 1.02 (t, J=7.20 Hz, 1H), 0.70 (t, J=7.20 Hz, 3H).

Example 114

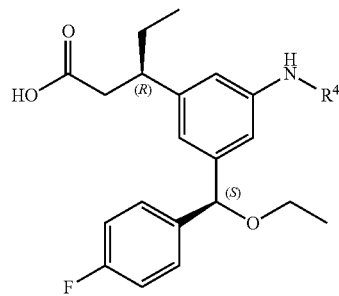

Example 114 Diastereomer 1 was prepared from 135C Enantiomer 1 and 6-bromo-2-methylbenzo[d]thiazole following the procedure described for the synthesis of Example 113 Diastereomer 1.

| Ex. No. | Name | R⁴ | Tr min | Method | (M + H) |
|---|---|---|---|---|---|
| 114 | (R)-3-(3-((S)-ethoxy(4-fluorophenyl)methyl)-5-((2-methylbenzo[d]thiazol-6-yl)amino)phenyl)pentanoic acid (absolute and relative stereochemistry not determined) | 2-methylbenzo[d]thiazol-6-yl | 1.934 | O | 493.2 |

Example 115

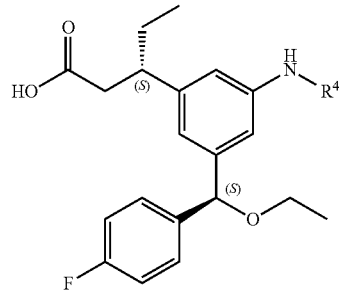

Example 115 Diastereomer 2 were prepared from 113C Enantiomer 1 and 6-bromo-2-methylbenzo[d]thiazole following the procedure described for the synthesis of Example 113 Diastereomer 2

| Ex. No. | Name | R⁴ | Tr min | Method | (M + H) |
|---|---|---|---|---|---|
| 115 | (S)-3-(3-((S)-ethoxy(4-fluorophenyl)methyl)-5-((2-methylbenzo[d]thiazol-6-yl)amino)phenyl)pentanoic acid (absolute and relative stereochemistry not determined) | 2-methylbenzo[d]thiazol-6-yl | 1.936 | O | 493.2 |

Example 116

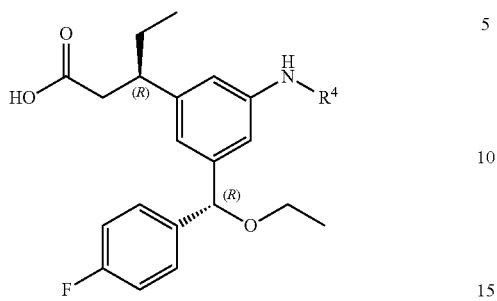

Example 116 Diastereomer 3 were prepared from 113C Enantiomer 2 and 6-bromo-2-methylbenzo[d]thiazole following the procedure described for the synthesis of Example 114 Diastereomer 3.

| Ex. No. | Name | R⁴ | Tr min | Method | (M + H) |
|---|---|---|---|---|---|
| 116 | (R)-3-(3-((R)-ethoxy(4-fluorophenyl)methyl)-5-((2-methylbenzo[d]thiazol-6-yl)amino)phenyl)pentanoic acid (absolute and relative stereochemistry not determined) | 2-methylbenzo[d]thiazol-6-yl | 1.949 | Method O | 493.2 |

Example 117

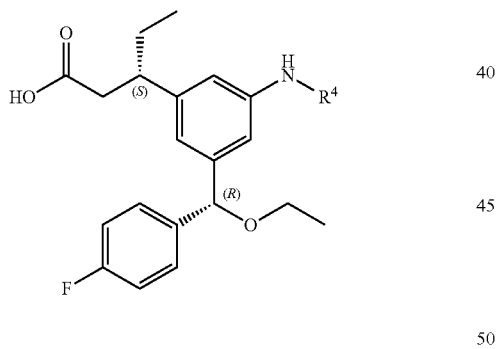

Example 117 Diastereomer 4 were prepared from 113C Enantiomer 2 and 6-bromo-2-methylbenzo[d]thiazole following the procedure described for the synthesis of Example 114 Diastereomer 4.

| Ex. No. | Name | R⁴ | Tr min | Method | (M + H) |
|---|---|---|---|---|---|
| 117 | (S)-3-(3-((R)-ethoxy(4-fluorophenyl)methyl)-5-((2-methylbenzo[d]thiazol-6-yl)amino)phenyl)pentanoic acid (absolute and relative stereochemistry not determined) | 2-methylbenzo[d]thiazol-6-yl | 1.925 | Method O | 493.2 |

Example 118

(Diastereomer 1, 2, 3, & 4) (R)-3-(3-((2-ethoxypyrimidin-5-yl)amino)-4-((R)-1-morpholinopropyl)phenyl)pentanoic Acid (S)-3-(3-((2-ethoxypyrimidin-5-yl)amino)-4-((R)-1-morpholinopropyl)phenyl)pentanoic Acid (R)-3-(3-((2-ethoxypyrimidin-5-yl)amino)-4-((S)-1-morpholinopropyl)phenyl)pentanoic Acid (S)-3-(3-((2-ethoxypyrimidin-5-yl)amino)-4-((S)-1-morpholinopropyl)phenyl)pentanoic Acid (Absolute and Relative Stereochemistry not Determined)

(Dia-1)

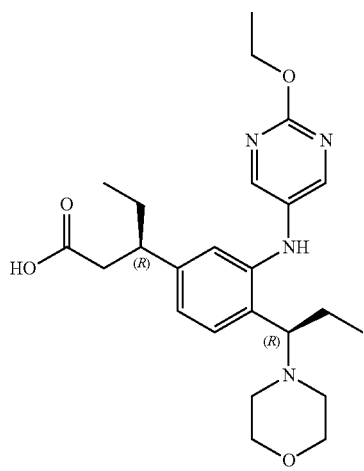

(Dia-2)

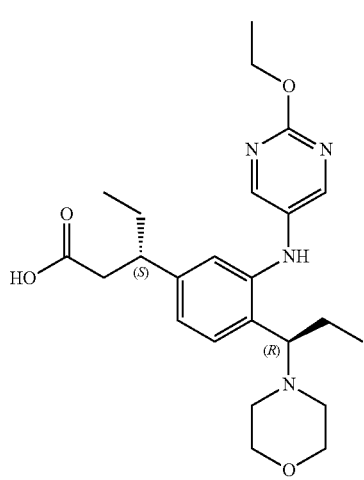

(Dia-3)

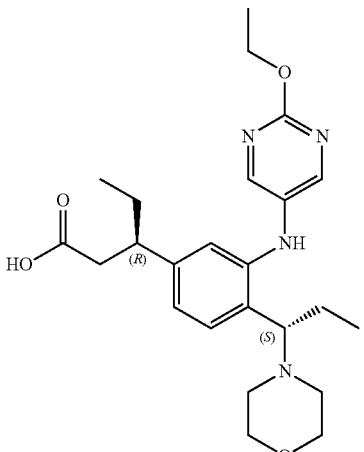

(Dia-4)

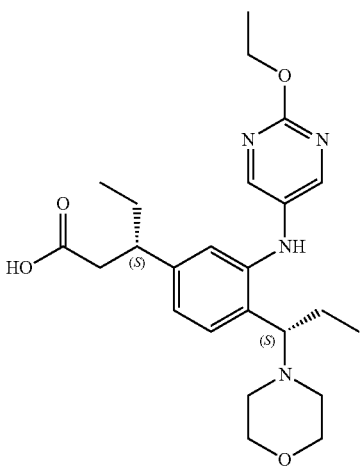

118A. methyl 2-amino-4-bromobenzoate

Thionyl chloride (30.4 mL, 417 mmol) was added drop wise to a solution of 2-amino-4-bromobenzoic acid (30 g, 139 mmol) in MeOH (300 mL) at 0° C. After complete addition the reaction mixture was heated at 60° C. for 24 h. The reaction mixture was concentrated under reduced pressure. The crude was partitioned between water (500 mL) and EtOAc (500 mL). The organic layer was washed with 10% NaHCO$_3$ solution (100 mL), followed by brine solution (100 mL), dried over anhydrous sodium sulfate, filtered and concentrated under reduced pressure to give the crude sample which was purified by flash chromatography to afford 118A (off-white solid, 15 g, 64.5 mmol, 46.5% yield). $^1$H NMR (400 MHz, DMSO-d$_6$) δ 7.60 (d, J=8.40 Hz, 1H), 7.01 (d, J=2.00 Hz, 1H), 6.82 (s, 2H), 6.67 (dd, J=2.00, 8.80 Hz, 1H), 3.78 (s, 3H).

118B. methyl 4-bromo-2-((tert-butoxycarbonyl)amino)benzoate

To a solution of 118A (7 g, 30.4 mmol) in DCM (100 mL) was added Boc$_2$O (7.77 mL, 33.5 mmol) and TEA (12.72 mL, 91 mmol) followed by DMAP (3.72 g, 30.4 mmol) under nitrogen atmosphere. Then the reaction was stirred at room temperature for 16 h. The reaction mixture was diluted with 200 mL of DCM, washed with water (100 mL), followed by brine solution (50 mL), dried over anhydrous sodium sulfate, filtered and concentrated under reduced pressure to give the crude sample which was purified by flash chromatography to afford 118B (white solid, 5.8 g, 16.69 mmol, 54.8% yield). 1H NMR (300 MHz, DMSO-$d_6$) δ 10.18 (s, 1H), 8.43 (d, J=1.80 Hz, 1H), 7.85 (d, J=8.40 Hz, 1H), 7.32 (dd, J=1.80, 8.55 Hz, 1H), 3.86 (s, 3H), 1.48 (s, 9H).

118C. tert-butyl (5-bromo-2-(hydroxymethyl)phenyl)carbamate

To a solution of 118B (5.8 g, 17.57 mmol) in MeOH (14 mL) added NaBH$_4$ (3.32 g, 88 mmol) at 0° C. and stirred at room temperature for 1 h. Then the reaction mixture was cooled to 0° C. and quenched with ice water, extracted with EtOAc (2×100 mL). The combined organic layer was washed with brine solution (50 mL), dried over anhydrous sodium sulfate, filtered and concentrated under reduced pressure to give the crude sample which was purified by flash chromatography to afford 118C (pale yellow oil, 5 g, 15.72 mmol, 89% yield). $^1$H NMR (400 MHz, DMSO-$d_6$) δ 8.67 (s, 1H), 7.83 (d, J=1.60 Hz, 1H), 7.27-7.22 (m, 2H), 5.52 (s, 1H), 4.49-4.48 (m, 2H), 1.47 (s, 9H).

118D. tert-butyl (5-bromo-2-formylphenyl)carbamate

To a solution of 118C (5.5 g, 18.20 mmol) in DCM (100 mL) was added Dess-Martin periodinane (11.58 g, 27.3 mmol) and stirred for 1 h at RT. The reaction mixture was filtered through Celite bed, and the Celite bed rinsed with DCM (200 ml). The filtrate was washed with NaHCO$_3$ solution (100 mL), dried over anhydrous sodium sulfate, filtered and concentrated under reduced pressure to give the crude sample which was purified by flash chromatography to afford 118D (pale yellow oil, 4 g, 12.66 mmol, 69.6% yield). $^1$H NMR (300 MHz, DMSO-$d_6$) δ 10.36 (s, 1H), 9.92 (s, 1H), 8.41 (d, J=1.50 Hz, 1H), 7.82 (d, J=8.40 Hz, 1H), 7.48-7.45 (m, 1H), 1.50 (s, 9H).

118E. tert-butyl (5-bromo-2-(1-hydroxypropyl)phenyl)carbamate

To a stirred solution of 118D (1.5 g, 5.00 mmol) in THF (15 mL) was cooled to 0° C. and added ethylmagnesium bromide (1.0 M in diethylether, 12.49 mL, 12.49 mmol). Then the reaction was stirred at −78° C. for 1 h. The reaction mixture was quenched with satd. NH$_4$Cl solution, extracted with EtOAc (2×100 mL). The combined organic layer was washed with brine solution (50 mL), dried over anhydrous sodium sulfate, filtered and concentrated under reduced pressure to give the crude sample which was purified by flash chromatography to afford 118E (pale yellow oil, 1.6 g, 4.60 mmol, 92% yield). $^1$H NMR (400 MHz, DMSO-$d_6$) δ 9.01 (s, 1H), 7.92 (d, J=1.60 Hz, 1H), 7.21-7.15 (m, 2H), 5.90 (d, J=4.00 Hz, 1H), 4.61-4.60 (m, 1H), 1.63-1.59 (m, 2H), 1.50 (s, 9H), 0.84 (t, J=7.20 Hz, 3H).

118F. tert-butyl (5-bromo-2-(1-morpholinopropyl)phenyl)carbamate

To a stirred solution of 118E (0.5 g, 1.514 mmol) in DCM (10 mL) was added TEA (0.422 mL, 3.03 mmol), then added methanesulfonyl chloride (0.142 mL, 1.817 mmol) at 0° C. slowly and allowed to stir at RT for 1 h. The reaction mixture was concentrated and the crude material was taken in morpholine (0.923 mL, 10.60 mmol) and heated at 70° C. for overnight. The reaction mixture was poured into water upon cooled to room temperature, extracted with DCM (2×50 mL). The combined organic layer was washed with brine (50 mL), dried over anhydrous sodium sulfate, filtered and concentrated under reduced pressure to give the crude sample which was purified by flash chromatography to afford 118F (pale yellow oil, 0.5 g, 1.190 mmol, 79% yield). $^1$H NMR (400 MHz, DMSO-$d_6$) δ 8.12 (d, J=2.00 Hz, 1H), 7.15-7.13 (m, 1H), 7.04 (d, J=8.00 Hz, 1H), 3.60-3.55 (m, 4H), 2.60-2.56 (m, 2H), 2.32-2.26 (m, 2H), 1.91-1.87 (m, 1H), 1.58-1.51 (m, 2H), 1.46 (s, 9H), 0.60 (t, J=7.20 Hz, 3H).

118G. tert-butyl(5-(5,5-dimethyl-1,3,2-dioxaborinan-2-yl)-2-(1-morpholinopropyl) phenyl)carbamate A mixture of 118F (0.5 g, 1.252 mmol), bis(neopentyl glycolato)diboron (0.368 g, 1.628 mmol) and potassium acetate (0.369 g, 3.76 mmol) in 1,4-Dioxane (10 mL), was purged with Argon for 20 minutes at room temperature in a sealable flask, then added the PdCl$_2$(dppf)-CH$_2$Cl$_2$ Adduct (0.031 g, 0.038 mmol). Then the flask was sealed and the reaction was heated at 80° C. for 6 hours. The reaction mixture was cooled to room temperature and poured into water (50 mL). The aqueous layer was extracted with EtOAc (2×50 mL). The combined organic layer was washed with brine (25 mL), dried over anhydrous sodium sulfate, filtered and concentrated under reduced pressure to give the crude sample which was purified by flash chromatography to afford 118G (pale yellow oil, 0.4 g, 0.879 mmol, 70.2% yield). $^1$H NMR (400 MHz, DMSO-$d_6$) δ 10.25 (s, 1H), 8.24 (s, 1H), 7.30-7.28 (m, 1H), 7.06 (d, J=7.60 Hz, 1H), 3.74 (s, 4H), 3.61-3.55 (m, 4H), 2.60-2.56 (m, 2H), 2.32-2.26 (m, 2H), 1.92-1.87 (m, 1H), 1.58-1.51 (m, 2H), 1.46 (s, 9H), 0.95 (s, 6H), 0.59 (t, J=7.60 Hz, 3H).

118H. methyl 3-(3-((tert-butoxycarbonyl)amino)-4-(1-morpholinopropyl)phenyl) pentanoate To a stirring solution of 118G (0.4 g, 0.925 mmol) and (E)-methyl pent-2-enoate (0.317 g, 2.78 mmol) in 1,4-Dioxane (10 mL) was added sodium hydroxide (0.845 mL, 0.845 mmol). Argon gas was purged through the solution for 20 min. Then chloro(1,5-cyclooctadiene)rhodium(I) dimer (9.12 mg, 0.019 mmol) was added. The reaction mixture was heated at 50° C. for 2 h in sealed vial. Reaction mixture was cooled to room temperature and quenched with acetic acid (0.048 mL, 0.833 mmol) and it was stirred for 5 minutes before partitioned between EtOAc (100 mL) and water (100 mL). Aqueous layer was extracted with ethyl acetate (50 mL). The combined organic layer was washed with brine (50 mL), dried over anhydrous sodium sulfate, filtered and concentrated under reduced pressure to give the crude sample which was purified by flash chromatography to afford 118H (yellow oil, 0.35 g, 0.725 mmol, 78% yield). LC-MS Analysis Calc'd for $C_{24}H_{38}N_2O_5$ 434.2, found [M+H] 435.2, Tr=0.85 min (Method BB).

118I. methyl 3-(3-amino-4-(1-morpholinopropyl)phenyl)pentanoate

To a solution of 118H (0.4 g, 0.920 mmol) in DCM (10 mL) was added TFA (0.709 mL, 9.20 mmol) under inert atmosphere. Then the reaction mixture was stirred for 1 h. The reaction mixture was concentrated under reduced pressure to give the crude material which was dissolved in (50 mL) DCM and washed with 10% w/w Sodium bicarbonate solution (50 mL). The combined organic phase was dried over anhydrous sodium sulfate, filtered and concentrated under reduced pressure to afford 118I (pale yellow oil, 0.25 g, 0.710 mmol, 77% yield). LC-MS Analysis Calc'd for $C_{19}H_{30}N_2O_3$ 334.2, found [M+H] 335.2, $T_r$=0.85 min (Method BC)

Example 118. 3-(3-((2-ethoxypyrimidin-5-yl) amino)-4-(1-morpholinopropyl)phenyl) pentanoic Acid (Absolute and Relative Stereochemistry not Determined)

To a solution of 118I (0.245 g, 0.537 mmol) in mixture of THF (3 mL), MeOH (3 mL) and Water (3 mL) was added LiOH.H$_2$O (0.051 g, 2.146 mmol) at RT and stirred for 16 h. The reaction mixture was concentrated under reduced pressure. The aqueous residue was acidified with saturated citric acid solution to pH ~4. The aqueous layer was extracted with EtOAc (2×50 mL). The combined organic layer was washed with brine (10 mL), dried over anhydrous sodium sulfate and concentrated under reduced pressure. The crude was separated by Prep-SFC to give Mixture A ($T_r$=6.16 min) and Mixture B ($T_r$=8.92 min) (Method EC).

The Mixture A was separated by Prep-SFC (Method DB) to afford Diastereomer 1($T_r$=3.59 min) and Diastereomer 2 ($T_r$=5.48 min).

Example 118 Diastereomer 1 (off-white solid, 12 mg, 0.027 mmol, 5.05% yield): LC-MS Analysis Calc'd for $C_{24}H_{34}N_4O_4$ 442.2, found [M+H] 443.2, $T_r$=1.683 min (Method O). 1H NMR (400 MHz, DMSO-d$_6$) δ 8.44 (s, 1H), 8.33 (s, 2H), 7.04 (d, J=7.60 Hz, 1H), 6.86 (s, 1H), 6.71 (d, J=7.20 Hz, 1H), 4.29 (q, J=6.80 Hz, 2H), 3.62 (s, 4H), 3.27-3.26 (m, 2H), 2.80-2.76 (m, 1H), 2.59-2.55 (m, 1H), 2.43-2.41 (m, 2H), 2.30-2.26 (m, 2H), 1.90-1.86 (m, 1H), 1.65-1.60 (m, 2H), 1.47-1.46 (m, 1H), 1.32 (t, J=7.20 Hz, 3H), 0.70 (t, J=7.60 Hz, 3H), 0.63 (t, J=7.60 Hz, 3H).

Example 118 Diastereomer 2 (off-white solid, 12 mg, 0.027 mmol, 5.0% yield): LC-MS Analysis Calc'd for $C_{24}H_{34}N_4O_4$ 442.2, found [M+H] 443.2, $T_r$=1.680 min (Method O). 1H NMR (400 MHz, DMSO-d$_6$) δ 8.45 (s, 1H), 8.33 (s, 2H), 7.04 (d, J=7.60 Hz, 1H), 6.86 (s, 1H), 6.70 (d, J=8.40 Hz, 1H), 4.29 (q, J=6.80 Hz, 2H), 3.62 (s, 4H), 3.27-3.26 (m, 2H), 2.80-2.76 (m, 1H), 2.59-2.55 (m, 1H), 2.43-2.41 (m, 2H), 2.30-2.26 (m, 2H), 1.90-1.86 (m, 1H), 1.65-1.60 (m, 2H), 1.47-1.46 (m, 1H), 1.32 (t, J=7.20 Hz, 3H), 0.70 (t, J=7.20 Hz, 3H), 0.63 (t, J=7.20 Hz, 3H).

The Mixture B was separated by Prep-SFC (Method BT) to afford Diastereomer 3 ($T_r$=3.17 min) and Diastereomer 4 ($T_r$=4.67 min).

Example 118 Diastereomer 3 (off-white solid, 2 mg, 0.004 mmol, 1% yield). LC-MS Analysis Calc'd for $C_{24}H_{34}N_4O_4$ 442.2, found [M+H] 443.2, $T_r$=1.682 min (Method O). 400 MHz, DMSO-d$_6$: δ 8.44 (s, 1H), 8.33 (s, 2H), 7.04 (d, J=7.20 Hz, 1H), 6.86 (s, 1H), 6.70 (d, J=7.60 Hz, 1H), 4.29 (q, J=7.20 Hz, 2H), 3.61 (s, 4H), 3.27-3.26 (m, 2H), 2.80-2.76 (m, 1H), 2.59-2.55 (m, 1H), 2.43-2.41 (m, 2H), 2.30-2.26 (m, 2H), 1.90-1.86 (m, 1H), 1.65-1.60 (m, 2H), 1.47-1.46 (m, 1H), 1.32 (t, J=6.80 Hz, 3H), 0.70 (t, J=7.60 Hz, 3H), 0.63 (t, J=7.20 Hz, 3H).

Example 118 Diastereomer 4 (off-white solid, 9 mg, 0.020 mmol, 3.79% yield). LC-MS Analysis Calc'd for $C_{24}H_{34}N_4O_4$ 442.2, found [M+H] 443.2, $T_r$=1.682 min (Method O). 1H NMR (400 MHz, DMSO-d$_6$) δ 8.44 (s, 1H), 8.33 (s, 2H), 7.05 (d, J=7.60 Hz, 1H), 6.87 (s, 1H), 6.71 (d, J=7.60 Hz, 1H), 4.29 (q, J=7.20 Hz, 2H), 3.62 (s, 4H), 3.27-3.26 (m, 2H), 2.80-2.76 (m, 1H), 2.59-2.55 (m, 1H), 2.43-2.41 (m, 2H), 2.30-2.26 (m, 2H), 1.90-1.86 (m, 1H), 1.65-1.60 (m, 2H), 1.47-1.46 (m, 1H), 1.32 (t, J=7.20 Hz, 3H), 0.70 (t, J=7.20 Hz, 3H), 0.63 (t, J=7.20 Hz, 3H).

Example 119

(R)-3-(3-((2-ethylpyrimidin-5-yl)amino)-4-((R)-1-morpholinopropyl)phenyl)pentanoic Acid (Absolute and Relative Stereochemistry not Determined)

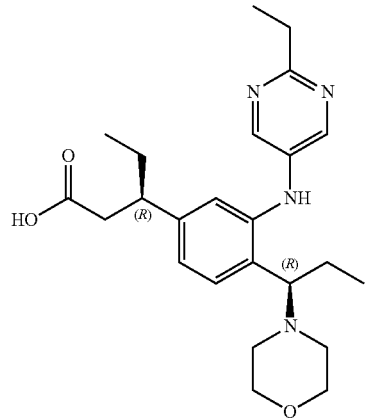

119A. methyl 3-(3-((tert-butoxycarbonyl)amino)-4-(1-morpholinopropyl)phenyl)pentanoate To a stirring solution of 118G (0.6 g, 1.388 mmol) and (E)-methyl pent-2-enoate (0.206 g, 1.804 mmol) in 1,4-Dioxane (12 mL) was added sodium hydroxide (1.249 mL, 1.249 mmol). Argon gas was purged through the solution for 20 min and chlorobis(ethylene)rhodium(1) dimer (8.10 mg, 0.021 mmol) and (S)-BINAP (0.019 g, 0.031 mmol) was added. Then the reaction mixture was heated at 50° C. for 2 h in sealed vial. Reaction mixture was cooled to room temperature and quenched with acetic acid (0.071 mL, 1.249 mmol) and it was stirred for 5 minutes before partitioned between EtOAc (100 mL) and water (100 mL). The aqueous layer was extracted with EtOAc (2×100 mL). The combined organic layer was washed with brine (50 mL), dried over anhydrous sodium sulfate, filtered and concentrated under reduced pressure to give the crude sample which was purified by flash chromatography to afford 119A (yellow oil, 0.4 g, 0.828 mmol, 59.7% yield). LC-MS Analysis Calc'd for $C_{24}H_{38}N_2O_5$ 434.5, found [M+H] 435.5, $T_r$=1.70 min (Method T)

119B. methyl 3-(3-amino-4-(1-morpholinopropyl) phenyl)pentanoate (Absolute and Relative Stereochemistry not Determined)

119A (0.4 g, 0.920 mmol) was taken in 4M HCl in 1,4-Dioxane (2.301 ml, 9.20 mmol) under inert atmosphere. Then the reaction mixture was stirred at RT for 1 h. The reaction mixture was concentrated under reduced pressure to give the crude sample which was dissolved in 50 mL of DCM and washed with Sodium bicarbonate solution (25 mL). The organic layers was dried over anhydrous sodium sulfate, filtered and concentrated under reduced pressure to afford 119B (Diastereomeric mixture).

The Diastereomeric mixture 119B was separated by Prep-SFC (Method CR) to afford Diastereomer 1($T_r$=3.17 min) and Diastereomer 2 ($T_r$=3.91 min).

119B Diastereomer 1 (0.08 g, 0.227 mmol, 24.69% yield). LC-MS Analysis Calc'd for $C_{19}H_{30}N_2O_3$ 334.2, found [M+H] 335.2, $T_r$=2.052 min (Method BB).

119B Diastereomer 2 (0.08 g, 0.227 mmol, 24.69% yield). LC-MS Analysis Calc'd for $C_{19}H_{30}N_2O_3$ 334.2, found [M+H] 335.2, $T_r$=2.057 min (Method BB)

119C. methyl 3-(3-((2-ethylpyrimidin-5-yl)amino)-4-(1-morpholinopropyl)phenyl)pentanoate (Absolute and Relative Stereochemistry not Determined)

To a stirring solution of 119B Diastereomer 1 (0.05 g, 0.149 mmol) in 1,4-Dioxane (2 mL) was added 5-bromo-2-ethylpyrimidine (0.034 g, 0.179 mmol), 4,5-bis(diphenylphosphino)-9,9-dimethylxanthene (0.017 g, 0.030 mmol), cesium carbonate (0.122 g, 0.374 mmol). Argon gas was purged through the solution for 10 min. Then bis(dibenzylideneacetone)palladium (8.60 mg, 0.015 mmol) was added. Then the reaction mixture was heated at 110° C. and stirred for 16 h in a sealed tube. The reaction mixture was poured into water (50 mL) and extracted with EtOAc (2×50 mL). The combined organic layer was dried over anhydrous sodium sulfate, filtered and concentrated under reduced pressure to afford 119C as crude (0.06 g, 0.116 mmol, 77% yield). LC-MS Analysis Calc'd for $C_{25}H_{36}N_4O_3$ 440.2, found [M+H] 441.5, $T_r$=1.49 min (Method T).

Example 119. (R)-3-(3-((2-ethylpyrimidin-5-yl)amino)-4-((R)-1-morpholinopropyl)phenyl)pentanoic Acid (Absolute and Relative Stereochemistry not Determined)

To a solution of 119C (0.06 g, 0.136 mmol) in mixture of THF (1 mL), MeOH (1 mL) and Water (1 mL) was added LiOH.$H_2O$ (0.013 g, 0.545 mmol) at RT and stirred for 16 h. The reaction mixture was concentrated under reduced pressure. The aqueous residue was acidified with saturated citric acid solution to pH ~4. The aqueous layer was extracted with EtOAc (2×50 mL). The combined organic layer was washed with brine (10 mL), dried over anhydrous sodium sulfate, filtered and concentrated under reduced pressure to give the crude which was purified by Prep-HPLC to afford Example 119 (off-white solid, 0.051 g, 0.117 mmol, 86% yield). LC-MS Analysis Calc'd for $C_{24}H_{34}N_4O_3$ 426.2, found [M+H] 427.2, $T_r$=1.492 min (Method O). 1H NMR (400 MHz, DMSO-$d_6$) δ 8.27 (s, 2H), 7.82 (s, 1H), 7.48 (d, J=8.00 Hz, 1H), 7.17-7.12 (m, 2H), 4.60-4.56 (m, 1H), 4.00-3.82 (m, 2H), 3.76-3.71 (m, 2H), 2.94-2.89 (m, 4H), 2.79 (q, J=7.60 Hz, 2H), 2.59-2.55 (m, 1H), 2.47-2.45 (m, 1H), 2.27-2.21 (m, 1H), 1.95-1.90 (m, 1H), 1.66-1.61 (m, 1H), 1.54-1.49 (m, 1H), 1.24 (t, J=7.60 Hz, 3H), 0.71 (t, J=7.20 Hz, 3H), 0.61 (t, J=7.20 Hz, 3H).

Example 120-123

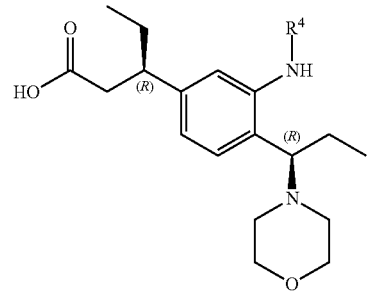

Example 120-123 were prepared from 119B Diastereomer 1 and corresponding halides following the procedure described for the synthesis of Example 119.

| Ex. No. | Name | $R^4$ | Tr min | Method | (M + H) |
|---|---|---|---|---|---|
| 120 | (R)-3-(3-((2-methylpyrimidin-5-yl)amino)-4-((R)-1-morpholinopropyl)phenyl)pentanoic acid (absolute and relative stereochemistry not determined) | | 1.338 | Method O | 413.2 |
| 121 | (R)-3-(3-((6-(methoxymethyl)pyridin-3-yl)amino)-4-((R)-1-morpholinopropyl)phenyl)pentanoic acid (absolute and relative stereochemistry not determined) | | 1.492 | Method O | 442.2 |
| 122 | (R)-3-(3-((4-cyanophenyl)amino)-4-((R)-1-morpholinopropyl)phenyl)pentanoic acid (absolute and relative stereochemistry not determined) | | 1.732 | Method O | 422.2 |
| 123 | (R)-3-(3-((4-chlorophenyl)amino)-4-((R)-1-morpholinopropyl)phenyl)pentanoic acid (absolute and relative stereochemistry not determined) | | 2.143 | Method O | 432.1 |

Example 124

(S)-3-(3-((4-cyanophenyl)amino)-4-((R)-1-morpholinopropyl)phenyl)pentanoic Acid (Absolute and Relative Stereochemistry not Determined)

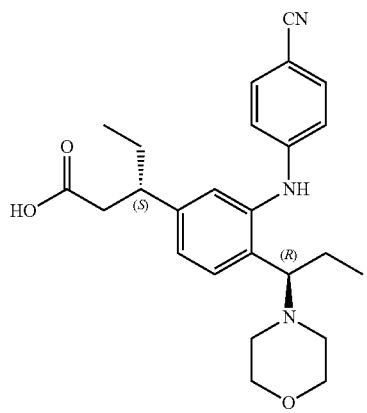

124A. methyl 3-(3-((tert-butoxycarbonyl)amino)-4-(1-morpholinopropyl)phenyl)pentanoate (Absolute and Relative Stereochemistry not Determined)

To a stirring solution of 118G (3.5 g, 8.10 mmol) and (E)-methyl pent-2-enoate (2.77 g, 24.29 mmol) in 1,4-Dioxane (70 mL) was added sodium hydroxide (7.29 mL, 7.29 mmol). Argon gas was purged through the solution for 20 min. Then chlorobis(ethylene)rhodium(1) dimer (0.047 g, 0.121 mmol) and (R)-BINAP (0.111 g, 0.178 mmol) was added. The reaction mixture was heated at 50° C. for 2 h in sealed vial. Reaction mixture was cooled to room temperature and quenched with acetic acid (0.417 mL, 7.29 mmol) and it was stirred for 5 minutes before partitioned between ethyl acetate (100 mL) and water (100 mL). The aqueous layer was extracted with ethyl acetate (2×100 mL). The combined organic layer was washed with brine (50 mL), dried over anhydrous sodium sulfate, filtered and concentrated under reduced pressure to give the crude sample was purified by flash chromatography to afford 124A (pale yellow oil, 3 g, 6.56 mmol, 81% yield). LC-MS Analysis Calc'd for $C_{24}H_{38}N_2O_5$ 434.5, found [M+H] 435.7, $T_r$=1.74 min (Method BA)

124B. methyl 3-(3-amino-4-(1-morpholinopropyl)phenyl)pentanoate (Absolute and Relative Stereochemistry not Determined)

124A (3 g, 6.90 mmol) was taken in 4M HCl in 1,4-Dioxane (17.26 ml, 69.0 mmol) under inert atmosphere. Then the reaction mixture was stirred at room temperature for 1 h. The reaction mixture was concentrated under reduced pressure to give the crude sample which was dissolved in 100 mL of DCM and washed with sodium bicarbonate solution (50 mL). The organic layers was dried over anhydrous sodium sulfate, filtered and concentrated under reduced pressure to afford 124B (Diastereomeric mixture).

The Diastereomeric mixture 124B was separated by Prep-SFC (Method CR) to afford Diastereomer 1($T_r$=2.54 min) and Diastereomer 2 ($T_r$=3.86 min).

124B Diastereomer 1. (0.98 g, 2.78 mmol, 40.30% yield). LC-MS Analysis Calc'd for $C_{19}H_{30}N_2O_3$ 334.2, found [M+H] 335.2, $T_r$=0.84 min (Method BC).

124B Diastereomer 2. (1.28 g, 3.64 mmol, 52.7% yield). LC-MS Analysis Calc'd for $C_{19}H_{30}N_2O_3$ 334.2, found [M+H] 335.2, $T_r$=0.84 min (Method BC).

124C. methyl 3-(3-((2-ethylpyrimidin-5-yl)amino)-4-(1-morpholinopropyl)phenyl)pentanoate (Absolute and Relative Stereochemistry not Determined)

To a stirring solution of 124B Diastereomer 2 (0.05 g, 0.149 mmol) in 1,4-Dioxane (2 mL) was added 4-bromobenzonitrile (0.033 g, 0.179 mmol), 4,5-bis(diphenylphosphino)-9,9-dimethylxanthene (0.017 g, 0.030 mmol), cesium carbonate (0.122 g, 0.374 mmol). Argon gas was purged through the solution for 10 min. Then bis(dibenzylideneacetone)palladium (8.60 mg, 0.015 mmol) was added. Then the reaction mixture was heated at 110° C. and stirred for 16 h in a sealed tube. The reaction mixture was poured into water (50 mL) and extracted with EtOAc (2×50 mL). The combined organic layer was dried over anhydrous sodium sulfate, filtered and concentrated under reduced pressure to afford 124C as crude (0.05 g, 0.098 mmol, 65.3% yield). LC-MS Analysis Calc'd for $C_{26}H_{33}N_3O_3$ 435.2, found [M+H] 436.5, $T_r$=1.59 min (Method T).

Example 124. (S)-3-(3-((4-cyanophenyl)amino)-4-((R)-1-morpholinopropyl)phenyl)pentanoic Acid (Absolute and Relative Stereochemistry not Determined)

To a solution of 124C (0.06 g, 0.136 mmol) in mixture of THF (1 mL), MeOH (1 mL) and Water (1 mL) was added LiOH. $H_2O$ (0.013 g, 0.545 mmol) at RT and stirred for 16 h. The reaction mixture was concentrated under reduced pressure. The aqueous residue was acidified with saturated citric acid solution to pH ~4. The aqueous layer was extracted with EtOAc (2×50 mL). The combined organic layer was washed with brine (10 mL), dried over anhydrous sodium sulfate, filtered and concentrated under reduced pressure to give the crude which was purified by Prep-HPLC to afford Example 124 (off-white solid, 0.051 g, 0.117 mmol, 86% yield). LC-MS Analysis Calc'd for $C_{25}H_{31}N_3O_3$ 421.2, found [M+H] 422.1, $T_r$=1.77 min (Method O). 1H NMR (400 MHz, DMSO-$d_6$) δ 7.56-7.55 (m, 3H), 7.25-7.20 (m, 2H), 6.80 (d, J=8.80 Hz, 2H), 3.70-3.55 (m, 4H), 2.92-2.87 (m, 4H), 2.64-2.58 (m, 3H), 2.47-2.45 (m, 1H), 2.24-2.23 (m, 1H), 1.92-1.90 (m, 1H), 1.65-1.62 (m, 1H), 1.56-1.51 (m, 1H), 0.73 (t, J=7.60 Hz, 3H), 0.59 (t, J=7.20 Hz, 3H).

Example 125

(R)-3-(3-((2-ethoxypyrimidin-5-yl)amino)-4-((S)-1-(tetrahydro-2H-pyran-4-yl)propyl)phenyl)pentanoic Acid (R)-3-(3-((2-ethoxypyrimidin-5-yl)amino)-4-((R)-1-(tetrahydro-2H-pyran-4-yl)propyl)phenyl)pentanoic Acid (Absolute and Relative Stereochemistry not Determined)

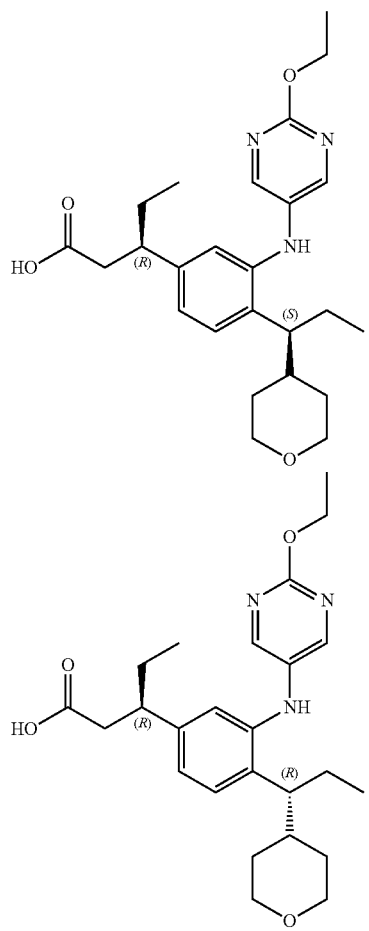

125A. methyl (R)-3-(4-bromophenyl)pentanoate (Absolute and Relative Stereochemistry not Determined)

To a stirred solution of 2-(4-bromophenyl)-4,4,5,5-tetramethyl-1,3,2-dioxaborolane (6 g, 21.20 mmol) in 1,4-Dioxane (60 mL) were added sodium hydroxide (19.08 mL, 19.08 mmol). To this argon gas was bubbled through the mixture for 15 mins and then (E)-methyl pent-2-enoate (2.420 g, 21.20 mmol), chlorobis(ethylene)rhodium(I) dimer (0.124 g, 0.318 mmol) and (S)-(−)-2,2'-bis(diphenylphosphino)-1,1'-binaphthyl (0.290 g, 0.466 mmol) were added at room temperature. Then the Argon gas was bubbled through it for 5 mins. Then the reaction mixture was stirred at room temperature for 12 h in a sealed tube. The reaction mixture was cooled to room temperature, quenched with acetic acid (1.214 mL, 21.20 mmol), stirred for 5 mins and diluted with water (100 mL). The aqueous layer was extracted with ethyl acetate (3×100 mL). The combined organic layer was washed with water (50 mL), brine (50 mL), dried over anhydrous sodium sulphate, filtered and concentrated under reduced pressure to afford the crude sample. The crude was purified by flash silica gel column chromatography to afford 125A (yellow oil, 3.6 g, 13.28 mmol, 62.6% yield). $^1$H NMR data: 400 MHz, CD$_3$OD: δ 7.43-7.46 (m, 2H), 7.13-7.16 (m, 2H), 3.72 (s, 3H), 2.95-2.99 (m, 1H), 2.67-2.73 (m, 1H), 2.54-2.60 (m, 1H), 1.61-1.75 (m, 2H), 0.80 (t, J=7.20 Hz, 3H).

125B. methyl 3-(4-bromo-3-nitrophenyl)pentanoate (Absolute and Relative Stereochemistry not Determined)

To a stirred solution of 125A (3.6 g, 13.28 mmol) in H$_2$SO$_4$ (40 mL, 750 mmol) at 0° C., potassium nitrate (1.342 g, 13.28 mmol) was added portion wise and stirred at 0° C. for 30 mins. The reaction mixture was added to cold water (200 mL) and extracted with ethyl acetate (2×200 mL). The combined organic layers were washed with saturated aqueous NaHCO$_3$ solution (100 mL), brine (100 mL), dried over sodium sulphate, filtered and evaporated under reduced pressure to afford 169B (light yellow oil, 3.6 g, 11.39 mmol, 86% yield). $^1$H NMR (400 MHz, CD$_3$OD) δ 7.74-7.77 (m, 2H), 7.42-7.44 (m, 1H), 3.61 (s, 3H), 3.08-3.13 (m, 1H), 2.04-2.80 (m, 2H), 2.01-2.03 (m, 2H), 1.64-1.80 (m, 2H), (t, J=Hz, 3H), 0.80 (t, J=7.20 Hz, 3H).

125C. methyl (3-(4-(5,5-dimethyl-1,3,2-dioxaborinan-2-yl)-3-nitrophenyl)pentanoate (Absolute and Relative Stereochemistry not Determined)

The mixture of 125 B (6.0 g, 18.98 mmol), 5,5,5',5'-tetramethyl-2,2'-bi(1,3,2-dioxaborinane) (8.57 g, 38.0 mmol), potassium acetate (5.59 g, 56.9 mmol) in Dioxane (90 mL) was stirred and argon gas was bubbled through the mixture for 5 min. PdCl$_2$(dppf)-CH$_2$Cl$_2$Adduct (0.620 g, 0.759 mmol) was added and the argon gas was bubbled through the mixture for another 5 min. The reaction mixture was heated at 88° C. for 4 h. Then the reaction mixture was cooled to room temperature and diluted with ethyl acetate (200 mL). The organic solvent was filtered through a pad of Celite, and the filtrate was washed with saturated aqueous sodium bicarbonate (150 mL), brine (150 mL), dried over sodium sulfate, filtered and evaporated under reduced pressure to afford brown colored residue. The residue was purified via flash chromatography to afford 125C (light yellow semi solid, 5.8 g, 16.61 mmol, 88% yield). $^1$H NMR (400 MHz, CD$_3$OD) δ 7.35-8.06 (m, 3H), 3.42-3.62 (m, 7H), 3.20-3.28 (m, 6H), 2.75-2.82 (m, 1H), 2.63-2.66 (m, 1H), 0.76 (s, 6H).

125D. 1-(tetrahydro-2H-pyran-4-yl)prop-1-en-1-yl trifluoromethanesulfonate (Absolute and Relative Stereochemistry not Determined)

To a stirred solution of 1-(tetrahydro-2H-pyran-4-yl)propan-1-one (1.0 g, 7.03 mmol) in dry THF (10 mL), argon gas was bubbled for 5 minutes. Then the solution was cooled to −78° C., LDA (11.72 mL, 21.10 mmol) was added drop wise and stirred for 30 mins. After that the reaction suspension was treated with drop wise addition of 1,1,1-trifluoro-N-phenyl-N-((trifluoromethyl) sulfonyl) methane sulfonamide (3.77 g, 10.55 mmol) and stirred for 2 h at −78° C. The resulting mixture was slowly warmed up to room temperature and stirred for 4 h. The reaction mixture was allowed to cool to 0° C. and quenched with saturated ammonium chloride solution (20 mL). The reaction mixture was diluted with ethyl acetate (20 mL), washed with water (20 mL), brine (20 mL), dried over sodium sulphate, filtered and evaporated under reduced pressure to afford a residue, which was purified via neutral alumina flash chromatography to afford 125D (brown oil, 0.7 g, 2.55 mmol, 36.3% yield). $^1$H (NMR (400 MHz, DMSO-d$^6$) δ 5.60-5.62 (m, 1H), 3.87-3.90 (m, 2H), 3.32-3.39 (m, 2H), 2.50-2.59 (m, 1H), 1.68-1.76 (m, 3H), 1.40-1.54 (m, 4H).

125E. methyl 3-(3-nitro-4-(1-(tetrahydro-2H-pyran-4-yl)prop-1-en-1-yl)phenyl) pentanoate (Absolute and Relative Stereochemistry not Determined)

A stirred solution of 125C (1.7 g, 4.87 mmol), 125D (4.01 g, 14.61 mmol), Na$_2$CO$_3$ (5.36 mL, 10.71 mmol) in Dioxane (20 mL), was purged with argon for 10 min in a pressure tube. PdCl$_2$ (dppf)-CH$_2$Cl$_2$Adduct (0.199 g, 0.243 mmol) was added and purged with argon for additional 10 min. The reaction mixture was heated at 85° C. for 1.5 h in a sealed pressure tube.

The reaction mixture was allowed to cool to room temperature and filtered through pad of celite. The celite pad was rinsed with excess of ethyl acetate (200 mL) and evaporated under reduced pressure to afford brown colored residue. The residue was purified via flash chromatography to afford 125E (light yellow oil, 1.4 g, 3.87 mmol, 80% yield). LC-MS Anal. Calc'd for C$_{20}$H$_{27}$NO$_5$ 361.189, found [M+H] 362.1, T$_r$=1.50 min (Method AY).

125F. methyl 3-(3-amino-4-(1-(tetrahydro-2H-pyran-4-yl)propyl)phenyl)pentanoate (Absolute and Relative Stereochemistry not Determined)

To a stirred solution of 125E (1.4 g, 3.10 mmol) in methanol (20 mL), was added 10% w/w palladium on carbon (0.330 g, 0.310 mmol) and the suspension was hydrogenated under pressure of 60 psi, at room temperature for 12 h. The suspension was filtered through a pad of celite and the filter cake was rinsed with ethyl acetate (200 mL). The combined organic layers were dried over anhydrous sodium sulphate, filtered and evaporated under reduced pressure to afford 169F as diastereomeric mixture (light yellow oil, 0.7 g, 1.97 mmol, 64.0%). LC-MS Anal. Calc'd for C$_{20}$H$_{31}$NO$_3$ 333.230, found [M+H] 334.2, Tr=2.774 min (Method BB).

125G. methyl 3-(3-((2-ethoxypyrimidin-5-yl) amino)-4-(1-(tetrahydro-2H-pyran-4-yl) propyl) phenyl) pentanoate (Absolute and Relative Stereochemistry not Determined)

A stirred solution of 125F Diastereomer mixture (70 mg, 0.210 mmol), 5-bromo-2-ethoxypyrimidine (51.1 mg, 0.252 mmol), Xantphos (18.22 mg, 0.031 mmol), Cs$_2$CO$_3$ (205 mg, 0.630 mmol) in dioxane (5 mL) was purged with nitrogen gas for 10 min. Then Bis (dibenzylideneacetone) palladium (6.04 mg, 10.50 μmol) was added to the reaction mixture and the solution was purged with nitrogen gas for 10 min. The reaction mixture was heated at 100° C. for 12 h in a sealed vial. The reaction mixture was allowed to cool to room temperature and evaporated under reduced pressure to afford the residue, which was purified via flash chromatography to afford 125G (brown oil, 50 mg, 0.110 mmol, 52.3% yield). LC-MS Anal. Calc'd for C$_{26}$H$_{37}$N$_3$O$_4$ 455.278, found [M+H] 456.2, Tr=3.449 min (Method N).

Example 125 Diastereomer 1 and Example 125 Diastereomer 2. (R)-3-(3-((2-ethoxypyrimidin-5-yl) amino)-4-((S)-1-(tetrahydro-2H-pyran-4-yl)propyl) phenyl)pentanoic acid and (R)-3-(3-((2-ethoxypyrimidin-5-yl)amino)-4-((R)-1-(tetrahydro-2H-pyran-4-yl)propyl)phenyl)pentanoic Acid (Absolute and Relative Stereochemistry not Determined)

To a stirred solution of 125G (50 mg, 0.110 mmol) in MeOH (2 mL), Water (2 mL) and THF (2 mL), was added LiOH (10.51 mg, 0.439 mmol) and stirred at room temperature for 4 h.

The organic solvents were evaporated and the aqueous solution was acidified with saturated citric acid solution (pH ~4), extracted with ethyl acetate (3×20 mL). The combined organic extracts were dried over sodium sulphate, filtered and evaporated under reduced pressure to afford brown colored residue. The residue was purified via Preparative HPLC to afford diastereomer mixture (off white solid, 25 mg, 56.689 mmol, 52%). LC-MS Anal. Calc'd for C$_{25}$H$_{35}$N$_3$O$_4$ 441.263, found [M+H] 442.3, Tr=1.26 min (Method AA).

Chiral SFC separation of Example 125 Diastereomer mixture gave Example 125 Diastereomer 1 Tr=5.59 min and Example 169 Diastereomer 2 Tr=7.71 min (Method DB).

Example 125 Diastereomer 1 (off white solid, 7.0 mg, 0.015 mmol, 13.72% yield), LC-MS Anal. Calc'd for C$_{25}$H$_{35}$N$_3$O$_4$ 441.263, found [M+H] 442.2, Tr=1.839 min (Method BB). $^1$H NMR (400 MHz, CD$_3$OD) δ 8.03 (s, 2H), 7.07 (d, J=8.00 Hz, 1H), 6.86-6.89 (m, 2H), 4.22-4.27 (m, 2H), 3.82-3.85 (m, 1H), 3.68-3.71 (m, 1H), 3.28-3.31 (m, 1H), 3.14-3.16 (m, 1H), 2.76-2.79 (m, 1H), 2.61-2.64 (m, 1H), 2.33-2.39 (m, 2H), 1.76-1.82 (m, 2H), 1.60-1.65 (m, 2H), 1.41-1.49 (m, 2H), 1.18-1.28 (m, 6H), 0.68 (t, J=7.20 Hz, 3H), 0.59 (t, J=7.20 Hz, 3H).

Example 125 Diastereomer 2 (off white solid, 7.0 mg, 0.015 mmol, 14.01% yield): LC-MS Anal. Calc'd for C$_{25}$H$_{35}$N$_3$O$_4$ 441.263, found [M+H] 442.4, Tr=1.876 min (Method BB). 400 MHz, CD$_3$OD: δ 8.14 (s, 2H), 7.19 (d, J=8.00 Hz, 1H), 6.99-7.01 (m, 2H), 4.33-4.39 (m, 2H), 3.95-3.98 (m, 1H), 3.81-3.84 (m, 1H), 3.40-3.43 (m, 1H), 3.25-3.28 (m, 1H), 2.90-2.93 (m, 1H), 2.74-2.77 (m, 1H), 2.49-2.53 (m, 2H), 1.87-1.90 (m, 2H), 1.71-1.77 (m, 2H), 1.53-1.59 (m, 2H), 1.31 (t, J=7.20 Hz, 3H), 1.20-1.25 (m, 3H), 0.80 (t, J=7.20 Hz, 3H), 0.71 (t, J=7.20 Hz, 3H).

Example 126 and 127

(R)-3-(3-((2-ethylpyrimidin-5-yl)amino)-4-((S)-1-(tetrahydro-2H-pyran-4-yl)propyl)phenyl)pentanoic Acid (R)-3-(3-((2-ethylpyrimidin-5-yl)amino)-4-((R)-1-(tetrahydro-2H-pyran-4-yl)propyl)phenyl)pentanoic Acid (Absolute and Relative Stereochemistry not Determined)

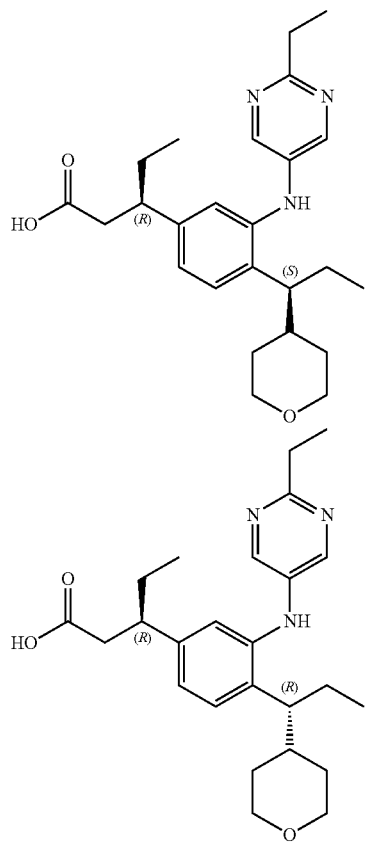

126A. methyl 3-(3-amino-4-(1-(tetrahydro-2H-pyran-4-yl)propyl)phenyl)pentanoate (Absolute and Relative Stereochemistry not Determined)

To a stirred solution of 169E (1.4 g, 3.10 mmol) in methanol (20 mL), was added 10% w/w palladium on carbon (0.330 g, 0.310 mmol) and the suspension was hydrogenated under pressure of 60 psi, at room temperature for 12 h. The suspension was filtered through a pad of celite and the filter cake was rinsed with ethyl acetate (200 mL). The combined organic layers were dried over anhydrous sodium sulphate, filtered and evaporated under reduced pressure to afford 170A as diastereomeric mixture (light yellow oil, 0.7 g, 1.97 mmol, 64.0%). LC-MS Anal. Calc'd for $C_{20}H_{31}NO_3$ 333.230, found [M+H] 334.2, Tr=2.774 min (Method BB).

Chiral SFC separation of 126A Diastereomer mixture gave 126A Diastereomer 1, Tr=3.55 min and 126A Diastereomer 2, $T_r$=5.24 min (Method AZ) as single diastereomers.

126A Diastereomer 1 (colorless oil, 250 mg, 0.750 mmol, 24.19% yield). LC-MS Anal. Calc'd for $C_{20}H_{31}NO_3$ 333.230, found [M+H] 334.2, $T_r$=3.027 min (Method N).

126A Diastereomer 2 (colorless oil, 270 mg, 0.810 mmol, 26.1% yield). LC-MS Anal. Calc'd for $C_{20}H_{31}NO_3$ 333.230, found [M+H] 334.2, $T_r$=2.772 min (Method BB).

126B. Methyl 3-(3-((2-ethylpyrimidin-5-yl) amino)-4-(1-(tetrahydro-2H-pyran-4-yl) propyl)phenyl)pentanoate (Absolute and Relative Stereochemistry not Determined)

126B was prepared from 126A Diastereomer 1 and 5-bromo-2-ethylpyrimidine following the procedure described for the synthesis of 169 G. LC-MS Analysis Calc'd for $C_{26}H_{37}N_3O_3$ 439.283, found [M+H] 440.4, $T_r$=1.23 min (Method AA).

Example 126 Diastereomer 1. (R)-3-(3-((2-ethylpyrimidin-5-yl)amino)-(R)-4-((S)-(1-(tetrahydro-2H-pyran-4-yl)propyl)phenyl)pentanoic Acid (Absolute and Relative Stereochemistry not Determined)

Example 126 Diastereomer 1 was prepared using 126A following the hydrolysis procedure described for the synthesis of Example 125. LC-MS Analysis Calc'd for $C_{25}H_{35}N_3O_3$ 425.268, found [M+H] 426.1, $T_r$=1.536 min (Method O). $^1$H NMR (400 MHz, CD$_3$OD) δ 8.27 (s, 2H), 7.29 (d, J=8.00 Hz, 1H), 7.12-7.15 (m, 2H), 3.93-3.94 (m, 1H), 3.78-3.81 (m, 1H), 3.25-3.42 (m, 3H), 2.85-2.94 (m, 3H), 2.64-2.70 (m, 1H), 2.50-2.56 (m, 1H), 1.87-1.90 (m, 2H), 1.72-1.77 (m, 2H), 1.54-1.65 (m, 2H), 1.30-1.35 (m, 4H), 1.17-1.21 (m, 2H), 0.83 (t, J=7.60 Hz, 3H), 0.69 (t, J=7.20 Hz, 3H).

Example 127

Absolute and Relative Stereochemistry not Determined

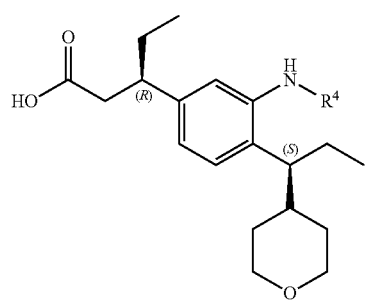

Examples 127 Diastereomer 1 was prepared using 126A Diastereomer 1and (5-bromo-2-(methoxymethyl)pyridine), following the procedure described for the synthesis of Example 126 Diastereomer 1.

| Ex. No. | Name | R⁴ | $T_R$ (min) | [M + H]⁺ |
|---|---|---|---|---|
| 127 | (R)-3-(3-((6-(methoxymethyl)pyridin-3-yl)amino)-4-((S)-1-(tetrahydro-2H-pyran-4-yl)propyl)phenyl)pentanoic acid (absolute and relative stereochemistry not determined) | pyridine-CH₂OMe | 1.556 Method O. | 441.1 |

Example 128

(R)-3-(3-((2-ethylpyrimidin-5-yl)amino)-4-((S)-(1-(tetrahydro-2H-pyran-4-yl)propyl)phenyl)pentanoic Acid (Absolute and Relative Stereochemistry not Determined)

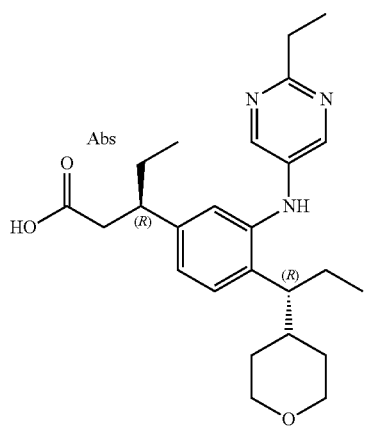

128A. Methyl 3-(3-((2-ethylpyrimidin-5-yl) amino)-4-(1-(tetrahydro-2H-pyran-4-yl) propyl)phenyl)pentanoate (Absolute and Relative Stereochemistry not Determined)

128A was prepared from 126A Diastereomer 2 and 5-bromo-2-ethylpyrimidine following the procedure described for the synthesis of 169 G. LC-MS Analysis Calc'd for $C_{26}H_{37}N_3O_3$ 439.283, found [M+H] 440.4, Tr=1.23 min (Method AA).

Example 128 Diastereomer 2. (R)-3-(3-((2-ethylpyrimidin-5-yl)amino)-4-((S)-(1-(tetrahydro-2H-pyran-4-yl)propyl)phenyl)pentanoic Acid (Absolute and Relative Stereochemistry not Determined)

Example 128 Diastereomer 2 was prepared from 128A following the procedure described for the synthesis of Example 126 Diastereomer 1. LC-MS Analysis Calc'd for $C_{25}H_{35}N_3O_3$ 425.268, found [M+H] 426.1, Tr=1.522 min (Method O). ¹H NMR (400 MHz, CD₃OD) δ 8.27 (s, 2H), 7.29 (d, J=8.00 Hz, 1H), 7.12-7.15 (m, 2H), 3.94-3.97 (m, 1H), 3.79-3.81 (m, 1H), 3.24-3.43 (m, 3H), 2.85-2.96 (m, 3H), 2.64-2.70 (m, 1H), 2.50-2.56 (m, 1H), 1.87-1.90 (m, 2H), 1.72-1.77 (m, 2H), 1.54-1.66 (m, 2H), 1.32-1.35 (m, 4H), 1.15-1.20 (m, 2H), 0.83 (t, J=7.20 Hz, 3H), 0.68 (t, J=7.60 Hz, 3H).

Example 129

Absolute and Relative Stereochemistry not Determined

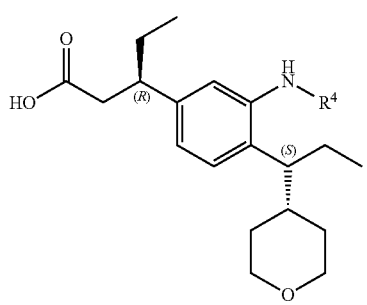

Examples 129 Diastereomer 2 were prepared using respectively the 126A Diastereomer 2 and (5-bromo-2-(methoxymethyl)pyridine), following the procedure described for the synthesis of Example 126 Diastereomer 1.

| Ex. No. | Name | R⁴ | $T_R$ (min) | [M + H]⁺ |
|---|---|---|---|---|
| 129 | (R)-3-(3-((6-(methoxymethyl)pyridin-3-yl)amino)-4-((S)-1-(tetrahydro-2H-pyran-4-yl)propyl)phenyl)pentanoic acid (absolute and relative stereochemistry not determined) | pyridine-CH₂OMe | 1.547 Method O | 441.2 |

Example 130-133

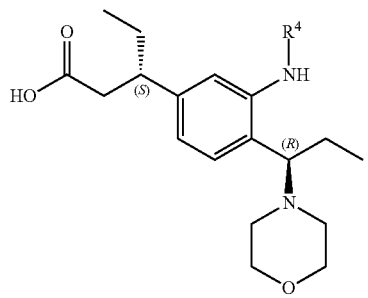

Example 130-133 were prepared from 124B Diastereomer 2 and corresponding halides following the procedure described for the synthesis of Example 119.

Example 134

1-(4-(2,6-dimethylheptan-4-yl)-2'-(2H-tetrazol-5-yl)-[1,1'-biphenyl]-3-yl)-3-(p-tolyl)urea

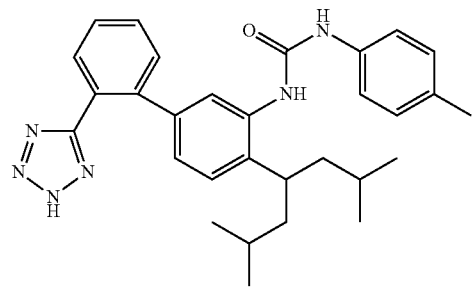 [SMILES: Cc1ccc(NC(=O)Nc2cc(-c3ccccc3-c3nn[nH]n3)ccc2C(CC(C)C)CC(C)C)cc1]

| Ex. NO | Name | $R^4$ | Tr min | Method | (M + H) |
|---|---|---|---|---|---|
| 130 | (S)-3-(4-((R)-1-morpholinopropyl)-3-((2-(trifluoromethyl)pyrimidin-5-yl)amino)phenyl)pentanoic acid (absolute and relative stereochemistry not determined) | $CF_3$ pyrimidine | 1.756 | Method O | 467.1 |
| 131 | (S)-3-(3-((6-(methoxymethyl)pyridin-3-yl)amino)-4-((R)-1-morpholinopropyl)phenyl)pentanoic acid (absolute and relative stereochemistry not determined) | methoxymethyl pyridine | 1.525 | Method O | 442.2 |
| 132 | (S)-3-(3-((4-chlorophenyl)amino)-4-((R)-1-morpholinopropyl)phenyl)pentanoic acid (absolute and relative stereochemistry not determined) | Cl-phenyl | 2.170 | Method O | 431.2 |
| 133 | (S)-3-(3-((5-(difluoromethoxy)pyridin-2-yl)amino)-4-((R)-1-morpholinopropyl)phenyl)pentanoic acid (absolute and relative stereochemistry not determined) | $OCHF_2$ pyridine | 1.783 | Method O | 464.1 |

134A Methyl 2-(4-bromo-2-nitrophenyl)-4-methyl-3-oxopentanoate

Methyl 4-methyl-3-oxopentanoate (8.78 g, 60.9 mmol) was dissolved in dry DMF (40 mL) under nitrogen. The reaction was cooled in an ice bath. Potassium carbonate (16.83 g, 122 mmol) was added and stirring continued for a few minutes. 4-Bromo-1-fluoro-2-nitrobenzene (5.0 mL, 40.6 mmol) was then added and the reaction was allowed to gradually warm to RT. Stirring was continued overnight. Hydrochloric acid (2.4 M, 200 mL) was mixed with ice. The reaction was added to this mixture with stirring. The quenched reaction was then extracted twice with methylene chloride. The combined organic layer was dried over magnesium sulfate, filtered and evaporated. The residue was dissolved in a solution of sodium hydroxide (60 mL, 1 N) and diluted with 120 mL of water. The dark red solution was washed twice with ether. Hydrochloric acid (1 N, 62 mL) was added and the suspension extracted with ether. The organic phase was washed with brine. Drying over magnesium sulfate, filtration and evaporation provided the crude product as a slowly solidifying orange oil (8.91 g, 25.9 mmol, 64%).

134B 1-(4-Bromo-2-nitrophenyl)-3-methylbutan-2-one

A flask was charged with methyl 2-(4-bromo-2-nitrophenyl)-4-methyl-3-oxopentanoate (3.6 g, 10.46 mmol) in DMSO (40 ml). Sodium chloride (1.223 ml, 20.92 mmol) was added and the flask was evacuated and flushed with argon. Water (0.377 ml, 20.92 mmol) was added and the reaction was warmed to 150° C. After heating for two hours, the cooled reaction was partitioned between ether and water. The organic layer was washed with another portion of water and then brine. Drying over magnesium sulfate, filtration and evaporation provided the crude product. The crude material was purified on a 120 g Isco silica gel column (0-50% ethyl acetate in hexanes). Evaporation of the product containing fractions provided 1-(4-bromo-2-nitrophenyl)-3-methylbutan-2-one (1.64 g, 5.73 mmol, 54.8% yield) as a tan solid. $^1$H NMR (400 MHz, CHLOROFORM-d) δ 8.28 (d, J=2.1 Hz, 1H), 7.72 (dd, J=8.2, 2.1 Hz, 1H), 7.16 (d, J=8.2 Hz, 1H), 4.18 (s, 2H), 2.83 (spt, J=6.9 Hz, 1H), 1.23 (d, J=7.0 Hz, 6H).

134C 4-(4-Bromo-2-nitrophenyl)-2,6-dimethylheptan-3-one 1-(4-Bromo-2-nitrophenyl)-3-methylbutan-2-one (1.64 g, 5.73 mmol) was dissolved in DMF (24 mL) under nitrogen. 1-Iodo-2-methylpropane (0.996 ml, 8.60 mmol) and 18-crown-6 (0.152 g, 0.573 mmol) were added and the reaction cooled in an ice bath. Upon addition of sodium hydride(0.275 g, 6.88 mmol), the reaction turned a beautiful blue color. The reaction was then warmed to 50° C. for ca. 2 hours when the blue color had been discharged. The cooled reaction was quenched with 1 M hydrochloric acid and transferred to a separatory funnel. Ethyl acetate was used to extract the crude product. The organic layer was then washed with water and brine. Drying over magnesium sulfate, filtration and evaporation provided the crude product. This material was applied to a 120 g Isco silica gel column and eluted with 0-100% ethyl acetate in hexanes. Evaporation provided 4-(4-bromo-2-nitrophenyl)-2,6-dimethylheptan-3-one (1.41 g, 4.12 mmol, 71.9% yield) as a yellow oil. $^1$H NMR (400 MHz, CHLOROFORM-d) δ 7.97 (d, J=2.1 Hz, 1H), 7.69 (dd, J=8.4, 2.1 Hz, 1H), 7.35 (d, J=8.6 Hz, 1H), 7.29 (s, 1H), 4.57 (t, J=7.2 Hz, 1H), 2.72 (spt, J=6.9 Hz, 1H), 2.02-1.90 (m, 1H), 1.61-1.51 (m, 2H), 1.37 (dquin, J=13.3, 6.6 Hz, 1H), 1.14 (d, J=7.0 Hz, 3H), 1.00 (d, J=6.8 Hz, 4H), 0.89 (t, J=6.7 Hz, 6H).

134D 4-Bromo-1-(2,6-dimethylhept-2-en-4-yl)-2-nitrobenzene 4-(4-Bromo-2-nitrophenyl)-2,6-dimethylheptan-3-one (142 mg, 0.415 mmol) was dissolved in ethanol (2 mL) under nitrogen. Sodium borohydride (47.1 mg, 1.245 mmol) was added and the reaction stirred overnight. A saturated solution of sodium potassium tartrate and ethyl acetate were added and the mixture stirred until clear. The layers were then separated and the organic phase washed with water and brine. Drying over magnesium sulfate, filtration and evaporation provided 138 mg of a yellow oil. This alcohol was dissolved in dry methylene chloride (2.0 mL) under nitrogen. Martin's sulfurane (335 mg, 0.498 mmol) was added and reaction continued overnight. The reaction was applied to a 24 g Isco silica gel column and eluted with 0-25% ethyl acetate in hexanes. Evaporation gave 4-bromo-1-(2,6-dimethylhept-2-en-4-yl)-2-nitrobenzene (98.5 mg, 0.302 mmol, 73%). This material appears to be nearly exclusively the deconjugated olefin isomer by $^1$H-NMR. $^1$H NMR (400 MHz, CHLOROFORM-d) δ 7.83 (d, J=2.1 Hz, 1H), 7.63 (dd, J=8.5, 2.0 Hz, 1H), 7.33 (d, J=8.4 Hz, 1H), 5.21 (dd, J=9.1, 1.2 Hz, 1H), 4.23-4.07 (m, 1H), 1.72 (s, 3H), 1.60 (s, 3H), 1.58-1.43 (m, 3H), 0.91 (dd, J=6.2, 2.8 Hz, 6H).

134E 5-(4'-(2,6-Dimethylhept-2-en-4-yl)-3'-nitro-[1,1'-biphenyl]-2-yl)-2H-tetrazole A reaction vial was charged with 4-bromo-1-(2,6-dimethylhept-2-en-4-yl)-2-nitrobenzene (98.5 mg, 0.302 mmol), (2-(2H-tetrazol-5-yl)phenyl)boronic acid (172 mg, 0.906 mmol) and potassium carbonate (1208 µl, 1.812 mmol, 1.5 M solution) in DMF (4.0 mL). The vial was subjected to three cycles of vacuum/nitrogen purge.

Tetrakis(triphenylphosphine)palladium(0) (69.8 mg, 0.060 mmol) was introduced and vacuum/nitrogen cycle repeated three times. The vial was then warmed to 90° C. for 4 hours. The cooled reaction was quenched with acetic acid (830 µl, 14.49 mmol), filtered and purified by RP-HPLC (methanol-water gradient+0.1% TFA). The product containing fractions were evaporated and azeotroped with ethanol. 5-(4'-(2,6-Dimethylhept-2-en-4-yl)-3'-nitro-[1,1'-biphenyl]-2-yl)-2H-tetrazole (94 mg, 0.240 mmol, 80% yield) was isolated as a yellow oil. $^1$H NMR (400 MHz, CHLOROFORM-d) δ 9.20 (br s, 1H), 7.84 (dd, J=7.6, 0.9 Hz, 1H), 7.69-7.60 (m, 1H), 7.58 (d, J=1.8 Hz, 1H), 7.57-7.51 (m, 1H), 7.47 (dd, J=7.7, 0.9 Hz, 1H), 7.36 (d, J=8.2 Hz, 1H), 7.16 (dd, J=8.1, 1.8 Hz, 1H), 5.19 (br d, J=9.3 Hz, 1H), 4.14 (td, J=9.0, 5.6 Hz, 1H), 1.70 (s, 3H), 1.59 (d, J=0.9 Hz, 3H), 1.57-1.44 (m, 3H), 0.89 (dd, J=6.3, 2.3 Hz, 6H). $^{13}$C NMR (101 MHz, CHLOROFORM-d) δ 155.2, 149.7, 140.6, 139.1, 137.6, 134.4, 132.9, 131.7, 130.9, 129.6, 128.9, 126.5, 124.2, 122.5, 46.7, 36.0, 25.9, 25.8, 23.3, 21.8, 18.2.

134F 4-(2,6-Dimethylheptan-4-yl)-2'-(2H-tetrazol-5-yl)-[1,1'-biphenyl]-3-amine A Parr bottle was charged with 5-(4'-(2,6-dimethylhept-2-en-4-yl)-3'-nitro-[1,1'-biphenyl]-2-yl)-2H-tetrazole (94 mg, 0.240 mmol) in ethyl acetate (ca. 10 mL). 10% Pd/C was added (60 mg, wet) and the bottle was pressurized with 50 psi hydrogen. After 2 hours, LCMS showed partial conversion. More Pd/C (46 mg) was added and the bottle was repressurized. After three hours, LCMS showed mostly desired product. Magnesium sulfate was added and the reaction was filtered through a pad of magnesium sulfate. Evaporation provided 81 mg of 4-(2,6-dimethylheptan-4-yl)-2'-(2H-tetrazol-5-yl)-[1,1'-biphenyl]-3-amine as a colorless oil. $^1$H NMR (400 MHz, CHLOROFORM-d) δ 8.16 (d, J=7.1 Hz, 1H), 7.59-7.53 (m, 1H), 7.52-7.46 (m, 1H), 7.42 (dd, J=7.5, 1.2 Hz, 1H), 7.12 (d, J=7.8 Hz, 1H), 6.61 (br d, J=7.8 Hz, 1H), 6.56 (d, J=1.5 Hz, 1H), 2.80 (quin, J=6.9 Hz, 1H), 1.62-1.42 (m, 6H), 0.90 (d, J=5.4 Hz, 12H).

134 1-(4-(2,6-Dimethylheptan-4-yl)-2'-(2H-tetrazol-5-yl)-[1,1'-biphenyl]-3-yl)-3-(p-tolyl)urea 4-(2,6-Dimethylheptan-4-yl)-2'-(2H-tetrazol-5-yl)-[1,1'-biphenyl]-3-amine (27 mg, 0.074 mmol) was dissolved in DMF (0.5 mL). 1-Isocyanato-4-methylbenzene (14.05 μl, 0.111 mmol) was added and reaction stirred overnight. The reaction was then diluted with methanol and purified by RP-HPLC (methanol-water gradient+0.1% TFA). Evaporation provided 1-(4-(2,6-dimethylheptan-4-yl)-2'-(2H-tetrazol-5-yl)-[1,1'-biphenyl]-3-yl)-3-(p-tolyl)urea (18.2 mg, 0.036 mmol, 49%). $^1$H NMR (500 MHz, DMSO-d$_6$) δ 8.80 (s, 1H), 7.76-7.65 (m, 2H), 7.65-7.52 (m, 3H), 7.34-7.27 (m, 3H), 7.13 (d, J=8.2 Hz, 1H), 7.07 (d, J=8.2 Hz, 2H), 6.77 (dd, J=8.1, 1.8 Hz, 1H), 3.01 (br, 1H), 2.24 (s, 3H), 1.49-1.31 (m, 6H), 0.83 (d, J=6.0 Hz, 6H), 0.79 (d, J=6.1 Hz, 6H). LC-MS Anal. Calc'd for $C_{30}H_{37}N_6O_1$ 496.3, found [M+H] 497.4, $T_r$=1.14 min (Method EH).

Example 135

1-(4-Chloro-2-fluorophenyl)-3-(4-(2,6-dimethylheptan-4-yl)-2'-(2H-tetrazol-5-yl)-[1,1'-biphenyl]-3-yl)urea

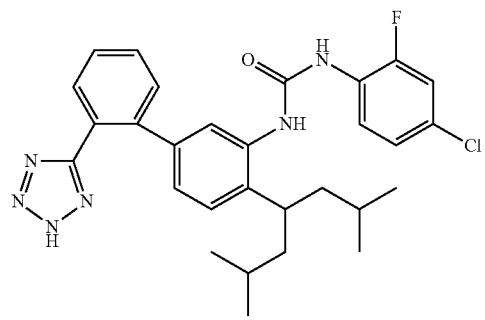 [SMILES: CC(C)CC(CC(C)C)c1ccc(-c2ccccc2-c2nn[nH]n2)cc1NC(=O)Nc1ccc(Cl)cc1F]

4-(2,6-Dimethylheptan-4-yl)-2'-(2H-tetrazol-5-yl)-[1,1'-biphenyl]-3-amine (27 mg, 0.074 mmol)(Intermediate 134F) was dissolved in DMF (0.5 mL). 4-Chloro-2-fluoro-1-isocyanatobenzene (14.12 μl, 0.111 mmol) was added and the reaction stirred overnight. The reaction was then diluted with methanol and purified by RP-HPLC (methanol-water gradient+0.1% TFA). Evaporation of the appropriate fractions provided 1-(4-chloro-2-fluorophenyl)-3-(4-(2,6-dimethylheptan-4-yl)-2'-(2H-tetrazol-5-yl)-[1,1'-biphenyl]-3-yl)urea (19.6 mg, 0.036 mmol, 49.0% yield). $^1$H NMR (400 MHz, CHLOROFORM-d) δ 8.91 (s, 1H), 8.18 (br s, 1H), 8.17-8.08 (m, 1H), 7.74-7.66 (m, 1H), 7.65-7.60 (m, 1H), 7.60-7.51 (m, 2H), 7.45 (dd, J=11.2, 2.4 Hz, 1H), 7.24 (d, J=1.7 Hz, 1H), 7.21 (br d, J=8.8 Hz, 1H), 7.15 (d, J=8.1 Hz, 1H), 6.82 (dd, J=8.1, 1.7 Hz, 1H), 3.02 (br s, 1H), 1.48-1.27 (m, 6H), 0.82 (d, J=5.7 Hz, 6H), 0.77 (d, J=5.9 Hz, 6H). LC-MS Anal. Calc'd for $C_{29}H_{32}ClFN_6O$ 534.2, found [M+H] 535.3, $T_r$=1.17 min (Method EH).

Example 136

1-(4-(2,6-Dimethylheptan-4-yl)-2'-(2H-tetrazol-5-yl)-[1,1'-biphenyl]-3-yl)-3-(5-methylisoxazol-3-yl)urea

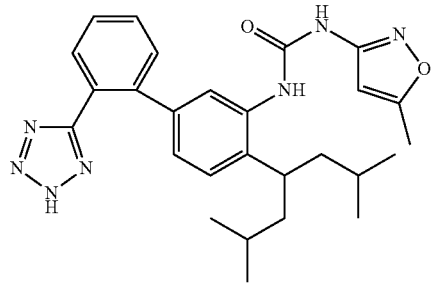 [SMILES: Cc1cc(NC(=O)Nc2cc(-c3ccccc3-c3nn[nH]n3)ccc2C(CC(C)C)CC(C)C)no1]

4-(2,6-Dimethylheptan-4-yl)-2'-(2H-tetrazol-5-yl)-[1,1'-biphenyl]-3-amine (27 mg, 0.074 mmol) (Intermediate 134F) was dissolved in DMF (0.5 mL). Phenyl (5-methylisoxazol-3-yl)carbamate (24.31 mg, 0.111 mmol) was added and the reaction warmed to 80° C. for 3 hours. The cooled reaction was diluted with DMF (1.5 mL) and purified using the following conditions: Column: XBridge C18, 19×200 mm, 5-μm particles; Mobile Phase A: 5:95 acetonitrile:water with 0.1% trifluoroacetic acid; Mobile Phase B: 95:5 acetonitrile: water with 0.1% trifluoroacetic acid; Gradient: 50-100% B over 20 minutes, then a 10-minute hold at 100% B; Flow: 20 mL/min. Fractions containing the desired product were combined and dried via centrifugal evaporation to give 1-(4-(2,6-dimethylheptan-4-yl)-2'-(2H-tetrazol-5-yl)-[1,1'-biphenyl]-3-yl)-3-(5-methylisoxazol-3-yl)urea (10.4 mg, 0.021 mmol, 29%). $^1$H NMR (500 MHz, DMSO-d$_6$) δ 9.83 (s, 1H), 7.64-7.56 (m, 2H), 7.51 (br d, J=4.4 Hz, 2H), 7.38 (br s, 1H), 7.11 (br d, J=8.1 Hz, 1H), 6.79 (br d, J=7.7 Hz, 1H), 6.36 (br s, 1H), 3.00 (br s, 1H), 2.35 (s, 3H), 1.36 (br dd, J=13.0, 6.6 Hz, 6H), 0.81 (br d, J=5.5 Hz, 6H), 0.78 (br d, J=5.6 Hz, 6H). LC-MS Anal. Calc'd for $C_{27}H_{33}N_7O_2$ 487.3, found [M+H] 488.1, $T_r$=2.22 min (Method EI).

Example 137

(S)-3-(4-(2,6-Dimethylheptan-4-yl)-3-(3-(p-tolyl)ureido)phenyl)pentanoic Acid

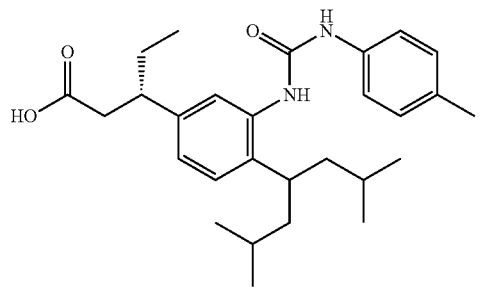 [SMILES: CC[C@@H](CC(=O)O)c1ccc(C(CC(C)C)CC(C)C)c(NC(=O)Nc2ccc(C)cc2)c1]

137A 2-(4-(2,6-Dimethylhept-2-en-4-yl)-3-nitrophenyl)-5,5-dimethyl-1,3,2-dioxaborinane A solution of 5,5,5',5'-tetramethyl-2,2'-bi(1,3,2-dioxaborinane) (155 mg, 0.685 mmol) and 4-bromo-1-(2,6-dimethylhept-2-en-4-yl)-2-nitrobenzene (172 mg, 0.527 mmol) (Intermediate 222D) and potassium acetate (155 mg, 1.582 mmol) in degassed DMSO (753 µl) was treated with 1,1'-bis(diphenylphosphino)ferrocenedichloro palladium(II) dichloromethane complex (19.29 mg, 0.026 mmol). This dark solution was placed under nitrogen and heated to 80° C. for 2 h then cooled to RT. The reaction was applied to a 24 g Isco silica gel column and eluted with 0-25% ethyl acetate in hexanes. Concentration of the appropriate fractions afforded 2-(4-(2,6-dimethylhept-2-en-4-yl)-3-nitrophenyl)-5,5-dimethyl-1,3,2-dioxaborinane (72 mg, 38.0% yield) as a pale yellow oil. $^1$H NMR (400 MHz, CHLOROFORM-d) δ 8.08 (d, J=1.1 Hz, 1H), 7.89 (dd, J=7.9, 1.3 Hz, 1H), 7.41 (d, J=7.8 Hz, 1H), 5.25 (dt, J=9.1, 1.3 Hz, 1H), 4.21-4.12 (m, 1H), 3.78 (s, 4H), 1.71 (d, J=1.1 Hz, 3H), 1.61 (d, J=1.2 Hz, 3H), 1.55-1.48 (m, 3H), 1.04 (s, 6H), 0.93-0.89 (m, 6H).

137B (3S)-Methyl 3-(4-(2,6-dimethylhept-2-en-4-yl)-3-nitrophenyl)pentanoate

A reaction vial was charged with 2-(4-(2,6-dimethylhept-2-en-4-yl)-3-nitrophenyl)-5,5-dimethyl-1,3,2-dioxaborinane(73 mg, 0.203 mmol) in dioxane (1 mL). The vial was subjected to three cycles of vacuum/nitrogen purge. R-Binap (2.78 mg, 4.47 µmol) and chlorobis(ethylene))rhodium(I) (1.185 mg, 3.05 µmol) were added. The vial was subjected to three additional cycles of vacuum/nitrogen purge. After stirring for 15 minutes, (E)-methyl pent-2-enoate (34.8 mg, 0.305 mmol) and NaOH (183 µl, 0.183 mmol) (1 M solution) were added. The vial was subjected to three final cycles of vacuum/nitrogen purge. After stirring for an hour, the reaction was warmed to 50° C. for 3 hours. After cooling, acetic acid (10.5 µl, 0.183 mmol) was added and the crude reaction was applied to 24 g Isco silica gel column. The column was eluted with 0-100% ethyl acetate in hexanes. Evaporation provided (3S)-methyl 3-(4-(2,6-dimethylhept-2-en-4-yl)-3-nitrophenyl)pentanoate (41 mg, 0.113 mmol, 55.8% yield) as a yellow film. $^1$H NMR (400 MHz, CHLOROFORM-d) δ 7.49 (s, 1H), 7.38-7.34 (m, 2H), 5.23 (dd, J=9.2, 1.2 Hz, 1H), 4.21-4.10 (m, 1H), 3.62 (s, 3H), 3.14-3.00 (m, 1H), 2.73-2.63 (m, 1H), 2.61-2.51 (m, 1H), 1.72 (s, 3H), 1.62 (d, J=1.2 Hz, 3H), 1.56-1.46 (m, 3H), 0.91 (d, J=6.1 Hz, 6H), 0.83 (t, J=7.3 Hz, 3H).

137C (S)-Methyl 3-(4-(2,6-dimethylheptan-4-yl)-3-(3-(p-tolyl)ureido)phenyl)pentanoate A Parr bottle was charged with (3S)-methyl 3-(4-(2,6-dimethylhept-2-en-4-yl)-3-nitrophenyl)pentanoate (41 mg, 0.113 mmol) in ethyl acetate (ca. 5 mL). 10% Pd/C (56 mg) was added and the vessel pressurized with hydrogen (45 psi). After 4 hours, the reaction was passed through a syringe filter. Evaporation provided (S)-methyl 3-(3-amino-4-(2,6-dimethylheptan-4-yl)phenyl)pentanoate in sufficient purity for the next transformation. (S)-methyl 3-(3-amino-4-(2,6-dimethylheptan-4-yl)phenyl)pentanoate (37.7 mg, 0.113 mmol) was dissolved in THF (1 mL) under nitrogen. 1-Isocyanato-4-methylbenzene (15 µL, 0.119 mmol) was added and the reaction stirred overnight. The crude reaction was applied to a 24 g Isco silica gel column and eluted with 0-50% ethyl acetate in hexanes. As this treatment resulted in partial purification, the sample was further purified by RP-HPLC (methanol-water gradient+0.1% TFA). Evaporation of the product containing fraction and lyophilization from frozen d6-benzene gave (S)-methyl 3-(4-(2,6-dimethylheptan-4-yl)-3-(3-(p-tolyl)ureido)phenyl)pentanoate (24 mg, 0.050 mmol, 45%). $^1$H NMR (500 MHz, BENZENE-d$_6$) δ 7.54 (d, J=8.4 Hz, 2H), 7.23 (s, 1H), 7.08 (d, J=8.1 Hz, 1H), 7.00-6.84 (m, 4H), 6.65 (s, 1H), 3.18 (s, 3H), 2.88 (tt, J=8.8, 6.1 Hz, 1H), 2.42-2.36 (m, 1H), 2.34-2.25 (m, 1H), 2.04 (s, 3H), 1.44-1.32 (m, 8H), 0.82 (d, J=5.3 Hz, 6H), 0.78 (d, J=6.1 Hz, 6H), 0.68 (t, J=7.3 Hz, 3H). LC-MS Anal. Calc'd for C$_{29}$H$_{42}$N$_2$O$_3$ 466.3, found [M+H] 467.5, T$_r$=1.26 min (Method EH).

137 (S)-3-(4-(2,6-Dimethylheptan-4-yl)-3-(3-(p-tolyl)ureido)phenyl)pentanoic Acid (S)-Methyl 3-(4-(2,6-dimethylheptan-4-yl)-3-(3-(p-tolyl)ureido)phenyl)pentanoate (22 mg, 0.047 mmol) was dissolved in THF(1 mL), methanol (0.3 mL) and water (0.3 mL). A 1 M solution of sodium hydroxide (141 µl, 0.141 mmol) was added and the reaction stirred overnight. The reaction was neutralized with 1 N hydrochloric acid (141 uL) and concentrated under a stream of nitrogen. The resultant solid was filtered and rinsed with water. The sample was dried in vacuo to give (S)-3-(4-(2,6-dimethylheptan-4-yl)-3-(3-(p-tolyl)ureido)phenyl)pentanoic acid (14.4 mg, 0.031 mmol, 66.1% yield) as a colorless solid. $^1$H NMR (500 MHz, DMSO-d$_6$) δ 12.03 (br d, J=2.1 Hz, 1H), 8.80 (s, 1H), 7.65 (br s, 1H), 7.32 (d, J=8.9 Hz, 2H), 7.29 (d, J=1.7 Hz, 1H), 7.12 (d, J=8.1 Hz, 1H), 7.07 (d, J=8.2 Hz, 2H), 6.95 (dd, J=8.0, 1.6 Hz, 1H), 3.00 (br s, 1H), 2.89-2.79 (m, 1H), 2.60-2.53 (m, 1H), 2.48-2.40 (m, 1H), 2.24 (s, 3H), 1.63 (tt, J=13.1, 7.3 Hz, 1H), 1.56-1.29 (m, 5H), 0.83 (d, J=5.8 Hz, 3H), 0.78 (d, J=6.1 Hz, 3H), 0.76-0.76 (m, 1H), 0.73 (t, J=7.3 Hz, 2H). LC-MS Anal. Calc'd for C$_{28}$H$_{40}$N$_2$O$_3$ 452.3, found [M+H] 453.4, T$_r$=1.16 min (Method EH).

Example 138

2-(4-(2,6-Dimethylheptan-4-yl)-3-(3-(p-tolyl)ureido)phenoxy)acetic acid

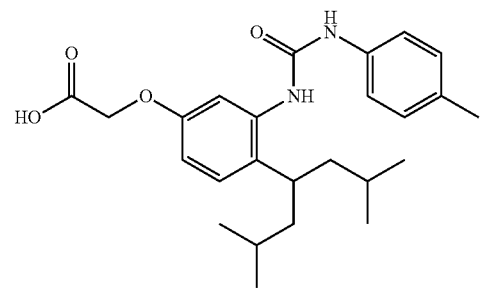 [SMILES: Cc1ccc(NC(=O)Nc2cc(OCC(=O)O)ccc2C(CC(C)C)CC(C)C)cc1]

138A 4-(2,6-Dimethylhept-2-en-4-yl)-3-nitrophenol 2-(4-(2,6-Dimethylhept-2-en-4-yl)-3-nitrophenyl)-5,5-dimethyl-1,3,2-dioxaborinane (46 mg, 0.128 mmol)(Intermediate 137A) was dissolved in THF (1.5 mL) and water (0.5 mL). Two portions of sodium perborate tetrahydrate (2×29 mg) were added and stirring continued until completion of the reaction. The reaction was partitioned between ethyl acetate and water. The organic phase was then washed with brine. Drying over magnesium sulfate, filtration and evaporation gave the crude product. This material was applied to a 12 g Isco silica gel column and eluted with 0-25% ethyl acetate in hexanes. Evaporation of the appropriate fractions gave 4-(2,6-dimethylhept-2-en-4-yl)-3-nitrophenol (14 mg, 0.053 mmol, 41.5% yield). $^1$H NMR (500 MHz, CHLOROFORM-d) δ 7.29 (d, J=8.5 Hz, 1H), 7.31-7.27 (m, 1H), 7.01 (dd, J=8.5, 2.7 Hz, 1H), 5.33 (br s, 1H), 5.19 (dt, J=9.2, 1.3 Hz, 1H), 4.12-4.04 (m, 1H), 1.69 (d, J=1.2 Hz, 3H), 1.59 (d, J=1.2 Hz, 3H), 1.55-1.42 (m, 3H), 0.88 (dd, J=6.3, 1.2 Hz, 6H). $^{13}$C NMR (126 MHz, CHLOROFORM-d) δ 153.4, 149.8, 133.5, 133.0, 130.3, 127.3, 120.2, 110.5, 46.9, 35.4, 25.9, 25.7, 23.2, 22.0, 18.1.

138B Ethyl 2-(4-(2,6-dimethylhept-2-en-4-yl)-3-nitrophenoxy)acetate

A reaction vial was charged with 4-(2,6-dimethylhept-2-en-4-yl)-3-nitrophenol (14 mg, 0.053 mmol) in DMF (0.5 mL). Cesium carbonate (20.79 mg, 0.064 mmol) was added followed by ethyl bromoacetate (8.88 μl, 0.080 mmol). The flask was then warmed to 60° C. After ca. 0.5 hour, another portion of ethyl bromoacetate (8.88 μl, 0.080 mmol) was added and heating continued. As the reaction still had not progressed to completion, additional cesium carbonate (20.79 mg, 0.064 mmol) and ethyl bromoacetate (8.88 μl, 0.080 mmol) were added and heating continued. The completed reaction was cooled and diluted with 3:1 hexanes-ethyl acetate. The mixture was transferred to a separatory funnel and washed successively with water and brine. Drying over magnesium sulfate, filtration and evaporation gave the crude product (approximately 19 mg) which was used without purification. LC-MS Anal. Calc'd for $C_{19}H_{27}NO_5$ 349.2, found [M+H] 350.2, $T_r$=1.21 min (Method EH).

138C Ethyl 2-(3-amino-4-(2,6-dimethylheptan-4-yl)phenoxy)acetate

A Parr bottle was charged with crude ethyl 2-(4-(2,6-dimethylhept-2-en-4-yl)-3-nitrophenoxy)acetate (0.019 g, 0.053 mmol) in ethyl acetate (ca. 5 mL). 10% Pd/C(21 mg) was added and the vessel was pressurized at 44 psi of hydrogen. After 4 hours, more catalyst (21 mg) was added and the sample was pressurized with hydrogen for 5 more hours. The reaction was passed through a syringe filter and evaporated to give the crude product. The material looked reasonable by LCMS and was used without purification. LC-MS Anal. Calc'd for $C_{19}H_{31}NO_3$ 321.4, found [M+H] 322.4, $T_r$=1.11 min (Method EH).

138 2-(4-(2,6-Dimethylheptan-4-yl)-3-(3-(p-tolyl)ureido)phenoxy)acetic Acid

Ethyl 2-(3-amino-4-(2,6-dimethylheptan-4-yl)phenoxy)acetate (17 mg, 0.053 mmol) was dissolved in THF (0.5 mL) under nitrogen. 1-Isocyanato-4-methylbenzene (8.02 μl, 0.064 mmol) was added and stirring continued overnight. Methanol (0.2 mL) and a 1 M solution of sodium hydroxide (159 μl, 0.159 mmol) were then added A precipitate formed and more methanol was added to solubilize the solid. The reaction was stirred for ca. 0.5 hour when it was neutralized with acetic acid (9.10 μl, 0.159 mmol). The sample was diluted with DMF and purified by RP-HPLC (methanol-water gradient+0.1% TFA). Evaporation provided 2-(4-(2,6-dimethylheptan-4-yl)-3-(3-(p-tolyl)ureido)phenoxy)acetic acid (8 mg, 0.018 mmol, 33.6% yield) as a waxy solid. $^1$H NMR (500 MHz, METHANOL-$d_4$) δ 7.32-7.27 (m, 2H), 7.18 (d, J=8.7 Hz, 1H), 7.11 (d, J=8.1 Hz, 2H), 7.06 (d, J=2.7 Hz, 1H), 6.82 (dd, J=8.7, 2.7 Hz, 1H), 4.67 (s, 2H), 3.08- 3.02 (m, 1H), 2.30 (s, 3H), 1.55-1.37 (m, 6H), 0.89 (d, J=6.0 Hz, 6H), 0.84 (d, J=6.1 Hz, 6H). LC-MS Anal. Calc'd for $C_{25}H_{34}N_2O_4$ 426.2, found [M+H] 427.3, $T_r$=1.09 min (Method EH).

Exemplary compounds were tested for inhibition of IDO activity. Experimental procedures and results are provided below.

Assessment of Inhibitor Activity in HeLa Cell-Based Indoleamine 23-Dioxygenase (IDO) Assay HeLa (ATCC® CCL-2) cells were obtained from the ATCC® and cultured in Dulbecco's Modified Eagle Medium supplemented with 4.5 g/L glucose, 4.5 g/L L-glutamine and 4.5 g/L sodium pyruvate (#10-013-CV, Corning), 2 mM L-alanyl-L-glutamine dipeptide (#35050-061, Gibco), 100U/mL penicillin, 100 μg/mL streptomycin (#SV30010, HyClone) and 10% fetal bovine serum (#SH30071.03 HyClone). Cells were maintained in a humidified incubator at 37° C. in 5% $CO_2$.

IDO activity was assessed as a function of kynurenine production as follows: HeLa cells were seeded in a 96-well culture plate at a density of 5,000 cells/well and allowed to equilibrate overnight. After 24 hours, the media was aspirated and replaced with media containing IFNγ (#285-IF/CF, R&D Systems) at a final concentration of 25 ng/mL. A serial dilution of each test compound was added to the cells in a total volume of 200 μL of culture medium. After a further 48 hour incubation, 170 μL of supernatant was transferred from each well to a fresh 96-well plate. 12.1 μL of 6.1N trichloroacetic acid (#T0699, Sigma-Aldrich) was added to each well and mixed, followed by incubation at 65° C. for 20 minutes to hydrolyze N-formylkynurenine, the product of indoleamine 2,3-dioxygenase, to kynurenine. The reaction mixture was then centrifuged for 10 mins at 500×g to sediment the precipitate. 100 μL of the supernatant was transferred from each well to a fresh 96-well plate. 100 μl of 2% (w/v) p-dimethylaminobenzaldehyde (#15647-7, Sigma-Aldrich) in acetic acid (#A6283, Sigma-Aldrich) was added to each well mixed and incubated at room temperature for 20 mins. Kynurenine concentrations were determined by measuring absorbance at 480 nm and calibrating against an L-kynurenine (#K8625, Sigma-Aldrich) standard curve using a SPECTRAMAX® M2e microplate reader (Molecular Devices). The percentage activity at each inhibitor concentration was determined and $IC_{50}$ values assessed using nonlinear regression.

Activity for compounds described herein is provided in FIG. 1, wherein potency levels are provided as follows: (Potency: IDO $IC_{50}$: A<0.01 μM; B<0.1 μM; C<10 μM)

Assessment of Inhibitor Activity in HEK293 Cell-Based Indoleamine 2,3-Dioxygenase (IDO) Assay HEK293 cells were transfected with a pCDNA-based mammalian expression vector harboring human IDO1 cDNA (NM 002164.2) by electroporation. They were cultured in medium (DMEM with 10% FBS) containing 1 mg/ml G418 for two weeks. Clones of HEK293 cells that stably expressed human IDO1 protein were selected and expanded for IDO inhibition assay.

The human IDO1/HEK293 cells were seeded at 10,000 cells per 50 μL per well with RPMI/phenol red free media contains 10% FBS in a 384-well black wall clear bottom tissue culture plate (Matrix Technologies LLC) 100 nL of certain concentration of compound was then added to each well using ECHO liquid handling systems. The cells were incubated for 20 hours in 37° C. incubator with 5% $CO_2$.

The compound treatments were stopped by adding trichloroacetic acid (Sigma-Aldrich) to a final concentration at 0.2%. The cell plate was further incubated at 50° C. for 30 minute. The equal volume supernatant (20 µL) and 0.2% (w/v) Ehrlich reagent (4-dimethylaminobenzaldehyde, Sigma-Aldrich) in glacial acetic acid were mixed in a new clear bottom 384-well plate. This plate was then incubated at room temperature for 30 minute. The absorbance at 490 nm was measured on Envision plate reader.

Compound $IC_{50}$ values were calculated using the counts of 500 nM of a reference standard treatment as one hundred percent inhibition, and counts of no compound but DMSO treatment as zero percent inhibition.

Activity for compounds described herein is provided in FIG. 1, wherein potency levels are provided as follows: (Potency: IDO $IC_{50}$: A<0.01 µM; B<0.1 µM; C<10 µM)

| Example # | IDO1 HEK Human IC50 (uM) | A < 50, B < 250, C < 2000 | IDO Hela IC50 (uM) | A < 50, B < 250, C < 2000 |
|---|---|---|---|---|
| 1 | 2.000 | C | | |
| 2 | 0.224 | C | | |
| 3 | 2.000 | C | | |
| 4 | 2.000 | C | | |
| 5 | 0.095 | B | | |
| 6 | 2.000 | C | | |
| 7 | | | 0.06 | B |
| 9 | | | 0.01 | A |
| 10 | | | 0.02 | A |
| 11 | 0.001 | A | 0.00 | A |
| 12 | | | 0.02 | A |
| 13 | | | 0.01 | A |
| 14 | | | 0.01 | A |
| 15 | | | 0.00 | A |
| 16 | | | 0.61 | C |
| 17 | | | 0.13 | B |
| 18 | | | 0.04 | A |
| 19 | | | 0.58 | C |
| 20 | | | 0.01 | A |
| 22 | | | 0.01 | A |
| 23 | 0.001 | A | | |
| 24 | | | 0.01 | A |
| 25 | | | 0.01 | A |
| 26 | | | 0.00 | A |
| 27 | | | 0.09 | B |
| 28 | | | 0.00 | A |
| 29 | | | 0.02 | A |
| 30 | | | 0.00 | A |
| 31 | | | 0.02 | A |
| 32 | | | 0.00 | A |
| 33 | | | 0.03 | A |
| 34 | 0.001 | A | 0.00 | A |
| 35 | | | | |
| 36 | | | 0.03 | A |
| 37 | | | 0.00 | A |
| 38 | | | 0.61 | C |
| 39 | | | 0.10 | B |
| 40 | | | 0.02 | A |
| 41 | | | 0.02 | A |
| 43 | | | 0.01 | A |
| 44 | | | | |
| 45 | | | 0.03 | A |
| 48 | | | 0.00 | A |
| 49 | | | 0.44 | C |
| 51 | | | 0.02 | A |
| 52 | | | 0.23 | B |
| 60 | | | 0.91 | C |
| 53 | | | 0.04 | A |
| 54 | | | 0.10 | B |
| 55 | | | 0.01 | A |
| 56 | | | 1.00 | C |
| 57 | | | 0.01 | A |
| 58 | | | 0.02 | A |
| 59 | | | 1.00 | C |
| 61 | | | 0.19 | B |
| 62 | | | 0.04 | A |
| 63 | | | 0.02 | A |
| 64 | | | 1.00 | C |
| 65 | | | 0.01 | A |
| 66 | | | 0.00 | A |
| 67 | | | 0.41 | C |
| 68 | | | 0.24 | B |
| 69 | | | 0.62 | C |
| 70 | | | 0.03 | A |
| 71 | | | 1.00 | C |
| 72 | | | 0.01 | A |
| 73 | | | 0.01 | A |
| 74 | | | 1.00 | C |
| 75 | | | 0.04 | A |
| 76 | | | 0.70 | C |
| 77 | | | 0.03 | A |
| 79 | | | 0.01 | A |
| 80 | | | 0.00 | A |
| 81 | | | 1.00 | C |
| 83-1 | | | 0.00 | A |
| 83-2 | | | 0.00 | A |
| 84-1 | | | 0.00 | A |
| 84-2 | | | 0.00 | A |
| 85 | | | 0.00 | A |
| 86 | | | 0.45 | C |
| 87 | | | 0.13 | B |
| 88 | | | 0.01 | A |
| 89 | | | 0.00 | A |
| 90 | | | 0.15 | B |
| 91 | | | 0.03 | A |
| 92 | | | 0.01 | A |
| 93 | | | 0.00 | A |
| 94 | | | 0.07 | B |
| 95 | | | 0.01 | A |
| 96 | | | 0.01 | A |
| 97 | | | 0.00 | A |
| 98 | | | 0.15 | B |
| 99 | | | 0.03 | A |
| 100 | | | 0.01 | A |
| 101-1 | | | 0.00 | A |
| 101-2 | | | 1.00 | C |
| 102 | | | 0.89 | C |
| 103 | | | 0.20 | B |
| 104 | | | 1.00 | C |
| 105 | | | 0.00 | A |
| 106 | | | 0.01 | A |
| 107 | | | 1.00 | C |
| 108 | | | 1.00 | C |
| 109 | | | 1.00 | C |
| 110 | | | 0.38 | B |
| 111 | | | 1.00 | C |
| 124 | | | 0.07 | B |
| 126-1 | | | 0.00 | A |
| 128 | | | 0.12 | B |
| 127 | | | 0.00 | A |
| 129 | | | 0.31 | B |
| 130 | | | 0.09 | B |
| 131 | | | 1.00 | C |
| 132 | | | 0.07 | B |
| 133 | | | 1.00 | C |
| 112-1 | 0.002 | A | 0.00 | A |
| 112-2 | 0.007 | A | 0.03 | A |
| 113-1 | 0.020 | A | 0.02 | A |
| 113-2 | 0.131 | B | | |
| 114 | 0.023 | A | 0.02 | A |
| 115 | 1.198 | C | | |
| 116 | 0.108 | B | | |
| 117 | 2.000 | C | | |
| 118-1 | | | 0.75 | C |
| 118-2 | | | 0.43 | C |

-continued

| Example # | IDO1 HEK Human IC50 (uM) | A < 50, B < 250, C < 2000 | IDO Hela IC50 (uM) | A < 50, B < 250, C < 2000 |
|---|---|---|---|---|
| 118-3 | | | 0.00 | A |
| 118-4 | | | 0.01 | A |
| 119 | | | 0.02 | A |
| 120 | | | 0.08 | B |
| 121 | | | 0.03 | A |
| 122 | | | 0.00 | A |
| 123 | | | 0.00 | A |
| 125-1 | | | 0.04 | A |
| 125-2 | | | 0.00 | A |
| 134 | 0.020 | A | | |
| 135 | 0.010 | A | 0.01 | A |
| 136 | 0.019 | A | | |
| 137 | 0.004 | A | 0.00 | A |
| 138 | 0.464 | C | | |

What is claimed:

1. A compound of formula I or II

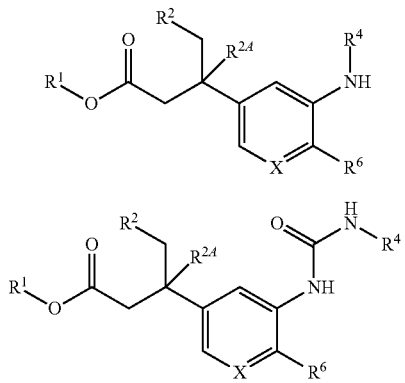

wherein

X is CH, N, or C—$V^a$—$R^3$;

$V^a$ is $C_1$-$C_6$alkylene optionally substituted with a phenyl that is optionally substituted with halogen;

$R^1$ is H or $C_{1-6}$alkyl;

$R^2$ is H, $C_{1-6}$alkyl, or $C_{0-6}$alk-$OC_{1-6}$alkyl, $R^{2A}$ is H or $C_{1-6}$alkyl, $R^6$ is H when X is C—$V^a$—$R^3$ or $R^6$ is —$V^b$—$R^3$ when X is CH or N;

$V^b$ is $C_1$-$C_6$alkylene optionally substituted with one, two, or three substituents independently selected from —OH, $C_{1-6}$alkyl, $C_{1-6}$haloalkyl, and heterocycloalkyl; or $V^b$ is $C_{2-6}$alkenylene optionally substituted with $C_{1-6}$alkyl;

$R^3$ is $C_{1-6}$alkyl optionally substituted with one, two or three —OH, or is $OC_{1-6}$alkyl optionally substituted with one, two or three —OH, $R^4$ is phenyl, pyridyl, pyrazinyl, pyridazinyl, pyrimidyl, or benzothiazolyl, each of which is optionally substituted with one, two or three substituents independently selected from halogen, $C_{1-6}$alkyl, $C_{1-6}$haloalkyl, $OC_{1-6}$haloalkyl, $C_{0-6}$alk-O—$C_{1-6}$alkyl, —CN, —COOH, and —COOC$_{1-6}$alkyl;

or a pharmaceutically acceptable salt thereof.

2. The compound of claim 1, wherein X is CH.
3. The compound of claim 1, wherein X is C—$V^a$—$R^3$.
4. The compound of claim 1, wherein X is N.
5. The compound of claim 1, wherein $R^1$ is H.
6. The compound of claim 1, wherein $R^1$ is $C_{1-6}$alkyl.
7. The compound of claim 1, wherein $R^2$ is H.
8. The compound of claim 1, wherein $R^2$ is $C_{1-6}$alkyl.
9. The compound of claim 1, wherein $R^2$ is $C_{0-6}$alk-$OC_{1-6}$alkyl.
10. The compound of claim 1, wherein $R^{2A}$ is H.
11. The compound of claim 1, wherein $R^{2A}$ is $C_{1-6}$alkyl.
12. The compound of claim 1, wherein $V^b$ is $C_1$alkylene substituted with one or two substituents that is independently $C_{1-6}$alkyl, $C_{1-6}$haloalkyl, or heterocycloalkyl.
13. The compound of claim 12, wherein the substituent is $CF_3$.
14. The compound of claim 3, wherein $V^a$ is $C_1$-$C_6$alkylene substituted with a phenyl that is optionally substituted with halogen.
15. The compound of claim 14, wherein the phenyl that is optionally substituted with halogen is 4-fluorophenyl.
16. The compound of claim 1, wherein $R^3$ is $C_{1-6}$alkyl optionally substituted with one, two or three —OH.
17. The compound of claim 1, wherein $R^3$ is $OC_{1-6}$alkyl optionally substituted with one, two, or three —OH.
18. The compound of claim 1, wherein $R^4$ is phenyl optionally substituted with one, two or three substituents independently selected from halogen, $C_{1-6}$alkyl, $C_{1-6}$haloalkyl, $OC_{1-6}$haloalkyl, $C_{0-6}$alk-O—$C_{1-6}$alkyl, —CN, —COOH, and —COOC$_{1-6}$alkyl.
19. The compound of claim 1, wherein $R^4$ is pyridyl optionally substituted with one, two or three substituents independently selected from halogen, $C_{1-6}$alkyl, $C_{1-6}$haloalkyl, $OC_{1-6}$haloalkyl, $C_{0-6}$alk-O—$C_{1-6}$alkyl, —CN, —COOH, and —COOC$_{1-6}$alkyl.
20. The compound of claim 1, wherein $R^4$ is pyrazinyl optionally substituted with one, two or three substituents independently selected from halogen, $C_{1-6}$alkyl, $C_{1-6}$haloalkyl, $OC_{1-6}$haloalkyl, $C_{0-6}$alk-O—$C_{1-6}$alkyl, —CN, —COOH, and —COOC$_{1-6}$alkyl.
21. The compound of claim 1, wherein $R^4$ is pyridazinyl optionally substituted with one, two or three substituents independently selected from halogen, $C_{1-6}$alkyl, $C_{1-6}$haloalkyl, $OC_{1-6}$haloalkyl, $C_{0-6}$alk-O—$C_{1-6}$alkyl, —CN, —COOH, and —COOC$_{1-6}$alkyl.
22. The compound of claim 1, wherein $R^4$ is pyrimidyl optionally substituted with one, two or three substituents independently selected from halogen, $C_{1-6}$alkyl, $C_{1-6}$haloalkyl, $OC_{1-6}$haloalkyl, $C_{0-6}$alk-O—$C_{1-6}$alkyl, —CN, —COOH, and —COOC$_{1-6}$alkyl.
23. The compound of claim 1, wherein $R^4$ is benzothiazolyl optionally substituted with one, two or three substituents independently selected from halogen, $C_{1-6}$alkyl, $C_{1-6}$haloalkyl, $OC_{1-6}$haloalkyl, $C_{0-6}$alk-O—$C_{1-6}$alkyl, —CN, —COOH, and —COOC$_{1-6}$alkyl.
24. The compound of claim 1 that is:
(R)-3-(4-(2-ethoxypropan-2-yl)-3-(3-(p-tolyl)ureido)phenyl)pentanoic acid;
(S)-3-(4-(2-ethoxypropan-2-yl)-3-(3-(p-tolyl)ureido)phenyl)pentanoic acid;
(R)-3-(4-(2-ethoxypropan-2-yl)-3-((2-methylbenzo[d]thiazol-6-yl)amino)phenyl)pentanoic acid;
(S)-3-(4-(2-ethoxypropan-2-yl)-3-((2-methylbenzo[d]thiazol-6-yl)amino)phenyl)pentanoic acid;
(S)-3-(3-((4-chlorophenyl)amino)-4-(2-ethoxypropan-2-yl)phenyl)pentanoic acid;
(S)-3-(4-(2-ethoxypropan-2-yl)-3-((2-ethoxypyrimidin-5-yl)amino)phenyl)pentanoic acid;
(R)-3-(4-((R)-1-ethoxy-2,2,2-trifluoroethyl)-3-(3-(p-tolyl)ureido)phenyl)pentanoic acid;

(S)-3-(4-((R)-1-ethoxy-2,2,2-trifluoroethyl)-3-(3-(p-tolyl)ureido)phenyl)pentanoic acid;
(R)-3-(4-((S)-1-ethoxy-2,2,2-trifluoroethyl)-3-(3-(p-tolyl)ureido)phenyl)pentanoic acid;
(S)-3-(4-((S)-1-ethoxy-2,2,2-trifluoroethyl)-3-(3-(p-tolyl) ureido)phenyl)pentanoic acid;
(R)-3-(3-(3-(4-cyanophenyl)ureido)-4-((R)-1-ethoxy-2,2,2-trifluoroethyl)phenyl)pentanoic acid;
(R)-3-(3-(3-(4-chloro-2-fluorophenyl)ureido)-4-((R)-1-ethoxy-2,2,2-trifluoroethyl)phenyl) pentanoic acid;
(R)-3-(4-((R)-1-ethoxy-2,2,2-trifluoroethyl)-3-((2-methoxypyrimidin-5-yl)amino)phenyl) pentanoic acid;
(R)-3-(3-((4-chlorophenyl)amino)-4-((R)-1-ethoxy-2,2,2-trifluoroethyl)phenyl)pentanoic acid;
(R)-3-(4-((R)-1-ethoxy-2,2,2-trifluoroethyl)-3-((2-ethoxypyrimidin-5-yl)amino)phenyl)pentanoic acid;
(R)-3-(4-((R)-1-ethoxy-2,2,2-trifluoroethyl)-3-((5-ethoxypyrazin-2-yl)amino)phenyl)pentanoic acid;
(R)-3-(4-((R)-1-ethoxy-2,2,2-trifluoroethyl)-3-((5-methoxypyrazin-2-yl)amino)phenyl)pentanoic acid;
(R)-3-(3-((4-cyanophenyl)amino)-4-((R)-1-ethoxy-2,2,2-trifluoroethyl)phenyl)pentanoic acid;
(R)-3-(4-((R)-1-ethoxy-2,2,2-trifluoroethyl)-3-((2-(methoxymethyl)pyrimidin-5-yl)amino) phenyl)pentanoic acid;
(R)-3-(4-((R)-1-ethoxy-2,2,2-trifluoroethyl)-3-((2-methylpyrimidin-5-yl)amino)phenyl)pentanoic acid;
(R)-3-(4-((R)-1-ethoxy-2,2,2-trifluoroethyl)-3-((2-ethylpyrimidin-5-yl)amino)phenyl)pentanoic acid;
(S)-3-(3-(3-(4-chloro-2-fluorophenyl)ureido)-4-((R)-1-ethoxy-2,2,2-trifluoroethyl)phenyl) pentanoic acid;
(S)-3-(3-(3-(4-cyanophenyl)ureido)-4-((R)-1-ethoxy-2,2,2-trifluoroethyl)phenyl)pentanoic acid;
(S)-3-(4-((R)-1-ethoxy-2,2,2-trifluoroethyl)-3-((2-methoxypyrimidin-5-yl)amino)phenyl) pentanoic acid;
(S)-3-(3-((4-chlorophenyl)amino)-4-((R)-1-ethoxy-2,2,2-trifluoroethyl)phenyl)pentanoic acid;
(S)-3-(4-((R)-1-ethoxy-2,2,2-trifluoroethyl)-3-((2-ethoxypyrimidin-5-yl)amino)phenyl)pentanoic acid;
(S)-3-(4-((R)-1-ethoxy-2,2,2-trifluoroethyl)-3-((5-methoxypyrazin-2-yl)amino)phenyl)pentanoic acid;
(S)-3-(3-((4-cyanophenyl)amino)-4-((R)-1-ethoxy-2,2,2-trifluoroethyl)phenyl)pentanoic acid;
(S)-3-(4-((R)-1-ethoxy-2,2,2-trifluoroethyl)-3-((2-(methoxymethyl)pyrimidin-5-yl)amino) phenyl)pentanoic acid;
(S)-3-(4-((R)-1-ethoxy-2,2,2-trifluoroethyl)-3-((2-methylpyrimidin-5-yl)amino)phenyl)pentanoic acid;
(S)-3-(4-((R)-1-ethoxy-2,2,2-trifluoroethyl)-3-((2-ethylpyrimidin-5-yl)amino)phenyl)pentanoic acid;
(S)-3-(4-((R)-1-ethoxy-2,2,2-trifluoroethyl)-3-((4-fluorophenyl)amino)phenyl)pentanoic acid;
(R)-3-(3-(3-(4-chloro-2-fluorophenyl)ureido)-4-((S)-1-ethoxy-2,2,2-trifluoroethyl)phenyl) pentanoic acid;
(R)-3-(4-((S)-1-ethoxy-2,2,2-trifluoroethyl)-3-((2-methoxypyrimidin-5-yl)amino)phenyl) pentanoic acid;
(R)-3-(3-((4-chlorophenyl)amino)-4-((S)-1-ethoxy-2,2,2-trifluoroethyl)phenyl)pentanoic acid;
(R)-3-(4-((S)-1-ethoxy-2,2,2-trifluoroethyl)-3-((2-ethoxypyrimidin-5-yl)amino)phenyl)pentanoic acid;
(R)-3-(4-((S)-1-ethoxy-2,2,2-trifluoroethyl)-3-((5-methoxypyrazin-2-yl)amino)phenyl)pentanoic acid;
(R)-3-(3-((4-cyanophenyl)amino)-4-((S)-1-ethoxy-2,2,2-trifluoroethyl)phenyl)pentanoic acid;
(R)-3-(4-((S)-1-ethoxy-2,2,2-trifluoroethyl)-3-((2-(methoxymethyl)pyrimidin-5-yl)amino) phenyl)pentanoic acid;
(R)-3-(4-((S)-1-ethoxy-2,2,2-trifluoroethyl)-3-((2-methylpyrimidin-5-yl)amino)phenyl)pentanoic acid;
(R)-3-(4-((S)-1-ethoxy-2,2,2-trifluoroethyl)-3-((2-ethylpyrimidin-5-yl)amino)phenyl)pentanoic acid;
(S)-3-(3-(3-(4-chloro-2-fluorophenyl)ureido)-4-((S)-1-ethoxy-2,2,2-trifluoroethyl)phenyl) pentanoic acid;
(S)-3-(4-((S)-1-ethoxy-2,2,2-trifluoroethyl)-3-((2-methoxypyrimidin-5-yl)amino)phenyl) pentanoic acid;
(S)-3-(3-((4-chlorophenyl)amino)-4-((S)-1-ethoxy-2,2,2-trifluoroethyl)phenyl)pentanoic acid;
(S)-3-(4-((S)-1-ethoxy-2,2,2-trifluoroethyl)-3-((2-ethoxypyrimidin-5-yl)amino)phenyl)pentanoic acid;
(S)-3-(4-((S)-1-ethoxy-2,2,2-trifluoroethyl)-3-((5-methoxypyrazin-2-yl)amino)phenyl)pentanoic acid;
(S)-3-(4-((S)-1-ethoxy-2,2,2-trifluoroethyl)-3-((4-fluorophenyl)amino)phenyl)pentanoic acid;
(S)-3-(4-((S)-1-ethoxy-2,2,2-trifluoroethyl)-3-((2-(methoxymethyl)pyrimidin-5-yl)amino) phenyl)pentanoic acid;
(R)-3-(4-((R)-1-ethoxy-2,2,2-trifluoroethyl)-3-(3-(p-tolyl)ureido)phenyl)-4-methoxybutanoic acid;
(S)-3-(4-((R)-1-ethoxy-2,2,2-trifluoroethyl)-3-(3-(p-tolyl)ureido)phenyl)-4-methoxybutanoic acid;
(R)-3-(3-(3-(4-chloro-2-fluorophenyl)ureido)-4-((R)-1-ethoxy-2,2,2-trifluoroethyl)phenyl)-4-methoxybutanoic acid;
3-(4-(1-ethoxy-2,2,2-trifluoroethyl)-3-((2-methoxypyrimidin-5-yl)amino)phenyl)-4-methoxybutanoic acid;
(R)-3-(3-((4-cyano-3-fluorophenyl)amino)-4-((R)-1-ethoxy-2,2,2-trifluoroethyl)phenyl)-4-methoxybutanoic acid;
(R)-3-(4-((R)-1-ethoxy-2,2,2-trifluoroethyl)-3-((5-fluoropyrimidin-2-yl)amino)phenyl)-4-methoxybutanoic acid;
(R)-3-(3-((4-cyanophenyl)amino)-4-((R)-1-ethoxy-2,2,2-trifluoroethyl)phenyl)-4-methoxybutanoic acid;
(R)-3-(3-((4-chlorophenyl)amino)-4-((R)-1-ethoxy-2,2,2-trifluoroethyl)phenyl)-4-methoxybutanoic acid;
(R)-3-(4-((R)-1-ethoxy-2,2,2-trifluoroethyl)-3-((2-methylpyrimidin-5-yl)amino)phenyl)-4-methoxybutanoic acid;
(S)-3-(3-(3-(4-chloro-2-fluorophenyl)ureido)-4-((R)-1-ethoxy-2,2,2-trifluoroethyl)phenyl)-4-methoxybutanoic acid;
(S)-3-(4-((R)-1-ethoxy-2,2,2-trifluoroethyl)-3-((2-methoxypyrimidin-5-yl)amino)phenyl)-4-methoxybutanoic acid;
(S)-3-(3-(3-(4-cyano-3-fluorophenyl)ureido)-4-((R)-1-ethoxy-2,2,2-trifluoroethyl)phenyl)-4-methoxybutanoic acid;
(S)-3-(4-((R)-1-ethoxy-2,2,2-trifluoroethyl)-3-((5-fluoropyrimidin-2-yl)amino)phenyl)-4-methoxybutanoic acid;
(S)-3-(3-((4-cyanophenyl)amino)-4-((R)-1-ethoxy-2,2,2-trifluoroethyl)phenyl)-4-methoxybutanoic acid;
(S)-3-(3-((4-chlorophenyl)amino)-4-((R)-1-ethoxy-2,2,2-trifluoroethyl)phenyl)-4-methoxybutanoic acid;
(S)-3-(4-((R)-1-ethoxy-2,2,2-trifluoroethyl)-3-((2-methylpyrimidin-5-yl)amino)phenyl)-4-methoxybutanoic acid;
(R)-3-(3-(3-(4-chloro-2-fluorophenyl)ureido)-4-((S)-1-ethoxy-2,2,2-trifluoroethyl)phenyl)-4-methoxybutanoic acid;
(R)-3-(4-((S)-1-ethoxy-2,2,2-trifluoroethyl)-3-((2-methoxypyrimidin-5-yl)amino)phenyl)-4-methoxybutanoic acid;

(R)-3-(3-((4-cyano-3-fluorophenyl)amino)-4-((S)-1-ethoxy-2,2,2-trifluoroethyl)phenyl)-4-methoxybutanoic acid;
(R)-3-(4-((S)-1-ethoxy-2,2,2-trifluoroethyl)-3-((5-fluoropyrimidin-2-yl)amino)phenyl)-4-methoxybutanoic acid;
(R)-3-(3-((4-chlorophenyl)amino)-4-((S)-1-ethoxy-2,2,2-trifluoroethyl)phenyl)-4-methoxybutanoic acid;
(R)-3-(3-((4-cyanophenyl)amino)-4-((S)-1-ethoxy-2,2,2-trifluoroethyl)phenyl)-4-methoxybutanoic acid;
(R)-3-(4-((S)-1-ethoxy-2,2,2-trifluoroethyl)-3-((2-methylpyrimidin-5-yl)amino)phenyl)-4-methoxybutanoic acid;
(S)-3-(3-(3-(4-chloro-2-fluorophenyl)ureido)-4-((S)-1-ethoxy-2,2,2-trifluoroethyl)phenyl)-4-methoxybutanoic acid;
(S)-3-(4-((S)-1-ethoxy-2,2,2-trifluoroethyl)-3-((2-methoxypyrimidin-5-yl)amino)phenyl)-4-methoxybutanoic acid;
(S)-3-(3-((4-cyano-3-fluorophenyl)amino)-4-((S)-1-ethoxy-2,2,2-trifluoroethyl)phenyl)-4-methoxybutanoic acid;
(S)-3-(4-((S)-1-ethoxy-2,2,2-trifluoroethyl)-3-((5-fluoropyrimidin-2-yl)amino)phenyl)-4-methoxybutanoic acid;
(S)-3-(3-((4-chlorophenyl)amino)-4-((S)-1-ethoxy-2,2,2-trifluoroethyl)phenyl)-4-methoxybutanoic acid;
(S)-3-(3-((4-cyanophenyl)amino)-4-((S)-1-ethoxy-2,2,2-trifluoroethyl)phenyl)-4-methoxybutanoic acid;
(S)-3-(4-((S)-1-ethoxy-2,2,2-trifluoroethyl)-3-((2-methylpyrimidin-5-yl)amino)phenyl)-4-methoxybutanoic acid;
(S)-3-(3-((4-chlorophenyl)amino)-4-((R)-2,2,2-trifluoro-1-methoxyethyl)phenyl)pentanoic acid;
(R)-3-(3-((4-chlorophenyl)amino)-4-((R)-2,2,2-trifluoro-1-methoxyethyl)phenyl)pentanoic acid;
(R)-3-(3-((4-chlorophenyl)amino)-4-((S)-2,2,2-trifluoro-1-methoxyethyl)phenyl)pentanoic acid;
(S)-3-(3-((4-chlorophenyl)amino)-4-((S)-2,2,2-trifluoro-1-methoxyethyl)phenyl)pentanoic acid;
(S)-3-(3-((4-cyanophenyl)amino)-4-((R)-2,2,2-trifluoro-1-methoxyethyl)phenyl)pentanoic acid;
(S)-3-(3-((2-methylpyrimidin-5-yl)amino)-4-((R)-2,2,2-trifluoro-1-methoxyethyl)phenyl) pentanoic acid;
(S)-3-(3-((2-ethoxypyrimidin-5-yl)amino)-4-((R)-2,2,2-trifluoro-1-methoxyethyl)phenyl) pentanoic acid;
(S)-3-(4-((R)-2,2,2-trifluoro-1-methoxyethyl)-3-((2-(trifluoromethyl)pyrimidin-5-yl)amino) phenyl)pentanoic acid;
(R)-3-(3-((4-cyanophenyl)amino)-4-((R)-2,2,2-trifluoro-1-methoxyethyl)phenyl)pentanoic acid;
(R)-3-(3-((2-methylpyrimidin-5-yl)amino)-4-((R)-2,2,2-trifluoro-1-methoxyethyl)phenyl) pentanoic acid;
(R)-3-(3-((2-ethoxypyrimidin-5-yl)amino)-4-((R)-2,2,2-trifluoro-1-methoxyethyl)phenyl) pentanoic acid;
(R)-3-(4-((R)-2,2,2-trifluoro-1-methoxyethyl)-3-((2-(trifluoromethyl)pyrimidin-5-yl)amino) phenyl)pentanoic acid;
(R)-3-(3-((4-cyanophenyl)amino)-4-((S)-2,2,2-trifluoro-1-methoxyethyl)phenyl)pentanoic acid;
(R)-3-(3-((2-methylpyrimidin-5-yl)amino)-4-((S)-2,2,2-trifluoro-1-methoxyethyl)phenyl) pentanoic acid;
(R)-3-(3-((2-ethoxypyrimidin-5-yl)amino)-4-((S)-2,2,2-trifluoro-1-methoxyethyl)phenyl) pentanoic acid;
(R)-3-(4-((S)-2,2,2-trifluoro-1-methoxyethyl)-3-((2-(trifluoromethyl)pyrimidin-5-yl)amino) phenyl)pentanoic acid;
(S)-3-(3-((4-cyanophenyl)amino)-4-((S)-2,2,2-trifluoro-1-methoxyethyl)phenyl)pentanoic acid;
(S)-3-(3-((2-methylpyrimidin-5-yl)amino)-4-((S)-2,2,2-trifluoro-1-methoxyethyl)phenyl) pentanoic acid;
(S)-3-(3-((2-ethoxypyrimidin-5-yl)amino)-4-((S)-2,2,2-trifluoro-1-methoxyethyl)phenyl) pentanoic acid;
(S)-3-(4-((S)-2,2,2-trifluoro-1-methoxyethyl)-3-((2-(trifluoromethyl)pyrimidin-5-yl)amino) phenyl)pentanoic acid;
(S)-3-(3-((4-cyanophenyl)amino)-4-((S)-1-morpholinopropyl)phenyl)-4-methoxybutanoic acid;
(S)-3-(3-((4-cyanophenyl)amino)-4-((R)-1-morpholinopropyl)phenyl)-4-methoxybutanoic acid;
(S)-3-(3-((2-ethylpyrimidin-5-yl)amino)-4-((S)-1-morpholinopropyl)phenyl)-4-methoxybutanoic acid;
(S)-3-(3-((2-ethoxypyrimidin-5-yl)amino)-4-((S)-1-morpholinopropyl)phenyl)-4-methoxybutanoic acid;
(S)-4-methoxy-3-(3-((6-(methoxymethyl)pyridin-3-yl)amino)-4-((S)-1-morpholinopropyl) phenyl)butanoic acid;
(S)-3-(3-((4-chlorophenyl)amino)-4-((S)-1-morpholinopropyl)phenyl)-4-methoxybutanoic acid;
(S)-3-(3-((4-fluorophenyl)amino)-4-((S)-1-morpholinopropyl)phenyl)-4-methoxybutanoic acid;
(S)-3-(3-((2-ethylpyrimidin-5-yl)amino)-4-((R)-1-morpholinopropyl)phenyl)-4-methoxybutanoic acid;
(S)-3-(3-((2-ethoxypyrimidin-5-yl)amino)-4-((R)-1-morpholinopropyl)phenyl)-4-methoxybutanoic acid;
(S)-4-methoxy-3-(3-((6-(methoxymethyl)pyridin-3-yl)amino)-4-((R)-1-morpholinopropyl) phenyl)butanoic acid;
(S)-3-(3-((4-chlorophenyl)amino)-4-((R)-1-morpholinopropyl)phenyl)-4-methoxybutanoic acid;
(S)-3-(3-((4-fluorophenyl)amino)-4-((R)-1-morpholinopropyl)phenyl)-4-methoxybutanoic acid;
(R)-3-(3-((4-chlorophenyl)amino)-5-((S)-ethoxy(4-fluorophenyl)methyl)phenyl)pentanoic acid;
(S)-3-(3-((4-chlorophenyl)amino)-5-((S)-ethoxy(4-fluorophenyl)methyl)phenyl)pentanoic acid;
3-(3-((4-chlorophenyl)amino)-5-(ethoxy(4-fluorophenyl)methyl)phenyl)pentanoic acid;
(R)-3-(3-((4-chlorophenyl)amino)-5-((R)-ethoxy(4-fluorophenyl)methyl)phenyl)pentanoic acid;
(S)-3-(3-((4-chlorophenyl)amino)-5-((R)-ethoxy(4-fluorophenyl)methyl)phenyl)pentanoic acid;
(R)-3-(3-((S)-ethoxy(4-fluorophenyl)methyl)-5-((2-methylbenzo[d]thiazol-6-yl)amino)phenyl)pentanoic acid;
(S)-3-(3-((S)-ethoxy(4-fluorophenyl)methyl)-5-((2-methylbenzo[d]thiazol-6-yl)amino)phenyl) pentanoic acid;
(R)-3-(3-((R)-ethoxy(4-fluorophenyl)methyl)-5-((2-methylbenzo[d]thiazol-6-yl)amino)phenyl) pentanoic acid;
(S)-3-(3-((R)-ethoxy(4-fluorophenyl)methyl)-5-((2-methylbenzo[d]thiazol-6-yl)amino)phenyl) pentanoic acid;
(R)-3-(3-((2-ethoxypyrimidin-5-yl)amino)-4-((R)-1-morpholinopropyl)phenyl)pentanoic acid;
(S)-3-(3-((2-ethoxypyrimidin-5-yl)amino)-4-((R)-1-morpholinopropyl)phenyl)pentanoic acid;
(R)-3-(3-((2-ethoxypyrimidin-5-yl)amino)-4-((S)-1-morpholinopropyl)phenyl)pentanoic acid;
(S)-3-(3-((2-ethoxypyrimidin-5-yl)amino)-4-((S)-1-morpholinopropyl)phenyl)pentanoic acid;
3-(3-((2-ethoxypyrimidin-5-yl)amino)-4-(1-morpholinopropyl)phenyl) pentanoic acid;

(R)-3-(3-((2-ethylpyrimidin-5-yl)amino)-4-((R)-1-morpholinopropyl)phenyl)pentanoic acid;
(R)-3-(3-((2-methylpyrimidin-5-yl)amino)-4-((R)-1-morpholinopropyl)phenyl)pentanoic acid;
(R)-3-(3-((6-(methoxymethyl)pyridin-3-yl)amino)-4-((R)-1-morpholinopropyl)phenyl)pentanoic acid;
(R)-3-(3-((4-cyanophenyl)amino)-4-((R)-1-morpholinopropyl)phenyl)pentanoic acid;
(R)-3-(3-((4-chlorophenyl)amino)-4-((R)-1-morpholinopropyl)phenyl)pentanoic acid;
(S)-3-(3-((4-cyanophenyl)amino)-4-((R)-1-morpholinopropyl)phenyl)pentanoic acid;
(R)-3-(3-((2-ethoxypyrimidin-5-yl)amino)-4-((S)-1-(tetrahydro-2H-pyran-4-yl)propyl)phenyl) pentanoic acid;
(R)-3-(3-((2-ethoxypyrimidin-5-yl)amino)-4-((R)-1-(tetrahydro-2H-pyran-4-yl)propyl)phenyl) pentanoic acid;
(R)-3-(3-((2-ethylpyrimidin-5-yl)amino)-4-((S)-(1-(tetrahydro-2H-pyran-4-yl)propyl)phenyl) pentanoic acid;
(R)-3-(3-((2-ethylpyrimidin-5-yl)amino)-4-((R)-1-(tetrahydro-2H-pyran-4-yl)propyl)phenyl) pentanoic acid;
(R)-3-(3-((6-(methoxymethyl)pyridin-3-yl)amino)-4-((S)-1-(tetrahydro-2H-pyran-4-yl)propyl) phenyl)pentanoic acid;
(S)-3-(4-((R)-1-morpholinopropyl)-3-((2-(trifluoromethyl)pyrimidin-5-yl)amino)phenyl) pentanoic acid;
(S)-3-(3-((6-(methoxymethyl)pyridin-3-yl)amino)-4-((R)-1-morpholinopropyl)phenyl)pentanoic acid;
(S)-3-(3-((4-chlorophenyl)amino)-4-((R)-1-morpholinopropyl)phenyl)pentanoic acid;
(S)-3-(3-((5-(difluoromethoxy)pyridin-2-yl)amino)-4-((R)-1-morpholinopropyl)phenyl)pentanoic acid;
(S)-3-(4-(2,6-Dimethylheptan-4-yl)-3-(3-(p-tolyl)ureido)phenyl)pentanoic acid;
or pharmaceutically acceptable salt thereof.

25. A compound that is an enantiomer or a diastereomer of a compound of claim 24, or a pharmaceutically acceptable salt thereof.

26. A compound that is
1-(4-(2,6-dimethylheptan-4-yl)-2'-(2H-tetrazol-5-yl)-[1,1'-biphenyl]-3-yl)-3-(p-tolyl)urea;
1-(4-Chloro-2-fluorophenyl)-3-(4-(2,6-dimethylheptan-4-yl)-2'-(2H-tetrazol-5-yl)-[1,1'-biphenyl]-3-yl)urea;
1-(4-(2,6-Dimethylheptan-4-yl)-2'-(2H-tetrazol-5-yl)-[1,1'-biphenyl]-3-yl)-3-(5-methylisoxazol-3-yl)urea; or
2-(4-(2,6-Dimethylheptan-4-yl)-3-(3-(p-tolyl)ureido)phenoxy)acetic acid; or
a pharmaceutically acceptable salt thereof.

27. A pharmaceutical composition comprising a compound of claim 1 and a pharmaceutically acceptable carrier.

28. The pharmaceutical composition of claim 27, further comprising ipilimumab (YERVOY), nivolumab (OPDIVO), or pembrolizumab (KEYTRUDA), or a combination thereof.

29. A method of treating melanoma, lung cancer, head or neck cancer, renal cell carcinoma, or bladder cancer in a patient in need of such treatment comprising administering to the patient a therapeutically effective amount of a compound according to claim 1.

30. The method of claim 29, further comprising administering to the patient ipilimumab (YERVOY), nivolumab (OPDIVO), or pembrolizumab (KEYTRUDA), or a combination thereof.

31. The method of claim 29, wherein the patient is human.

32. The method of claim 29, wherein the cancer is bladder cancer.

* * * * *